(12) United States Patent
Jheng et al.

(10) Patent No.: US 12,428,479 B2
(45) Date of Patent: Sep. 30, 2025

(54) CLDN18.2-TARGETING ANTIBODY, BISPECIFIC ANTIBODY AND USE THEREOF

(71) Applicant: HARBOUR BioMed (Shanghai) Co., Ltd, Shanghai (CN)

(72) Inventors: Ming-Jin Jheng, Shanghai (CN); Yongqiang Wang, Shanghai (CN); Yun Zhang, Shanghai (CN); Chuchu Zhao, Shanghai (CN); Yunxing Yang, Shanghai (CN); Fei Chen, Shanghai (CN); Beibei Qin, Shanghai (CN); Yuetao Wu, Shanghai (CN); Yi Ding, Shanghai (CN)

(73) Assignee: HARBOUR BioMed (Shanghai) Co., Ltd, Shanghai (CN)

( * ) Notice: Subject to any disclaimer, the term of this patent is extended or adjusted under 35 U.S.C. 154(b) by 0 days.

(21) Appl. No.: 17/818,072

(22) Filed: Aug. 8, 2022

(65) Prior Publication Data
US 2023/0134183 A1 May 4, 2023

(30) Foreign Application Priority Data
Aug. 9, 2021 (CN) .................. 202110909032.3

(51) Int. Cl.
| C07K 16/28 | (2006.01) |
| A61K 39/00 | (2006.01) |
| A61K 39/395 | (2006.01) |
| A61K 45/06 | (2006.01) |
| A61K 47/68 | (2017.01) |
| A61P 35/00 | (2006.01) |

(52) U.S. Cl.
CPC .......... *C07K 16/28* (2013.01); *A61K 39/3955* (2013.01); *A61K 45/06* (2013.01); *A61K 47/6849* (2017.08); *A61P 35/00* (2018.01); *C07K 16/2809* (2013.01); *A61K 2039/505* (2013.01); *C07K 2317/14* (2013.01); *C07K 2317/24* (2013.01); *C07K 2317/31* (2013.01); *C07K 2317/51* (2013.01); *C07K 2317/515* (2013.01); *C07K 2317/52* (2013.01); *C07K 2317/522* (2013.01); *C07K 2317/524* (2013.01); *C07K 2317/526* (2013.01); *C07K 2317/53* (2013.01); *C07K 2317/55* (2013.01); *C07K 2317/56* (2013.01); *C07K 2317/565* (2013.01); *C07K 2317/567* (2013.01); *C07K 2317/569* (2013.01); *C07K 2317/622* (2013.01); *C07K 2317/73* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| 5,858,358 | A | 1/1999 | June et al. |
| 5,883,223 | A | 3/1999 | Gray |
| 5,892,019 | A | 4/1999 | Schlom et al. |
| 6,352,694 | B1 | 3/2002 | June et al. |
| 6,534,055 | B1 | 3/2003 | June et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 2004/0101519 | A1 | 5/2004 | June et al. |
| 2006/0034810 | A1 | 2/2006 | Riley et al. |
| 2006/0121005 | A1 | 6/2006 | Berenson et al. |
| 2018/0282389 | A1 | 10/2018 | Sahin et al. |
| 2021/0214433 | A1 | 7/2021 | Lin et al. |
| 2022/0184126 | A1 | 6/2022 | Wang et al. |

FOREIGN PATENT DOCUMENTS

| CN | 112480248 A | 3/2021 | |
| WO | WO-2014075788 A1 * | 5/2014 | ....... A61K 39/39558 |
| WO | WO-2019133761 A1 * | 7/2019 | ............. A61P 35/00 |

(Continued)

OTHER PUBLICATIONS

Vauquelin et al. British Journal of Pharmacology. Apr. 2013. 168(8): 1771-1785 (Year: 2013).*
Chamow et al. BioProcess International. May 24, 2020. Retrieved online on Mar. 19, 2024 from URL: https://www.bioprocessintl.com/chromatography/capture-of-ch1-containing-bispecific-antibodies-evaluating-an-alternative-to-protein-a (Year: 2020).*
Schroeder et al. J Allergy Clin Immunol. Feb. 2010 ; 125(2 0 2): S41-S52 (Year: 2010).*
Adusumilli P.S., et al., "Mesothelin-Targeted CAR T-cell Therapy in Patients with Malignant Pleural Disease, in Combination with the Anti-PD-1 Agent Pembrolizumab", Cancer Discovery, Nov. 2021, vol. 11, No. 11, pp. 2748-2763. (Year: 2021).*

(Continued)

*Primary Examiner* — Anne M. Gussow
*Assistant Examiner* — Brianna K Swartwout

(57) ABSTRACT

The present invention discloses CLDN18.2-targeting antibodies, bispecific antibodies and use thereof. The CLDN18.2-targeting antibody is a single-domain heavy-chain antibody that has high affinity for tumor cells endogenously expressing CLDN18.2 and can induce high endocytic activity. The bispecific antibody can target CLDN18.2 and CD3 and retains the binding effect of an Fc to an FcRn; meanwhile, a mutant Fc is preferred so as to reduce the binding to an FcgR and thus the activation of non-specific T cells caused by the cross-linking of an FcgR. The CD3-terminus activity is optimized so that the release of common cytokines in CRS, such as IL6 and TNFα can be reduced.

17 Claims, 38 Drawing Sheets

Specification includes a Sequence Listing.

(56) References Cited

FOREIGN PATENT DOCUMENTS

| WO | 2020025792 A1 | 2/2020 | |
|---|---|---|---|
| WO | 2020238730 A1 | 12/2020 | |
| WO | 2021011885 A1 | 1/2021 | |
| WO | WO-2021009692 A1 * | 1/2021 | ......... A61K 31/4709 |
| WO | 2021129765 A1 | 7/2021 | |
| WO | WO-2021222578 A1 * | 11/2021 | ............. A61P 35/00 |
| WO | WO-2022104267 A1 * | 5/2022 | ............. A61P 35/00 |

OTHER PUBLICATIONS

Altschul S.F., et al., "Basic Local Alignment Search Tool," Journal of Molecular Biology, Oct. 1990, vol. 215 (3), Elsevier, Netherlands, pp. 403-410. (Year: 1990).*

Altschul S.F., et al., "Gapped BLAST and PSI-Blast: A New Generation of Protein Database Search Programs," Nucleic Acids Research, Oxford University Press, England, 1997, vol. 25 (17), pp. 3389-3402. (Year: 1997).*

Bird R.E., et al., "Single-Chain Antigen-Binding Proteins," Science, vol. 242, 1988, pp. 423-426. (Year: 1988).*

Gattinoni L., et al., "A Human Memory T Cell Subset with Stem Cell-Like Properties", Nature Medicine, vol. 17, No. 10, Oct. 2011, pp. 1290-1297. (Year: 2011).*

Haanen J.B.A.G., et al., "Selective Expansion of Cross-reactive CD81 Memory T Cells by Viral Variants", Journal of Experimental Medicine, vol. 90, No. 9, Nov. 1, 1999, pp. 1319-1328. (Year: 1999).*

Henderson D.J., et al., "Comparison of the Effects of FK-506, Cyclosporin A and Rapamycin on IL-2 Production", Immunology, vol. 73, No. 3, Jul. 1991, pp. 316-321. (Year: 1991).*

Huston J.S., et al., "Protein Engineering of Antibody Binding Sites: Recovery of Specific Activity in an Anti-digoxin Single-chain Fv Analogue Produced in Escherichia Coli," Proceedings of the National Academy of Sciences, USA, Aug. 1988, vol. 85, No. 16, pp. 5879-5883. (Year: 1988).*

Liu J., et al., "Calcineurin is a Common Target of Cyclophilin-Cyclosporin A and FKBP-FK506 Complexes", Cell, vol. 66, No. 4, 807 -815, Aug. 23, 1991, 9 Pages. (Year: 1991).*

Needleman S.B., et al., "A General Method Applicable to the Search for Similarities in the Amino Acid Sequence of Two Proteins" , Journal of Molecular Biology, vol. 48, No. 3, 1970, pp. 443-453. (Year: 1970).*

Qi C., et al., "Claudin18.2-Specific CAR T Cells in Gastrointestinal Cancers: Phase 1 Trial Interim Results", Nature Medicine, vol. 28, Jun. 2022, pp. 1189-1198. (Year: 2022).*

Ten Berge I.J., "Selective Expansion of a Peripheral Blood CD8+ Memory T Cell Subset Expressing Both Granzyme B and L-Selectin During Primary Viral Infection in Renal Allograft Recipients", Transplantation Proceedings, vol. 30, No. 8, 1998, pp. 3975-3977. (Year: 1998).*

Ward E.S., et al., "Binding Activities of a Repertoire of Single Immunoglobulin Variable Domains Secreted From Escherichia Coli", Nature, 1989, vol. 341, pp. 544-546. (Year: 1989).*

Wells D.A., et al., "A Review of CAR T-Cell Therapies Approved for the Treatment of Relapsed and Refractory B-Cell Lymphomas", Journal of Hematology Oncology Pharmacy, vol. 12, No. 1, Feb. 2022, pp. 30-42. (Year: 2022).*

Yu L., et al., "GD2-Specific Chimeric Antigen Receptor-Modified T Cells for the Treatment of Refractory and/or Recurrent Neuroblastoma in Pediatric Patients", Journal of Cancer Research and Clinical Oncology, vol. 148, 2022, pp. 2643-2652. (Year: 2022).*

Zheng X., et al., "Glypican-3: A Novel and Promising Target for the Treatment of Hepatocellular Carcinoma", Frontiers in Oncology , vol. 12, Feb. 16, 2022, pp. 1-11. (Year: 2022).*

Drabek D., et al., "Expression Cloning and Production of Human Heavy-Chain-Only Antibodies from Murine Transgenic Plasma Cells", Frontiers In Immunology, vol. 7, Dec. 19, 2016, pp. 1-10, XP055418377, DOI: 10.3389/fimmu.2016.00619.

International Search Report and Written Opinion for International Application No. PCT/CN2022/110314, mailed Jan. 12, 2023, 26 Pages.

Janssens R., et al., "Generation of Heavy-Chain-Only Antibodies in Mice", Proceedings of the National Academy of Sciences, vol. 103, No. 41, Oct. 10, 2006, pp. 15130-15135, XP055781470, ISSN: 0027-8424, DOI: 10.1073/pnas.0601108103.

Adusumilli P.S., et al., "Mesothelin-Targeted CAR T-cell Therapy in Patients with Malignant Pleural Disease, in Combination with the Anti-PD-1 Agent Pembrolizumab", Cancer Discovery, Nov. 2021, vol. 11, No. 11, pp. 2748-2763.

Altschul S.F., et al., "Basic Local Alignment Search Tool," Journal of Molecular Biology, Oct. 1990, vol. 215 (3), Elsevier, Netherlands, pp. 403-410.

Altschul S.F., et al., "Gapped BLAST and PSI-BLAST: A New Generation of Protein Database Search Programs," Nucleic Acids Research, Oxford University Press, England, 1997, vol. 25 (17), pp. 3389-3402.

Bierer B.E., et al., "Cyclosporin A and FK506: Molecular Mechanisms of Immunosuppression and Probes for Transplantation Biology", Current Opinion in Immunology, Oct. 1993, vol. 5, No. 5, pp. 763-773, doi: 10.1016/0952-7915(93)90135-f.

Bird R.E., et al., "Single-Chain Antigen-Binding Proteins," Science, vol. 242, 1988, pp. 423-426.

Gattinoni L., et al., "A Human Memory T Cell Subset with Stem Cell-Like Properties", Nature Medicine, vol. 17, No. 10, Oct. 2011, pp. 1290-1297.

Haanen J.B.A.G., et al., "Selective Expansion of Cross-reactive CD81 Memory T Cells by Viral Variants", Journal of Experimental Medicine, vol. 90, No. 9, Nov. 1, 1999, pp. 1319-1328.

Henderson D.J., et al., "Comparison of the Effects of FK-506, Cyclosporin A and Rapamycin on IL-2 Production", Immunology, vol. 73, No. 3, Jul. 1991, pp. 316-321.

Huston J.S., et al., "Protein Engineering of Antibody Binding Sites: Recovery of Specific Activity in an Anti-digoxin Single-chain Fv Analogue Produced in Escherichia Coli," Proceedings of the National Academy of Sciences, USA, Aug. 1988, vol. 85, No. 16, pp. 5879-5883.

International Search Report and Written Opinion for International Application No. PCT/US2023/076117, mailed May 15, 2024, 18 Pages.

Liu J., et al., "Calcineurin is a Common Target of Cyclophilin-Cyclosporin A and FKBP-FK506 Complexes", Cell, vol. 66, No. 4, 807-815, Aug. 23, 1991, 9 Pages.

Mackensen A., et al., "BNT211: A Phase I/Ii Trial to Evaluate Safety and Efficacy of CLDN6 Car-T Cells and Vaccine-Mediated In Vivo Expansion in Patients with CLDN6-Positive Advanced Solid Tumors", The Journal of Immunotherapy of Cancer, 2021, vol. 9, (Suppl 2): A1-A1054, 1 Page.

Majzner R.G. et al., "Tuning the Antigen Density Requirement for CAR T-cell Activity", Cancer Discovery, May 2020, vol. 10, No. 5, pp. 702-723.

Needleman S.B., et al., "A General Method Applicable to the Search for Similarities in the Amino Acid Sequence of Two Proteins", Journal of Molecular Biology, vol. 48, No. 3, 1970, pp. 443-453.

Qi C., et al., "Claudin18.2-Specific CAR T Cells in Gastrointestinal Cancers: Phase 1 Trial Interim Results", Nature Medicine, vol. 28, Jun. 2022, pp. 1189-1198.

Ten Berge I.J., "Selective Expansion of a Peripheral Blood CD8+ Memory T Cell Subset Expressing Both Granzyme B and L-Selectin During Primary Viral Infection in Renal Allograft Recipients", Transplantation Proceedings, vol. 30, No. 8, 1998, pp. 3975-3977.

Ward E.S., et al., "Binding Activities of a Repertoire of Single Immunoglobulin Variable Domains Secreted From *Escherichia coli*", Nature, 1989, vol. 341, pp. 544-546.

Wells D.A., et al., "A Review of CAR T-Cell Therapies Approved for the Treatment of Relapsed and Refractory B-Cell Lymphomas", Journal of Hematology Oncology Pharmacy, vol. 12, No. 1, Feb. 2022, pp. 30-42.

Yu L., et al., "GD2-Specific Chimeric Antigen Receptor-Modified T Cells for the Treatment of Refractory and/or Recurrent Neuroblastoma in Pediatric Patients", Journal of Cancer Research and Clinical Oncology, vol. 148, 2022, pp. 2643-2652.

(56) References Cited

OTHER PUBLICATIONS

Zheng X., et al., "Glypican-3: A Novel and Promising Target for the Treatment of Hepatocellular Carcinoma", Frontiers in Oncology, vol. 12, Feb. 16, 2022, pp. 1-11.

* cited by examiner

Structure (1)     Fab-Fc-Dual VH

Structure (2)     HCAb_HC-Fab

Structure (7)    Fab-Fc-VH-VH-VH

Structure (8)    Fab-Fc-scFv(VH-VL)

FIG 5g
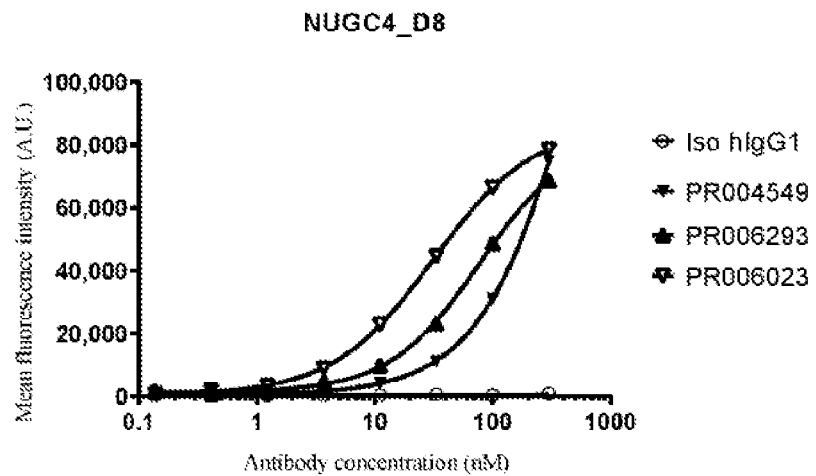
FIG 5h
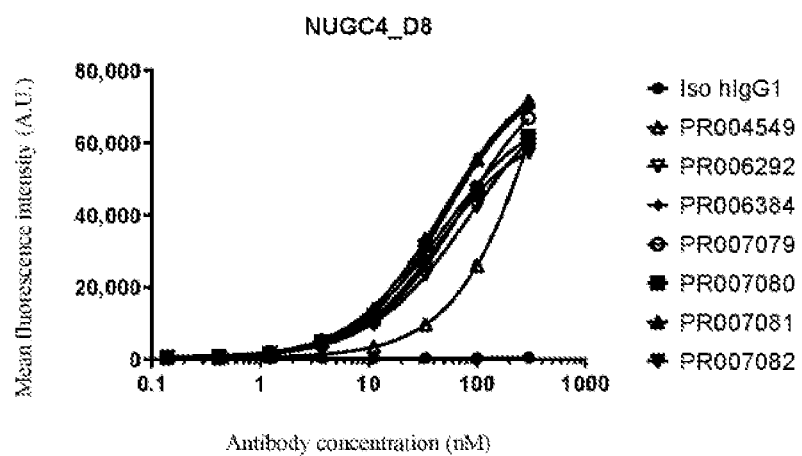
FIG 5i
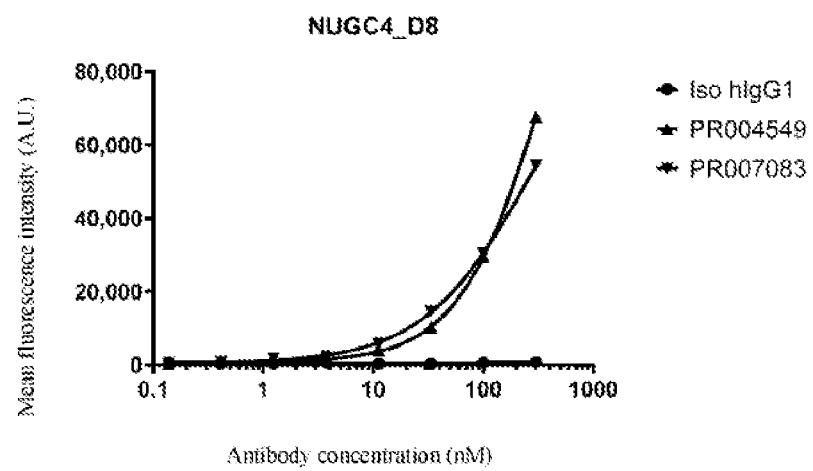
FIG. 5

CLDN18.2-TARGETING ANTIBODY, BISPECIFIC ANTIBODY AND USE THEREOF

CROSS-REFERENCE TO RELATED APPLICATION

This application Ser. No. 17/818,072 filed on Aug. 8, 2022 claims benefit under 35 U.S.C. § 119(b) of the following Chinese Provisional Application No. 202110909032.3 filed Aug. 9, 2021.

REFERENCE TO THE SEQUENCE LISTING

This application incorporates by reference a Sequence Listing submitted with this application as text file entitled "2022-08-08—CLDN18T-100_Sequence_Listing_NEW.xml" created on Aug. 8, 2022 and having a size of 348,484 bytes.

TECHNICAL FIELD

The present invention relates to the field of biomedicine, and particularly to a CLDN18.2-targeting antibody, a bispecific antibody and use thereof.

BACKGROUND

Cancer is one of the deadliest diseases in humans today. According to the World Health Organization (WHO) Report 2018, there are about 18.07 million new cases of cancer each year. Approximately 9.55 million people each year die of cancer. According to WHO estimates, gastric cancer is ranked fifth among the most commonly diagnosed cancers in the world. Gastric cancer is ranked third (for men) and fourth (for women) among the causes of cancer-related deaths. There are one million new cases of gastric cancer worldwide each year. Approximately 35% of patients who are primarily diagnosed with gastric cancer in the U.S. are those with metastatic gastric cancer. The five-year survival rate for those diagnosed with advanced gastric cancer is 5%, and the median survival is about 6 months. First-line medication for treating patients with metastatic/recurrent gastric cancer is divided into two cases: (1) for HER2-neu positive patients, Transtuzumab is employed in combination with chemotherapeutic drugs; (2) for HER2-neu negative patients, the treatment is limited to chemotherapeutic drugs; however, the treatment outcome is not good (*Front Pharmacol.* 2018 Sep. 13; 9: 404).

The splice variant 1 (CLD18A1, namely CLDN18.1, under the Genbank accession number NP_057453, NM016369) and the splice variant 2 (CLD18A2, namely CLDN18.2, under the Genbank accession number NM_001002026, NP_001002026) of the CLDN18 (Claudin18) molecule are integral transmembrane proteins having a molecular weight of approximately 27.9/27.72 kD. Claudins are integral membrane proteins located in the tight junction of an epithelium and endothelium. The other two major proteins of the tight-junction family are occludin and the junctional adhesion molecule (JAM). Claudins are essential components of the tight junctions, and play an important role in maintaining the polarity of epithelial cells, controlling the paracellular diffusion, and regulating the growth and differentiation of cells. It is speculated that claudins can hardly get near antibodies in well-constructed epithelia but become exposed in tumor cells. The claudin molecule crosses a cell membrane four times, with both the N- and C-termini in the cytoplasm. The human CLDN18.2 (Claudin 18.2) protein is a transmembrane protein having 261 amino acids in full length, among which 1-23 forms a signal peptide; it has two extramembranous regions following the signal peptide, extracellular loop 1 (ECL1) of about 55 amino acids and ECL2 of about 23 amino acids. CLDN18.1 (Claudin 18.1) and CLDN18.2 differ in the first 21 amino acids of the N-terminus including the first TM and loop 1 (i.e., ECL1) but have identical primary protein sequences at the C-terminus. The ECL1 regions of human CLDN18.2 and human CLDN18.1 are very similar, and the ECL2 regions of human CLDN18.2 and human CLDN18.1 are identical. Thus, the development of antibodies for human CLDN18.2 protein targets requires the search for antibodies targeted at the ECL1 region or the spatial structure of the human CLDN18.2 protein. This makes the work in this aspect more difficult. CLDN18.1 is selectively expressed in the epithelium of the normal lungs and stomach (*Mol Cell Biol.* 2001 November; 21(21): 7380-90). Expression of CLDN18.2 in normal tissues is highly limited to differentiated cells of the gastric epithelium and absent from the gastric stem cell region. But it is highly expressed in several types of cancer, including gastric, esophageal, pancreatic and lung tumors, as well as human cancer cell lines. The molecular weight of the protein varies in some cancers and adjacent normal tissues. The proteins with a high molecular weight observed in healthy tissues can be converted to those with the same molecular weight as observed in cancer by treating the tissue lysate with the deglycosylating compound PNGaseF. This suggests that claudin is less N-glycosylated in cancer than in its normal tissue counterpart. This structural difference is likely to give rise to an altered epitope. A classical N-glycosylation motif is in the amino acid at position 116 within the loop D3 domain of the molecule. (CN103509110B).

At present, studies on monoclonal antibodies for CLDN18.2 are limited to the phase II and phase III clinical trials of the Claudiximab (IMAB362) antibody (see WO 2014/146672). IMAB362 is capable of inducing ADCC (antibody-dependent cell-mediated cytotoxicity) and CDC (complement dependent cytotoxicity) effects, as well as mediating tumor killing. IMAB362 showed an encouraging effect in the phase I and II clinical trials for the treatment of advanced gastro-esophageal cancer (*Eur J Cancer.* 2018 September; 100: 17-26). However, IMAB362 is a human or murine chimeric antibody and thus involves an immunogenicity risk, and the affinity is not high. Due to the unmet medical need for a large number of malignancies, there is a need for other CLDN18.2 antibodies with more desirable pharmaceutical characteristics. Therefore, there is a lack in the art of effective antibodies targeting the human CLDN18.2 protein, particularly fully human monoclonal antibodies, as well as monoclonal antibodies with better cell-binding activity.

At present, the CLDN18.2×CD3 bispecific antibody under clinical development includes AMG910 of Amgen. AMG910 can induce a TDCC (T-cell-dependent-cellular-cytotoxicity) effect to mediate tumor killing. However, the antibodies in the prior art may have the problems of short half-lives, poor drug effects, causing cytokine release syndrome (CRS), etc. Therefore, there is an urgent need to develop safer and more effective bispecific antibodies that target both human CLDN18.2 and CD3 and can bind to cynomolgus CLDN18.2 and CD3.

SUMMARY

To solve the technical problems in the prior art that safe and effective monoclonal antibodies targeting human CLDN18.2 and bispecific antibodies that target both human CLDN18.2 and CD3 and can bind to cynomolgus CLDN18.2 and CD3 are lacking, the present invention provides a CLDN18.2-targeting monoclonal antibody, a CLDN18.2 and CD3-targeting bispecific antibody and use thereof.

To solve the above technical problems, a first aspect of the present invention provides a CLDN18.2-targeting antibody comprising a heavy chain variable region comprising HCDR1, HCDR2 and HCDR3, wherein the HCDR1 comprises an amino acid sequence as set forth in any one of SEQ ID NOs: 16-18, the HCDR2 comprises an amino acid sequence as set forth in any one of SEQ ID NOs: 42-46 and SEQ ID NOs: 48-54, and the HCDR3 comprises an amino acid sequence as set forth in any one of SEQ ID NOs: 77-82.

In a preferred embodiment of the present invention, the HCDR1, the HCDR2 and the HCDR3 comprise amino acid sequences as set forth in SEQ ID NO: 16, SEQ ID NO: 42 and SEQ ID NO: 77, respectively; or
the HCDR1, the HCDR2 and the HCDR3 comprise amino acid sequences as set forth in SEQ ID NO: 16, SEQ ID NO: 43 and SEQ ID NO: 78, respectively; or
the HCDR1, the HCDR2 and the HCDR3 comprise amino acid sequences as set forth in SEQ ID NO: 16, SEQ ID NO: 44 and SEQ ID NO: 79, respectively; or
the HCDR1, the HCDR2 and the HCDR3 comprise amino acid sequences as set forth in SEQ ID NO: 17, SEQ ID NO: 45 and SEQ ID NO: 80, respectively; or
the HCDR1, the HCDR2 and the HCDR3 comprise amino acid sequences as set forth in SEQ ID NO: 18, SEQ ID NO: 43 and SEQ ID NO: 80, respectively; or
the HCDR1, the HCDR2 and the HCDR3 comprise amino acid sequences as set forth in SEQ ID NO: 18, SEQ ID NO: 43 and SEQ ID NO: 78, respectively; or
the HCDR1, the HCDR2 and the HCDR3 comprise amino acid sequences as set forth in SEQ ID NO: 16, SEQ ID NO: 43 and SEQ ID NO: 81, respectively; or
the HCDR1, the HCDR2 and the HCDR3 comprise amino acid sequences as set forth in SEQ ID NO: 16, SEQ ID NO: 46 and SEQ ID NO: 82, respectively; or
the HCDR1, the HCDR2 and the HCDR3 comprise amino acid sequences as set forth in SEQ ID NO: 16, SEQ ID NO: 48 and SEQ ID NO: 78, respectively; or
the HCDR1, the HCDR2 and the HCDR3 comprise amino acid sequences as set forth in SEQ ID NO: 16, SEQ ID NO: 49 and SEQ ID NO: 78, respectively; or
the HCDR1, the HCDR2 and the HCDR3 comprise amino acid sequences as set forth in SEQ ID NO: 16, SEQ ID NO: 50 and SEQ ID NO: 78, respectively; or
the HCDR1, the HCDR2 and the HCDR3 comprise amino acid sequences as set forth in SEQ ID NO: 16, SEQ ID NO: 51 and SEQ ID NO: 78, respectively; or
the HCDR1, the HCDR2 and the HCDR3 comprise amino acid sequences as set forth in SEQ ID NO: 16, SEQ ID NO: 52 and SEQ ID NO: 78, respectively; or
the HCDR1, the HCDR2 and the HCDR3 comprise amino acid sequences as set forth in SEQ ID NO: 16, SEQ ID NO: 53 and SEQ ID NO: 79, respectively; or
the HCDR1, the HCDR2 and the HCDR3 comprise amino acid sequences as set forth in SEQ ID NO: 16, SEQ ID NO: 54 and SEQ ID NO: 78, respectively.

The above combinations of amino acid sequences for the HCDR1, the HCDR2 and the HCDR3 are detailed in Table a below.

TABLE a

The HCDR combination of the CLDN18.2-targeting antibody

| HCDRs Antibody No. | No. | HCDR1 SEQ ID NOs: | Corresponding sequences | HCDR2 SEQ ID NOs: | Corresponding sequences | HCDR3 SEQ ID NOs: | Corresponding sequences |
|---|---|---|---|---|---|---|---|
| 1 | PR004227 | 16 | GFTFSSY | 42 | NNDGSS | 77 | APPYGNYERDY |
| 2 | PR004533 | 16 | GFTFSSY | 43 | NSDGSR | 78 | GEDHDILTGYPI |
| 3 | PR004536 | 16 | GFTFSSY | 44 | NSDGST | 79 | DFPVLGGSHFDFQH |
| 4 | PR004540 | 17 | GFTFSIY | 45 | SSDGNY | 80 | GEDHDMLTGYPV |
| 5 | PR004949 | 18 | GFTFSAY | 43 | NSDGSR | 80 | GEDHDMLTGYPV |
| 6 | PR004950 | 18 | GFTFSAY | 43 | NSDGSR | 78 | GEDHDILTGYPI |
| 7 | PR004952 | 16 | GFTFSSY | 43 | NSDGSR | 81 | GEDHDILTGYPV |
| 8 | PR004953 | 16 | GFTFSSY | 46 | GYDGRN | 82 | HFPSLPGTTDTFDI |
| 9 | PR007242 | 16 | GFTFSSY | 48 | NFDSSR | 78 | GEDHDILTGYPI |
| 10 | PR007243 | 16 | GFTFSSY | 49 | SSAGSR | 78 | GEDHDILTGYPI |
| 11 | PR007244 | 16 | GFTFSSY | 50 | DSRGSR | 78 | GEDHDILTGYPI |
| 12 | PR007245 | 16 | GFTFSSY | 51 | SSDASR | 78 | GEDHDILTGYPI |
| 13 | PR007246 | 16 | GFTFSSY | 52 | SSTGSR | 78 | GEDHDILTGYPI |
| 14 | PR007247 | 16 | GFTFSSY | 53 | NPLGST | 79 | DFPVLGGSHFDFQH |
| 15 | PR007248 | 16 | GFTFSSY | 54 | NHDSSR | 78 | GEDHDILTGYPI |

In a preferred embodiment of the present invention, the heavy chain variable region further comprises framework regions, among which the HFR1 comprises an amino acid sequence as set forth in SEQ ID NO: 6 or 7, the HFR2 comprises an amino acid sequence as set forth in any one of SEQ ID NOs: 28-34, the HFR3 comprises an amino acid sequence as set forth in any one of SEQ ID NOs: 63-68, and the HFR4 comprises an amino acid sequence as set forth in any one of SEQ ID NOs: 84 and 86-89.

In a preferred embodiment of the present invention, the heavy chain variable region comprises an amino acid sequence as set forth in any one of SEQ ID NOs: 150-157 and SEQ ID NOs: 159-165. See Table b below for details.

TABLE b

The heavy chain variable region of the CLDN18.2-targeting antibody

| SEQ ID NOs: | Corresponding sequences |
|---|---|
| 150 | EVQLVESGGGLVQPGGSLRLSCAASGFTFSSYWMHWVRQAPGKGLEWVSYINNDGSSTRYADSVKGRFTISRDNAKNTLYLQMNSLRAEDTAVYYCTEAPPYGNYERDYWGQGTLVTVSS |
| 151 | EVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSS |
| 152 | EVQLVESGGGLVQPGGSLRLSCAASGFTFSSYWMYWVRQVPGKGLVWVSHINSDGSTTQYADSVKGRFTISRDNAKNMLYLQMNSLRAEDTAVYYCARDFPVLGGSHFDFQHWGQGTLVTVSS |
| 153 | EVQLVESGGGLVQPGGSLRLSCAASGFTFSIYWMHWVRQVPGKGLVLVSRISSDGNYTSYADSVKGRFTISRDNAKNTLYLQMNSLRAEDTAVYLCARGEDHDMLTGYPVRGQGTTVTVSS |
| 154 | EVQLVESGGGLVQPGGSLRLSCAASGFTFSAYWMHWVRQVPGRGLVWVSRINSDGSRTIYADSVKGRFTISRDNAKNTLYLQMNSLRAEDTAVYLCARGEDHDMLTGYPVRGQGTMVTVSS |
| 155 | EVQLVESGGGLVQPGGSLRLSCAASGFTFSAYWMHWVRQVPGKGLVWVSRINSDGSRTIYADSVKGRFTISRDNAKNTLYLQMNSLRAEDTAVYYCARGEDHDILTGYPIRGQGTMVTVSS |
| 156 | EVQLVESGGGLVQPGGSLRLSCAASGFTFSSYWMHWVRQAPGKGLVWVSRINSDGSRTIYADSVKGRFTISRDNAKNTLYLQMNSLRAEDTAVYYCARGEDHDILTGYPVRGQATVTVSS |
| 157 | EVQLVESGGGVVQPGRSLRLSCAASGFTFSSYGMHWVRQAPGKGLEWVAVIGYDGRNKYYADSVKGRFTISRDNSKNTLFLQMDNLRAEDTALYYCARHFPSLPGTTDTFDIRGPGTMVTVSS |
| 159 | EVQLVESGGGLVQPGGSLRLSCAASGFTFSSYWMHWVRQVPGKGLVWVSRINFDSSRTIYADSVKGRFTISRDNAKNTLYLQMNSLRAEDTAVYYCARGEDHDILTGYPIRGQGTTVTVSS |
| 160 | EVQLVESGGGLVQPGGSLRLSCAASGFTFSSYWMHWVRQVPGKGLVWVSRISSAGSRTIYADSVKGRFTISRDNAKNTLYLQMNSLRAEDTAVYYCARGEDHDILTGYPIRGQGTTVTVSS |
| 161 | EVQLVESGGGLVQPGGSLRLSCAASGFTFSSYWMHWVRQVPGKGLVWVSRIDSRGSRTIYADSVKGRFTISRDNAKNTLYLQMNSLRAEDTAVYYCARGEDHDILTGYPIRGQGTTVTVSS |
| 162 | EVQLVESGGGLVQPGGSLRLSCAASGFTFSSYWMHWVRQVPGKGLVWVSRISSDASRTIYADSVKGRFTISRDNAKNTLYLQMNSLRAEDTAVYYCARGEDHDILTGYPIRGQGTTVTVSS |

TABLE b-continued

The heavy chain variable region of the CLDN18.2-targeting antibody

| SEQ ID NOs: | Corresponding sequences |
|---|---|
| 163 | EVQLVESGGGLVQPGGSLRLSCAASGFTFSSYWMHWVRQVPGKGLVWVSRISSTGSRTIYADSVKGRFTISRDNAKNTLYLQMNSLRAEDTAVYYCARGEDHDILTGYPIRGQGTTVTVSS |
| 164 | EVQLVESGGGLVQPGGSLRLSCAASGFTFSSYWMYWVRQVPGKGLVWVSHINPLGSTTQYADSVKGRFTISRDNAKNMLYLQMNSLRAEDTAVYYCARDFPVLGGSHFDFQHWGQGTLVTVSS |
| 165 | EVQLVESGGGLVQPGGSLRLSCAASGFTFSSYWMHWVRQVPGKGLVWVSRINHDSSRTIYADSVKGRFTISRDNAKNTLYLQMNSLRAEDTAVYYCARGEDHDILTGYPIRGQGTTVTVSS |

In a preferred embodiment of the present invention, the antibody further comprises a heavy chain constant region. More preferably, the heavy chain constant region is selected from hIgG1, hIgG2, hIgG3 and hIgG4 and a variant thereof. Even more preferably, the heavy chain constant region is hIgG1.

In a preferred embodiment of the present invention, the antibody is a full-length antibody, an Fab, an Fab', an F(ab')$_2$, an Fv, an scFv, a bispecific antibody, a multispecific antibody, a heavy-chain antibody or a single-domain antibody, or a monoclonal or polyclonal antibody prepared from the antibodies above.

In a more preferred embodiment of the present invention, the antibody is a single-domain antibody comprising an amino acid sequence as set forth in any one of SEQ ID NOs: 182-189 and SEQ ID NOs: 191-197. See Table c below for details.

TABLE c

The heavy chain of the CLDN18.2-targeting antibody

| SEQ ID NOs: | Corresponding sequences |
|---|---|
| 182 | EVQLVESGGGLVQPGGSLRLSCAASGFTFSSYWMHWVRQAPGKGLEWVSYINNDGSSTRYADSVKGRFTISRDNAKNTLYLQMNSLRAEDTAVYYCTEAPPYGNYERDYWGQGTLVTVSSGQAGQEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 183 | EVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSEPKSSDKTHTCPPCPAPELLGGPSVFLFPPKPKDTLMISRTPEVTCVVVDVSHEDPEVKFNWYVDG |

TABLE c-continued

The heavy chain of the CLDN18.2-targeting antibody

| SEQ ID NOs: | Corresponding sequences |
|---|---|
|  | VEVHNAKTKPREEQYNSTYRVVSVLTVLHQD WLNGKEYKCKVSNKALPAPIEKTISKAKGQP REPQVYTLPPSREEMTKNQVSLTCLVKGFYP SDIAVEWESNGQPENNYKTTPPVLDSDGSFF L YSKLTVDKSRWQQGNVFSCSVMHEALHNHYT QKSLSLSPGK |
| 184 | EVQLVESGGGLVQPGGSLRLSCAASGFTFSS YWMYWVRQVPGKGLVWVSHINSDGSTTQYA DSVKGRFTISRDNAKNMLYLQMNSLRAEDTA VYYCARDFPVLGGSHFDFQHWGQGTLVTVS SEPKSSDKTHTCPPCPAPELLGGPSVFLFPP KPKDTLMISRTPEVTCVVVDVSHEDPEVKFN WY VDGVEVHNAKTKPREEQYNSTYRVVSVLTVL HQDWLNGKEYKCKVSNKALPAPIEKTISKA KGQPREPQVYTLPPSREEMTKNQVSLTCLVK GFYPSDIAVEWESNGQPENNYKTTPPVLDSD G SFFLYSKLTVDKSRWQQGNVFSCSVMHEALH NHYTQKSLSLSPGK |
| 185 | EVQLVESGGGLVQPGGSLRLSCAASGFTFSI YWMHWVRQVPGKGLVLVSRISSDGNYTSYAD SVKGRFTISRDNAKNTLYLQMNSLRAEDTAV YLCARGEDHDMLTGYPVRGQGTTVTVSSEP KSSDKTHTCPPCPAPELLGGPSVFLFPPKPK DTLMISRTPEVTCVVVDVSHEDPEVKFNWYV D GVEVHNAKTKPREEQYNSTYRVVSVLTVLHQ DWLNGKEYKCKVSNKALPAPIEKTISKAKG QPREPQVYTLPPSREEMTKNQVSLTCLVKGF YPSDIAVEWESNGQPENNYKTTPPVLDSDGS F FLYSKLTVDKSRWQQGNVFSCSVMHEALHN HYTQKSLSLSPGK |
| 186 | EVQLVESGGGLVQPGGSLRLSCAASGFTFSA YWMHWVRQVPGRGLVWVSRINSDGSRTIYA DSVKGRFTISRDNAKNTLYLQMNSLRAEDTA VYLCARGEDHDMLTGYPVRGQGTMVTVSSE PKSSDKTHTCPPCPAPELLGGPSVFLFPPKP KDTLMISRTPEVTCVVVDVSHEDPEVKFNWY V DGVEVHNAKTKPREEQYNSTYRVVSVLTVLH QDWLNGKEYKCKVSNKALPAPIEKTISKAK GQPREPQVYTLPPSREEMTKNQVSLTCLVKG FYPSDIAVEWESNGQPENNYKTTPPVLDSDG S FFLYSKLTVDKSRWQQGNVFSCSVMHEALHN HYTQKSLSLSPGK |
| 187 | EVQLVESGGGLVQPGGSLRLSCAASGFTFSA YWMHWVRQVPGKGLVWVSRINSDGSRTIYA DSVKGRFTISRDNAKNTLYLQMNSLRAEDTA VYYCARGEDHDILTGYPIRGQGTMVTVSSEP KSSDKTHTCPPCPAPELLGGPSVFLFPPKPK DTLMISRTPEVTCVVVDVSHEDPEVKFNWYV D GVEVHNAKTKPREEQYNSTYRVVSVLTVLHQ DWLNGKEYKCKVSNKALPAPIEKTISKAKG QPREPQVYTLPPSREEMTKNQVSLTCLVKGF YPSDIAVEWESNGQPENNYKTTPPVLDSDGS F FLYSKLTVDKSRWQQGNVFSCSVMHEALHN HYTQKSLSLSPGK |
| 188 | EVQLVESGGGLVQPGGSLRLSCAASGFTFSS YWMHWVRQAPGKGLVWVSRINSDGSRTIYA DSVKGRFTISRDNAKNTLYLQMNSLRAEDTA VYYCARGEDHDILTGYPVRGQGATVTVSSEP KSSDKTHTCPPCPAPELLGGPSVFLFPPKPK DTLMISRTPEVTCVVVDVSHEDPEVKFNWYV D GVEVHNAKTKPREEQYNSTYRVVSVLTVLHQ DWLNGKEYKCKVSNKALPAPIEKTISKAKG QPREPQVYTLPPSREEMTKNQVSLTCLVKGF YPSDIAVEWESNGQPENNYKTTPPVLDSDGS F FLYSKLTVDKSRWQQGNVFSCSVMHEALHNH YTQKSLSLSPGK |
| 189 | EVQLVESGGGVVQPGRSLRLSCAASGFTFSS YGMHWVRQAPGKGLEWVAVIGYDGRNKYY ADSVKGRFTISRDNSKNTLFLQMDNLRAEDT ALYYCARHFPSLPGTTDTFDIRGPGTMVTVS S EPKSSDKTHTCPPCPAPELLGGPSVFLFPPK PKDTLMISRTPEVTCVVVDVSHEDPEVKFNW YV DGVEVHNAKTKPREEQYNSTYRVVSVLTVLH QDWLNGKEYKCKVSNKALPAPIEKTISKAK GQPREPQVYTLPPSREEMTKNQVSLTCLVKG FYPSDIAVEWESNGQPENNYKTTPPVLDSDG S FFLYSKLTVDKSRWQQGNVFSCSVMHEALHN HYTQKSLSLSPGK |
| 191 | EVQLVESGGGLVQPGGSLRLSCAASGFTFSS YWMHWVRQVPGKGLVWVSRINFDSSRTIYAD SVKGRFTISRDNAKNTLYLQMNSLRAEDTAV YYCARGEDHDILTGYPIRGQGTTVTVSSEPK S SDKTHTCPPCPAPELLGGPSVFLFPPKPKDT LMISRTPEVTCVVVDVSHEDPEVKFNWYVDG V EVHNAKTKPREEQYNSTYRVVSVLTVLHQDW LNGKEYKCKVSNKALPAPIEKTISKAKGQPR EPQVYTLPPSREEMTKNQVSLTCLVKGFYPS DIAVEWESNGQPENNYKTTPPVLDSDGSFFL Y SKLTVDKSRWQQGNVFSCSVMHEALHNHYTQ KSLSLSPGK |
| 192 | EVQLVESGGGLVQPGGSLRLSCAASGFTFSS YWMHWVRQVPGKGLVWVSRISSAGSRTIYAD SVKGRFTISRDNAKNTLYLQMNSLRAEDTAV YYCARGEDHDILTGYPIRGQGTTVTVSSEPK S SDKTHTCPPCPAPELLGGPSVFLFPPKPKDT LMISRTPEVTCVVVDVSHEDPEVKFNWYVDG V EVHNAKTKPREEQYNSTYRVVSVLTVLHQDW LNGKEYKCKVSNKALPAPIEKTISKAKGQPR EPQVYTLPPSREEMTKNQVSLTCLVKGFYPS DIAVEWESNGQPENNYKTTPPVLDSDGSFFL Y SKLTVDKSRWQQGNVFSCSVMHEALHNHYTQ KSLSLSPGK |
| 193 | EVQLVESGGGLVQPGGSLRLSCAASGFTFSS YWMHWVRQVPGKGLVWVSRIDSRGSRTIYAD SVKGRFTISRDNAKNTLYLQMNSLRAEDTAV YYCARGEDHDILTGYPIRGQGTTVTVSSEPK S SDKTHTCPPCPAPELLGGPSVFLFPPKPKDT LMISRTPEVTCVVVDVSHEDPEVKFNWYVDG V EVHNAKTKPREEQYNSTYRVVSVLTVLHQDW LNGKEYKCKVSNKALPAPIEKTISKAKGQPR EPQVYTLPPSREEMTKNQVSLTCLVKGFYPS DIAVEWESNGQPENNYKTTPPVLDSDGSFFL Y |

TABLE c-continued

The heavy chain of the CLDN18.2-targeting antibody

| SEQ ID NOs: | Corresponding sequences |
|---|---|
|  | SKLTVDKSRWQQGNVFSCSVMHEALHNHYTQKSLSLSPGK |
| 194 | EVQLVESGGGLVQPGGSLRLSCAASGFTFSSYWMHWVRQVPGKGLVWVSRISSDASRTIYADSVKGRFTISRDNAKNTLYLQMNSLRAEDTAVYYCARGEDHDILTGYPIRGQGTTVTVSSEPKS<br>SDKTHTCPPCPAPELLGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLY<br>SKLTVDKSRWQQGNVFSCSVMHEALHNHYTQKSLSLSPGK |
| 195 | EVQLVESGGGLVQPGGSLRLSCAASGFTFSSYWMHWVRQVPGKGLVWVSRISSTGSRTIYADSVKGRFTISRDNAKNTLYLQMNSLRAEDTAVYYCARGEDHDILTGYPIRGQGTTVTVSSEPKS<br>SDKTHTCPPCPAPELLGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLY<br>SKLTVDKSRWQQGNVFSCSVMHEALHNHYTQKSLSLSPGK |
| 196 | EVQLVESGGGLVQPGGSLRLSCAASGFTFSSYWMYWVRQVPGKGLVWVSHINPLGSTTQYADSVKGRFTISRDNAKNMLYLQMNSLRAEDTAVYYCARDFPVLGGSHFDFQHWGQGTLVTVSSEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDG<br>SFFLYSKLTVDKSRWQQGNVFSCSVMHEALHNHYTQKSLSLSPGK |
| 197 | EVQLVESGGGLVQPGGSLRLSCAASGFTFSSYWMHWVRQVPGKGLVWVSRINHDSSRTIYADSVKGRFTISRDNAKNTLYLQMNSLRAEDTAVYYCARGEDHDILTGYPIRGQGTTVTVSSEPK<br>SSDKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFL<br>YSKLTVDKSRWQQGNVFSCSVMHEALHNHYTQKSLSLSPGK |

In the present invention, an "Fab fragment" consists of one light chain and CH1 and the variable region of one heavy chain. The heavy chain of an Fab molecule cannot form disulfide bonds with another heavy chain molecule. An "Fc" region contains two heavy chain fragments comprising the CH1 and CH2 domains of an antibody. The two heavy chain fragments are held together by two or more disulfide bonds and the hydrophobic interaction of the CH3 domains. An "Fab' fragment" contains one light chain and part of one heavy chain comprising the VH domain and the CH1 domain and the region between the CH1 and CH2 domains, so that interchain disulfide bonds can be formed between the two heavy chains of two Fab' fragments to provide an F(ab')$_2$ molecule. An "F(ab')$_2$ fragment" contains two light chains and two heavy chains comprising part of the constant region between the CH1 and CH2 domains, such that interchain disulfide bonds are formed between the two heavy chains. Thus, an F(ab')$_2$ fragment consists of two Fab' fragments held together by disulfide bonds between the two heavy chains. The term "Fv" refers to an antibody fragment consisting of the VL and VH domains of a single arm of an antibody, but lacks the constant region.

In the present invention, the scFv (single chain antibody fragment) may be a conventional single chain antibody in the art, which comprises a heavy chain variable region, a light chain variable region, and a short peptide of 15-20 amino acids. In the scFv, the VL and VH domains are paired to form a monovalent molecule via a linker that enables them to produce a single polypeptide chain [see, e.g., Bird et al, Science 242:423-426 (1988) and Huston et al, Proc. Natl. Acad. Sci. USA 85:5879-5883 (1988)]. Such scFv molecules may have a general structure: NH2-VL-linker-VH-COOH or NH2-VH-linker-VL-COOH. An appropriate linker in the prior art consists of repeated $G_4S$ amino acid sequences or a variant thereof. For example, linkers having the amino acid sequence $(G_4S)_4$ or $(G_4S)_3$ may be used, but a variant thereof may also be used.

The term "multispecific antibody" is used in its widest sense to encompass antibodies having multi-epitope specificity. These multispecific antibodies include, but are not limited to: an antibody comprising a heavy chain variable region (VH) and a light chain variable region (VL), the VH-VL unit having multi-epitope specificity; an antibody having two or more VL and VH regions, each VH-VL unit binding to a different target or a different epitope of the same target; an antibody having two or more single variable regions, each single variable region binding to a different target or a different epitope of the same target; full length antibodies, antibody fragments, bispecific antibodies, triabodies, antibody fragments linked together covalently or non-covalently, and the like.

The antibody of the present invention includes a monoclonal antibody. The monoclonal antibody or mAb or Ab of the present invention refers to an antibody obtained from a single clonal cell line, which is not limited to eukaryotic, prokaryotic, or phage clonal cell lines.

In the present invention, the "heavy-chain antibody", also referred to as HCAbs, refers to an antibody comprising only one heavy chain variable region (VHH) and two conventional CH2 and CH3 regions.

In the present invention, the "single-domain antibody", also referred to as "nanobody", refers to a VHH structure cloned from a heavy-chain antibody. It is the smallest unit known to be able to bind to a target antigen.

To solve the above technical problems, a second aspect of the present invention provides a bispecific antibody comprising a first protein functional region targeting CD3 and a second protein functional region targeting CLDN18.2;

the first protein functional region is in the form of an Fab, and the second protein functional region is in the form of VHs and preferably comprises 2 or 3 VHs; when the second protein functional region comprises 3 VHs linked in series, the first protein functional region and the second protein functional region are each linked to an Fc's double strand; when the second protein functional region comprises 2 VHs linked in series, the first protein functional region and the second protein functional region are each linked to an Fc's double strand; when the second protein functional region comprises 3 VHs and one of the 3 VHs is linked to the first protein functional region, the remaining two VHs are linked in series, and the first protein functional region and the two VHs linked in series of the second protein functional region are each linked to an Fc's double strand; alternatively, the first protein functional region is in the form of an Fab and the second protein functional region is in the form of an HCAb; alternatively, the first protein functional region is in the form of an Fab and the second protein functional region is in the form of a VH-HCAb, the second protein functional region preferably comprising a total of 4 VHs.

In the present invention, the "first" and "second" in the first protein functional region and the second protein functional region have no practical meaning, and are only used to distinguish antigen-binding domains for different targets. One protein functional region may comprise a plurality of antigen-binding domains in the same form or different forms; the antigen-binding domains of different protein functional regions may be operably linked together, and different antigen-binding domains of the same protein functional region may not be linked to each other.

For example, in the present invention, the first protein functional region may be a CD3-targeting antigen-binding domain, and the second protein functional region may be a CLDN18.2-targeting antigen-binding domain.

In a preferred embodiment of the present invention, the second protein functional region comprises a heavy chain variable region comprising HCDR1, HCDR2 and HCDR3, wherein the HCDR1 comprises an amino acid sequence as set forth in any one of SEQ ID NOs: 16-18, the HCDR2 comprises an amino acid sequence as set forth in any one of SEQ ID NOs: 42-46 and SEQ ID NOs: 48-54, and the HCDR3 comprises an amino acid sequence as set forth in any one of SEQ ID NOs: 77-82.

More preferably, the HCDR1, the HCDR2 and the HCDR3 comprise amino acid sequences as set forth in SEQ ID NO: 16, SEQ ID NO: 42 and SEQ ID NO: 77, respectively; or the HCDR1, the HCDR2 and the HCDR3 comprise amino acid sequences as set forth in SEQ ID NO: 16, SEQ ID NO: 43 and SEQ ID NO: 78, respectively; or the HCDR1, the HCDR2 and the HCDR3 comprise amino acid sequences as set forth in SEQ ID NO: 16, SEQ ID NO: 44 and SEQ ID NO: 79, respectively; or the HCDR1, the HCDR2 and the HCDR3 comprise amino acid sequences as set forth in SEQ ID NO: 16, SEQ ID NO: 48 and SEQ ID NO: 78, respectively; or the HCDR1, the HCDR2 and the HCDR3 comprise amino acid sequences as set forth in SEQ ID NO: 16, SEQ ID NO: 49 and SEQ ID NO: 78, respectively; or the HCDR1, the HCDR2 and the HCDR3 comprise amino acid sequences as set forth in SEQ ID NO: 16, SEQ ID NO: 50 and SEQ ID NO: 78, respectively; or the HCDR1, the HCDR2 and the HCDR3 comprise amino acid sequences as set forth in SEQ ID NO: 16, SEQ ID NO: 51 and SEQ ID NO: 78, respectively; or the HCDR1, the HCDR2 and the HCDR3 comprise amino acid sequences as set forth in SEQ ID NO: 16, SEQ ID NO: 52 and SEQ ID NO: 78, respectively; or the HCDR1, the HCDR2 and the HCDR3 comprise amino acid sequences as set forth in SEQ ID NO: 16, SEQ ID NO: 53 and SEQ ID NO: 79, respectively; or the HCDR1, the HCDR2 and the HCDR3 comprise amino acid sequences as set forth in SEQ ID NO: 16, SEQ ID NO: 54 and SEQ ID NO: 78, respectively. See Table d below for details.

TABLE d

The HCDR combination of the second protein functional region of the bispecific antibody

| HCDRs No. | Antibody No. | HCDR1 SEQ ID NOs: | HCDR1 Corresponding sequences | HCDR2 SEQ ID NOs: | HCDR2 Corresponding sequences | HCDR3 SEQ ID NOs: | HCDR3 Corresponding sequences |
|---|---|---|---|---|---|---|---|
| 1 | PR004603 | 16 | GFTFSSY | 42 | NNDGSS | 77 | APPYGNYERDY |
| 2 | PR005072, PR005354, PR005518, PR005519, PR005520, PR005521, PR005522, PR005525, | 16 | GFTFSSY | 43 | NSDGSR | 78 | GEDHDILTGYPI |
| 3 | PR005076 | 16 | GFTFSSY | 44 | NSDGST | 79 | DFPVLGGSHFDFQH |
| 4 | PR005397, PR006384, PR006023 | 16 | GFTFSSY | 52 | SSTGSR | 78 | GEDHDILTGYPI |
| 5 | PR005398, PR007081 | 16 | GFTFSSY | 48 | NFDSSR | 78 | GEDHDILTGYPI |
| 6 | PR005399, PR007079 | 16 | GFTFSSY | 49 | SSAGSR | 78 | GEDHDILTGYPI |
| 7 | PR005401, PR007080 | 16 | GFTFSSY | 50 | DSRGSR | 78 | GEDHDILTGYPI |
| 8 | PR005411, PR006292, PR007083, PR006293 | 16 | GFTFSSY | 51 | SSDASR | 78 | GEDHDILTGYPI |
| 9 | PR005422 | 16 | GFTFSSY | 53 | NPLGST | 79 | DFPVLGGSHFDFQH |
| 10 | PR007082 | 16 | GFTFSSY | 54 | NHDSSR | 78 | GEDHDILTGYPI |

Even more preferably, the heavy chain variable region comprises an amino acid sequence as set forth in any one of SEQ ID NOs: 150-152 and SEQ ID NOs: 159-165, all of which have been listed in Table b.

In a specific embodiment of the present invention, the first protein functional region comprises a light chain variable region comprising LCDR1, LCDR2 and LCDR3 as set forth in SEQ ID NO: 101, SEQ ID NO: 116 and SEQ ID NO: 131, respectively, and a heavy chain variable region comprising HCDR1, HCDR2 and HCDR3 as set forth in SEQ ID NO: 11, SEQ ID NO: 38 and SEQ ID NO: 72, respectively.

Preferably, the heavy chain variable region comprises an amino acid sequence as set forth in SEQ ID NO: 149 or SEQ ID NO: 144 and the light chain comprises an amino acid sequence as set forth in SEQ ID NO: 168.

The amino acid sequence of the first protein functional region above is shown in Table e below.

TABLE e

The amino acid sequences related to the first protein functional region of the bispecific antibody

| First protein functional region | SEQ ID NOs: | Corresponding sequences | SEQ ID NOs: | Corresponding sequences | SEQ ID NOs: | Corresponding sequences |
|---|---|---|---|---|---|---|
| Heavy chain variable region HCDR | 11 | GFTFSTY | 38 | RSKYNNYA | 72 | HGNFGNSYVSWFAY |
| Light chain variable region LCDR | 101 | RSSTGAVTTSNYAN | 116 | GTNKRAP | 131 | ALWYSNLWV |

| First protein functional region | SEQ ID NOs: | Corresponding sequences |
|---|---|---|
| Heavy chain variable region | 144 | EVQLLESGGGLVQPGGSLRLSCAAS GFTFSTYAMNWVRQAPGKGLEWVSR IRSKYNNYATYYADSVKDRFTISRD DSKSTLYLQMNSLRAEDTAVYYCVR HGNFGNSYVSWFAYWGQGTLVTVSS |
| | 149 | EVQLVESGGGLVQPGGSLKLSCAAS GFTFSTYAMNWVRQASGKGLEWVGR IRSKYNNYATYYADSVKDRFTISRD DSKNTAYLQMNSLKTEDTAVYYCTR HGNFGNSYVSWFAYWGQGTLVTVSS |
| Light chain variable region | 168 | QAVVTQEPSLTVSPGGTVTLTCRSS TGAVTTSNYANWVQQKPGQAPRGLI GTNKRAPWTPARFSGSLLGDKAALT LLGAQPEDEAEYFCALWYSNLWVG FGGGTKLTVL |

Preferably, the bispecific antibody comprises three polypeptide chains in the following forms:

two N-termini of the Fc are linked to the Fab and the VH, respectively; preferably, the bispecific antibody has a first polypeptide chain as shown in formula: $VH_{CLDN18.2}$-$VH_{CLDN18.2}$-hinge-CH2-CH3 or $VH_{CLDN18.2}$-$VH_{CLDN18.2}$-$VH_{CLDN18.2}$-hinge-CH2-CH3, a second polypeptide chain as shown in formula: $VH_{CD3}$-CH1-hinge-CH2-CH3 and a third polypeptide chain as shown in formula: $VL_{CD3}$-CL;

alternatively, one C-terminus of the HCAb is linked to a VH or VL of the Fab; preferably, the bispecific antibody has a first polypeptide chain as shown in formula: $VH_{CLDN18.2}$-hinge-CH2-CH3, a second polypeptide chain as shown in formula: $VH_{CLDN18.2}$-hinge-CH2-CH3-$VH_{CD3}$-CH1 and a third polypeptide chain as shown in formula: $VL_{CD3}$-CL; alternatively, the bispecific antibody has a first polypeptide chain as shown in formula: $VH_{CLDN18.2}$-hinge-CH2-CH3, a second polypeptide chain as shown in formula: $VH_{CLDN18.2}$-hinge-CH2-CH3-$VL_{CD3}$-CL and a third polypeptide chain as shown in formula: $VH_{CD3}$-CH1; alternatively, the bispecific antibody has a first polypeptide chain as shown in formula: $VH_{CLDN18.2}$-$VH_{CLDN18.2}$-hinge-CH2-CH3, a second polypeptide chain as shown in formula: $VH_{CLDN18.2}$-$VH_{CLDN18.2}$-hinge-CH2-CH3-$VH_{CD3}$-CH1 and a third polypeptide chain as shown in formula: $VL_{CD3}$-CL; alternatively, the bispecific antibody has a first polypeptide chain as shown in formula: $VH_{CLDN18.2}$-$VH_{CLDN18.2}$-hinge-CH2-CH3, a second polypeptide chain as shown in formula: $VH_{CLDN18.2}$-$VH_{CLDN18.2}$-hinge-CH2-CH3-$VL_{CD3}$-CL and a third polypeptide chain as shown in formula: $VH_{CD3}$-CH1; alternatively, the N-terminus of the heavy chain of the Fab is linked to one $VH_{CLDN18.2}$, the C-terminus of the heavy chain is linked to one N-terminus of the Fc, and the C-terminus of the VHs linked in series is linked to the other N-terminus of the Fc; preferably, the bispecific antibody has a first polypeptide chain as shown in formula: $VH_{CLDN18.2}$-$VH_{CLDN18.2}$-hinge-CH2-CH3, a second polypeptide chain as shown in formula: $VH_{CLDN18.2}$-$VH_{CD3}$-CH1-hinge-CH2-CH3 and a third polypeptide chain as shown in formula: $VL_{CD3}$-CL.

More preferably, different functional units such as VH, CH2-CH3 and VL are operably linked by linker peptides preferably comprising an amino acid sequence as set forth in any one of SEQ ID NOs: 244-248, preferably the sequence set forth in SEQ ID NO: 246. See Table f for details.

TABLE f

Linker peptide sequences

| SEQ ID NOs: | Corresponding sequences | Names |
|---|---|---|
| 244 | GGGGS | GS_5 |
| 245 | GGGGSGGGGS | GS_10 |
| 246 | GGGGSGGGGSGGGGS | GS_15 |
| 247 | GGGGSGGGGSGGGGSGGGGS | GS_20 |
| 248 | GGGGSGGGGSGGGGSGGGGSGGGGS | GS_25 |

In one embodiment of the present invention, two N-termini of the Fc are linked to the Fab and the VH, respectively; preferably, the bispecific antibody has a first polypeptide chain as shown in formula: $VH_{CLDN18.2}$-linker peptide-$VH_{CLDN18.2}$-hinge-CH2-CH3 or $VH_{CLDN18.2}$-linker peptide-$VH_{CLDN18.2}$-linker peptide-$VH_{CLDN18.2}$-hinge-CH2-CH3, a second polypeptide chain as shown in formula: $VH_{CD3}$-CH1-hinge-CH2-CH3 and a third polypeptide chain as shown in formula: $VL_{CD3}$-CL; see structures (1) and (7) of FIG. 4 for specific examples;

alternatively, one C-terminus of the HCAb is linked to a VH or VL of the Fab; preferably, the bispecific antibody has a first polypeptide chain as shown in formula: $VH_{CLDN18.2}$-hinge-CH2-CH3, a second polypeptide chain as shown in formula: $VH_{CLDN18.2}$-hinge-CH2-CH3-linker peptide-$VH_{CD3}$-CH1 and a third polypeptide chain as shown in formula: $VL_{CD3}$-CL; alternatively, the bispecific antibody has a first polypeptide chain as shown in formula: $VH_{CLDN18.2}$-hinge-CH2-CH3, a second polypeptide chain as shown in formula: $VH_{CLDN18.2}$-hinge-CH2-CH3-linker peptide-$VL_{CD3}$-CL and a third polypeptide chain as shown in formula: $VH_{CD3}$-CH1; see structures (2) and (3) of FIG. 4 for specific examples;

alternatively, one C-terminus of the VH-HCAb is linked to a VH or VL of the Fab; preferably, the bispecific antibody has a first polypeptide chain as shown in formula: $VH_{CLDN18.2}$-linker peptide-$VH_{CLDN18.2}$-hinge-CH2-CH3, a second polypeptide chain as shown in formula: $VH_{CLDN18.2}$-linker peptide-$VH_{CLDN18.2}$- hinge-CH2-CH3-linker peptide-VH$_{CD3}$-CH1 and a third polypeptide chain as shown in formula: VL$_{CD3}$-CL; alternatively, the bispecific antibody has a first polypeptide chain as shown in formula: VH$_{CLDN18.2}$-linker peptide-VH$_{CLDN18.2}$-hinge-CH2-CH3, a second polypeptide chain as shown in formula: VH$_{CLDN18.2}$-linker peptide-VH$_{CLDN18.2}$-hinge-CH2-CH3-linker peptide-VL$_{CD3}$-CL and a third polypeptide chain as shown in formula: VH$_{CD3}$-CH1; see structures (4) and (5) of FIG. 4 for specific examples;

alternatively, the N-terminus of the heavy chain of the Fab is linked to one VH$_{CLDN18.2}$, the C-terminus of the heavy chain is linked to one N-terminus of the Fc, and the C-terminus of the VHs linked in series is linked to the other N-terminus of the Fc; preferably, the bispecific antibody has a first polypeptide chain as shown in formula: VH$_{CLDN18.2}$-linker peptide-VH$_{CLDN18.2}$-hinge-CH2-CH3, a second polypeptide chain as shown in formula: VH$_{CLDN18.2}$-linker peptide-VH$_{CD3}$-CH1-hinge-CH2-CH3 and a third polypeptide chain as shown in formula: VL$_{CD3}$-CL; see structure (6) of FIG. 4 for a specific example.

In a specific embodiment of the present invention, the first polypeptide chain comprises an amino acid sequence as set forth in SEQ ID NO: 214, the second polypeptide chain comprises an amino acid sequence as set forth in SEQ ID NO: 213, and the third polypeptide chain comprises an amino acid sequence as set forth in SEQ ID NO: 200;

alternatively, the first polypeptide chain comprises an amino acid sequence as set forth in SEQ ID NO: 219, the second polypeptide chain comprises an amino acid sequence as set forth in SEQ ID NO: 213, and the third polypeptide chain comprises an amino acid sequence as set forth in SEQ ID NO: 200;

alternatively, the first polypeptide chain comprises an amino acid sequence as set forth in SEQ ID NO: 220, the second polypeptide chain comprises an amino acid sequence as set forth in SEQ ID NO: 213, and the third polypeptide chain comprises an amino acid sequence as set forth in SEQ ID NO: 200;

alternatively, the first polypeptide chain comprises an amino acid sequence as set forth in SEQ ID NO: 221, the second polypeptide chain comprises an amino acid sequence as set forth in SEQ ID NO: 213, and the third polypeptide chain comprises an amino acid sequence as set forth in SEQ ID NO: 200;

alternatively, the first polypeptide chain comprises an amino acid sequence as set forth in SEQ ID NO: 222, the second polypeptide chain comprises an amino acid sequence as set forth in SEQ ID NO: 213, and the third polypeptide chain comprises an amino acid sequence as set forth in SEQ ID NO: 200;

alternatively, the first polypeptide chain comprises an amino acid sequence as set forth in SEQ ID NO: 223, the second polypeptide chain comprises an amino acid sequence as set forth in SEQ ID NO: 213, and the third polypeptide chain comprises an amino acid sequence as set forth in SEQ ID NO: 200;

alternatively, the first polypeptide chain comprises an amino acid sequence as set forth in SEQ ID NO: 224, the second polypeptide chain comprises an amino acid sequence as set forth in SEQ ID NO: 213, and the third polypeptide chain comprises an amino acid sequence as set forth in SEQ ID NO: 200;

alternatively, the first polypeptide chain comprises an amino acid sequence as set forth in SEQ ID NO: 225, the second polypeptide chain comprises an amino acid sequence as set forth in SEQ ID NO: 213, and the third polypeptide chain comprises an amino acid sequence as set forth in SEQ ID NO: 200;

alternatively, the first polypeptide chain comprises an amino acid sequence as set forth in SEQ ID NO: 226, the second polypeptide chain comprises an amino acid sequence as set forth in SEQ ID NO: 213, and the third polypeptide chain comprises an amino acid sequence as set forth in SEQ ID NO: 200;

alternatively, the first polypeptide chain comprises an amino acid sequence as set forth in SEQ ID NO: 227, the second polypeptide chain comprises an amino acid sequence as set forth in SEQ ID NO: 228, and the third polypeptide chain comprises an amino acid sequence as set forth in SEQ ID NO: 200;

alternatively, the first polypeptide chain comprises an amino acid sequence as set forth in SEQ ID NO: 227, the second polypeptide chain comprises an amino acid sequence as set forth in SEQ ID NO: 230, and the third polypeptide chain comprises an amino acid sequence as set forth in SEQ ID NO: 229;

alternatively, the first polypeptide chain comprises an amino acid sequence as set forth in SEQ ID NO: 219, the second polypeptide chain comprises an amino acid sequence as set forth in SEQ ID NO: 231, and the third polypeptide chain comprises an amino acid sequence as set forth in SEQ ID NO: 200;

alternatively, the first polypeptide chain comprises an amino acid sequence as set forth in SEQ ID NO: 219, the second polypeptide chain comprises an amino acid sequence as set forth in SEQ ID NO: 232, and the third polypeptide chain comprises an amino acid sequence as set forth in SEQ ID NO: 229;

alternatively, the first polypeptide chain comprises an amino acid sequence as set forth in SEQ ID NO: 219, the second polypeptide chain comprises an amino acid sequence as set forth in SEQ ID NO: 233, and the third polypeptide chain comprises an amino acid sequence as set forth in SEQ ID NO: 200;

alternatively, the first polypeptide chain comprises an amino acid sequence as set forth in SEQ ID NO: 234, the second polypeptide chain comprises an amino acid sequence as set forth in SEQ ID NO: 213, and the third polypeptide chain comprises an amino acid sequence as set forth in SEQ ID NO: 200;

alternatively, the first polypeptide chain comprises an amino acid sequence as set forth in SEQ ID NO: 219, the second polypeptide chain comprises an amino acid sequence as set forth in SEQ ID NO: 209, and the third polypeptide chain comprises an amino acid sequence as set forth in SEQ ID NO: 200;

alternatively, the first polypeptide chain comprises an amino acid sequence as set forth in SEQ ID NO: 221, the second polypeptide chain comprises an amino acid sequence as set forth in SEQ ID NO: 209, and the third polypeptide chain comprises an amino acid sequence as set forth in SEQ ID NO: 200;

alternatively, the first polypeptide chain comprises an amino acid sequence as set forth in SEQ ID NO: 236, the second polypeptide chain comprises an amino acid sequence as set forth in SEQ ID NO: 235, and the third polypeptide chain comprises an amino acid sequence as set forth in SEQ ID NO: 200;

alternatively, the first polypeptide chain comprises an amino acid sequence as set forth in SEQ ID NO: 236, the second polypeptide chain comprises an amino acid sequence as set forth in SEQ ID NO: 237, and the third polypeptide chain comprises an amino acid sequence as set forth in SEQ ID NO: 200;
alternatively, the first polypeptide chain comprises an amino acid sequence as set forth in SEQ ID NO: 238, the second polypeptide chain comprises an amino acid sequence as set forth in SEQ ID NO: 235, and the third polypeptide chain comprises an amino acid sequence as set forth in SEQ ID NO: 200;
alternatively, the first polypeptide chain comprises an amino acid sequence as set forth in SEQ ID NO: 239, the second polypeptide chain comprises an amino acid sequence as set forth in SEQ ID NO: 235, and the third polypeptide chain comprises an amino acid sequence as set forth in SEQ ID NO: 200;
alternatively, the first polypeptide chain comprises an amino acid sequence as set forth in SEQ ID NO: 240, the second polypeptide chain comprises an amino acid sequence as set forth in SEQ ID NO: 235, and the third polypeptide chain comprises an amino acid sequence as set forth in SEQ ID NO: 200;
alternatively, the first polypeptide chain comprises an amino acid sequence as set forth in SEQ ID NO: 241, the second polypeptide chain comprises an amino acid sequence as set forth in SEQ ID NO: 235, and the third polypeptide chain comprises an amino acid sequence as set forth in SEQ ID NO: 200;
alternatively, the first polypeptide chain comprises an amino acid sequence as set forth in SEQ ID NO: 242, the second polypeptide chain comprises an amino acid sequence as set forth in SEQ ID NO: 235, and the third polypeptide chain comprises an amino acid sequence as set forth in SEQ ID NO: 200;
alternatively, the first polypeptide chain comprises an amino acid sequence as set forth in SEQ ID NO: 243, the second polypeptide chain comprises an amino acid sequence as set forth in SEQ ID NO: 235, and the third polypeptide chain comprises an amino acid sequence as set forth in SEQ ID NO: 200.

Information about the sequences in the specific embodiment above is shown in Table g below.

TABLE g

Information about the polypeptide chain sequences of the bispecific antibody

| SEQ ID NOs: | Corresponding sequences |
| --- | --- |
| 200 | QAVVTQEPSLTVSPGGTVTLTCRSSTGAVTT SNYANWVQQKPGQAPRGLIGGTNKRAPWTP ARFSGSLLGDKAALTLLGAQPEDEAEYFCAL WYSNLWVFGGGTKLTVLGQPKAAPSVTLFPP SSEELQANKATLVCLISDFYPGAVTVAWKAD SSPVKAGVETTTPSKQSNNKYAASSYLSLTP E QWKSHRSYSCQVTHEGSTVEKTVAPTECS |
| 209 | EVQLLESGGGLVQPGGSLRLSCAASGFTFST YAMNWVRQAPGKGLEWVSRIRSKYNNYATY YADSVKDRFTISRDDSKSTLYLQMNSLRAED TAVYYCVRHGNFGNSYVSWFAYWGQGTLV TVSSASTKGPSVFPLAPSSKSTSGGTAALGC LVKDYFPEPVTVSWNSGALTSGVHTFPAVLQ S SGLYSLSSVVTVPSSSLGTQTYICNVNHKPS NTKVDKKVEPKSCDKTHTCPPCPAPEAAGGP S VFLFPPKPKDTLMISRTPEVTCVVVDVSHED PEVKFNWYVDGVEVHNAKTKPREEQYNSTYR VVSVLTVLHQDWLNGKEYKCKVSNKALPAPI EKTISKAKGQPREPQVYTLPPCREEMTKNQV SLWCLVKGFYPSDIAVEWESNGQPENNYKTT PPVLDSDGSFFLYSKLTVDKSRWQQGNVFSC SVMHEALHNHYTQKSLSLSPGK |
| 213 | EVQLVESGGGLVQPGGSLKLSCAASGFTFST YAMNWVRQASGKGLEWVGRIRSKYNNYATY YADSVKDRFTISRDDSKNTAYLQMNSLKTED TAVYYCTRHGNFGNSYVSWFAYWGQGTLV TVSSASTKGPSVFPLAPSSKSTSGGTAALGC LVKDYFPEPVTVSWNSGALTSGVHTFPAVLQ S SGLYSLSSVVTVPSSSLGTQTYICNVNHKPS NTKVDKKVEPKSCDKTHTCPPCPAPEAAGGP S VFLFPPKPKDTLMISRTPEVTCVVVDVSHED PEVKFNWYVDGVEVHNAKTKPREEQYNSTYR VVSVLTVLHQDWLNGKEYKCKVSNKALPAPI EKTISKAKGQPREPQVYTLPPCREEMTKNQV SLWCLVKGFYPSDIAVEWESNGQPENNYKTT PPVLDSDGSFFLYSKLTVDKSRWQQGNVFSC SVMHEALHNHYTQKSLSLSPGK |
| 214 | EVQLVESGGGLVQPGGSLRLSCAASGFTFSS YWMHWVRQAPGKGLEWVSYINNDGSSTRYA DSVKGRFTISRDNAKNTLYLQMNSLRAEDTA VYYCTEAPPYGNYERDYWGQGTLVTVSSGG GGSGGGGSGGGGSEVQLVESGGGLVQPGGSL RLSCAASGFTFSSYWMHWVRQAPGKGLEW VSYINNDGSSTRYADSVKGRFTISRDNAKNT LYLQMNSLRAEDTAVYYCTEAPPYGNYERDY WGQGTLVTVSSASEPKSSDKTHTCPPCPAPE AAGGPSVFLFPPKPKDTLMISRTPEVTCVVV D VSHEDPEVKFNWYVDGVEVHNAKTKPREEQY NSTYRVVSVLTVLHQDWLNGKEYKCKVSN KALPAPIEKTISKAKGQPREPQVCTLPPSRE EMTKNQVSLSCAVKGFYPSDIAVEWESNGQP E NNYKTTPPVLDSDGSFFLVSKLTVDKSRWQQ GNVFSCSVMHEALHNHYTQKSLSLSPGK |
| 219 | EVQLVESGGGLVQPGGSLRLSCAASGFTFSS YWMHWVRQVPGKGLVWVSRINSDGSRTIYA DSVKGRFTISRDNAKNTLYLQMNSLRAEDTA VYYCARGEDHDILTGYPIRGQGTTVTVSSGG GGSGGGGSGGGGSEVQLVESGGGLVQPGGSL RLSCAASGFTFSSYWMHWVRQVPGKGLVW VSRINSDGSRTIYADSVKGRFTISRDNAKNT LYLQMNSLRAEDTAVYYCARGEDHDILTGYP I RGQGTTVTVSSASEPKSSDKTHTCPPCPAPE AAGGPSVFLFPPKPKDTLMISRTPEVTCVVV DV SHEDPEVKFNWYVDGVEVHNAKTKPREEQYN STYRVVSVLTVLHQDWLNGKEYKCKVSNK ALPAPIEKTISKAKGQPREPQVCTLPPSREE MTKNQVSLSCAVKGFYPSDIAVEWESNGQPE N NYKTTPPVLDSDGSFFLVSKLTVDKSRWQQG NVFSCSVMHEALHNHYTQKSLSLSPGK |
| 220 | EVQLVESGGGLVQPGGSLRLSCAASGFTFSS YWMYWVRQVPGKGLVWVSHINSDGSTTQYA DSVKGRFTISRDNAKNMLYLQMNSLRAEDTA VYYCARDFPVLGGSHFDPQHWGQGTLVTVS SGGGGSGGGGSGGGGSEVQLVESGGGLVQPG GSLRLSCAASGFTFSSYWMYWVRQVPGKG LVWVSHINSDGSTTQYADSVKGRFTISRDNA KNMLYLQMNSLRAEDTAVYYCARDFPVLGG SHFDFQHWGQGTLVTVSSASEPKSSDKTHTC PPCPAPEAAGGPSVFLFPPKPKDTLMISRTP EV |

TABLE g-continued

Information about the polypeptide chain sequences of the bispecific antibody

| SEQ ID NOs: | Corresponding sequences |
|---|---|
|  | TCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 221 | EVQLVESGGGLVQPGGSLRLSCAASGFTFSSYWMHWVRQVPGKGLVWVSRISSTGSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRISSTGSRTIYADSVKGRFTISRDNAKNTLYLQMNSLRAEDTAVYYCARGEDHDILTGYPIRGQGTTVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 222 | EVQLVESGGGLVQPGGSLRLSCAASGFTFSSYWMHWVRQVPGKGLVWVSRINFDSSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRINFDSSRTIYADSVKGRFTISRDNAKNTLYLQMNSLRAEDTAVYYCARGEDHDILTGYPIRGQGTTVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 223 | EVQLVESGGGLVQPGGSLRLSCAASGFTFSSYWMHWVRQVPGKGLVWVSRISSAGSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRISSAGSRTIYADSVKGRFTISRDNAKNTLYLQMNSLRAEDTAVYYCARGEDHDILTGYPIRGQGTTVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 224 | EVQLVESGGGLVQPGGSLRLSCAASGFTFSSYWMHWVRQVPGKGLVWVSRIDSRGSRTIYADSVKGRFTISRDNAKNTLYLQMNSLRAEDTAVYYCARGEDHDILTGYPIRGQGTTVTVSSGG GGSGGGGSGGGGSEVQLVESGGGLVQPGGSLRLSCAASGFTFSSYWMHWVRQVPGKGLVWVSRIDSRGSRTIYADSVKGRFTISRDNAKNTLYLQMNSLRAEDTAVYYCARGEDHDILTGYPIRGQGTTVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 225 | EVQLVESGGGLVQPGGSLRLSCAASGFTFSSYWMHWVRQVPGKGLVWVSRISSDASRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRISSDASRTIYADSVKGRFTISRDNAKNTLYLQMNSLRAEDTAVYYCARGEDHDILTGYPIRGQGTTVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 226 | EVQLVESGGGLVQPGGSLRLSCAASGFTFSSYWMYWVRQVPGKGLVWVSHINPLGSTTQYADSVKGRFTISRDNAKNMLYLQMNSLRAEDTAVYYCARDFPVLGGSHFDFQHWGQGTLVTVSSGGGGSGGGGSGGGGSEVQLVESGGGLVQPGGSLRLSCAASGFTFSSYWMYWVRQVPGKGLVWVSHINPLGSTTQYADSVKGRFTISRDNAKNMLYLQMNSLRAEDTAVYYCARDFPVLGGSHFDFQHWGQGTLVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 227 | EVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 228 | EVQLVESGGGLVQPGGSLRLSCAASGFTFSSYWMHWVRQVPGKGLVWVSRINSDGSRTIYADSVKGRFTISRDNAKNTLYLQMNSLRAEDTA |

TABLE g-continued

Information about the polypeptide chain sequences of the bispecific antibody

| SEQ ID NOs: | Corresponding sequences |
|---|---|
|  | VYYCARGEDHDILTGYPIRGQGTTVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGGGGGSGGGGSGGGGSRTEVQLLESGGGLVQPGGSLRLSCAASGFTFSTYAMNWVRQAPGKGLEWVSRIRSKYNNYATYYADSVKDRFTISRDDSKSTLYLQMNSLRAEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 229 | EVQLLESGGGLVQPGGSLRLSCAASGFTFSTYAMNWVRQAPGKGLEWVSRIRSKYNNYATYYADSVKDRFTISRDDSKSTLYLQMNSLRAEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 230 | EVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGGGGGSGGGGSGGGGSRTQAVVTQEPSLTVSPGGTVTLTCRSSTGAVTTSNYANWVQQKPGQAPRGLIGGTNKRAPWTPARFSGSLLGDKAALTLLGAQPEDEAEYFCALWYSNLWVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| 231 | EVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGGGGGSGGGGSGGGGSRTEVQLLESGGGLVQPGGSLRLSCAASGFTFSTYAMNWVRQAPGKGLEWVSRIRSKYNNYATYYADSVKDRFTISRDDSKSTLYLQMNSLRAEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 232 | EVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSASEPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGGGGSGGGGSGGGGSRTQAVVTQEPSLTVSPGGTVTLTCRSSTGAVTTSNYANWVQQKPGQAPRGLIGGTNKRAPWTPARFSGSLLGDKAALTLLGAQPEDEAEYFCALWYSNLWVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| 233 | EVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSGGGGSGGGGSGGGGSEVQLLESGGGLVQPGGSLRLSCAASGFTFSTYAMNWVRQAPGKGLEWVSRIRSKYNNYATYYADSVKDRFTISRDDSKSTLYLQMNSLRAEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGK |
| 234 | EVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRINSDGSRTIYADSVKGRFTISRDNAKNTLYLQMNSLRAEDTAVYYCARGEDHDILTGYPIRGQGTTVTVSSASEPKSSDKTHTCPPCPAPEAAGGPSVFLFPPKPKDTLM |

TABLE g-continued

Information about the polypeptide chain sequences of the bispecific antibody

| SEQ ID NOs: | Corresponding sequences |
|---|---|
| | ISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 235 | EVQLVESGGGLVQPGGSLKLSCAASGFTFSTYAMNWVRQASGKGLEWVGRIRSKYNNYATYYADSVKDRFTISRDDSKNTAYLQMNSLKTEDTAVYYCTRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGK |
| 236 | EVQLVESGGGLVQPGGSLRLSCAASGFTFSSYWMHWVRQVPGKGLVWVSRISSDASRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRISSDASRTIYADSVKGRFTISRDNAKNTLYLQMNSLRAEDTAVYYCARGEDHDILTGYPIRGQGTTVTVSSASEPKSSDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 237 | EVQLLESGGGLVQPGGSLRLSCAASGFTFSTYAMNWVRQAPGKGLEWVSRIRSKYNNYATYYADSVKDRFTISRDDSKSTLYLQMNSLRAEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGK |
| 238 | EVQLVESGGGLVQPGGSLRLSCAASGFTFSSYWMHWVRQVPGKGLVWVSRISSTGSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRISSTGSRTIYADSVKGRFTISRDNAKNTLYLQMNSLRAEDTAVYYCARGEDHDILTGYPIRGQGTTVTVSSASEPKSSDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 239 | EVQLVESGGGLVQPGGSLRLSCAASGFTFSSYWMHWVRQVPGKGLVWVSRISSAGSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRISSAGSRTIYADSVKGRFTISRDNAKNTLYLQMNSLRAEDTAVYYCARGEDHDILTGYPIRGQGTTVTVSSASEPKSSDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 240 | EVQLVESGGGLVQPGGSLRLSCAASGFTFSSYWMHWVRQVPGKGLVWVSRIDSRGSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRIDSRGSRTIYADSVKGRFTISRDNAKNTLYLQMNSLRAEDTAVYYCARGEDHDILTGYPIRGQGTTVTVSSASEPKSSDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 241 | EVQLVESGGGLVQPGGSLRLSCAASGFTFSSYWMHWVRQVPGKGLVWVSRINFDSSRTIYADSVKGRFTISRDNAKNTLYLQMNSLRAEDTAVYYCARGEDHDILTGYPIRGQGTTVTVSSGGGGSGGGGSGGGGSEVQLVESGGGLVQPGGSLRLSCAASGFTFSSYWMHWVRQVPGKGLVWVSRINFDSSRTIYADSVKGRFTISRDNAKNTLYLQMNSLRAEDTAVYYCARGEDHDILTGYPIRGQGTTVTVSSASEPKSSDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |

TABLE g-continued

Information about the polypeptide chain
sequences of the bispecific antibody

| SEQ ID NOs: | Corresponding sequences |
|---|---|
| 242 | EVQLVESGGGLVQPGGSLRLSCAASGFTFSS YWMHWVRQVPGKGLVWVSRINHDSSRTIYA DSVKGRFTISRDNAKNTLYLQMNSLRAEDTA VYYCARGEDHDILTGYPIRGQGTTVTVSSGG GGSGGGGSGGGGSEVQLVESGGGLVQPGGSL RLSCAASGFTFSSYWMHWVRQVPGKGLVW VSRINHDSSRTIYADSVKGRFTISRDNAKNT LYLQMNSLRAEDTAVYYCARGEDHDILTGYP I RGQGTTVTVSSASEPKSSDKTHTCPPCPAPE AAGAPSVFLFPPKPKDTLMISRTPEVTCVVV DV SHEDPEVKFNWYVDGVEVHNAKTKPREEQYN STYRVVSVLTVLHQDWLNGKEYKCKVSNK ALPAPIEKTISKAKGQPREPQVCTLPPSREE MTKNQVSLSCAVKGFYPSDIAVEWESNGQPE N NYKTTPPVLDSDGSFFLVSKLTVDKSRWQQG NVFSCSVMHEALHNHYTQKSLSLSPGK |
| 243 | EVQLVESGGGLVQPGGSLRLSCAASGFTFSS YWMHWVRQVPGKGLVWVCRISSDASRTIYA DSVKGRFTCSRDNAKNTLYLQMNSLRAEDTA VYYCARGEDHDILTGYPIRGQGTTVTVSSGG GGSGGGGSGGGGSEVQLVESGGGLVQPGGSL RLSCAASGFTFSSYWMHWVRQVPGKGLVW VCRISSDASRTIYADSVKGRFTCSRDNAKNT LYLQMNSLRAEDTAVYYCARGEDHDILTGYP I RGQGTTVTVSSASEPKSSDKTHTCPPCPAPE AAGAPSVFLFPPKPKDTLMISRTPEVTCVVV DV SHEDPEVKFNWYVDGVEVHNAKTKPREEQYN STYRVVSVLTVLHQDWLNGKEYKCKVSNK ALPAPIEKTISKAKGQPREPQVCTLPPSREE MTKNQVSLSCAVKGFYPSDIAVEWESNGQPE N NYKTTPPVLDSDGSFFLVSKLTVDKSRWQQG NVFSCSVMHEALHNHYTQKSLSLSPGK |

To solve the above technical problems, a third aspect of the present invention provides an isolated nucleic acid encoding the antibody according to the first aspect of the present invention or the bispecific antibody according to the second aspect of the present invention.

The preparation method for the nucleic acid is a conventional preparation method in the art, and preferably comprises the following steps: obtaining a nucleic acid molecule encoding the above antibody by gene cloning technology, or obtaining a nucleic acid molecule encoding the above antibody by artificial complete sequence synthesis.

It is known to those skilled in the art that substitutions, deletions, alterations, insertions or additions may be appropriately introduced into the base sequence encoding the amino acid sequence of the above antibody to provide a polynucleotide homologue. The polynucleotide homologue of the present invention may be produced by substituting, deleting or adding one or more bases of a gene encoding the antibody sequence within a range in which the activity of the antibody is maintained.

To solve the above technical problems, a fourth aspect of the present invention provides a recombinant expression vector comprising the isolated nucleic acid according to the third aspect of the present invention. The recombinant expression vector may be obtained by using conventional methods in the art, i.e., by linking the nucleic acid molecule of the present invention to various expression vectors. The expression vector is any conventional vector in the art, provided that it can carry the aforementioned nucleic acid molecule.

Preferably, the recombinant expression vector is a plasmid, a cosmid, a phage or a viral vector, wherein the viral vector is preferably a retroviral vector, a lentiviral vector, an adenoviral vector or an adeno-associated viral vector.

To solve the above technical problems, a fifth aspect of the present invention provides a transformant comprising the recombinant expression vector according to the fourth aspect of the present invention in a host cell; preferably, the host cell is an *E. coli* TG1, BL21 cell, or CHO-K1 cell.

The recombinant expression transformant may be prepared by using conventional methods in the art, e.g., by transforming the above recombinant expression vector into a host cell. The host cell is any conventional host cell in the art, provided that it can enable the stable replication of the above recombinant expression vector and the nucleic acid carried can be efficiently expressed. Preferably, the host cell is an *E. coli* TG1 or BL21 cell (expressing a single-chain antibody or an Fab antibody), or a CHO-K1 cell (expressing a full-length IgG antibody). The preferred recombinant expression transformant of the present invention can be obtained by transforming the aforementioned recombinant expression plasmid into a host cell. The transformation method is a conventional transformation method in the art, preferably a chemical transformation method, a heat shock method or an electric transformation method.

In the present invention, the CLDN18.2-targeting antibody may be used to prepare a chimeric antigen receptor (CAR) or the like so as to modify it onto cells such as T cells or NK cells. Thus, a sixth aspect of the present invention provides a chimeric antigen receptor (CAR) comprising the antibody according to the first aspect of the present invention or the bispecific antibody according to the second aspect of the present invention.

For example, the chimeric antigen receptor may comprise the following structure: (a) an extracellular binding domain scFv that specifically recognizes CLDN18.2; (b) a hinge domain; (c) a transmembrane domain; (d) a co-stimulatory intracellular domain; and (e) a signaling domain; wherein the extracellular binding domain comprises the CLDN18.2-targeting antibody according to the first aspect of the present invention.

To solve the above technical problems, a seventh aspect of the present invention provides a genetically modified cell comprising the antibody according to the first aspect of the present invention or the bispecific antibody according to the second aspect of the present invention. Preferably, the genetically modified cell is a eukaryotic cell, preferably an isolated human cell, and more preferably an immune cell such as a T cell or an NK cell.

To solve the above technical problems, an eighth aspect of the present invention provides a method for preparing a bispecific antibody comprising culturing the transformant according to the fifth aspect of the present invention, and obtaining the antibody or the bispecific antibody from the culture.

To solve the above technical problems, a ninth aspect of the present invention provides an antibody-drug conjugate (ADC) comprising a cytotoxic agent, and the antibody according to the first aspect of the present invention or the bispecific antibody according to the second aspect of the present invention; preferably, the cytotoxic agent is MMAF or MMAE.

The preparation method for the antibody-drug conjugate may be a conventional method in the art, and preferably the preparation method described in Doronina, 2006, *Bioconjugate Chem.* 17, 114-124. Preferably, the preparation method produces antibody-drug conjugates with a minimal low conjugate fraction (LCF) of less than 10%.

The antibody-drug conjugate can be present in any physical form known in the art, preferably as a clear solution.

To solve the above technical problems, a tenth aspect of the present invention provides a pharmaceutical composition comprising the antibody according to the first aspect of the present invention or the bispecific antibody according to the second aspect of the present invention, and a pharmaceutically acceptable carrier.

Preferably, the pharmaceutical composition further comprises one or more of the group consisting of a hormonal agent, a small molecule-targeted agent, a proteasome inhibitor, an imaging agent, a diagnostic agent, a chemotherapeutic agent, an oncolytic drug, a cytotoxic agent, a cytokine, an activator of a costimulatory molecule, an inhibitor of an inhibitory molecule, and a vaccine.

To solve the above technical problems, an eleventh aspect of the present invention provides use of the antibody according to the first aspect of the present invention or the bispecific antibody according to the second aspect of the present invention or the pharmaceutical composition according to the tenth aspect of the present invention in the manufacture of a medicament for the prevention or treatment of a CD3 and/or CLDN18.2-associated disease;

the disease is preferably cancer, wherein the cancer is preferably breast cancer, ovarian cancer, endometrial cancer, renal cancer, melanoma, lung cancer, gastric cancer, liver cancer, esophageal cancer, cervical cancer, head and neck tumor, cholangiocarcinoma, gallbladder cancer, bladder cancer, sarcoma or colorectal cancer; preferably, the cancer is breast cancer, ovarian cancer, endometrial cancer, renal cancer or cholangiocarcinoma; more preferably, the cancer is breast cancer.

To solve the above technical problems, a twelfth aspect of the present invention provides a kit comprising the antibody according to the first aspect of the present invention or the bispecific antibody according to the second aspect of the present invention, the chimeric antigen receptor according to the sixth aspect of the present invention, the genetically modified cell according to the seventh aspect of the present invention, or the antibody-drug conjugate according to the ninth aspect of the present invention or the pharmaceutical composition according to the tenth aspect of the present invention;

preferably, the kit further comprises (i) a device for administering the antibody or an antigen-binding fragment thereof or the antibody-drug conjugate or the pharmaceutical composition; and/or (ii) instructions.

To solve the above technical problems, a thirteenth aspect of the present invention provides a kit of parts comprising a kit A and a kit B, wherein:

the kit A comprises the antibody according to the first aspect of the present invention or the bispecific antibody according to the second aspect of the present invention, the chimeric antigen receptor according to the sixth aspect of the present invention, the genetically modified cell according to the seventh aspect of the present invention, the antibody-drug conjugate according to the ninth aspect of the present invention and/or the pharmaceutical composition according to the tenth aspect of the present invention;

the kit B comprises other anti-tumor antibodies or a pharmaceutical composition comprising the other anti-tumor antibodies, and/or one or more of the group consisting of a hormonal agent, a small molecule-targeted agent, a proteasome inhibitor, an imaging agent, a diagnostic agent, a chemotherapeutic agent, an oncolytic drug, a cytotoxic agent, a cytokine, an activator of a co-stimulatory molecule, an inhibitor of an inhibitory molecule, and a vaccine.

The kit A and the kit B may be used simultaneously, or the kit A may be used prior to the use of the kit B, or the kit B may be used prior to the use of the kit A. The sequence of use can be determined according to actual requirements in a specific application.

To solve the above technical problems, a fourteenth aspect of the present invention provides a method for diagnosing, treating and/or preventing a CLDN18.2-mediated disease or disorder comprising administering to a patient in need thereof a therapeutically effective amount of the antibody according to the first aspect of the present invention or the bispecific antibody according to the second aspect of the present invention, the chimeric antigen receptor according to the sixth aspect of the present invention, the antibody-drug conjugate according to the ninth aspect of the present invention or the pharmaceutical composition according to the tenth aspect of the present invention, or treating a patient in need thereof using the kit of parts according to the thirteenth aspect of the present invention.

Preferably, the disease or disorder is a tumor, preferably a CLDN18.2 positive tumor, and more preferably gastric cancer, esophageal cancer, lung cancer, ovarian cancer, melanoma, renal cancer, breast cancer, colorectal cancer, liver cancer, pancreatic cancer, bladder cancer, head and neck cancer, bronchial carcinoma, glioma and/or leukemia.

The "CLDN18.2 positive" used in the present invention refers to the overexpression of the CLDN18.2 protein, e.g., the CLDN18.2-positive cell NUGC4_D8 cell lines; otherwise, it is referred to as "CLDN18.2 negative".

To solve the above technical problems, a fifteenth aspect of the present invention provides a method of immunodetection or determination of CLDN18.2 comprising using the antibody according to the first aspect of the present invention or the bispecific antibody according to the second aspect of the present invention, the chimeric antigen receptor according to the sixth aspect of the present invention, the antibody-drug conjugate according to the ninth aspect of the present invention, or the pharmaceutical composition according to the tenth aspect of the present invention. Preferably, the detection is for non-diagnostic and/or therapeutic purposes.

To solve the above technical problems, a sixteenth aspect of the present invention provides a combination therapy comprising administering to a patient in need thereof the antibody according to the first aspect of the present invention or the bispecific antibody according the second aspect of the present invention, the chimeric antigen receptor according to the sixth aspect of the present invention, the antibody-drug conjugate according to the ninth aspect of the present invention or the pharmaceutical composition according to the tenth aspect of the present invention, and a second therapeutic agent; the second therapeutic agent preferably comprises other anti-tumor antibodies or a pharmaceutical composition comprising the other anti-tumor antibodies, and/or one or more of the group consisting of a hormonal agent, a small molecule-targeted agent, a proteasome inhibitor, an imaging agent, a diagnostic agent, a chemotherapeutic agent, an oncolytic drug, a cytotoxic agent, a cytokine, an activator of a co-stimulatory molecule, an inhibitor of an inhibitory molecule, and a vaccine.

In the present application, the amino acid sequences of the listed CDRs are all shown according to the Chothia scheme (the sequences in the claims of the present invention are also shown according to the Chothia scheme). However, it is well known to those skilled in the art that the CDRs of an antibody can be defined in the art using a variety of methods, such as the Kabat scheme based on sequence variability (see Kabat et al., *Sequences of Proteins of Immunological Interest*, Fifth Edition, National Institutes of Health (U.S.), Bethesda, Maryland (1991)), and the Chothia scheme based on the location of the structural loop regions (see *J Mol Biol* 273: 927-48, 1997). In the present application, the Combined scheme comprising the Kabat scheme and the Chothia scheme can also be used to determine the amino acid residues in a variable domain sequence. The Combined scheme combines the Kabat scheme with the Chothia scheme to obtain a larger range. See Table 1 for details. It will be understood by those skilled in the art that unless otherwise specified, the terms "CDR" and "complementary determining region" of a given antibody or a region (e.g., variable region) thereof are construed as encompassing complementary determining regions as defined by any one of the above known schemes described herein. Although the scope claimed in the claims of the present invention is the sequences shown based on the Chothia scheme, the amino acid sequences corresponding to the other CDR-defined schemes shall also fall within the scope of the present invention.

TABLE 1

The definition scheme for the CDRs of the antibody of the present invention (see http://bioinf.org.uk/abs/)

|  | Kabat | Chothia | Combined |
|---|---|---|---|
| VL CDR1 | L24--L34 | L24--L34 | L24-L34 |
| VL CDR2 | L50--L56 | L50--L56 | L50-L56 |
| VL CDR3 | L89--L97 | L89--L97 | L89-L97 |
| VH CDR1 | H31--H35 | H26--H32 | H26-H35 |
| VH CDR2 | H50--H65 | H52--H56 | H50-H65 |
| VH CDR3 | H95--H102 | H95--H102 | H95-H102 |

In the Chothia scheme, Laa-Lbb can refer to an amino acid sequence from position aa to position bb beginning at the N-terminus of the light chain of the antibody; and Haa-Hbb can refer to an amino acid sequence from position aa to position bb beginning at the N-terminus of the heavy chain of the antibody. For example, L24-L34 can refer to the amino acid sequence from position 24 to position 34 according to the Chothia scheme beginning at the N-terminus of the light chain of the antibody; H26-H32 can refer to the amino acid sequence from position 26 to position 32 according to the Chothia scheme beginning at the N-terminus of the heavy chain of the antibody. It is well known to those skilled in the art that there are positions where insertion sites are present in numbering CDRs with the Chothia scheme.

In the present invention, unless otherwise defined, the scientific and technical terms used herein have the meanings generally understood by those skilled in the art. In addition, the laboratory operations of cell culture, molecular genetics, nucleic acid chemistry and immunology used herein are the routine procedures widely used in the corresponding fields. Meanwhile, in order to better understand the present invention, the definitions and explanations of the relevant terms are provided below.

The three-letter codes and single-letter codes for amino acids used in the present invention are known to those skilled in the art, or are described in *J. Biol. Chem*, 243, p 3558 (1968).

As used herein, the term "include/includes/including" or "comprise/comprises/comprising" is intended to mean that a composition and a method include the elements described but does not exclude other elements; but the case of "consist/consists/consisting of" is also included as the context dictates.

The term "CLDN18.2" includes isotypes, mammalian (e.g., human) CLDN18.2, species homologues of human CLDN18.2 and analogues comprising at least one common epitope with CLDN18.2. The amino acid sequence of CLDN18.2 (e.g., human CLDN18.2) is known in the art, as shown in the NCBI database.

The term "CLDN18.1" includes isotypes, mammalian (e.g., human) CLDN18.1, species homologues of human CLDN18.1 and analogues comprising at least one common epitope with CLDN18.1. The amino acid sequence of CLDN18.1 (e.g., human CLDN18.1) is known in the art, as shown in the NCBI database.

The term "epitope" refers to moieties of an antigen (e.g., human CLDN18.2) that specifically interact with an antibody molecule. The term "competitive" in the present invention refers to the ability of an antibody molecule to interfere with the binding of an anti-CLDN18.2 antibody molecule to a target (e.g., human CLDN18.2). The interference with the binding may be direct or indirect (e.g., through the allosteric modulation of an antibody molecule or target). Competitive binding assays (e.g., FACS assays, ELISA, or BIACORE assays) can be used to determine the extent to which whether an antibody molecule is able to interfere with the binding of another antibody molecule to its target.

The term "antibody" used in the present invention includes an immunoglobulin, which is a tetrapeptide chain structure formed by connection between two identical heavy chains and two identical light chains by interchain disulfide bonds. Immunoglobulins differ in amino acid composition and arrangement of their heavy chain constant regions and therefore in their antigenicity. Accordingly, immunoglobulins can be classified into five classes, or isotypes of immunoglobulins, namely IgM, IgD, IgG, IgA and IgE, with their corresponding heavy chains being the μ, δ, γ, α and ε chains, respectively. The Ig of the same class can be divided into different subclasses according to the differences in amino acid composition of the hinge regions and the number and location of disulfide bonds in the heavy chains; for example, IgG can be divided into IgG1, IgG2, IgG3, and IgG4. Light chains are classified into κ or λ chains by the difference in the constant regions. Each of the five classes of Ig can have a κ chain or a λ chain.

In the present invention, the light chain variable region of the antibody of the present invention may further comprise a light chain constant region comprising a human κ or λ chain or a variant thereof. In the present invention, the heavy chain variable region of the antibody of the present invention may further comprise a heavy chain constant region comprising human IgG1, IgG2, IgG3, IgG4 or a variant thereof.

The sequences of about 110 amino acids of the heavy and light chains of the antibody near the N-terminus vary considerably and thus are referred to as variable regions (V regions); the remaining amino acid sequences near the C-terminus are relatively stable and thus are referred to as constant regions (C regions). The variable regions comprise 3 hypervariable regions (HVRs) and 4 framework regions (FWRs) with relatively conservative sequences. The 3 hypervariable regions determine the specificity of the antibody and thus are also known as complementarity determining regions (CDRs). Each light chain variable region (VL) or heavy chain variable region (VH) consists of 3 CDR regions and 4 FWR regions arranged from the amino-terminus to the carboxy-terminus in the following order: FWR1, CDR1, FWR2, CDR2, FWR3, CDR3, and FWR4. The 3 CDR regions of the light chain refer to LCDR1, LCDR2, and LCDR3; the 3 CDR regions of the heavy chain refer to HCDR1, HCDR2 and HCDR3.

In light chains and heavy chains, the variable region and constant region are linked by a "J" region of about 12 or more amino acids, and the heavy chain further comprises a "D" region of about 3 or more amino acids. Each heavy chain consists of a heavy chain variable region (VH) and a heavy chain constant region (CH). The heavy chain constant region consists of 3 domains (CH1, CH2 and CH3). Each light chain consists of a light chain variable region (VL) and a light chain constant region (CL). The light chain constant region consists of one domain CL. The constant region of the antibody can mediate the binding of immunoglobulins to host tissues or factors, including the binding of various cells of the immune system (e.g., effector cells) to the first component (C1q) of classical complement system. The VH and VL regions can be further subdivided into hypervariable regions (called complementarity determining regions (CDRs)), between which conservative regions called framework regions (FWRs) are distributed. Each VH and VL consists of 3 CDRs and 4 FWRs arranged from the amino-terminus to the carboxy-terminus in the following order: FWR1, CDR1, FWR2, CDR2, FWR3, CDR3, and FWR4. The corresponding variable regions (VH and VL) of each heavy chain/light chain form an antibody-binding site, respectively. In particular, the heavy chain may also comprise 3 or more CDRs, such as 6, 9, or 12 CDRs. For example, in the bispecific antibody of the present invention, the heavy chain may be a ScFv with the N-terminus of the heavy chain of IgG antibody linked to another antibody, and in this case, the heavy chain comprises 9 CDRs.

The term "human antibody" includes antibodies having variable and constant regions of human germline immunoglobulin sequences. The human antibody of the present invention may include amino acid residues not encoded by human germline immunoglobulin sequences (e.g., mutations introduced by in vitro random or site-directed mutagenesis or in vivo somatic mutation). However, the term "human antibody" does not include antibodies in which CDR sequences derived from the germline of another mammalian species, such as a mouse, have been grafted into human framework sequences (i.e., "humanized antibodies").

As used herein, the term "specific" with respect to an antibody means that an antibody recognizes a specific antigen but does not substantially recognize or bind to other molecules in a sample. For example, an antibody that specifically binds to an antigen from one species may also bind to the antigen from one or more species. However, such interspecies cross-reactivity per se does not change the classification of antibodies by specificity. In another example, an antibody that specifically binds to an antigen may also bind to the antigen in different allelic forms. However, such cross-reactivity per se does not change the classification of antibodies by specificity. In some cases, the term "specificity" or "specific binding" may be used to refer to the interaction of an antibody, a protein or a peptide with a second chemical, meaning that the interaction is dependent on the presence of a particular structure (e.g., an antigenic determinant or epitope) in the chemical; for example, an antibody generally recognizes and binds to a particular protein structure rather than a protein. If an antibody is specific to an epitope "A", then in a reaction containing labeled "A" and the antibody, the presence of a molecule containing the epitope A (or free, unlabeled A) will reduce the amount of labeled A bound to by the antibody.

The term "chimeric antigen receptor" or "CAR" used herein includes extracellular domains (extracellular binding domains), hinge domains, transmembrane domains (transmembrane regions) capable of binding to antigens and polypeptides that causes passes a cytoplasmic signal to a domain (i.e., an intracellular signal domain). The hinge domain may be considered as a part for providing flexibility to an extracellular antigen-binding region. The intracellular signal domain refers to a protein that transmits information into a cell via a determined signaling pathway by generating a second messenger to regulate the activity of the cell, or a protein that functions as an effector by corresponding to such a messenger. It generates a signal that can promote the immune effector function of a cell of the CAR (e.g., a CART cell). The intracellular signal domain includes a signaling domain, and may also include a co-stimulatory intracellular domain derived from a co-stimulatory molecule.

"Homology", "variant sequence" or "mutation" refers to sequence similarity between two polynucleotide sequences or between two polypeptide sequences. When positions in two compared sequences are all occupied by the same base or amino acid monomer subunit, for example, if a position in each of two DNA molecules is occupied by adenine, the molecules are homologous at that position. The identity percentage between two sequences is a function of the number of matched or homologous positions shared by the two sequences divided by the number of the compared positions×100%. For example, when sequences are optimally aligned, if 6 out of 10 positions in two sequences match or are homologous, the two sequences are 60% homologous. In general, the comparison is made when two aligned sequences give the greatest identity percentage. The "optimization" refers to a mutation that maintains or improves the binding of an antibody to an antigen. In the present invention, it refers to a mutation that maintains, preserves or improves the binding to CLDN18.2.

The terms "polypeptide", "peptide" and "protein" (if single-stranded) are used interchangeably in the present invention. The terms "nucleic acid", "nucleic acid sequence", "nucleotide sequence" or "polynucleotide sequence" and "polynucleotide" are used interchangeably.

The term "mutation" includes substitutions, additions and/or deletions of amino acids or nucleotides. The "amino acid substitution" and "conservative amino acid substitution" are replacement of an amino acid residue by another amino acid residue and replacement by an amino acid residue with similar side chains, respectively.

The "lentivirus" used herein refers to a genus of the Retroviridae family. Lentiviruses are unique among retroviruses and are capable of infecting non-dividing cells; they are capable of delivering a considerable amount of genetic information into the DNA of a host cell, and are thus one of the most efficient methods of gene delivery vectors. HIV, SIV and FIV are all examples of lentiviruses. Vectors derived from lentiviruses provide a means to achieve significant horizontal gene transfer in vivo.

The term "vector" used herein is a composition that comprises an isolated nucleic acid and is useful for delivering the isolated nucleic acid to the interior of a cell. Many vectors are known in the art. They include, but are not limited to, linear polynucleotides, polynucleotides associated with ionic or amphiphilic compounds, plasmids, and viruses. Thus, the term "vector" includes autonomously replicating plasmids or viruses. The term should also be construed as including non-plasmid and non-viral compounds that facilitate the transfer of nucleic acids into cells, such as polylysine compounds and liposomes. Examples of viral vectors include, but are not limited to, adenoviral vectors, adeno-associated viral vectors, retroviral vectors, etc.

The expressions "cell" and "cell line" used in the present invention are used interchangeably and all such designations include progeny. The term "host cell" refers to a cell to which a vector can be introduced, including, but not limited to, prokaryotic cells such as E. coli, fungal cells such as yeast cells, or animal cells such as fibroblasts, CHO cells, COS cells, NSO cells, HeLa cells, BHK cells, HEK 293 cells, or human cells.

The term "transfection" refers to the introduction of an exogenous nucleic acid into a eukaryotic cell. Transfection may be accomplished by a variety of means known in the art, including calcium phosphate-DNA co-precipitation, DEAE-dextran mediated transfection, polybrene-mediated transfection, electroporation, microinjection, liposome fusion, lipofection, protoplast fusion, retroviral infection, and biolistics.

The term "immune cell" refers to a cell that can elicit an immune response. The "immune cell" and other grammatical variations thereof may refer to an immune cell of any origin. The "immune cell" includes, for example, white blood cells (leukocytes) and lymphocytes (T cells, B cells, and natural killer (NK) cells) derived from hematopoietic stem cells (HSCs) produced in the bone marrow, and bone marrow-derived cells (neutrophils, eosinophils, basophils, monocytes, macrophages, dendritic cells). The term "immune cell" may also refers to a human or non-human immune cell.

As used herein, the term "T cell" refers to a class of lymphocytes that mature in the thymus. T cells play an important role in cell-mediated immunity and are different from other lymphocytes (e.g., B cells) in that T cell receptors are present on the cell surface. The "T cell" includes all types of immune cells that express CD3, including T helper cells (CD4+ cells), cytotoxic T cells (CD8+ cells), natural killer T cells, T regulatory cells (Tregs), and γ-δT cells. The "cytotoxic cells" include CD8+ T cells, natural killer (NK) cells and neutrophils, which are capable of mediating a cytotoxic response. As used herein, the term "NK cell" refers to a class of lymphocytes that originate in the bone marrow and play an important role in the innate immune system. NK cells provide a rapid immune response against virus-infected cells, tumor cells or other stressed cells, even in the absence of antibodies and major histocompatibility complexes on the cell surface.

For example, the immune cells may be derived from the blood, such as autologous T cells, allogeneic T cells, autologous NK cells and allogeneic NK cells, or from cell lines, such as NK cell lines prepared by infection with the EBV virus, NK cells obtained by induced differentiation of embryonic stem cells and iPSCs, as well as NK92 cell lines.

The term "optional", "optionally", "any" or "any one of" means that the event or circumstance subsequently described may, but not necessarily, occur, and that the description includes instances where the event or circumstance occurs or does not occur. For example, "optionally comprising 1 antibody heavy chain variable region" means that the antibody heavy chain variable region of a particular sequence may, but not necessarily, be present. As used herein, the "a"

and "an" are used in the present invention to refer to one or more grammatical objects. Unless otherwise specifically stated in the content, the term "or" is used in the present invention to mean, and is interchangeable with, the term "and/or". The "about" and "approximately" shall generally mean an acceptable degree of error in the measured quantity in view of the nature or accuracy of the measurement. Exemplary degrees of error are typically within 10% thereof and more typically within 5% thereof. The method and composition disclosed in the present invention encompass polypeptides and nucleic acids having a specified sequence, a variant sequence, or a sequence substantially identical or similar thereto, e.g., a sequence that is at least 85%, 90%, 95%, 99% or more identical to the sequence specified. In the context of amino acid sequences, the term "substantially identical" is used in the present invention to refer to a first amino acid sequence.

As used herein, the term $EC_{50}$ refers to the concentration for 50% of maximal effect, i.e., the concentration that can cause 50% of the maximal effect.

As used herein, the terms "antibody-drug conjugate" and "ADC" are used interchangeably.

Auristatin is a fully synthetic drug whose chemical structural formula is relatively easy to modify so as to optimize its physical properties and druggability. Auristatin derivatives used for conjugation with antibodies mainly include monomethyl auristatin E (MMAE) and monomethyl auristatin F (MMAF), wherein the former is synthesized by adding 2-amino-1-phenylpropyl-1-ol to the C-terminus of a synthetic pentapeptide derived from a natural tubulin polymerase inhibitor dolastatin-10. The inhibitory activity of MMAE against various human tumor cell lines is less than one nanomole. In order to reduce the cytotoxic activity of MMAE, a phenylalanine is added to the C-terminus of dolastatin-10 in MMAF. The cell membrane trafficability of MMAF is poor for the carboxyl introduced in the structure. Therefore, the bioactivity for cells is significantly reduced, but the inhibitory activity against cells is greatly improved after conjugation with an antibody (U.S. Pat. No. 7,750,116).

In some embodiments, an antibody-cytotoxic drug conjugate or a pharmaceutically acceptable salt or solvate thereof comprises the antibody of the present invention conjugated with one or more maytansinoid molecules. Maytansinoids are mitotic inhibitors that disable tubulin by inhibiting polymerization of tubulin. Maytansine was originally isolated from the East African shrub Maytenus serrata (U.S. Pat. No. 3,896,111). It was subsequently discovered that certain microorganisms also produce maytansinoids, such as maytansinol and C-3 maytansinol vinegar (U.S. Pat. No. 4,151,042). Maytansinoid drug modules are appealing drug modules in antibody-drug conjugates as they are: (i) relatively easy to prepare by fermentation or chemical modification or derivatization of the fermentation product; (ii) readily derivatized with functional groups suitable for conjugation to antibodies through non-disulfide linkers; (iii) stable in plasma; and (iv) effective for a variety of tumor cell lines. Maytansine compounds suitable for use as maytansinoid drug modules are well known in the art and can be isolated from natural sources according to known methods or produced using genetic engineering techniques (see Yu et al. (2002) PNAS 99: 7968-7973). Maytansinol and maytansinol analogues can also be prepared synthetically according to known methods. Exemplary embodiments of maytansinoid drug modules include: DM1, DM3 and DM4, as disclosed herein.

The method, composition and combination therapy of the present invention may be combined with other active agents or therapeutic modalities, the method comprising administering to a subject the anti-CLDN18.2 antibody molecule of the present invention in an amount that is effective in treating or preventing diseases (e.g., cancer), optionally in combination with one or more inhibitors of PD-1, PD-L1, PD-L2, LAG-3, CTLA-4, Tim-3 antibody (immunotherapy) or other tumor therapy antibodies, Her-2, EGFR, VEGF, VEGFR antibodies, etc., as well as ADCs (e.g., T-DM1), bispecific antibodies, chemotherapeutic agents, etc., and further comprising administering an anti-CLDN18.2 antibody molecule, an additional active agent or all in an amount or at a dose that is higher, lower or equal to the amount or dose for each active agent when used alone (e.g., as a monotherapy). The amount or dose for the anti-CLDN18.2 antibody, the additional active agent or all administered is, e.g., at least 20%, at least 30%, at least 40% or at least 50%, lower than the amount or dose for each active agent when used alone (e.g., as a monotherapy).

Furthermore, as described in the examples of the present invention, the anti-CLDN18.2 antibody and the drug conjugate of the CLDN18.2 antibody can bind to CLDN18.2 to induce apoptosis of target cells (tumor cells), to inhibit the growth of tumor cells, and to increase the effector cells' ADCC and CDC killing effects on tumor cells in vivo, thereby achieving the purpose of treating cancer patients. Thus, in certain embodiments, the anti-CLDN18.2 antibody and drug conjugate of the CLDN18.2 antibody described in the present invention show the anti-tumor effects of the antibody of the present invention, as well as methods for inhibiting the growth of tumor cells comprising administering to a subject a therapeutically effective amount of the anti-CLDN18.2 antibody and drug conjugate of the CLDN18.2 antibody of the present invention, through these mechanisms. The method is suitable for the in vivo treatment of cancer. To achieve a targeted specific therapeutic effect, the anti-CLDN18.2 antibody molecule may be administered together with other antibodies. In administering the CLDN18.2 antibody and the drug conjugate of the CLDN18.2 antibody in combination with one or more active agents, the combination may be administered in any order or simultaneously to a patient with a type of cancer, particularly a tumor patient with high expression of CLDN18.2. In certain aspects, treatment (e.g., reduction or amelioration) of a hyperproliferative symptom or disease (e.g., cancer) in a subject is provided. The method comprises administering to a subject one or more anti-CLDN18.2 antibodies or drug conjugates of the CLDN18.2 antibodies of the present invention, either alone or in combination with other active agents or therapeutic modalities.

The anti-CLDN18.2 antibody molecule, alone or in combination with another immunomodulatory agent (e.g., anti-LAG-3, anti-Tim-3, anti-PD-L or anti-PD-L1, and anti-CTLA-4 antibody molecules), is employed to treat gastric cancer, pancreatic cancer, lung cancer, esophageal cancer, ovarian cancer, etc. The anti-CLDN18.2 antibody molecule may be administered in combination with one or more of: an immunity-based strategy, a targeted drug (e.g., a VEGF inhibitor such as a monoclonal antibody against VEGF); VEGF tyrosine kinase inhibitors such as sunitinib, sorafenib and apatinib; RNAi inhibitors or inhibitors of downstream mediators of the VEGF signaling, e.g., inhibitors of rapamycin mammalian target (mTOR).

As used herein, the terms "cancer," "cancer patient" are intended to include all types of cancerous growths or oncogenic processes, metastatic tissues or malignantly transformed cells, tissues or organs, regardless of their histopathological types or stages of invasiveness. Examples include, but are not limited to, solid tumors, hematologic cancer, soft tissue tumors and metastatic lesions.

Non-limiting examples of cancers that may be suitably treated using the CLDN18.2-targeting antibody disclosed in the present invention include gastric cancer, esophageal cancer, lung cancer, melanoma, renal cancer, breast cancer, colorectal cancer, liver cancer, pancreatic cancer, bladder cancer, glioma and/or leukemia and the like, or metastatic lesions thereof.

The above preferred conditions may be combined arbitrarily to obtain preferred embodiments of the present invention on the basis of the general knowledge in the art.

The reagents and starting materials used in the present invention are commercially available.

The beneficial effects of the present invention are as follows:

1. The present invention describes anti-CLDN18.2 HCAb antibodies with excellent affinity, specificity and endocytic activity. The antibody is a brand-new fully human antibody containing a "heavy chain" only with a molecular weight that is only about half of that of a conventional IgG antibody. Due to the absence of a light chain, the antibody can be used for the development of bispecific antibodies, and the common problems of light chain mismatching and heterodimerization in the development of bispecific antibodies are avoided. It also has the potential to be developed into ADCs. In certain preferred embodiments, the HCAb antibody has great affinity for tumor cells endogenously expressing CLDN18.2 and can induce great endocytic activity compared to an IMAB362 analogue.

2. The present invention also describes CLDN18.2×CD3 bispecific antibodies with excellent in vitro TDCC activity and in vivo drug effect. The bispecific antibody of the present invention has the activity of specifically binding to CLDN18.2, and has a better killing effect on tumor cells than a patent bispecific antibody analogue of Amgen. In certain preferred embodiments, the bispecific antibody has a Fc fragment and thus retains the binding effect of the Fc to an FcRn; meanwhile, a mutant Fc is preferred so as to reduce the binding to an FcgR and thus the activation of non-specific T cells caused by the cross-linking of an FcgR. The CD3-termini activity is optimized so that the release of common cytokines in CRS, such as IL6 and TNFα can be reduced. The CLDN18.2 termini is in the form of VHHs linked in series, avoiding the common problem of mismatching of light and heavy chains, retaining the excellent hydrophilicity and improving the selectivity for tumor cells with high expression of CLDN18.2. The antibody has good in vivo stability and long in vivo half-life and shows great in vivo anti-tumor activity.

DETAILED DESCRIPTION

Figure 1A:
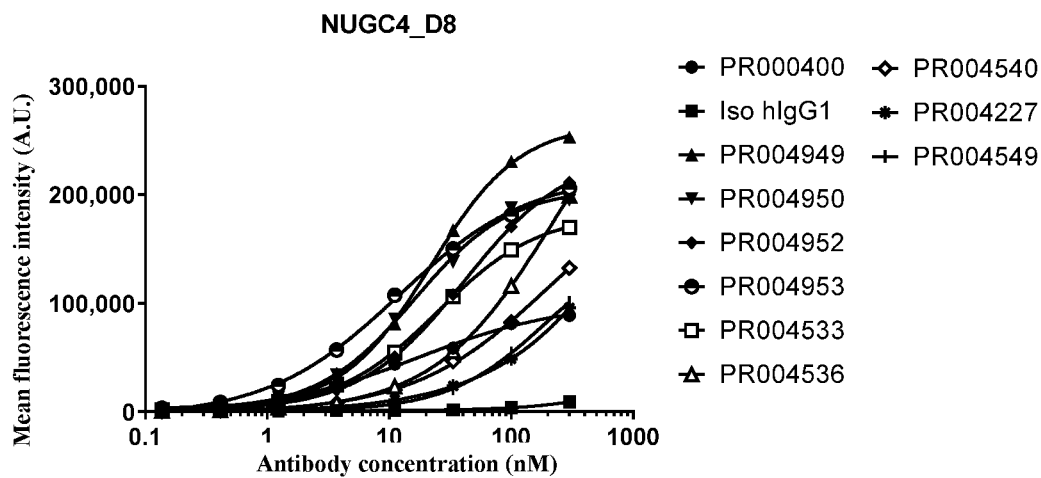
FIGS. 1a-f show the binding affinity of HCAB antibodies for (a-b) NUGC4_D8, (c) SNU601, (d) HEK293/hCLDN18.2, and (e-f) HEK293/hCLDN18.1 cells.

The present invention is further illustrated by the following examples, which are not intended to limit the present invention. Experimental procedures without specified conditions in the following examples are performed in accordance with conventional procedures and conditions, or in accordance with instructions.

Example 1

Preparation of Expression Vector and Stably Transfected Cell Lines and Immunization of Mice 1.1. Preparation of Expression Vector for Immunizing Mice A human CLDN18.2 expression vector for immunizing fully humanized transgenic mice was prepared as follows: a cDNA sequence encoding human CLDN18.2 (Uniprot ID P56856-iso2) was synthesized, and the coding sequence of the human CLDN18.2 gene was cloned into a pCAGGS plasmid (YOUBIO, VT1076) by enzymatic digestion.

1.2. Preparation of Stably Transfected Cell Lines

HEK293 (ATCC, Cat #: CRL-1573) cell lines stably expressing human CLDN18.1 or CLDN18.2 were constructed specifically as follows: plasmids encoding human CLDN18.1 (GenScript, OHu29174D) or CLDN18.2 (GenScript, OHu03374D) were transfected into HEK293 cells to produce stable cell lines overexpressing human CLDN18.1 or CLDN18.2. The expression of CLDN18.1 and CLDN18.2 was detected by fluorescence activated cell sorting (FACS). Specifically, 20,000 transfected cells were plated in each well of a 96-well plate, followed by the addition of a commercially-available rabbit anti-human CLDN18 antibody (LifeSpan Bio, LS-C168812-400). After 1 h of incubation at 4° C., the cells were washed 2 times with PBS, and then an AF-680-conjugated secondary goat anti-rabbit IgG antibody (Invitrogen, A21109) was added. After 1 h of incubation at 4° C., the cells were washed 3 times with PBS, and then the fluorescence intensity of the cells was monitored using an FACS instrument (IntelliCytiQue Plus BR).

1.3. Immunization of Mice

Fully humanized transgenic mice (commercially available Harbour HCAB 1.0 mice, purchased from Harbour BioMed) were immunized with the human CLDN18.2 expression vector and CLDN18.2-expressing HEK293 cells (HEK293/hCLDN18.2 cells) prepared above. Bullets for a gene gun were prepared with the human CLDN18.2 expression vector and gold powder. Mice were immunized at multiple sites of the abdomen using the gene gun. The mice were immunized with the expression vector DNA (50 μg each time) at 2-week intervals. After three immunizations, the mice were then immunized with HEK293/hCLDN18.2 cells at 2-week intervals, with $4 \times 10^6$ cells per mouse for each immunization. After two immunizations, the blood was collected for titer measurement. The mouse serum was assayed for binding affinity by FACS using human CLDN18.2-expressing CHOK1 cells (kyinno, KC-1180). Mice were selected according to the results of the titer measurement for screening of HCAB monoclonal antibodies. The mice were subjected to boosted immunization 3 days prior to the screening, with HEK293/hCLDN18.2 cells, $4 \times 10^6$ cells per mouse, as immunogen-.

Example 2

Production and Screening of Anti-CLDN18.2 HCAB Single-Domain Antibodies

The mice with high anti-CLDN18.2 antibody serum titer obtained in Example 1 were selected. The spleens of these mice were collected, and B cells were isolated. CD138 (BD, 558626) positive plasma cells were sorted using a BD FACS AriaIII cell sorter, and CLDN18.2 (CHOK1/hCLDN18.2, kyinno, KC-1180) positive B Cell populations were enriched using magnetic beads (Thermofisher, 11206D). The RNA of the B cells was extracted and reverse transcribed into cDNA (SuperScript IV First-Strand synthesis system, Invitrogen, 18091200), and human VH genes were amplified by PCR using specific primers. PCR primers:

(SEQ ID NO: 249)
5'-GGTGTCCAGTGTSAGGTGCAGCTG-3'

(SEQ ID NO: 250)
5'-AATCCCTGGGCACTGAAGAGACGGTGACC-3'

The amplified VH gene fragments were constructed into mammalian cell expression plasmid pCAG vectors encoding the sequence of heavy chain Fc domain of human IgG1 antibody.

The constructed plasmids were transfected into HEK293 mammalian host cells (ATCC, CRL-1573) to obtain an expression supernatant of the HCAb antibody. Primary screening was performed by Mirrorball using CHOK1/hCLDN18.2 expressing human CLDN18.2. Positive clones were selected for secondary screening. The secondary screening was performed by FACS using HEK293/hCLDN18.1 and HEK293/hCLDN18.2 cells.

While 295 monoclonal antibodies specifically binding to human CLDN18.2 were obtained, the nucleotide sequences encoding the variable domains of the antibody molecules and the corresponding amino acid sequences were obtained using conventional sequencing means. After the removal of repeated sequences, 211 fully human CLDN18.2 HCAb monoclonal antibodies having unique sequences and specifically binding to human CLDN18.2 were obtained. 54 antibodies with top comprehensive ranking were selected for recombinant expression according to the primary screening result and the secondary screening result. The purified monoclonal antibodies were further screened for binding ability to tumor cells endogenously expressing human CLDN18.2 by flow cytometry, and the top 8 antibody sequences in the comprehensive rankings were selected as candidate molecules, as shown in Table 3.

It is well known to those skilled in the art that the CDRs of an antibody can be defined in the art using a variety of methods, such as the Kabat scheme based on sequence variability (see Kabat et al., *Sequences of Proteins of Immunological Interest*, Fifth Edition, National Institutes of Health (U.S.), Bethesda, Maryland (1991)), and the Chothia scheme based on the location of the structural loop regions (see *J Mol Biol* 273: 927-48, 1997). In the present application, the Combined scheme comprising the Kabat scheme and the Chothia scheme can also be used to determine the amino acid residues in a variable domain sequence. The Combined scheme combines the Kabat scheme with the Chothia scheme to obtain a larger range, which is detailed in Table 1 of the summary of the present invention. The germline gene analysis and the PTM site analysis obtained after sequencing from this example are shown in Table 2 below. The sequence numbers of the antigen-binding proteins are shown in Table 3 below.

TABLE 2

Germline gene analysis and post-translational modification site (PTM) analysis of sequences of HCAb antibodies

| No. | Clone No. | Antibody | VH germline V gene | VH PTM |
|---|---|---|---|---|
| 1 | R1029P(CG20)001B02 | PR004227 | IGHV3-74*01 | DG (HCDR2) |
| 2 | R1029P021E10 | PR004533 | IGHV3-74*03 | NS (HCDR2), DG (HCDR2) |
| 3 | R1029P028A11 | PR004536 | IGHV3-74*01 | NS (HCDR2), DG (HCDR2) |
| 4 | R1029P037B07 | PR004540 | IGHV3-74*01 | DG (HCDR2), NxS/T (HCDR2) |
| 5 | R1029P021C02 | PR004949 | IGHV3-74*03 | NS (HCDR2), DG (HCDR2) |
| 6 | R1029P021F07 | PR004950 | IGHV3-74*01 | NS (HCDR2), DG (HCDR2) |
| 7 | R1029P021H07 | PR004952 | IGHV3-74*03 | NS (HCDR2), DG (HCDR2) |
| 8 | R1029P024B07 | PR004953 | IGHV3-30*03 | DG (HCDR2) |

TABLE 3

Sequence numbers of anti-CLDN18.2 HCAb

| | SEQ ID NOs: | | | | |
|---|---|---|---|---|---|
| Antibody | Heavy chain | VH | HCDR1 | HCDR2 | HCDR3 |
| PR004227 | 182 | 150 | 16 | 42 | 77 |
| PR004533 | 183 | 151 | 16 | 43 | 78 |
| PR004536 | 184 | 152 | 16 | 44 | 79 |
| PR004540 | 185 | 153 | 17 | 45 | 80 |
| PR004949 | 186 | 154 | 18 | 43 | 80 |
| PR004950 | 187 | 155 | 18 | 43 | 78 |
| PR004952 | 188 | 156 | 16 | 43 | 81 |
| PR004953 | 189 | 157 | 16 | 46 | 82 |

Example 3

Removal of Post-Translational Modification Site of Anti-CLDN18.2 HCAB Antibodies PR004533 and PR004536 both have an isomerization site and a deamidation site in the CDR2 region of the heavy chain. For the post-translational modification site in the CDR2 region, four amino acids of NS and DG were randomly mutated by PCR. The PCR products were electrically transfected into *E. coli* to establish a random mutation library of four amino acid sites. The mutant library was screened by Mirrorball using CHOK1/hCLDN18.1 and CHOK1/hCLDN18.2 cells, and positive molecules that specifically bind to CLDN18.2 were selected for sequencing. The sequence numbers of the molecules are shown in Table 4 below.

TABLE 4

Part of the sequence numbers of PR004533 and PR004536 mutant molecules

| Antibody | Heavy chain | VH | HCDR1 | HCDR2 | HCDR3 | Mutant clone |
|---|---|---|---|---|---|---|
| PR007242 | 191 | 159 | 16 | 48 | 78 | 4533_M10E1 |
| PR007243 | 192 | 160 | 16 | 49 | 78 | 4533_M3D9 |

TABLE 4-continued

Part of the sequence numbers of PR004533
and PR004536 mutant molecules

| Antibody | Heavy chain | VH | HCDR1 | HCDR2 | HCDR3 | Mutant clone |
|---|---|---|---|---|---|---|
| PR007244 | 193 | 161 | 16 | 50 | 78 | 4533_M4H6 |
| PR007245 | 194 | 162 | 16 | 51 | 78 | 4533_M6E6 |
| PR007246 | 195 | 163 | 16 | 52 | 78 | 4533_M3F10 |
| PR007247 | 196 | 164 | 16 | 53 | 79 | 4536_M8A6 |
| PR007248 | 197 | 165 | 16 | 54 | 78 | 4533_M10E7 |

Example 4

Preparation and Characterization of Full-Length Anti-CLDN18.2 HCAb Single-Domain Antibodies 4.1. Preparation of Recombinant HCAb Single-Domain Antibodies After obtaining the sequence of the heavy chain variable domain encoding the HCAb single-domain antibody molecules, the sequence of the heavy chain variable domain can be fused with the corresponding sequence of the heavy chain constant domain of the human antibody and expressed using conventional recombinant DNA techniques to obtain recombinant HCAb single-domain antibody molecules. In this example, the sequence of the heavy chain variable domain (VH) of the antibody was genetically synthesized and cloned into a mammalian cell expression plasmid vector encoding the sequence of the heavy chain constant domain of the human IgG1 antibody to encode a full-length sequence producing the HCAb single-domain antibody. In this example, the sequences of the variable domains of the monoclonal antibody molecules obtained from immunized Harbour HCAb mice were human antibody sequences, therefore, a fully human anti-CLDN18.2 recombinant HCAb antibody was also obtained from this example.

The plasmids encoding recombinant HCAb single-domain antibodies were transfected into mammalian host cells (e.g., Chinese Hamster Ovary (CHO) cells), and the corresponding purified recombinant antibody can be obtained using conventional recombinant protein expression and purification techniques. Specifically, ExpiCHO-S™ cells (Gibco, A29127) were expanded in ExpiCHO™ Expression Medium (Gibco, A2910001). Before the transient transfection, the cells were adjusted to a concentration of $3 \times 10^6$ to $4 \times 10^6$ cells/mL, and cultured in an 8% $CO_2$ shaker at 37° C. for 24 h, leading to a cell concentration of $7 \times 10^6$ to $10 \times 10^6$ cells/mL. The cells were then diluted to $6 \times 10^6$ cells/mL, and 10 mL of the cultured cells was prepared. 8 µg of the above plasmids encoding HCAb single-domain antibodies (the ratio of the plasmids to cells is 0.8 µg:1 mL) was dissolved in 0.4 mL of OptiPRO™ SFM medium (Gibco, 12309019). The resulting mixture was filtered through a 0.22 µm filter for sterilization. Then 32 µL of ExpiFectamine™ CHO reagent (Gibco, A29129) was added to 0.37 mL of OptiPRO™ SFM medium (Gibco, 12309019). The ExpiFectamine™ CHO reagent solution was immediately added slowly to the plasmid solution. The mixture was inverted to be well mixed. The mixed solution of plasmid and transfection reagent was slowly added dropwise while shaking the flask. The cells were cultured in an 8% $CO_2$ shaker at 37° C. for 8-9 days. The Cell viability was observed after 8 days.

The culture was collected and centrifuged at 3,300 g for 10 min, and then the supernatant was collected and centrifuged at high speed to remove impurities. A gravity column (Bio-Rad, #7311550) containing MabSelect™ (GE Healthcare Life Science, 71-5020-91 AE) was equilibrated with PBS (pH 7.4) and rinsed with 2-5 column volumes of PBS. The supernatant sample was loaded onto a column. The column was rinsed with 5-10 column volumes of PBS. The target protein was eluted with 0.1 M glycine (pH 3.5). The eluate was adjusted to neutrality with Tris-HCl (pH 8.0), and concentrated and buffer exchanged into PBS buffer with an ultrafiltration tube (Millipore, UFC901024) to obtain a purified antibody solution. Then, the purified antibody solution was subjected to concentration determination using NanoDrop (Thermo Scientific™ NanoDrop™ One), subpackaged and stored for later use.

4.2. Antibody Characterization by SEC-HPLC, HIC-HPLC and DSF

A proper amount of the purified sample above was loaded onto an analytical SEC column TSKgel G3000SW×1 (HPLC system model: Agilent 1260 Infinity II) for the measurement of purity. In this method, the following parameters and conditions were used: mobile phase: 1×PBS, pH 7.4 (Sangon, E607016); room temperature; flow rate: 1.0 mL/min; sample concentration: 1 mg/mL; injection volume: 20 µL; detection wavelength: 280 nm. After being recorded, the chromatogram was integrated using ChemStation software and relevant data were calculated. An analysis was generated, with the retention times reported for different components in the sample.

A proper amount of the purified sample above was loaded onto an analytical HIC column TSKgel Butyl-NPR 4.6*35 (HPLC system model: Agilent 1260 Infinity II) for the measurement of purity and hydrophobicity. The method consisted of a linear gradient from 100% mobile phase A (20 mM PB, 1.8 M $(NH4)_2SO_4$, pH 6.0) to 100% mobile phase B (20 mM PB, pH 6.0) within 16 min. The flow rate was set at 0.7 mL/min, the sample concentration was 1 mg/mL, the injection volume was 20 µL, and the detection wavelength was 280 nm. After being recorded, the chromatogram was integrated using ChemStation software and relevant data were calculated. An analysis was generated, with the retention times reported for different components in the sample.

In this example, the thermal denaturation temperature (Tm) of a protein molecule was measured by differential scanning fluorimetry (DSF). 10 µg of protein was added to a 96-well PCR plate (Thermo, AB-0700/W), followed by the addition of 2 µL of 100× diluted dye SYPRO™ (Invitrogen, 2008138), and then buffer was added to give a final volume of 40 µL per well. The PCR plate was sealed, placed in a real-time fluorescent quantitative PCR instrument (Bio-Rad CFX96 PCR System), incubated at 25° C. for 5 min, then gradually warmed from 25° C. to 95° C. at a gradient of 0.2° C./0.2 min, and cooled to 25° C. at the end of the test. The FRET scanning mode was used and data analysis was performed using Bio-Rad CFX Maestro software to calculate the Tm of the sample. The results of the above characterization are shown in Table 5 below.

TABLE 5

Characterization of anti-CLDN18.2 HCAB antibodies

| Antibody | SEC-HPLC purity (%) | HIC-HPLC purity (%) | HIC-HPLC retention time (min) | Tm1 (° C.) | Tm2 (° C.) |
|---|---|---|---|---|---|
| PR004227 | 87.8 | 86.5 | 19.2 | 52.2 | 64.4 |
| PR004533 | 99.2 | 100.0 | 17.2 | NA | 64.2 |
| PR004536 | 97.6 | 100.0 | 17.1 | 52.8 | 66.0 |
| PR004540 | 99.4 | 100.0 | 17.5 | 52.8 | 65.4 |
| PR004949 | 99.2 | 100.0 | 16.0 | 59.0 | NA |
| PR004950 | 98.7 | 100.0 | 16.2 | NA | 65.4 |
| PR004952 | 100.0 | 100.0 | 15.8 | 61.2 | NA |
| PR004953 | 98.2 | 100.0 | 18.9 | 60.0 | NA |
| PR007242 | 94.3 | 100.0 | 15.7 | 56.6 | 65.4 |
| PR007243 | 99.1 | 92.5 | 15.3 | 55.6 | 64.8 |
| PR007244 | 99.1 | 94.3 | 15.3 | 59.6 | NA |
| PR007245 | 98.9 | 94.5 | 15.2 | 59.8 | NA |
| PR007246 | 99.1 | 93.9 | 15.2 | 59.0 | 64.6 |
| PR007247 | 98.1 | 94.3 | 16.3 | 52.0 | 65.2 |
| PR007248 | 99.3 | 100.0 | 15.4 | 60.6 | NA |
| Trastuzumab | 100.0 | 100.0 | 16.0 | 67.8 | 79.2 |

Example 5

Binding Affinity of Anti-CLDN18.2 HCAB Antibodies to Cells

The binding affinity of an antibody was detected by FACS using human CLDN18.1-expressing HEK293 cells, human CLDN18.2-expressing HEK293 cells, NUGC4_D8 cells and SNU601 cells endogenously expressing human CLDN18.2 (Cobioer, CBP60507). Subcloned NUGC4_D8 cells were screened by limiting dilution using NUGC4 cells (JCRB, JCRB0834). The binding affinity was determined as follows: cells were centrifuged at 300 g for 5 min and then resuspended in FACS buffer (PBS containing 2% FBS). The cell density was adjusted to $10^6$ cells/mL, and 50 μL of the cell suspension was added to each well of a 96-well plate. Antibodies were diluted to different concentrations with FACS buffer, and 50 μL of the antibody dilution was added to each well of the 96-well plate. After 2 h of incubation at 4° C., the plate was washed twice with FACS buffer. Then, FACS buffer containing an APC-conjugated goat anti-human IgG secondary antibody (Jackson, 109-605-098) was added. After 1 h of incubation at 4° C., the plate was washed twice with FACS buffer. The cells were resuspended in fixative solution, and then the fluorescence of the cells was monitored using an FACS instrument (ACEA NovoCyte). PR000400, an IMAB362 analogue (produced in-house, see WO 2014/146672, having the same variable region as IMAB362, differing from IMAB362 in only a few amino acids in the constant region), was used as a positive control for CLDN18.2 binding. PR004549, a CL-1xI2C scFc analogue (produced in-house, see WO2020025792A1, having the same variable region as CL-1xI2C scFc, differing from CL-1xI2C scFc in only a few amino acids in the constant region), was used as a positive control for CLDN18.2 binding. PR002725 antibody was used as a positive control for CLDN18.1 binding. See CN2020/118650 (Table 6, Table 7, and Table 8). Iso hIgG1 (CrownBio, C0001-4) antibody was used as a negative control.

FIGS. 1(a-b), Table 9 and Table 10 show the binding affinity of antibodies for NUGC4_D8 cells endogenously expressing CLDN18.2. The test antibodies were able to bind to NUGC4_D8 cells in a dose-dependent manner. The results show that: PR004533, PR004949, PR004950, PR004952, PR004953, PR007242, PR007243, PR007244, PR007245, PR007246 and PR007248 antibodies exhibit higher affinity for NUGC4_D8 cells endogenously expressing CLDN18.2 than PR000400. FIG. 1c and Table 11 show the binding affinity of antibodies for SNU601 cells endogenously expressing CLDN18.2. The test antibodies were able to bind to SNU601 cells in a dose-dependent manner. The results show that: PR004227, PR004533, PR004536, PR004540, PR004949, PR004950 and PR004952 antibodies exhibit higher affinity for SNU601 cells endogenously expressing CLDN18.2 than PR000400. FIG. 1d and Table 12 show the binding affinity of antibodies for HEK293 cells overexpressing human CLDN18.2 (HEK293/hCLDN18.2). FIGS. 1(e-f) show the binding affinity of antibodies to HEK293 cells overexpressing human CLDN18.1 (HEK293/hCLDN18.1). The test antibodies have low binding affinity for HEK293/hCLDN18.1 cells. From the above results, it can be inferred that the test antibodies bind to human CLDN18.2 protein at ECL1 (Extracellular loop 1) rather than ECL2.

TABLE 6

| | Description for reference antibody molecules | |
|---|---|---|
| Antibody | Target | Description |
| PR000400 | CLDN18.2 | An anti-CLDN18.2 IgG1 monoclonal antibody with a sequence from patent WO2014/146672. |
| PR001861 | CLDN18.1 | An anti-CLDN18.1 IgG1 monoclonal antibody, produced in-house by Harbour BioMed. |
| PR002725 | CLDN18.1 | An anti-CLDN18.1 IgG1 monoclonal antibody with a sequence from patent PCT/CN2020/118650. |

TABLE 6-continued

Description for reference antibody molecules

| Antibody | Target | Description |
|---|---|---|
| PR002726 | CLDN18.2 | An anti-CLDN18.2 IgG1 monoclonal antibody with a sequence from patent PCT/CN2020/118650. |
| PR000325 | Chicken lysozyme | A chicken lysozyme-targeting IgG1 monoclonal antibody, used as an isotype control. |
| PR001848 | CD3 | An anti-CD3 IgG1 monoclonal antibody with a sequence from patent PCT/CN2020/118606. |
| PR003886 | CD3 | An anti-CD3 IgG1 monoclonal antibody with a sequence from patent PCT/CN2020/118606. |
| PR005080 | CLDN2 | An anti-CLDN2 IgG1 monoclonal antibody with a sequence from patent EP3567053A1. |
| PR003767 | TRBC1 | An anti-TRBC1 IgG1 monoclonal antibody, used as a control for ADCC experiments. |
| PR004549 | CLDN18.2/CD3 | A CLDN18.2 × CD3 bispecific antibody with a sequence from patent WO2020025792A1. |
| PR004931 | CEA/CD3 | A CEA × CD3 bispecific antibody with a sequence from patent WO2017055389A1. |
| PR002199 | BCMA/CD3 | A BCMA × CD3 bispecific antibody with a sequence from patent WO2018052503. |
| PR004312 | Chicken lysozyme/CD3 | A lysozyme and CD3-targeting bispecific antibody, constructed using the sequences of PR000325 and PR001848. |
| PR004313 | CLDN18.1/CD3 | A CLDN18.1 and CD3-targeting bispecific antibody, constructed using the sequences of PR001861 and PR001848. |

TABLE 7

Sequence numbers of reference antibodies (monoclonal antibodies)

| Antibody | Light chain | Heavy chain | VL | VH | LCDR1 | LCDR2 | LCDR3 | HCDR1 | HCDR2 | HCDR3 |
|---|---|---|---|---|---|---|---|---|---|---|
| PR000400 | 199 | 175 | 167 | 143 | 100 | 115 | 130 | 10 | 37 | 71 |
| PR001861 | 201 | 177 | 169 | 145 | 102 | 117 | 132 | 12 | 39 | 73 |
| PR002725 | 202 | 178 | 170 | 146 | 103 | 117 | 132 | 13 | 39 | 74 |
| PR002726 | 203 | 179 | 171 | 147 | 104 | 118 | 133 | 14 | 40 | 75 |
| PR000325 | 198 | 174 | 166 | 142 | 99 | 114 | 129 | 9 | 36 | 70 |
| PR001848 | 200 | 176 | 168 | 144 | 101 | 116 | 131 | 11 | 38 | 72 |
| PR003886 | 200 | 181 | 168 | 149 | 101 | 116 | 131 | 11 | 38 | 72 |
| PR005080 | 205 | 190 | 173 | 158 | 106 | 120 | 135 | 19 | 47 | 83 |
| PR003767 | 204 | 180 | 172 | 148 | 105 | 119 | 134 | 15 | 41 | 76 |

TABLE 8

Sequence numbers of reference antibodies (bispecific antibodies)

| Antibody | SEQ ID NOs: | | | |
|---|---|---|---|---|
| | Polypeptide chain-1 | Polypeptide chain-2 | Polypeptide chain-3 | Polypeptide chain-4 |
| PR004549 | 212 | | | |
| PR004931 | 218 | 215 | 217 | 216 |
| PR002199 | 206 | 207 | 208 | |
| PR004312 | 210 | 209 | 200 | |
| PR004313 | 211 | 209 | 200 | |

TABLE 9

The binding affinity of anti-CLDN18.2 antibodies (with post-translational modification sites in CDRs) for NUGC4_D8 cells (see FIG. 1a)

| Antibody | Titer $EC_{50}$ (nM) | Efficacy $E_{max}$ (MFI) |
|---|---|---|
| PR000400 | 17.0 | 100,612 |
| PR004227 | NA | NA |
| PR004533 | 25.0 | 183,235 |
| PR004536 | NA | NA |
| PR004540 | NA | NA |
| PR004949 | 21.8 | 265,481 |
| PR004950 | 16.1 | 206,071 |
| PR004952 | 41.0 | 239,521 |
| PR004953 | 12.0 | 218,991 |
| PR004549 | NA | NA |

TABLE 10

Figure 1B:
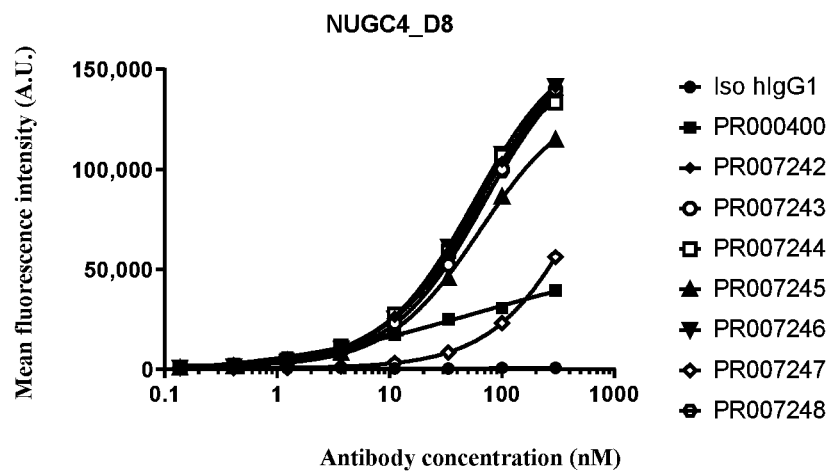
Figure 1C:
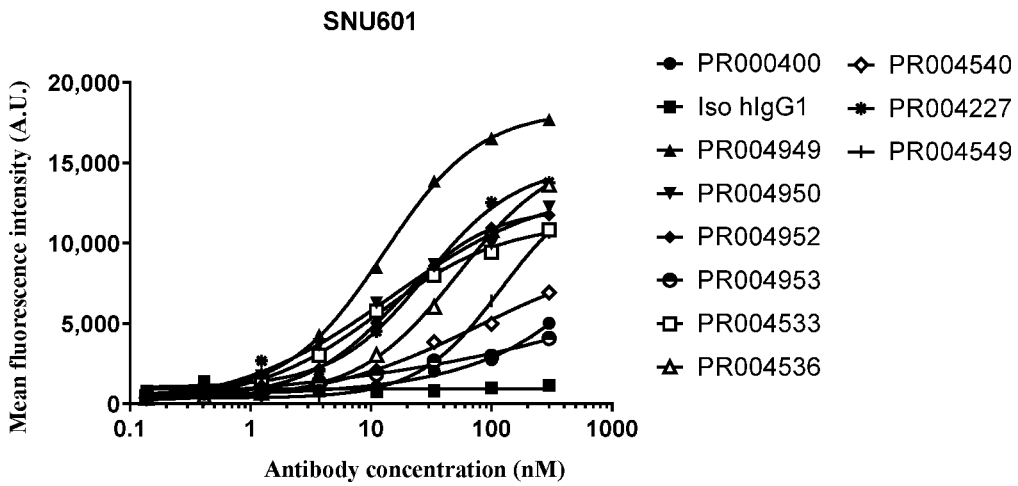
Figure 1D:
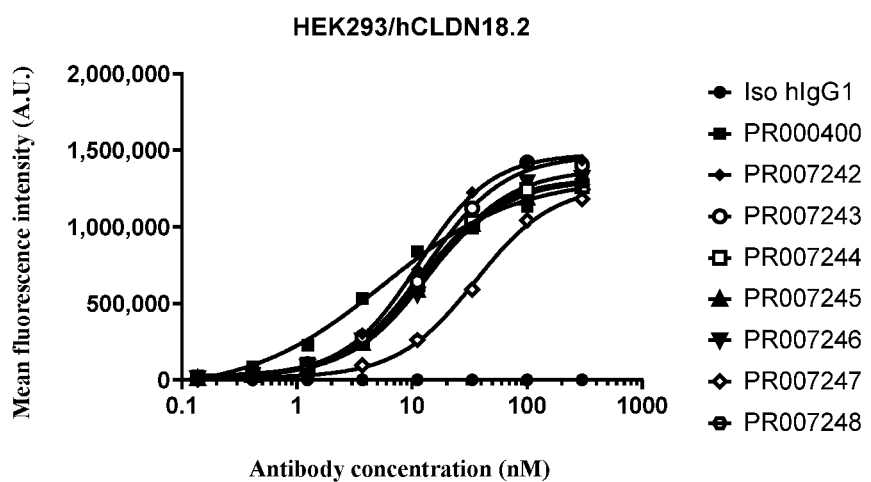
Figure 1E:
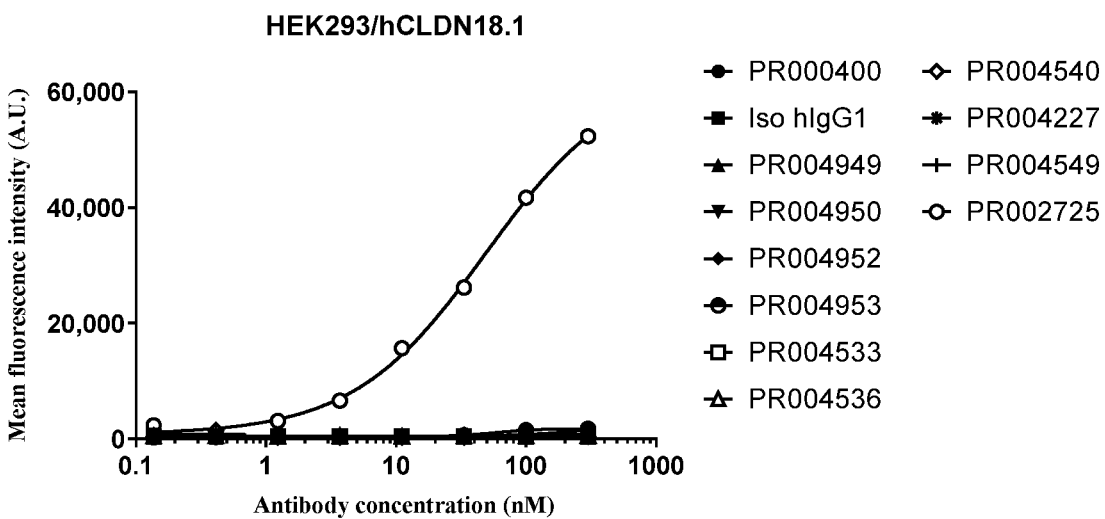
Figure 1F:
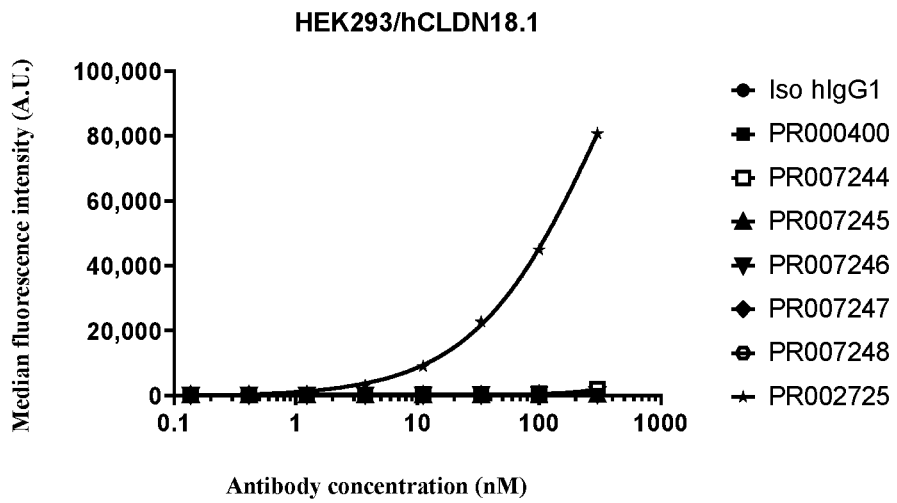

The binding affinity of PR004533 and PR004536 mutant antibodies for NUGC4_D8 cells (see FIG. 1b)

| Antibody | Titer $EC_{50}$ (nM) | Efficacy $E_{max}$ (MFI) |
|---|---|---|
| PR000400 | 56.4 | 58,383 |
| PR007242 | 69.5 | 176,098 |
| PR007243 | 78.2 | 176,068 |
| PR007244 | 49.2 | 152,567 |
| PR007245 | 63.2 | 136,796 |

TABLE 10-continued

The binding affinity of PR004533 and PR004536 mutant
antibodies for NUGC4_D8 cells (see FIG. 1b)

| Antibody | Titer EC$_{50}$ (nM) | Efficacy E$_{max}$ (MFI) |
|---|---|---|
| PR007246 | 55.9 | 165,611 |
| PR007247 | NA | NA |
| PR007248 | 74.6 | 174,113 |

TABLE 11

The binding affinity of anti-CLDN18.2
antibodies for SNU601 cells

| Antibody | Titer EC$_{50}$ (nM) | Efficacy E$_{max}$ (MFI) |
|---|---|---|
| PR000400 | NA | NA |
| PR004227 | 28.5 | 14,849 |
| PR004533 | 11.9 | 11,308 |
| PR004536 | 52.7 | 15,799 |
| PR004540 | NA | NA |
| PR004949 | 12.8 | 18,260 |
| PR004950 | 14.6 | 13,574 |
| PR004952 | 16.4 | 12,179 |
| PR004953 | NA | NA |
| PR004549 | NA | NA |

TABLE 12

The binding affinity of anti-CLDN18.2
antibodies for HEK293/hCLDN18.2 cells

| Antibody | Titer EC$_{50}$ (nM) | Efficacy E$_{max}$ (MFI) |
|---|---|---|
| PR000400 | 5.60 | 1,319,493 |
| PR007242 | 11.3 | 1,478,230 |
| PR007243 | 13.3 | 1,467,203 |
| PR007244 | 11.7 | 1,301,214 |
| PR007245 | 13.0 | 1,307,122 |
| PR007246 | 14.4 | 1,374,904 |
| PR007247 | 35.3 | 1,272,613 |
| PR007248 | 12.8 | 1,313,402 |

Example 6

Competitive Binding Activity of Anti-CLDN18.2 HCAb Antibodies

This example is to study the binding of anti-human CLDN18.2 HCAb monoclonal antibodies to the epitope region of human CLDN18.2 antigen. Competitive binding experiments were performed at the cellular level using HEK293/hCLDN18.2 cells overexpressing human CLDN18.2. Briefly, the anti-human CLDN18.2 antibodies PR000400 and PR004549 were biotinylated using a biotinylation kit (ThermoFisher, A35358) according to the instructions. 50 μL of the biotinylated anti-human CLDN18.2 antibodies PR000400 or PR004549 were each mixed well with 50 μL of a corresponding serially diluted non-biotinylated anti-human CLDN18.2 antibody in a 96-well V-bottom plate (Corning, 3894). Then suspension of HEK293/hCLDN18.2 cells overexpressing human CLDN18.2 were adjusted to 3×10$^6$ cells/mL, seeded 50 μL/well. The cells were co-incubated at 4° C. for 2 h. The cells in each well were washed twice with 200 μL of pre-cooled FACS buffer (2% FBS in PBS) and centrifuged at 500 g at 4° C. for 5 min, and then the supernatant was discarded. After washed twice, a fluorescent secondary antibody (BD, 554060, final concentration of 1 μg/mL) was added and incubated in the dark at 4° C. for 1 h. The cells in each well were washed twice with 200 μL of pre-cooled FACS buffer (2% FBS in PBS) and centrifuged at 500 g at 4° C. for 5 min, and then the supernatant was discarded. Finally, the cells in each well were resuspended in 200 μL of pre-cooled FACS buffer, and the fluorescence signal values were read using a BD FACS CANTOII. The inhibition rate was calculated using the formula, inhibition rate (%)=(A−B)/A×100 (note: A: fluorescence signal after interaction of biotinylated antibody with ISO hIgG1 (Crownbio, C0001-4); B: fluorescence signal after interaction of biotinylated antibody with non-biotinylated antibody).

Figure 2A:
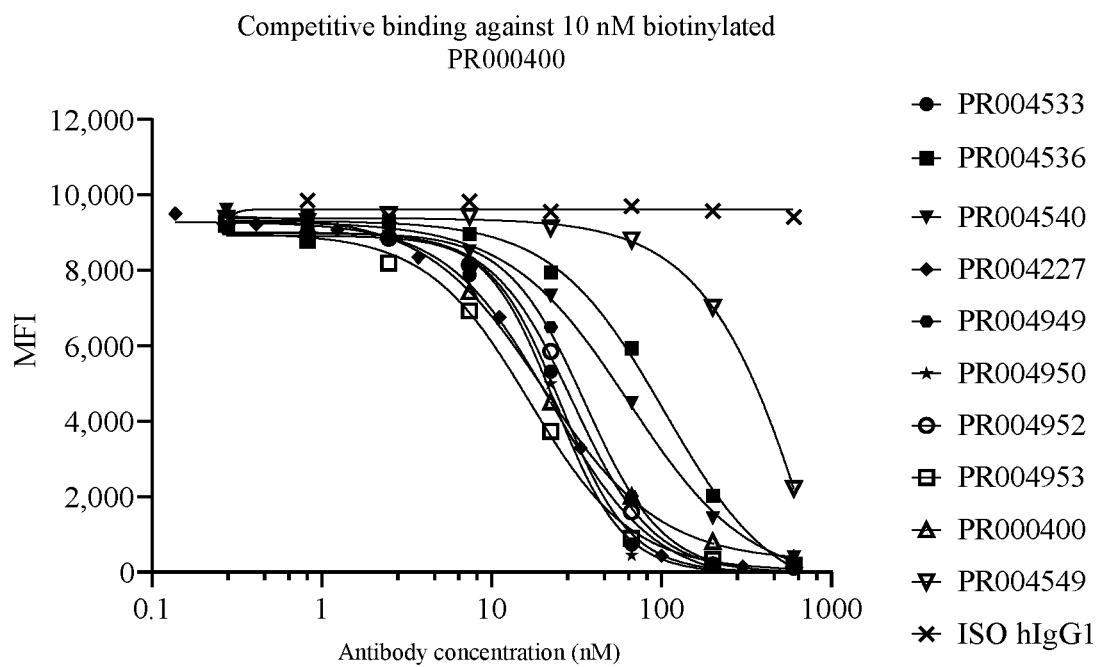
FIGS. 2a-b show the competitive binding activity of HCAB antibodies against (a) PR000400 and (b) PR004549 for HEK293/hCLDN18.2 cells.
Figure 2B:
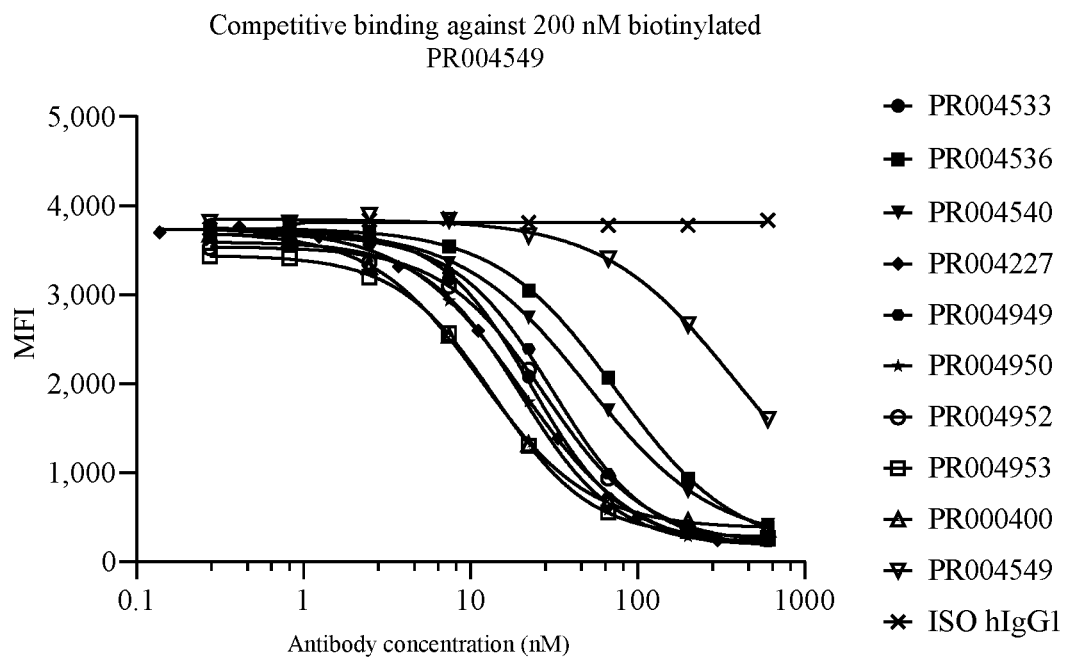

As shown in FIGS. 2(a-b) and Table 13, the anti-CLDN18.2 HCAb antibodies of the present invention are all able to block the binding of PR000400 or PR004549 to human CLDN18.2, and the detected blocking ability of the antibodies increases with the antibody concentration in a positively correlated manner; the inhibition rate can reach >80%, indicating that the test HCAb has very similar epitopes to those of PR000400 and PR004549. The test antibodies have low binding affinity for HEK293/hCLDN18.1 cells. From the above results, it can be inferred that the test antibodies bind to human CLDN18.2 protein at ECL1 (Extracellular loop 1) rather than ECL2.

TABLE 13

The competitive binding ability of anti-CLDN18.2
antibodies against PR000400 and PR004549

| | 10 nM biotinylated PR000400 | | 200 nM biotinylated PR004549 | |
|---|---|---|---|---|
| Antibody | IC50 (nM) | Maximum inhibition rate (%) | IC50 (nM) | Maximum inhibition rate (%) |
| PR004533 | 25.5 | 98.6 | 23.2 | 93.7 |
| PR004536 | 103 | 98.0 | 74.1 | 90.1 |
| PR004540 | 64.1 | 95.8 | 50.0 | 89.2 |
| PR004227 | 22.3 | 98.3 | 20.3 | 93.8 |
| PR004949 | 35.4 | 98.5 | 31.0 | 94.2 |
| PR004950 | 23.5 | 98.5 | 19.9 | 94.3 |
| PR004952 | 30.1 | 98.5 | 27.8 | 93.3 |
| PR004953 | 16.7 | 98.0 | 13.8 | 93.2 |
| PR000400 | 20.1 | 96.4 | 11.5 | 90.7 |
| PR004549 | 946 | 76.5 | 379 | 58.4 |
| Iso hIgG1 | NA | 0.00 | NA | 0.00 |

Example 7

Endocytic Activity of Anti-CLDN18.2 HCAB Antibodies

Figure 3A:
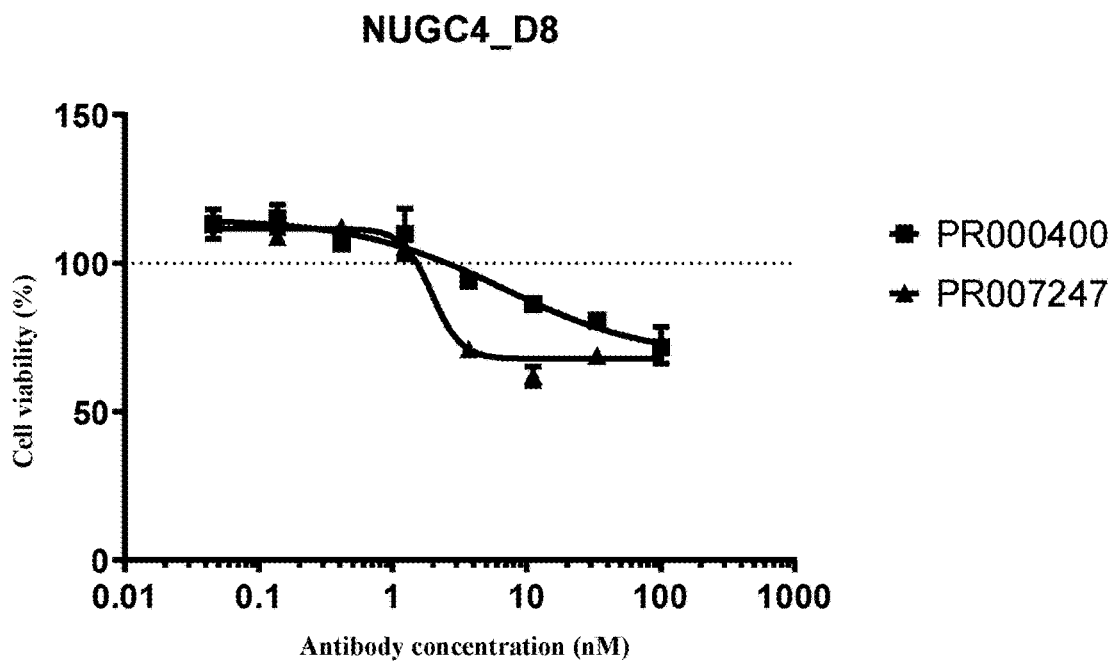
FIGS. 3a-b show the viability of target cells when co-cultured with test antibodies and an MMAF-coupled anti-human IgG antibody.
Figure 3B:
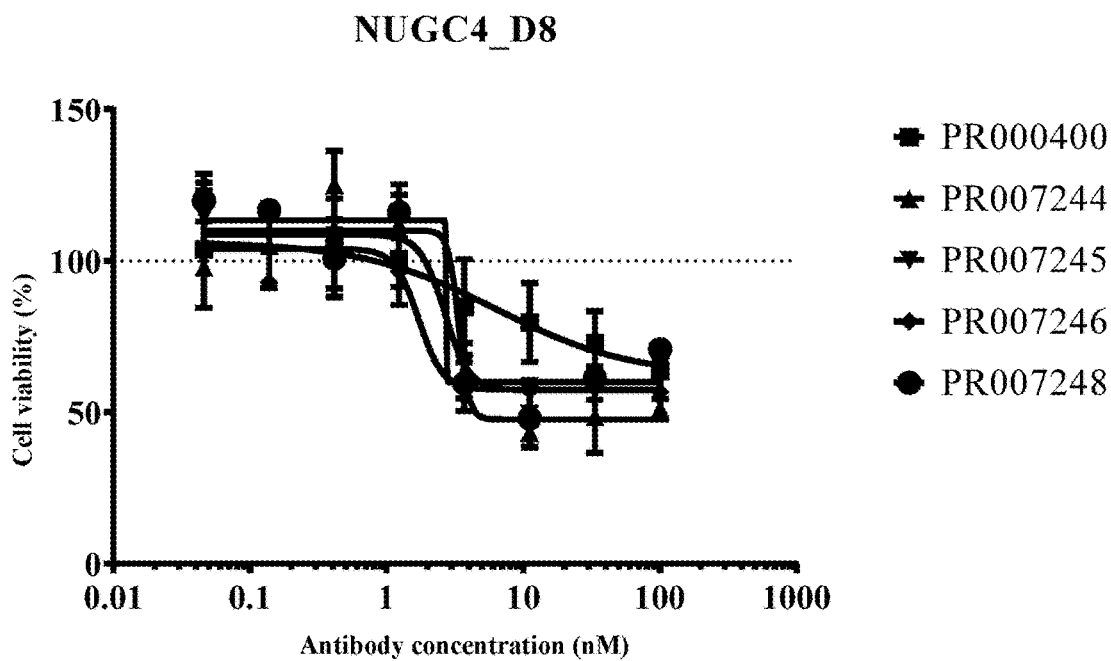
Figure 4A:
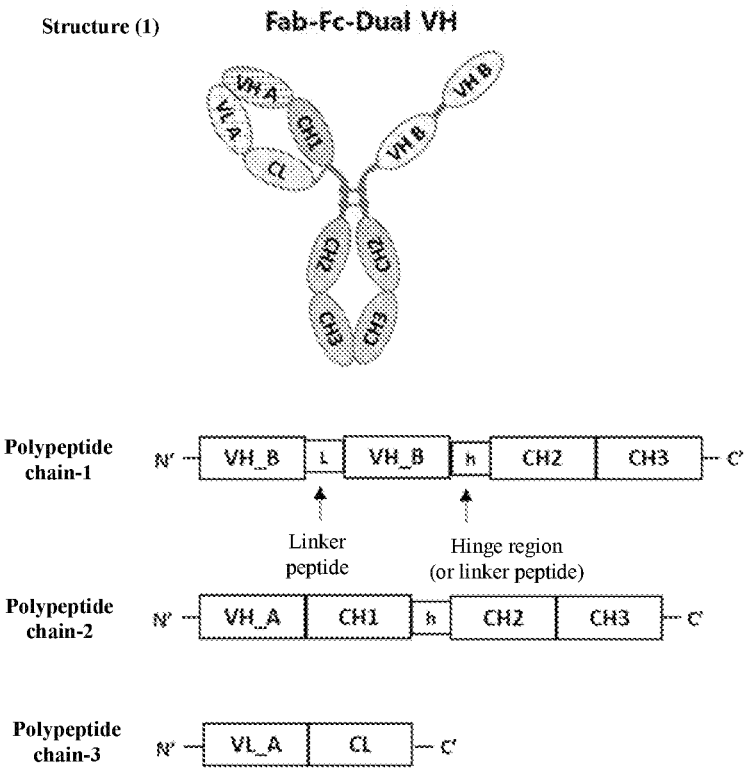
FIGS. 4a-h show the structures of CLDN18.2×CD3 bispecific antibodies.
Figure 4B:
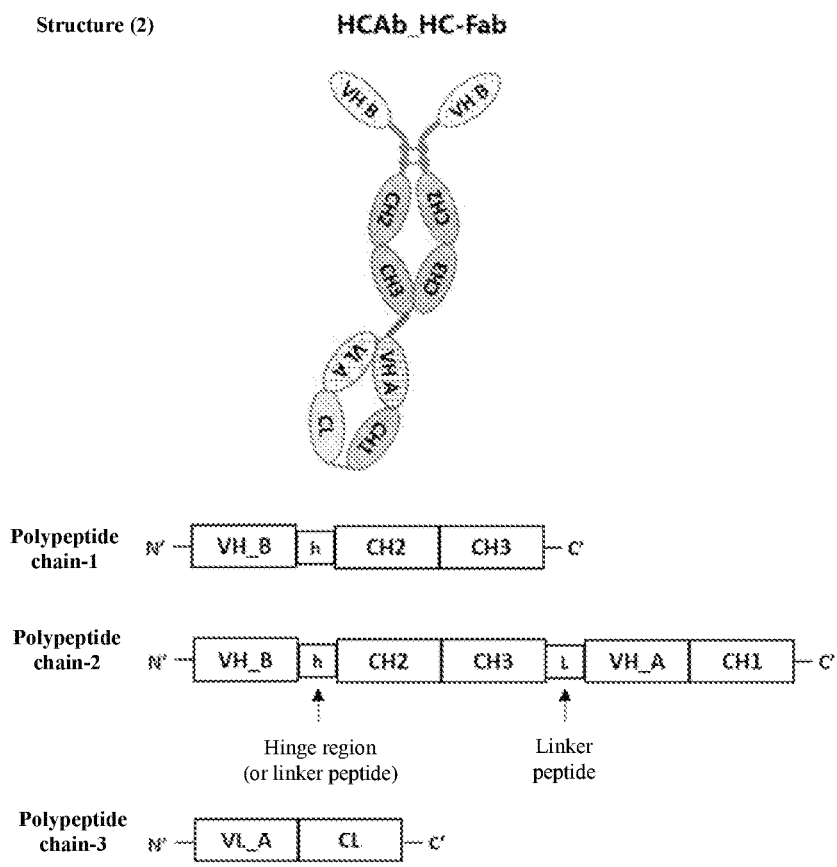
Figures 4C, 4D:
Figure 4E:
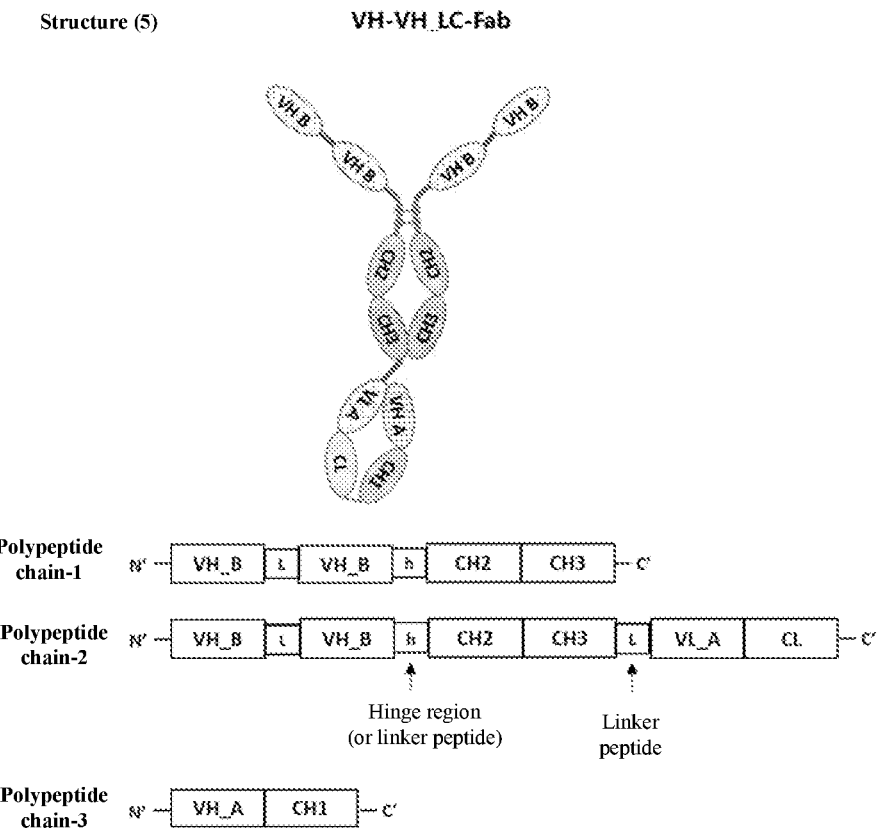
Figure 4F:
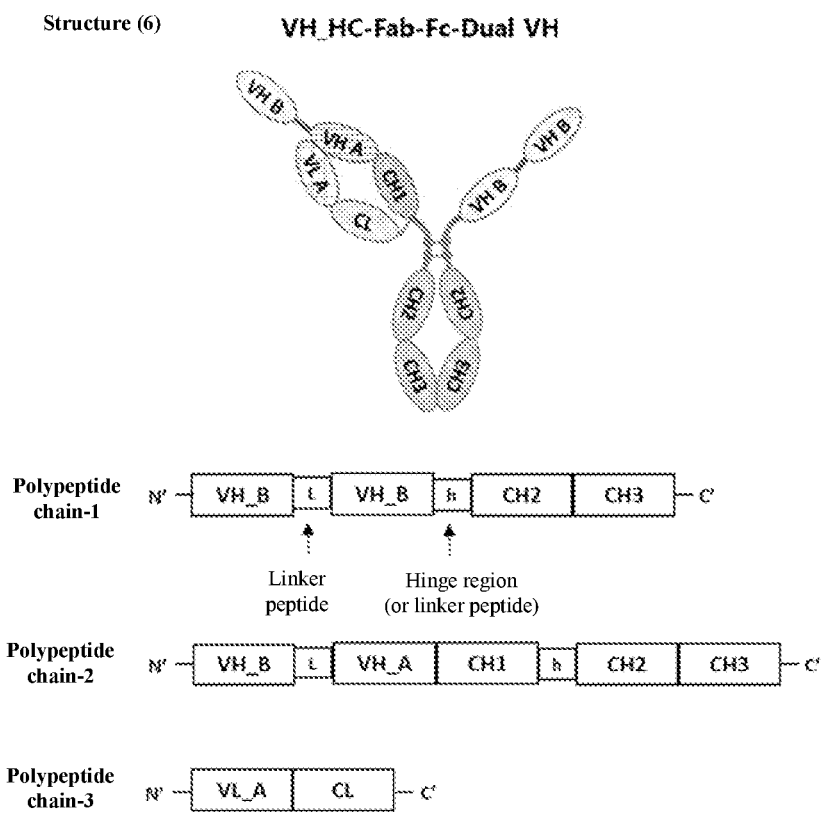
Figure 4G:
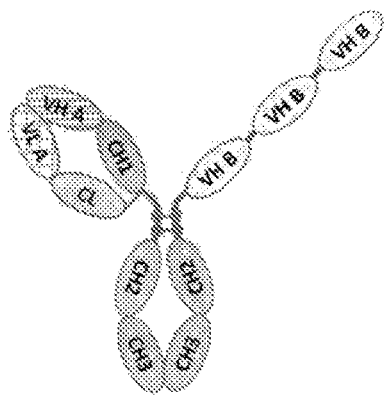
Figure 4G:
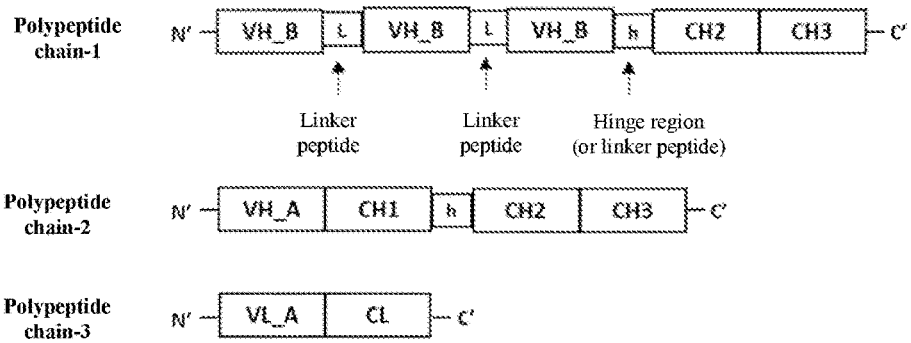
Figure 4H:
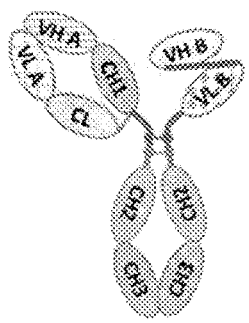
Figure 4H:
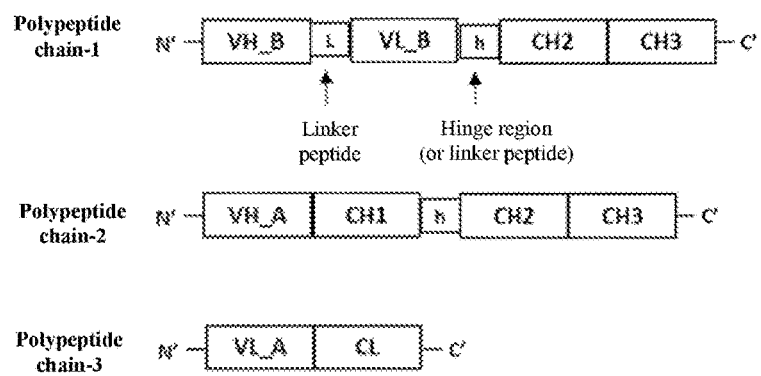
Figure 5A:
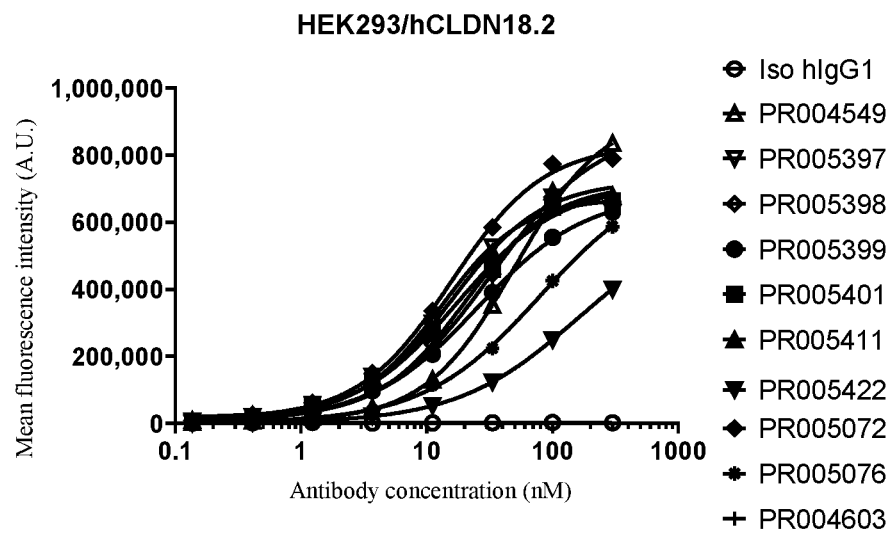
FIGS. 5a-s show the binding affinity of CLDN18.2×CD3 bispecific antibodies for (a-c) HEK293/hCLDN18.2, (d-i) NUGC4_D8, (j-o) Jurkat, and (p-s) HEK293/hCLDN18.1 cells.
Figure 5B:
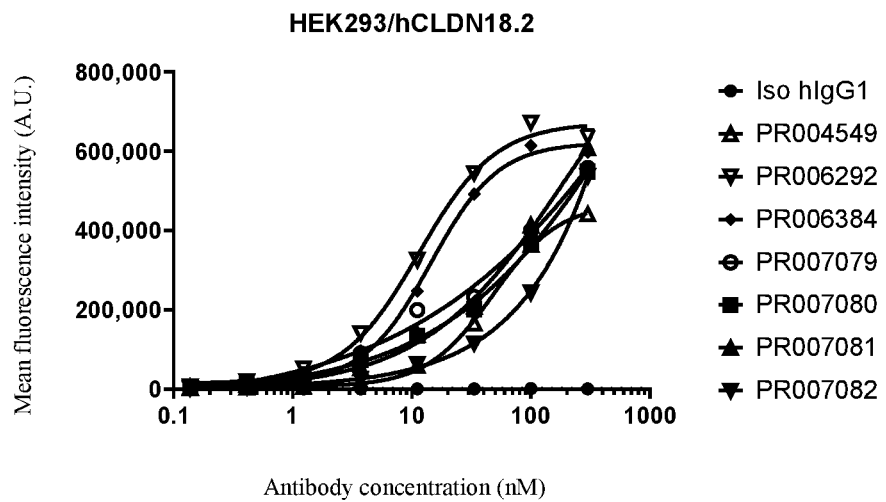
Figure 5C:
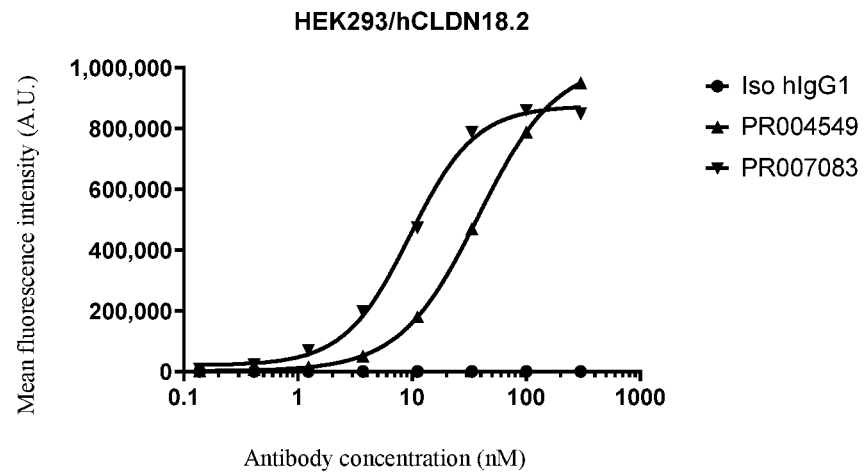
Figure 5D:
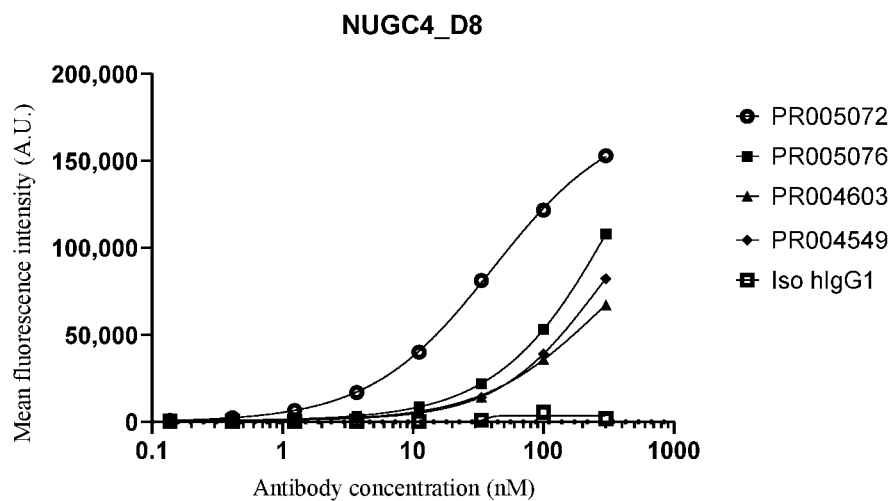
Figure 5E:
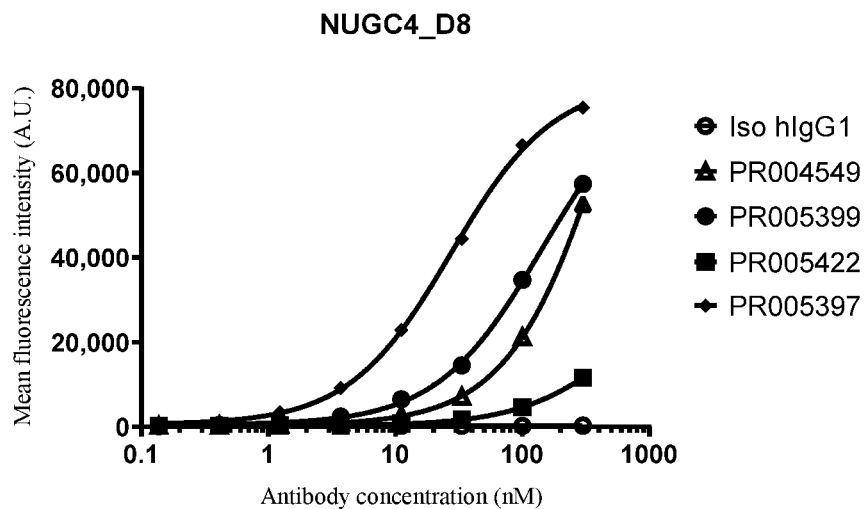
Figure 5F:
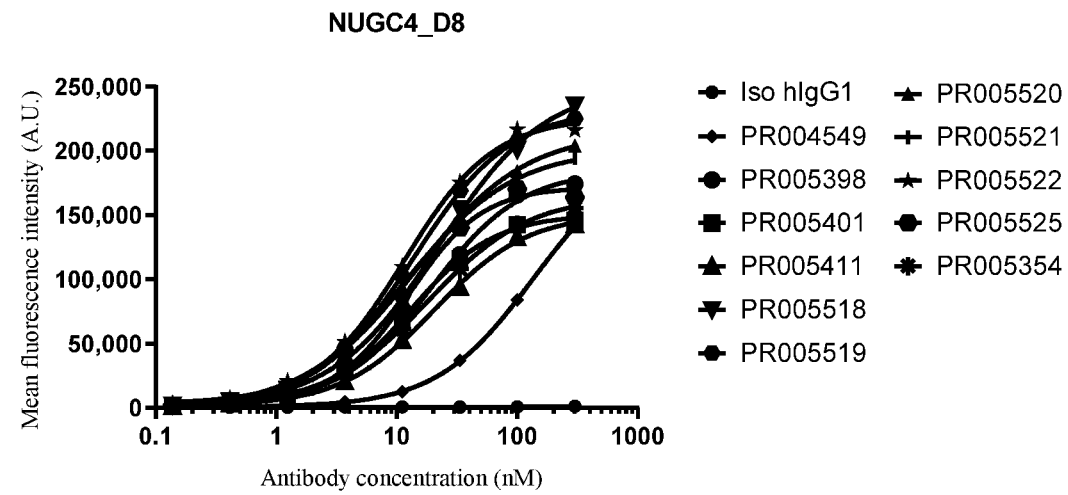
Figure 5J:
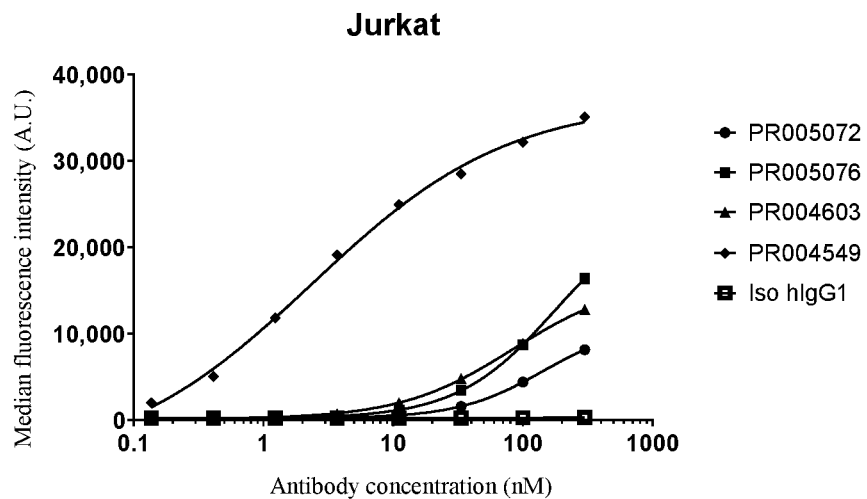
Figure 5K:
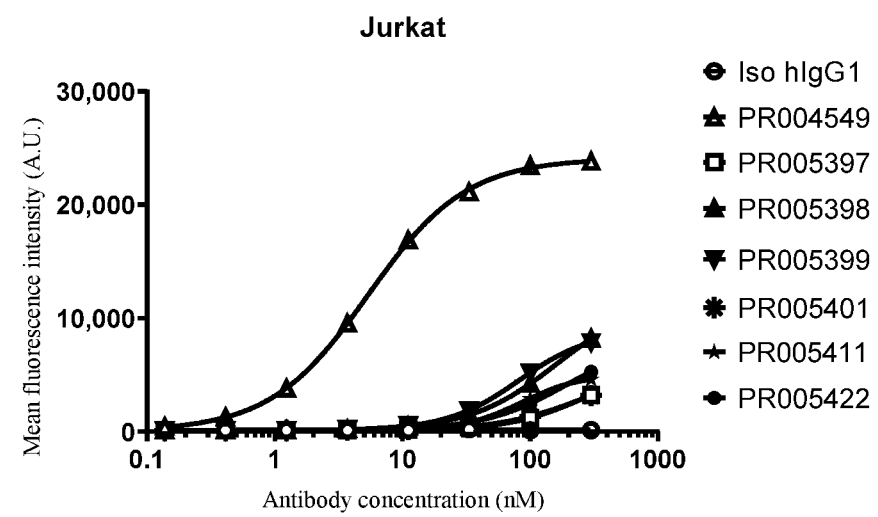
Figure 5L:
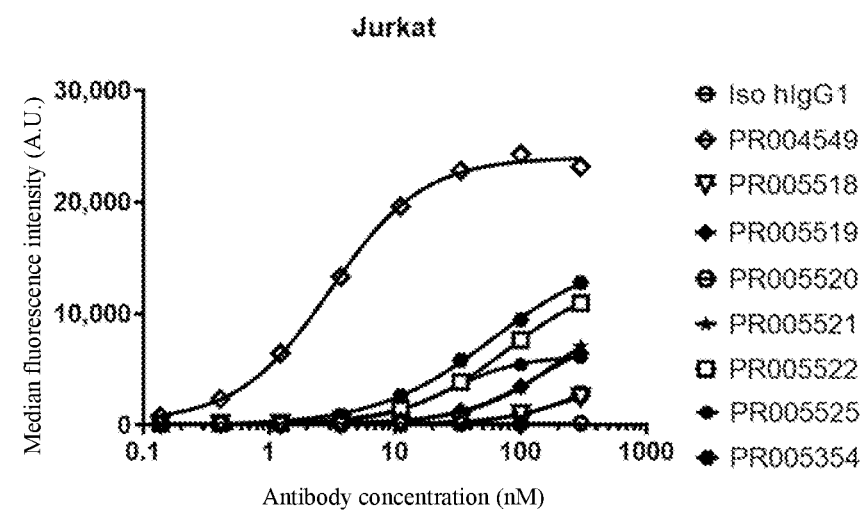
Figure 5M:
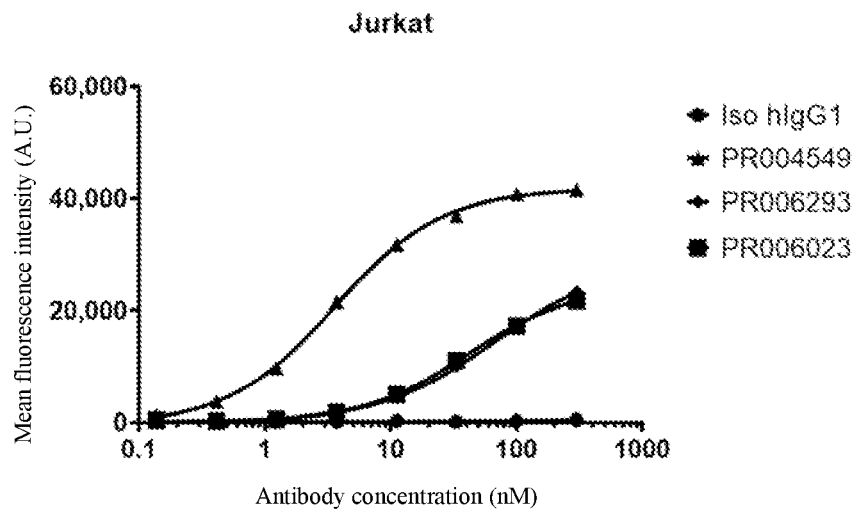
Figure 5N:
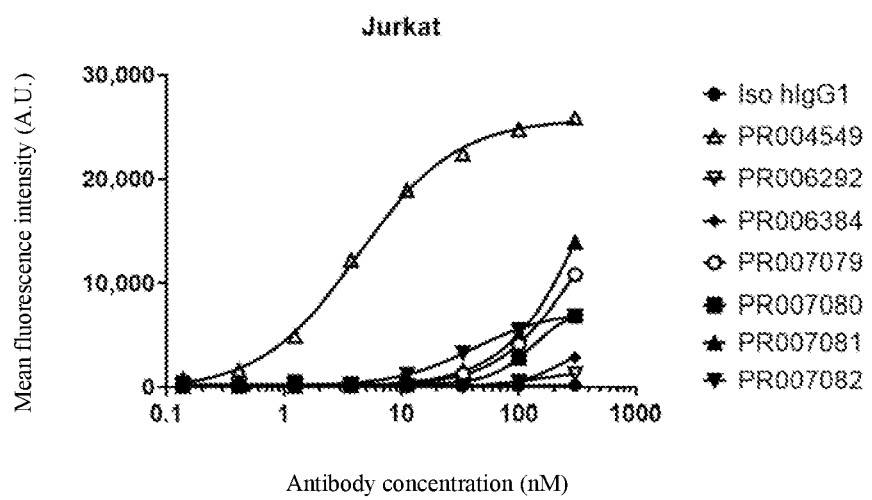
Figure 5O:
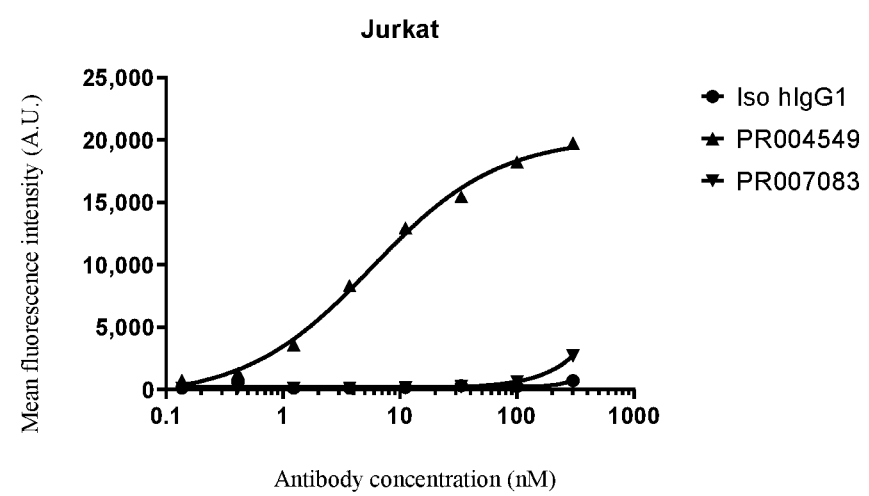
Figure 5P:
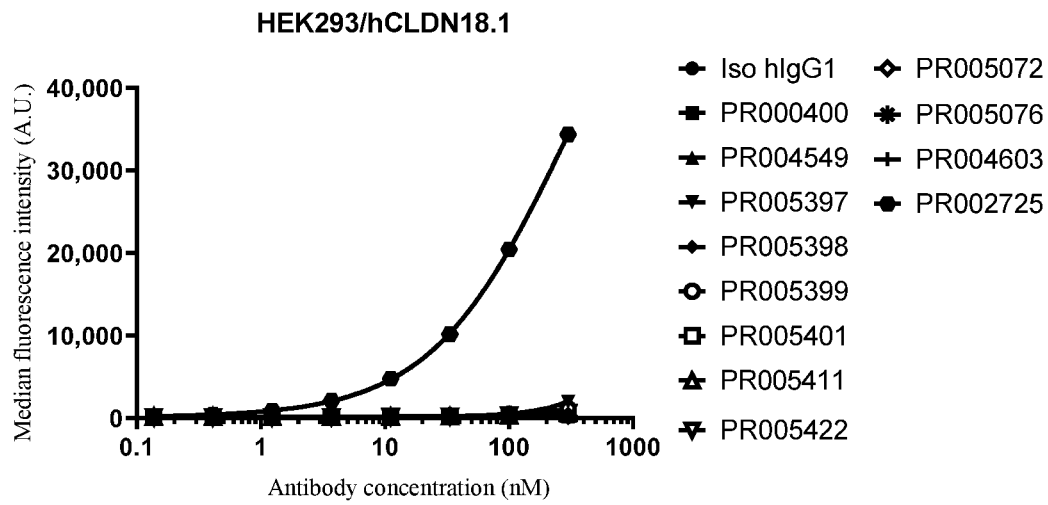
Figure 5Q:
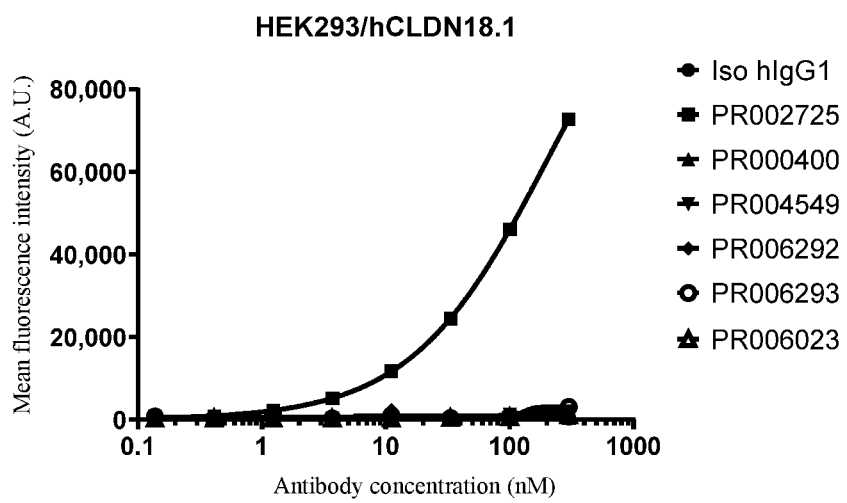
Figure 5R:
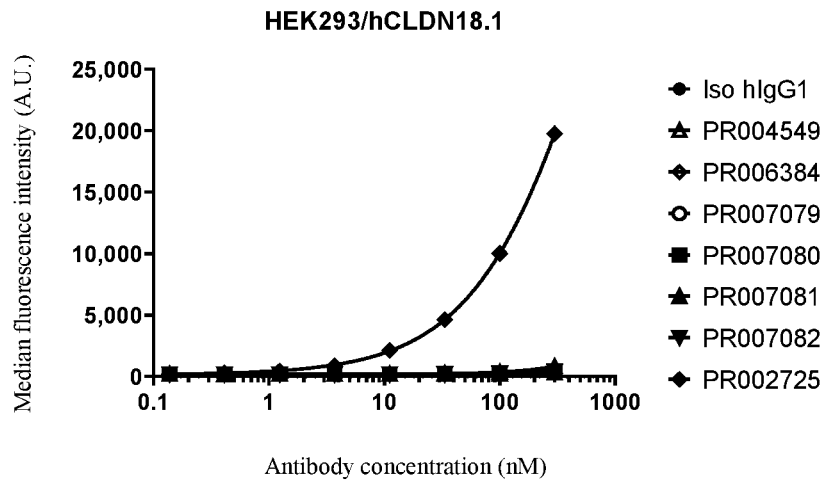
Figure 5S:
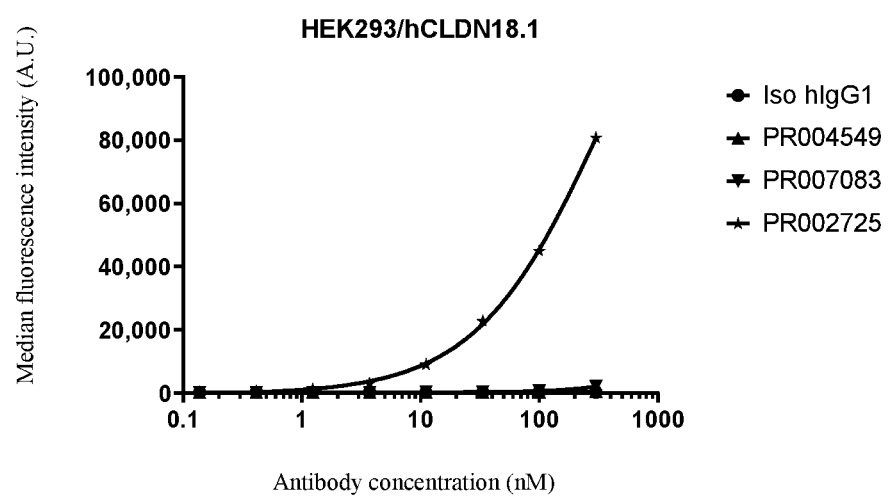
Figure 6A:
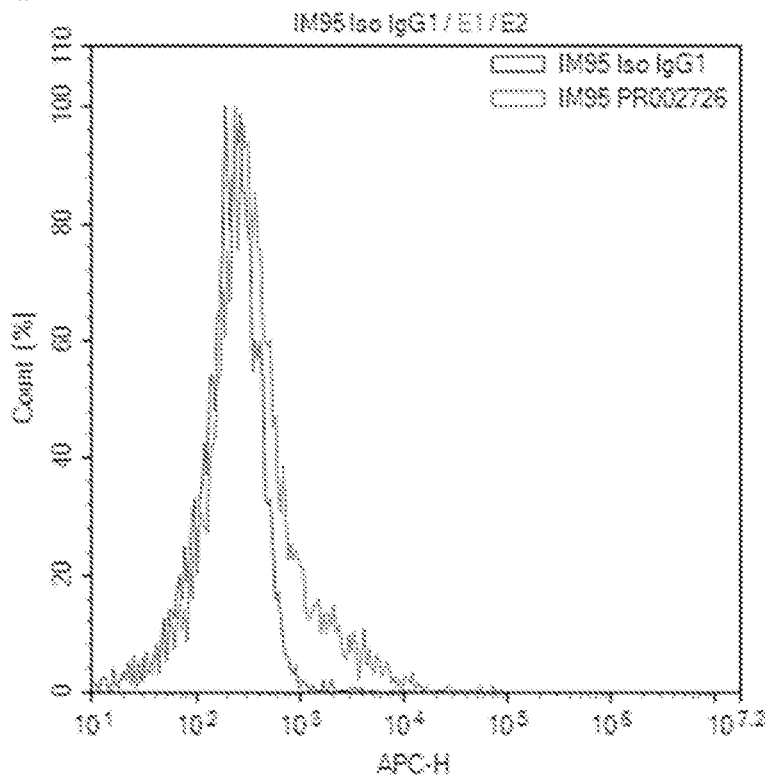
FIGS. 6a-w show (a) the expression yield of CLDN18.2 by IM95 cells, and the TDCC activity of bispecific antibodies against (b-k) NUGC4_D8, (l-o) IM95, (p-s) HEK293/hCLDN18.1, and (t-w) SNU620 cells.
Figure 6B:
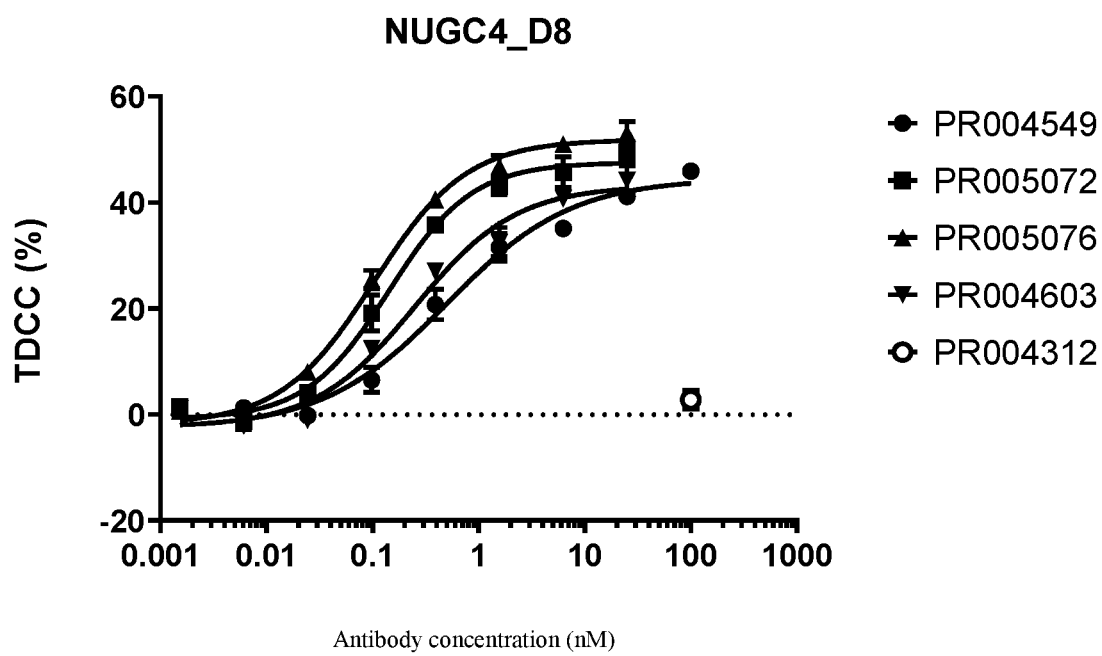
Figure 6C:
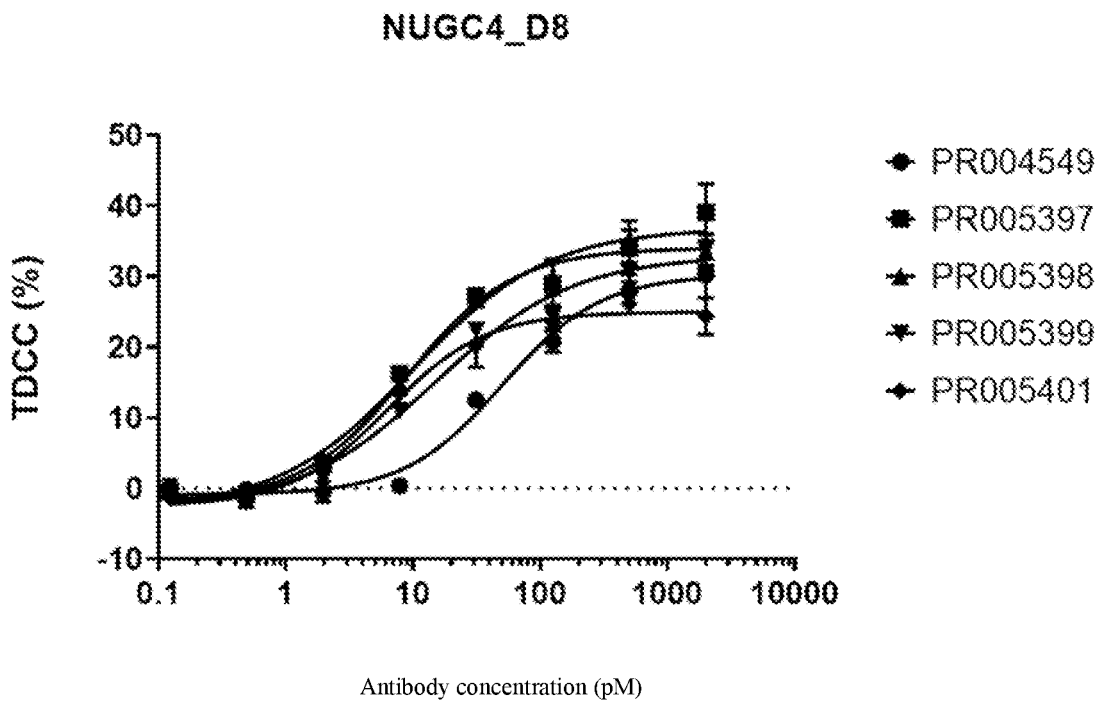
Figure 6D:
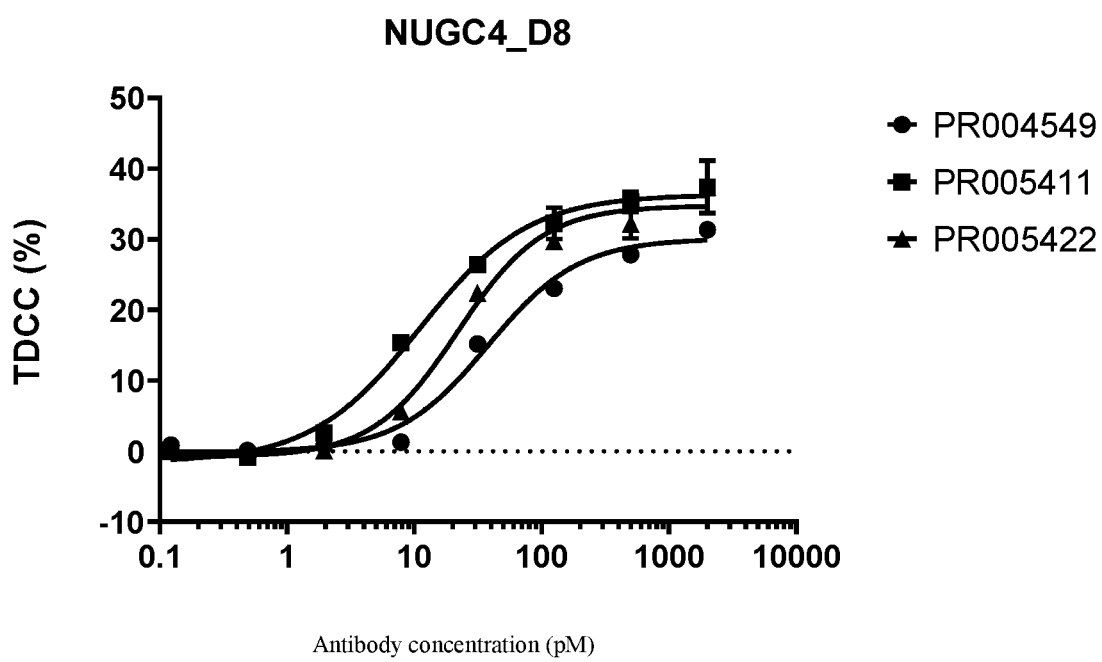
Figure 6E:
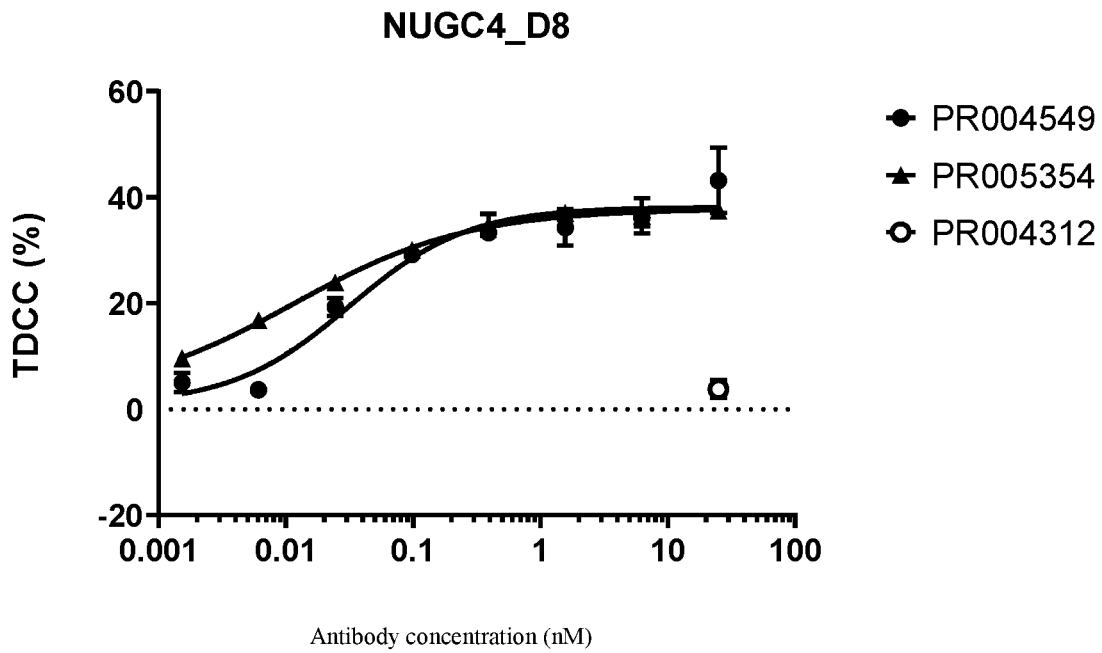
Figure 6F:
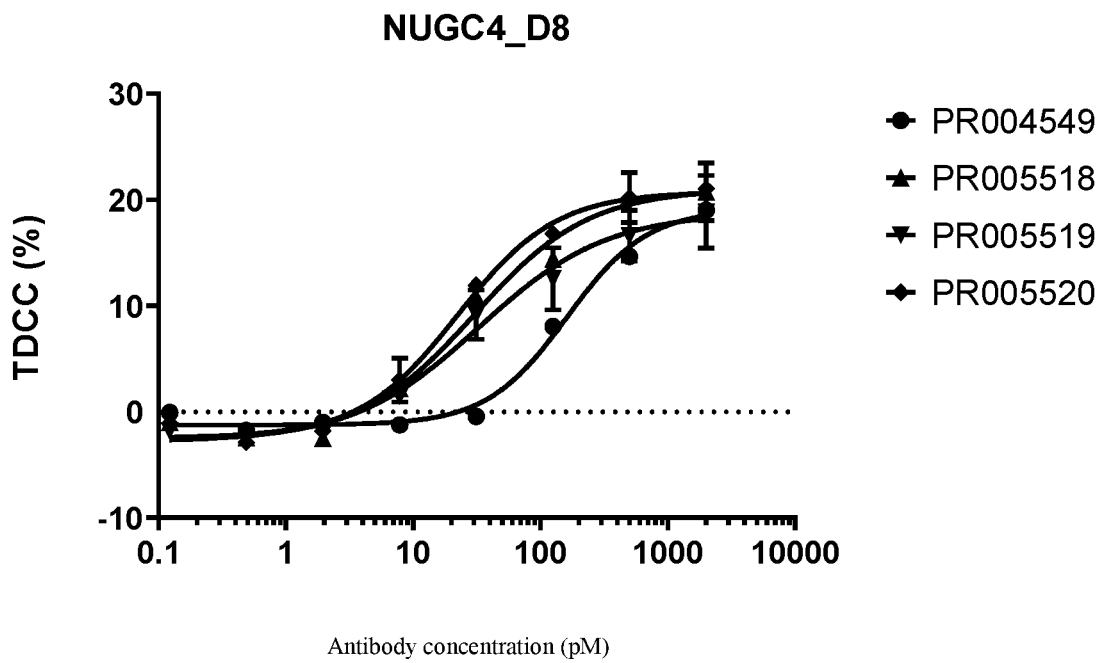
Figure 6G:
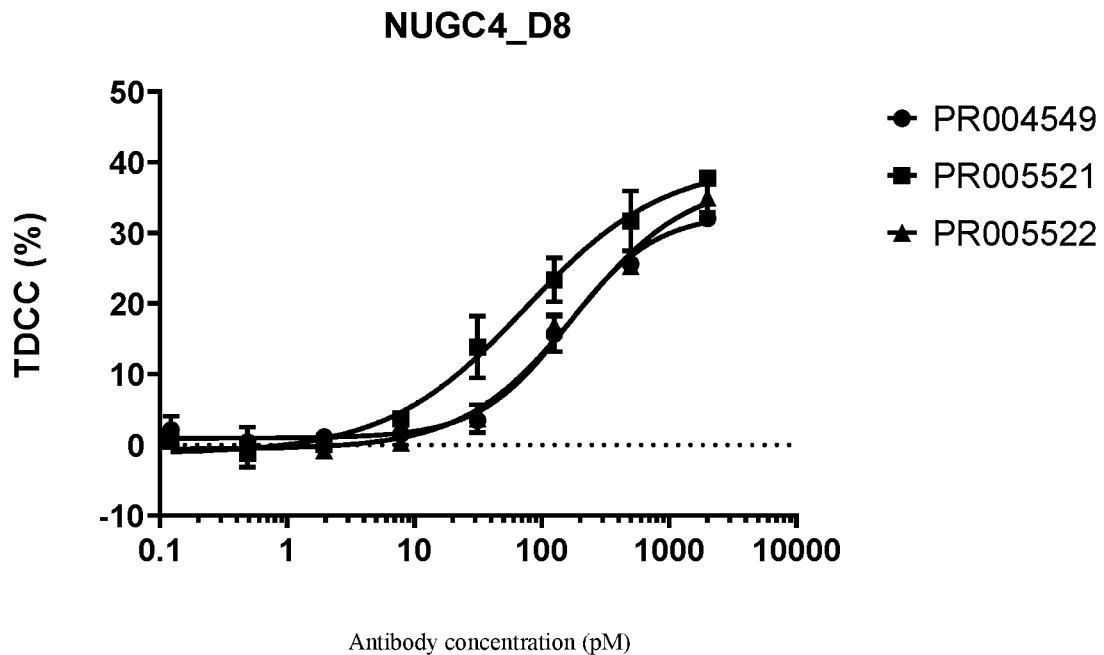
Figure 6H:
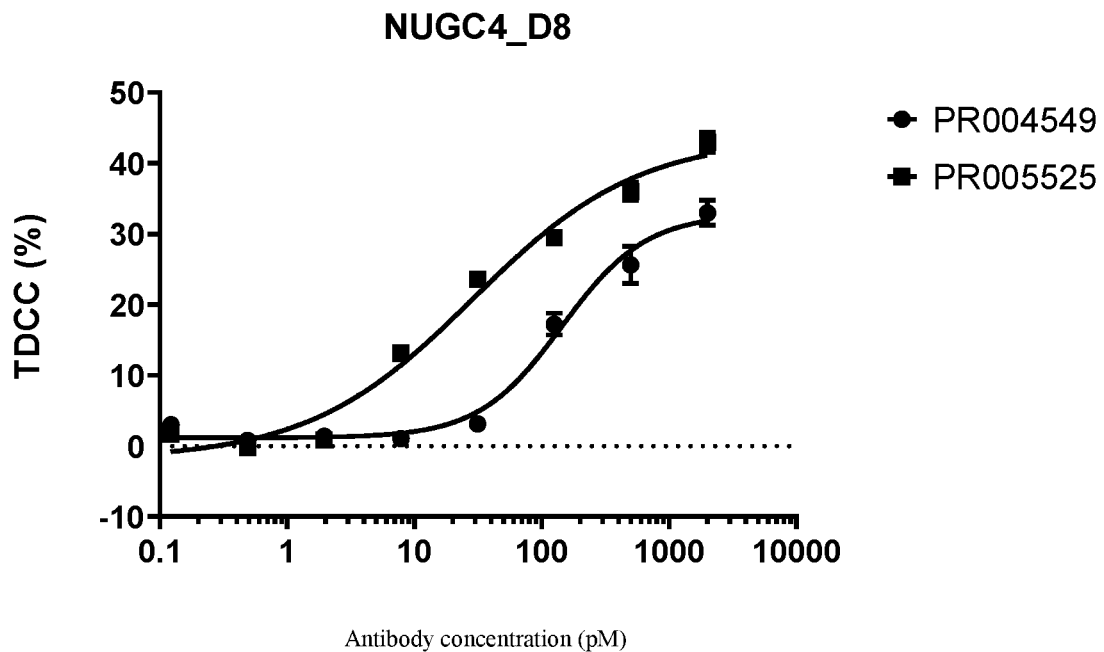
Figure 6I:
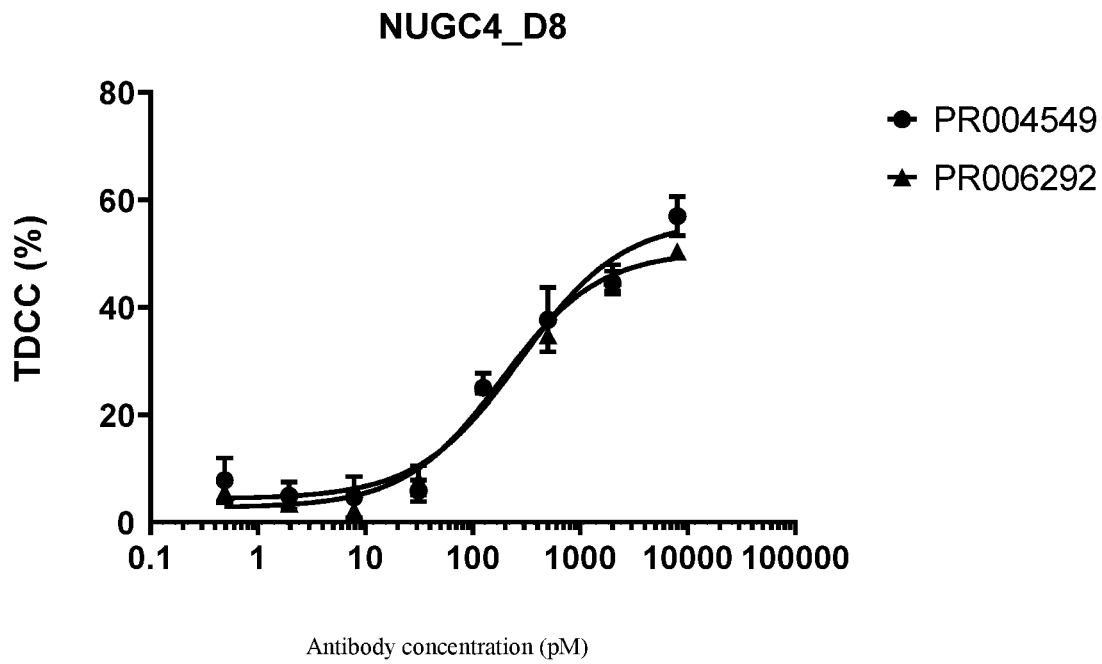
Figure 6J:
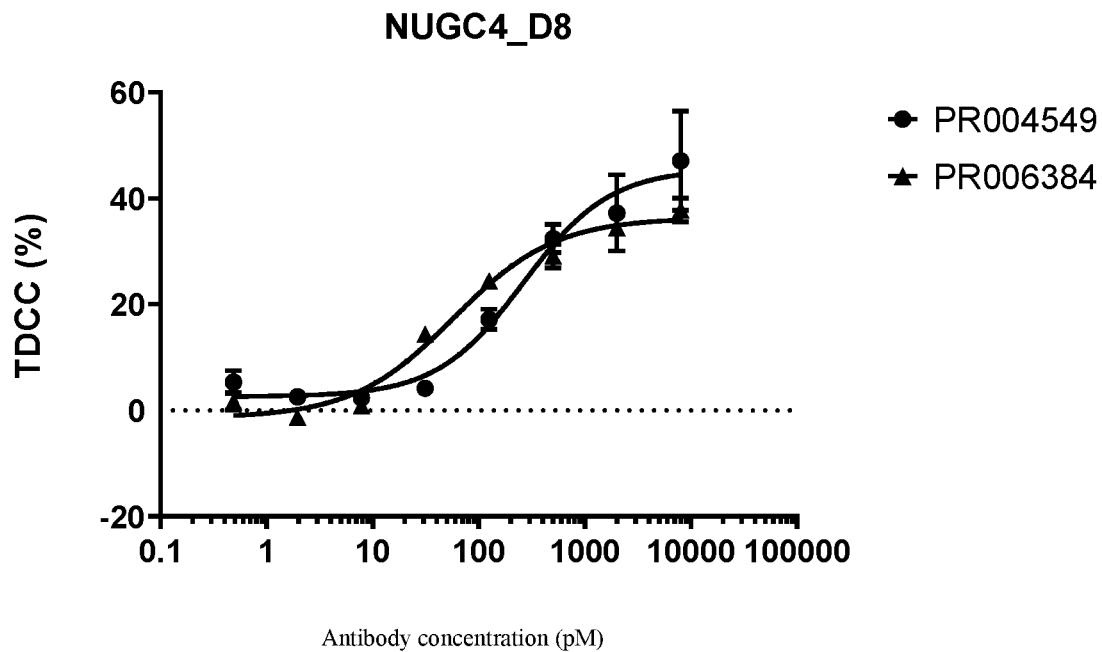
Figure 6K:
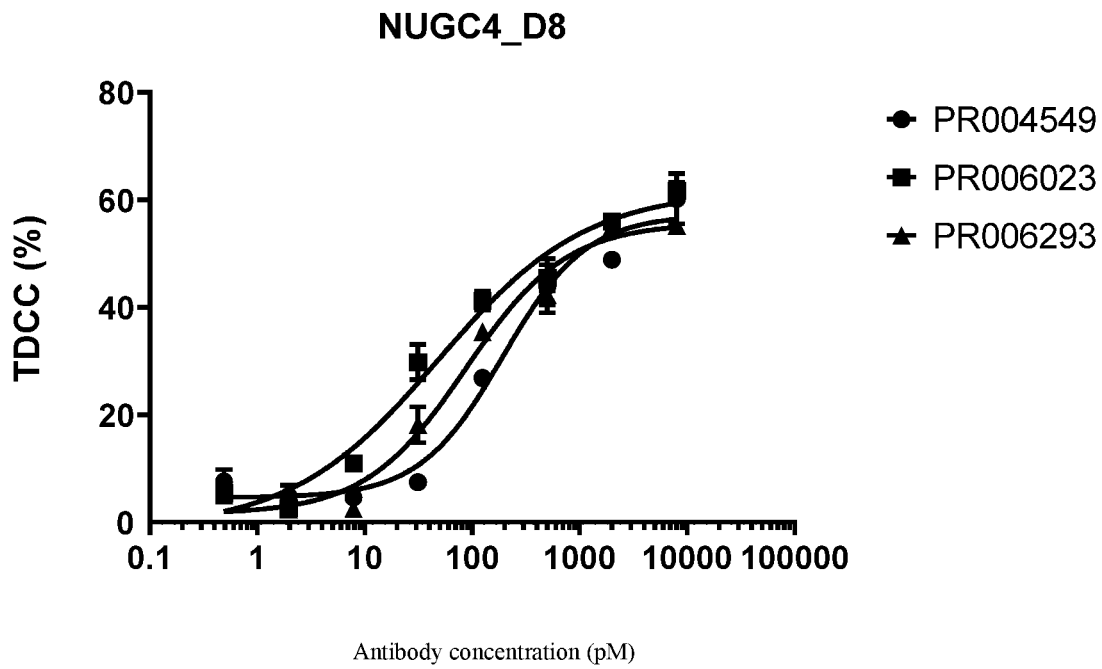
Figure 6L:
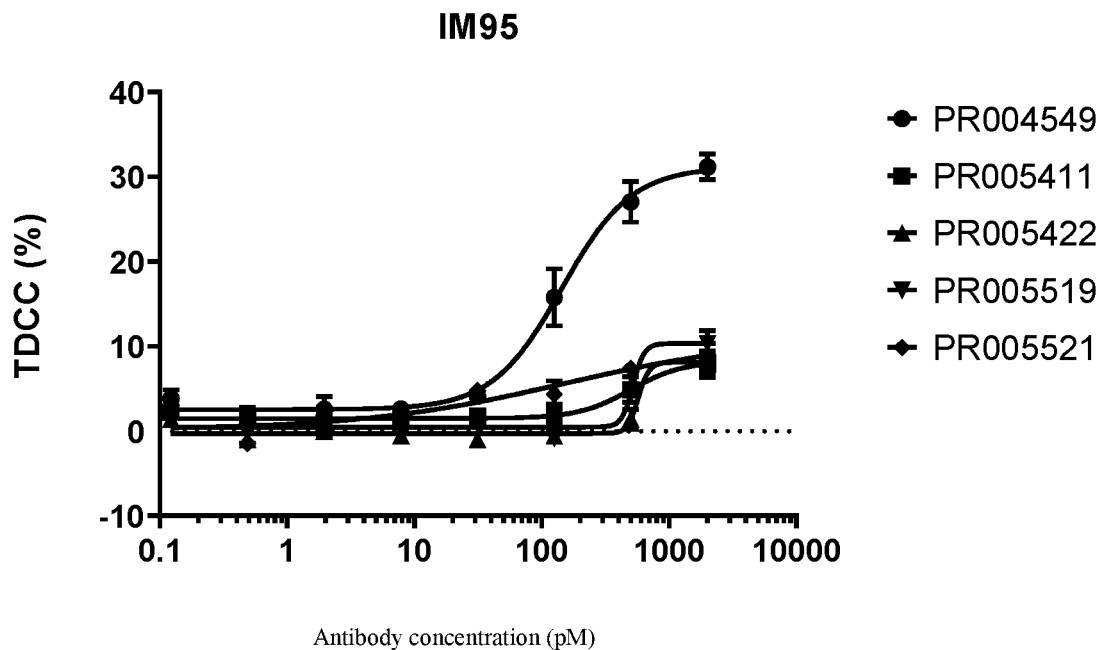
Figure 6M:
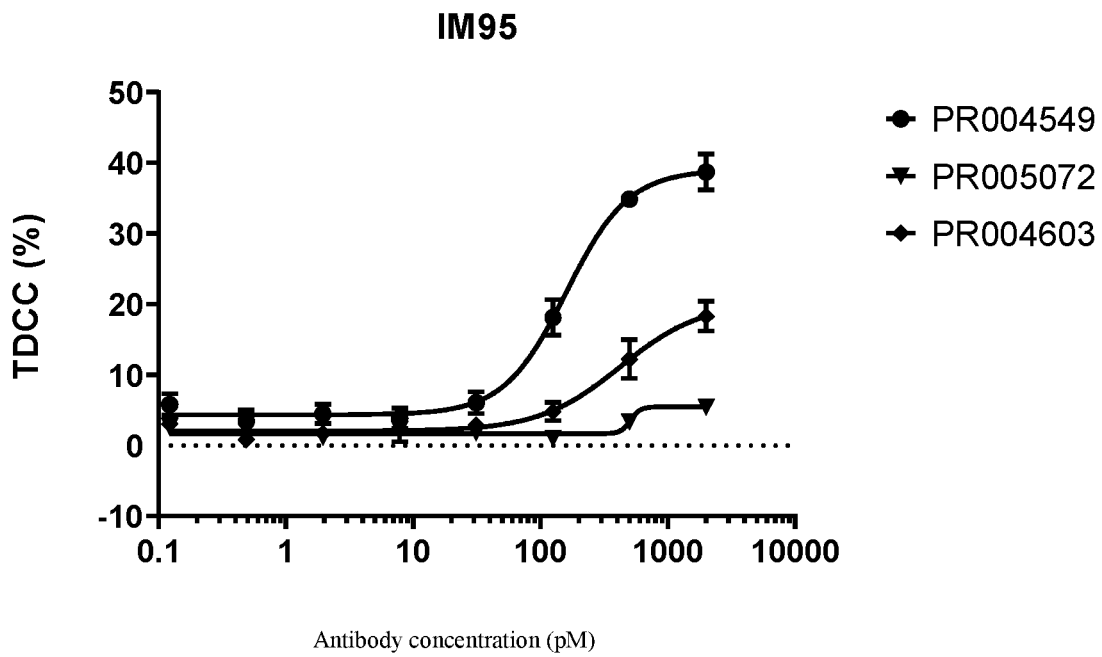
Figure 6N:
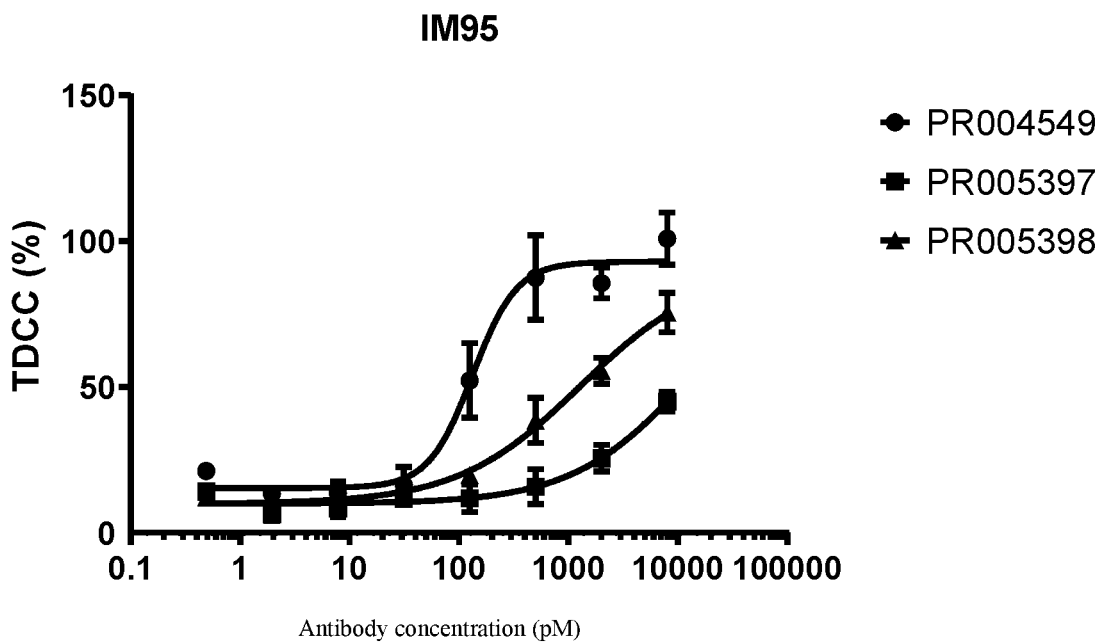
Figure 6O:
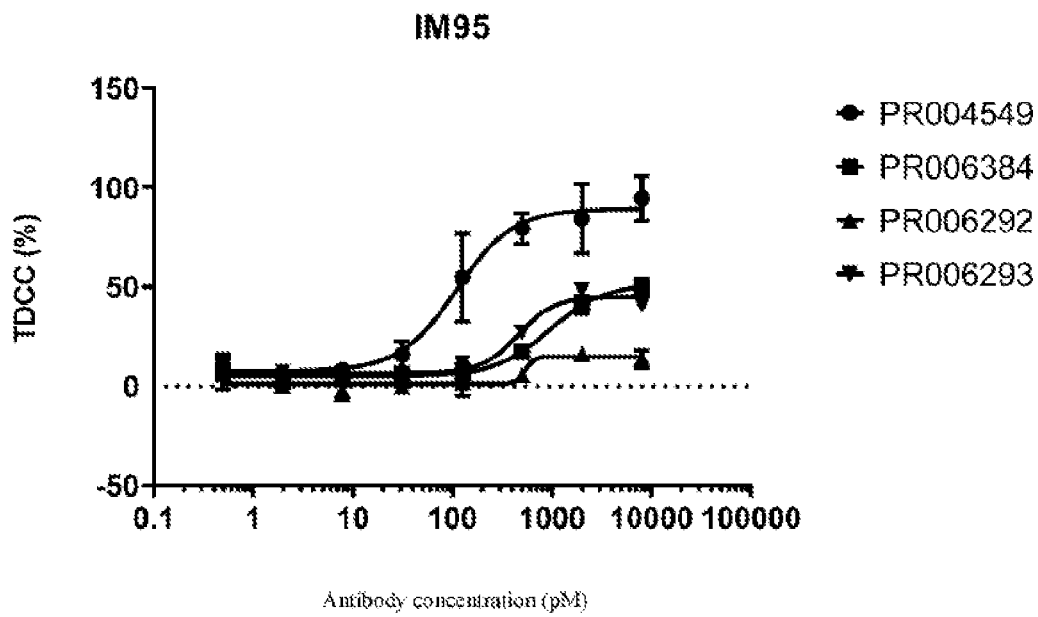
Figure 6P:
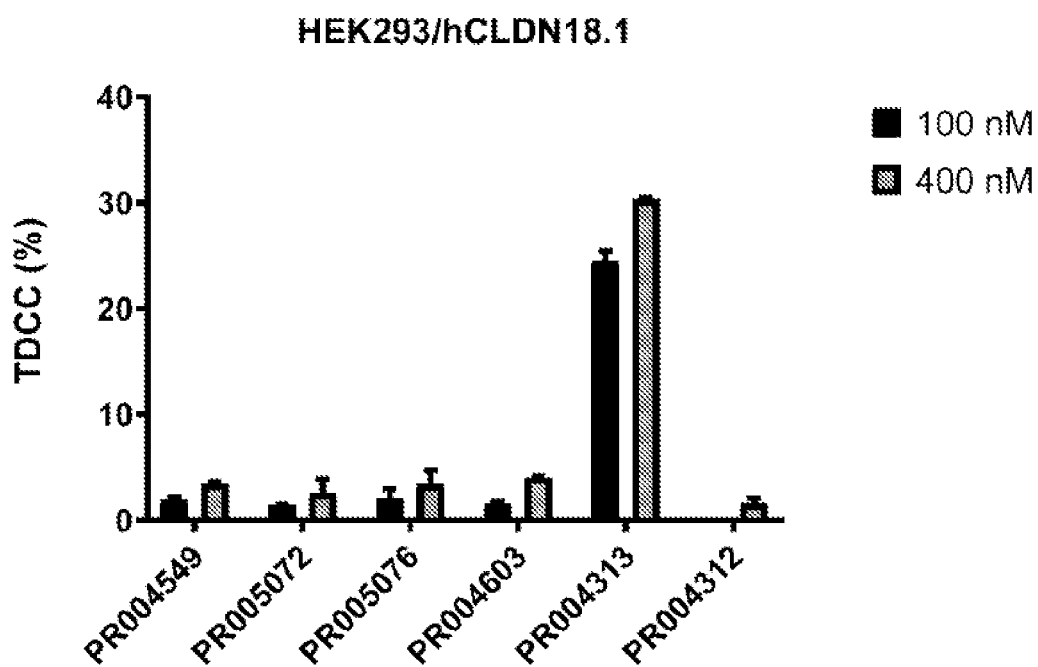
Figure 6Q:
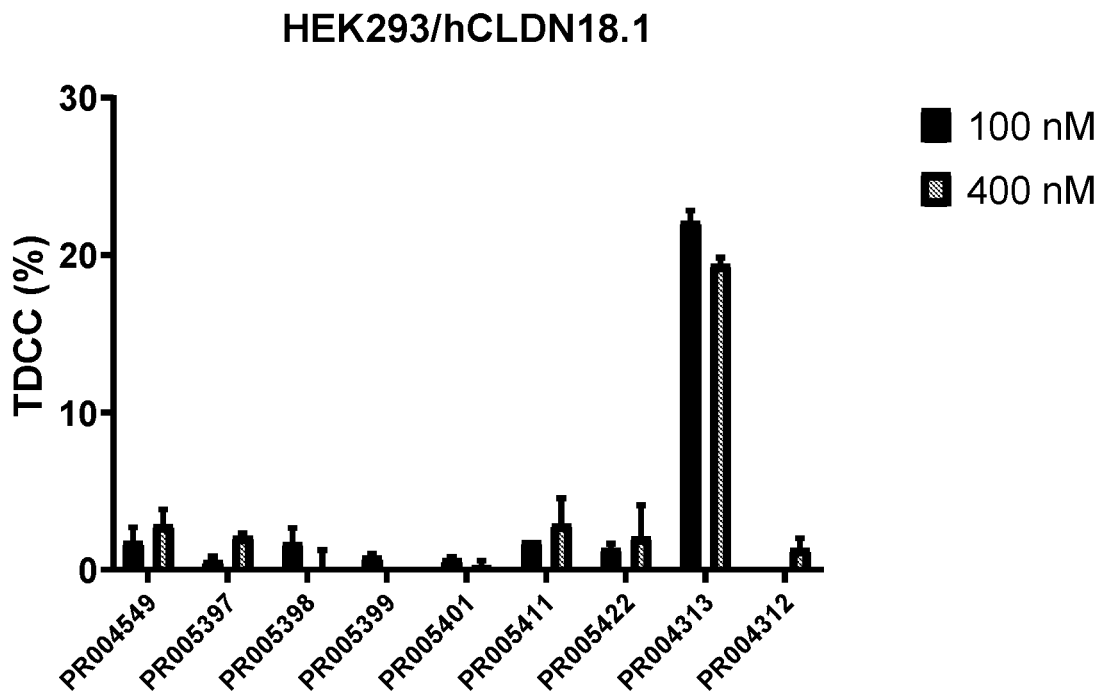
Figure 6R:
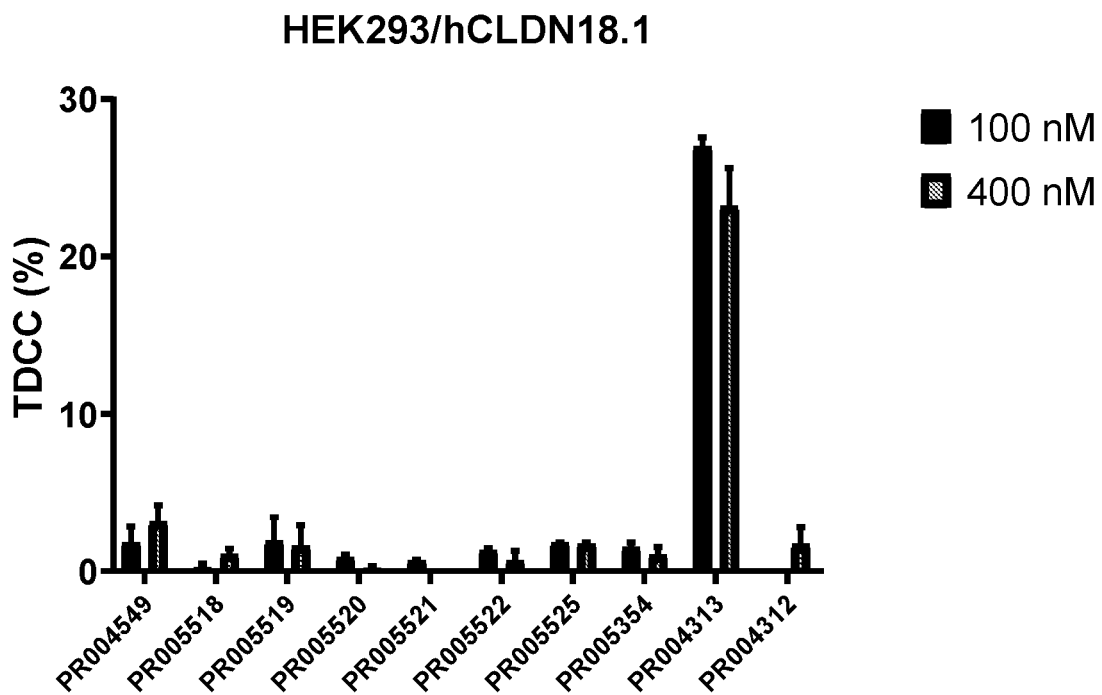
Figure 6S:
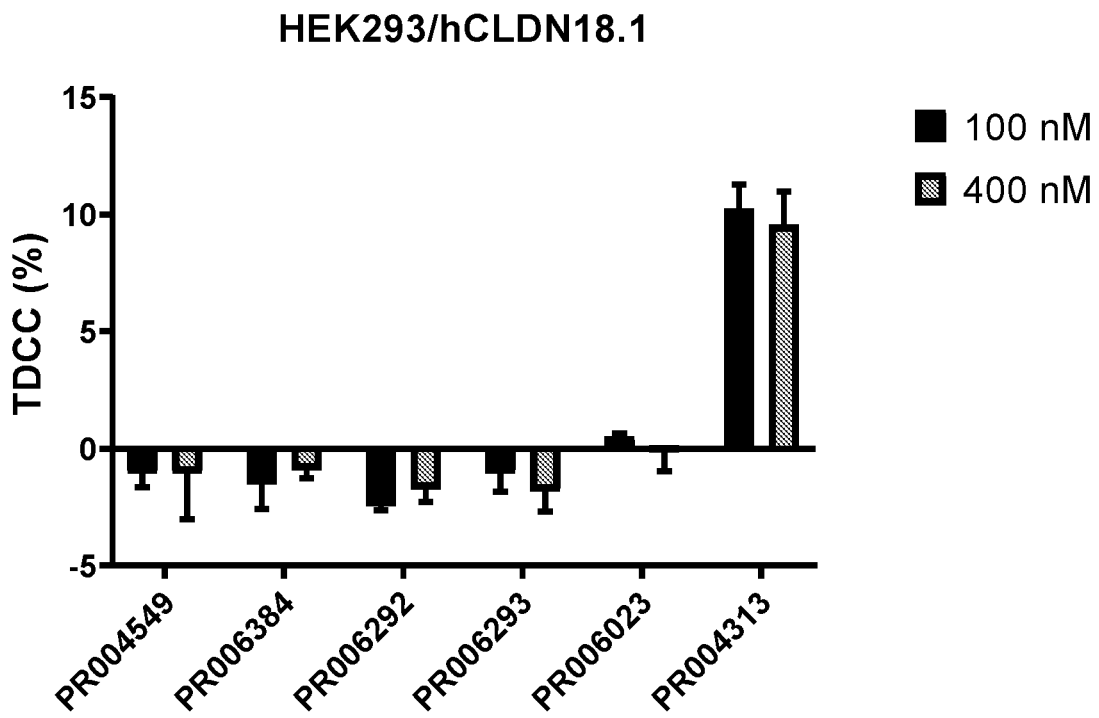
Figure 6T:
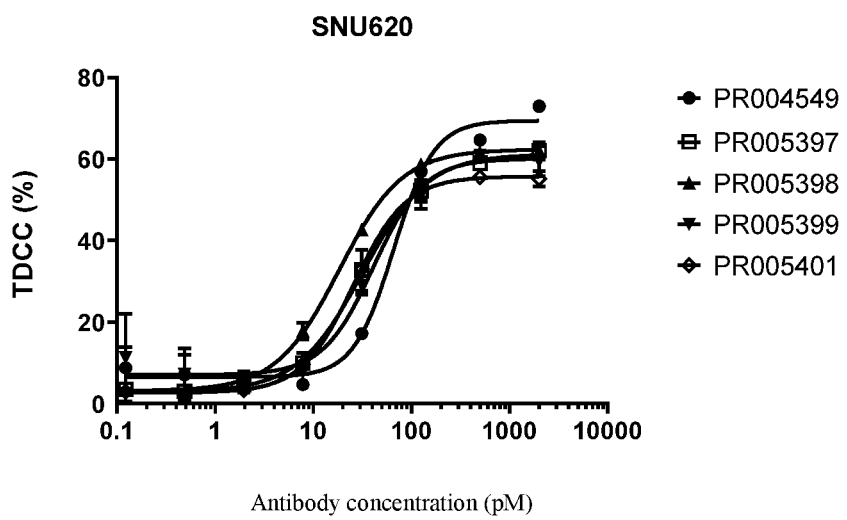
Figure 6U:
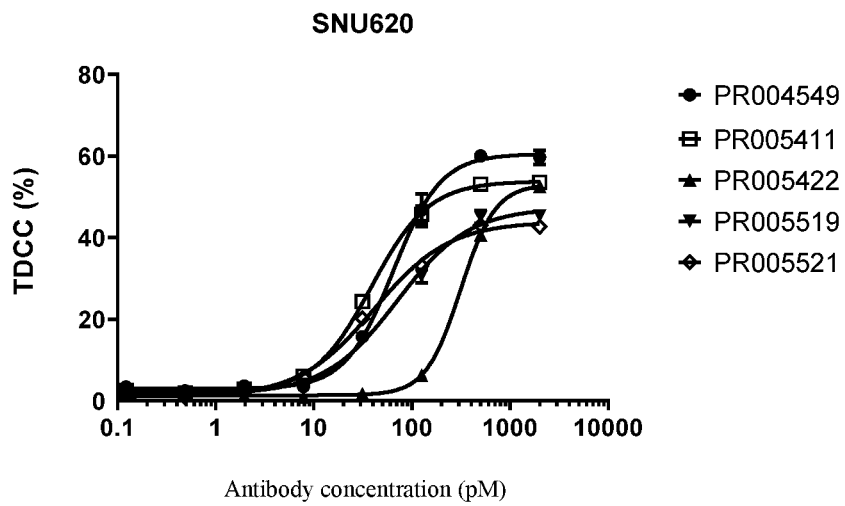
Figure 6V:
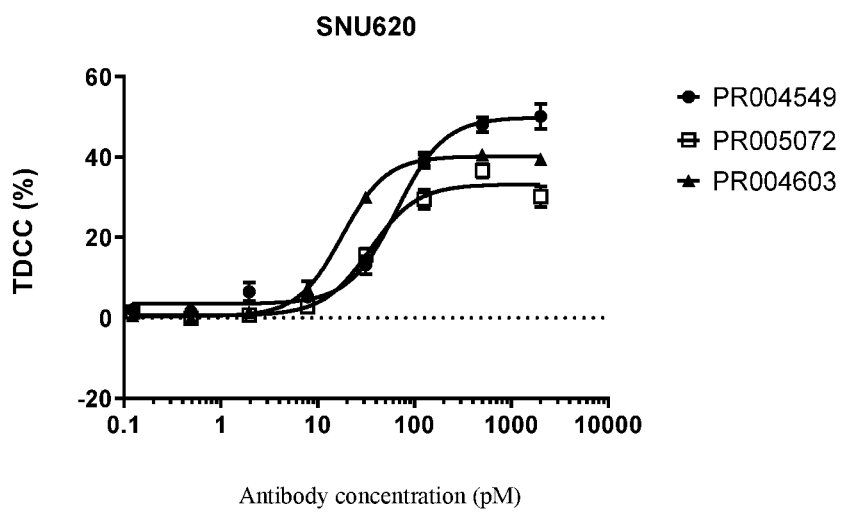
Figure 6W:
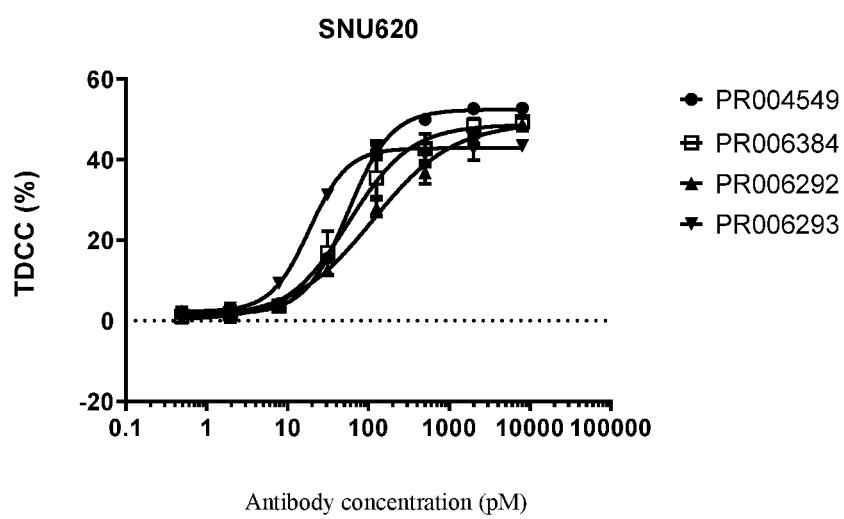

Antibodies were assayed for ability to induce cytotoxic killing against NUGC4_D8 cells when co-cultured with an MMAF-conjugated anti-human IgG antibody (Moradec, Cat #: AH-102-AF) using a CellTiter-Glo luminescent cell viability assay kit (Promega, G7573). NUGC4_D8 cells were centrifuged at 300 g for 5 min and then resuspended in culture medium (RPMI1640+10% FBS) to adjust the density of the cells to 2×10$^4$ cells/mL. 50 μL of the cell suspension was added to each well of a 96-well plate. The cells were incubated at 37° C. overnight. Antibodies were diluted to different concentrations with medium, and 25 μL of the antibody dilution was added to each well of the 96-well plate. The MMAF-conjugated anti-human IgG antibody was diluted with medium, and 25 μL of the antibody dilution was added to each well of a 96-well plate to a final concentration of 6.6 nM. The cells were incubated with the antibody at 37° C. for 3 days. The 96-well plate was left standing at room temperature for 30 min, and 100 μL of CellTiter-Glo chromogenic solution was added to each well at room temperature. Then, the sample was incubated in the dark at room temperature for 10 min. The plate was read with PE Enspire. Cell viability (%)=[(luminescent sample)/(luminescent mock control)]×100. PR000400 (IMAB362 analogue) was used as a positive control and Iso hIgG1 (CrownBio, C0001-4) antibody as a negative control. FIGS. 3(a-b) show the viability of target cells. When co-cultured with the MMAF-conjugated anti-human IgG antibody, the test antibodies exhibit a better cytotoxic effect against NUGC4_D8 cells in a dose-dependent manner, compared to PR000400.

Example 8

Structure and Design of CLDN18.2×CD3 Bispecific Antibodies

Selected anti-CLDN8.2 and anti-CD3 antibodies were used to prepare a bispecific antibody. The prepared CLDN18.2×CD3 bispecific antibody can bind to two targets simultaneously, with one terminus capable of recognizing CLDN18.2 specifically expressed on tumor cell surfaces and the other terminus capable of binding to CD3 molecules on T cells. After binding to the surface of tumor cells, the CLDN18.2×CD3 bispecific antibody molecule can recruit and activate T cells around the tumor cells, thereby kill the tumor cells.

As shown in FIG. 4, the structure (1) is a molecule with "2+1" Fab-Fc-Dual VH asymmetric structure; for the molecule with "2+1" asymmetric structure, the structure involves three protein chains comprising the heavy and light chains of the corresponding anti-CD3 antibody and the Dual VH polypeptide chain of the anti-CLDN18.2 antibody, respectively; the structures (2) and (3) were molecules with "2+1" HCAb-Fc-Fab asymmetric structure, which involves three protein chains comprising the heavy and light chains of the corresponding anti-CD3 antibody and the HCAb polypeptide chain of the anti-CLDN18.2 antibody, respectively.

The structure (4) is a molecule with "4+1" VH-VH_HC-Fab asymmetric structure, which involves three protein chains comprising the heavy and light chains of the corresponding anti-CD3 antibody and the tetravalent VH polypeptide chain of the anti-CLDN18.2 antibody, respectively.

The structure (5) is a molecule with "4+1" VH-VH_LC-Fab asymmetric structure, which involves three protein chains comprising the heavy and light chains of the corresponding anti-CD3 antibody and the tetravalent VH polypeptide chain of the anti-CLDN18.2 antibody, respectively.

The structure (6) is a molecule with "3+1" VH_HC-Fab-Fc-Dual VH asymmetric structure, which involves three protein chains comprising the heavy and light chains of an anti-CD3 antibody with the corresponding N-terminus linked to a monovalent VH of the anti-CLDN18.2 antibody and the bivalent VH polypeptide chain of the anti-CLDN18.2 antibody, respectively.

The structure (7) is a molecule with "3+1" Fab-Fc-VH-VH-VH asymmetric structure, which involves three protein chains comprising the heavy and light chains of the corresponding anti-CD3 antibody and the trivalent VH polypeptide chain of the anti-CLDN18.2 antibody, respectively.

The structure (8) is a molecule with "1+1" Fab-Fc-scFv asymmetric structure, which involves two protein chains comprising the heavy and light chains of the corresponding anti-CD3 antibody and the scFv polypeptide chain of the anti-Lysozyme or anti-CLDN18.1 antibody, respectively.

To minimize the formation of byproducts with mis-matched heavy chains (e.g., mismatching of two heavy chains of the anti-CD3 antibody), a mutant heterodimeric Fc region was used. It carries a "knob-hole" mutation and a modified disulfide bond, as described in WO2009080251 and WO2009080252. The CLDN18.2×CD3 bispecific antibody has an Fc of IgG1 and carries L234A, L235A or L234A, L235A and G237A (numbered according to the EU index) mutations on CH3 of the Fc. Each bispecific antibody was generated by co-transfecting simultaneously three or four different mammalian expression vectors encoding: 1) the heavy chain of the corresponding anti-CLDN18.2 antibody, which carries a "Hole" mutation in the Fc region so as to produce a heterodimeric antibody, CH3 of the Fc carrying L234A, L235A or L234A, L235A and G237A mutations; 2) the heavy chain of the corresponding anti-CD3 antibody, which carries a "knob" mutation in the Fc region so as to produce a heterodimeric antibody, CH3 of the Fc carrying L234A, L235A or L234A, L235A and G237A mutations; and 3) the light chain of the corresponding anti-CD3 antibody. The "knob" mutation in the Fc region of human IgG1 consists of: T366W, and the "Hole" mutation consists of: T366S, L368A, and Y407V. In addition, S354C in the "knob" Fc region and "Hole" Y349C may be included; they form a pair of disulfide bonds to increase the stability and the yield of the heterodimeric antibody.

Specific information about the CLDN18.2×CD3 bispecific antibodies constructed in the present invention is shown in Tables 14, 15 and 16.

TABLE 14

The CLDN18.2 × CD3 bispecific antibodies constructed according to the structures (1)-(8) of this example

| Structure | Bispecific antibodies molecule | CD3 antibody | CLDN18.2 antibody | CD3-terminus structure | CLDN18.2-terminus structure | Linker peptide | Fc type of CD3 end (mutation) | Fc type of CLDN18.2 terminus (mutation) |
|---|---|---|---|---|---|---|---|---|
| 1 | PR004603 | PR003886 | PR004227 | Fab | Dual VH | GS_15 | Human IgG1 (knob, LALA) | Human IgG1 (hole, LALA) |
| 1 | PR005072 | PR003886 | PR004533 | Fab | Dual VH | GS_15 | Human IgG1 (knob, LALA) | Human IgG1 (hole, LALA) |
| 1 | PR005076 | PR003886 | PR004536 | Fab | Dual VH | GS_15 | Human IgG1 (knob, LALA) | Human IgG1 (hole, LALA) |
| 1 | PR005354 | PR001848 | PR004533 | Fab | Dual VH | GS_15 | Human IgG1 (knob, LALA) | Human IgG1 (hole, LALA) |
| 1 | PR005397 | PR003886 | PR007246 | Fab | Dual VH | GS_15 | Human IgG1 (knob, LALA) | Human IgG1 (hole, LALA) |

TABLE 14-continued

The CLDN18.2 × CD3 bispecific antibodies constructed according to the structures (1)-(8) of this example

| Structure | Bispecific antibodies molecule | CD3 antibody | CLDN18.2 antibody | CD3-terminus structure | CLDN18.2-terminus structure | Linker peptide | Fc type of CD3 end (mutation) | Fc type of CLDN18.2 terminus (mutation) |
|---|---|---|---|---|---|---|---|---|
| 1 | PR005398 | PR003886 | PR007242 | Fab | Dual VH | GS_15 | Human IgG1 (knob, LALA) | Human IgG1 (hole, LALA) |
| 1 | PR005399 | PR003886 | PR007243 | Fab | Dual VH | GS_15 | Human IgG1 (knob, LALA) | Human IgG1 (hole, LALA) |
| 1 | PR005401 | PR003886 | PR007244 | Fab | Dual VH | GS_15 | Human IgG1 (knob, LALA) | Human IgG1 (hole, LALA) |
| 1 | PR005411 | PR003886 | PR007245 | Fab | Dual VH | GS_15 | Human IgG1 (knob, LALA) | Human IgG1 (hole, LALA) |
| 1 | PR005422 | PR003886 | PR007247 | Fab | Dual VH | GS_15 | Human IgG1 (knob, LALA) | Human IgG1 (hole, LALA) |
| 1 | PR006023 | PR001848 | PR007246 | Fab | Dual VH | GS_15 | Human IgG1 (knob, LALA) | Human IgG1 (hole, LALA) |
| 1 | PR006292 | PR003886 | PR007245 | Fab | Dual VH | GS_15 | Human IgG1 (knob, AAA) | Human IgG1 (hole, AAA) |
| 1 | PR006293 | PR001848 | PR007245 | Fab | Dual VH | GS_15 | Human IgG1 (knob, AAA) | Human IgG1 (hole, AAA) |
| 1 | PR006384 | PR003886 | PR007246 | Fab | Dual VH | GS_15 | Human IgG1 (knob, AAA) | Human IgG1 (hole, AAA) |
| 1 | PR007079 | PR003886 | PR007243 | Fab | Dual VH | GS_15 | Human IgG1 (knob, AAA) | Human IgG1 (hole, AAA) |
| 1 | PR007080 | PR003886 | PR007244 | Fab | Dual VH | GS_15 | Human IgG1 (knob, AAA) | Human IgG1 (hole, AAA) |
| 1 | PR007081 | PR003886 | PR007242 | Fab | Dual VH | GS_15 | Human IgG1 (knob, AAA) | Human IgG1 (hole, AAA) |
| 1 | PR007082 | PR003886 | PR007248 | Fab | Dual VH | GS_15 | Human IgG1 (knob, AAA) | Human IgG1 (hole, AAA) |
| 1 | PR007083 | PR003886 | PR007245 | Fab | Dual VH | GS_15 | Human IgG1 (knob, AAA) | Human IgG1 (hole, AAA) |
| 2 | PR005518 | PR001848 | PR004533 | Fab | VH | GS_15 | Human IgG1 (knob, LALA) | Human IgG1 (hole, LALA) |
| 3 | PR005519 | PR001848 | PR004533 | Fab | VH | GS_15 | Human IgG1 (knob, LALA) | Human IgG1 (hole, LALA) |
| 4 | PR005520 | PR001848 | PR004533 | Fab | Dual VH | GS_15 | Human IgG1 (knob, LALA) | Human IgG1 (hole, LALA) |
| 5 | PR005521 | PR001848 | PR004533 | Fab | Dual VH | GS_15 | Human IgG1 (knob, LALA) | Human IgG1 (hole, LALA) |
| 6 | PR005522 | PR001848 | PR004533 | Fab | Trivalent VH | GS_15 | Human IgG1 (knob, LALA) | Human IgG1 (hole, LALA) |
| 7 | PR005525 | PR003886 | PR004533 | Fab | Trivalent VH | GS_15 | Human IgG1 (knob, LALA) | Human IgG1 (hole, LALA) |
| 8 | PR004312 | PR001848 | PR000325 | Fab | scFv | GS_20 | Human IgG1 (knob, LALA) | Human IgG1 (hole, LALA) |
| 8 | PR004313 | PR001848 | PR001861 | Fab | scFv | GS_20 | Human IgG1 (knob, LALA) | Human IgG1 (hole, LALA) |

TABLE 15

The sequence numbers of the CLDN18.2 × CD3 bispecific antibody of the present invention

| Antibody | SEQ ID NOs: | | |
|---|---|---|---|
| | Polypeptide chain-1 | Polypeptide chain-2 | Polypeptide chain-3 |
| PR004603 | 214 | 213 | 200 |
| PR005072 | 219 | 213 | 200 |
| PR005076 | 220 | 213 | 200 |
| PR005397 | 221 | 213 | 200 |
| PR005398 | 222 | 213 | 200 |
| PR005399 | 223 | 213 | 200 |
| PR005401 | 224 | 213 | 200 |
| PR005411 | 225 | 213 | 200 |
| PR005422 | 226 | 213 | 200 |
| PR005518 | 227 | 228 | 200 |
| PR005519 | 227 | 230 | 229 |
| PR005520 | 219 | 231 | 200 |
| PR005521 | 219 | 232 | 229 |
| PR005522 | 219 | 233 | 200 |
| PR005525 | 234 | 213 | 200 |
| PR005354 | 219 | 209 | 200 |
| PR006023 | 221 | 209 | 200 |
| PR006292 | 236 | 235 | 200 |
| PR006293 | 236 | 237 | 200 |
| PR006384 | 238 | 235 | 200 |
| PR007079 | 239 | 235 | 200 |
| PR007080 | 240 | 235 | 200 |
| PR007081 | 241 | 235 | 200 |
| PR007082 | 242 | 235 | 200 |
| PR007083 | 243 | 235 | 200 |

TABLE 16

The sequence numbers of the CDRs of the antigen-binding domain of the CLDN18.2 × CD3 bispecific antibody of the present invention

| Structure number | Molecule number | Antigen-binding domain number | LCDR1 | LCDR2 | LCDR3 | HCDR1 | HCDR2 | HCDR3 |
|---|---|---|---|---|---|---|---|---|
| 1 | PR004603 | #1 | 101 | 116 | 131 | 11 | 38 | 72 |
|   |   | #2 |   |   |   | 16 | 42 | 77 |
| 1 | PR005072 | #1 | 101 | 116 | 131 | 11 | 38 | 72 |
|   |   | #2 |   |   |   | 16 | 43 | 78 |
| 1 | PR005076 | #1 | 101 | 116 | 131 | 11 | 38 | 72 |
|   |   | #2 |   |   |   | 16 | 44 | 79 |
| 1 | PR005354 | #1 | 101 | 116 | 131 | 11 | 38 | 72 |
|   |   | #2 |   |   |   | 16 | 43 | 78 |
| 1 | PR005397, PR006384 | #1 | 101 | 116 | 131 | 11 | 38 | 72 |
|   |   | #2 |   |   |   | 16 | 52 | 78 |
| 1 | PR005398, PR007081 | #1 | 101 | 116 | 131 | 11 | 38 | 72 |
|   |   | #2 |   |   |   | 16 | 48 | 78 |
| 1 | PR005399, PR007079 | #1 | 101 | 116 | 131 | 11 | 38 | 72 |
|   |   | #2 |   |   |   | 16 | 49 | 78 |
| 1 | PR005401, PR007080 | #1 | 101 | 116 | 131 | 11 | 38 | 72 |
|   |   | #2 |   |   |   | 16 | 50 | 78 |
| 1 | PR005411, PR006292, PR007083 | #1 | 101 | 116 | 131 | 11 | 38 | 72 |
|   |   | #2 |   |   |   | 16 | 51 | 78 |
| 1 | PR005422 | #1 | 101 | 116 | 131 | 11 | 38 | 72 |
|   |   | #2 |   |   |   | 16 | 53 | 79 |
| 1 | PR006023 | #1 | 101 | 116 | 131 | 11 | 38 | 72 |
|   |   | #2 |   |   |   | 16 | 52 | 78 |
| 1 | PR006293 | #1 | 101 | 116 | 131 | 11 | 38 | 72 |
|   |   | #2 |   |   |   | 16 | 51 | 78 |
| 1 | PR007082 | #1 | 101 | 116 | 131 | 11 | 38 | 72 |
|   |   | #2 |   |   |   | 16 | 54 | 78 |
| 2 | PR005518 | #1 | 101 | 116 | 131 | 11 | 38 | 72 |
|   |   | #2 |   |   |   | 16 | 43 | 78 |
| 3 | PR005519 | #1 | 101 | 116 | 131 | 11 | 38 | 72 |
|   |   | #2 |   |   |   | 16 | 43 | 78 |
| 4 | PR005520 | #1 | 101 | 116 | 131 | 11 | 38 | 72 |
|   |   | #2 |   |   |   | 16 | 43 | 78 |
| 5 | PR005521 | #1 | 101 | 116 | 131 | 11 | 38 | 72 |
|   |   | #2 |   |   |   | 16 | 43 | 78 |
| 6 | PR005522 | #1 | 101 | 116 | 131 | 11 | 38 | 72 |
|   |   | #2 |   |   |   | 16 | 43 | 78 |
| 7 | PR005525 | #1 | 101 | 116 | 131 | 11 | 38 | 72 |
|   |   | #2 |   |   |   | 16 | 43 | 78 |

Example 9

Preparation and Characterization of CLDN18.2×CD3 Bispecific Antibodies 9.1. Preparation of Recombinant CLDN18.2×CD3 Bispecific Antibodies A plurality of plasmids encoding recombinant CLDN18.2×CD3 bispecific antibodies were transfected into mammalian host cells (e.g., Chinese Hamster Ovary (CHO) cells) according to a certain proportion, and the corresponding purified recombinant antibody can be obtained using conventional recombinant protein expression and purification techniques. Specifically, ExpiCHO-S™ cells (Gibco, A29127) were expanded in ExpiCHO™ Expression Medium (Gibco, A2910001). Before the transient transfection, the cells were adjusted to a concentration of $3 \times 10^6$ to $4 \times 10^6$ cells/mL, and cultured in an 8% $CO_2$ shaker at 37° C. for 24 h, leading to a cell concentration of $7 \times 10^6$ to $10 \times 10^6$ cells/mL. The cells were then diluted to $6 \times 10^6$ cells/mL, and 10 mL of the cultured cells was prepared. A total of 8 μg of the above plasmids encoding CLDN18.2×CD3 bispecific antibodies (the ratio of the plasmids to cells is 0.8 μg:1 mL) was dissolved in 0.4 mL of OptiPRO™ SFM medium (Gibco, 12309019). The resulting mixture was filtered through a 0.22 μm filter for sterilization. Then 32 μL of ExpiFectamine™ CHO reagent (Gibco, A29129) was added to 0.37 mL of OptiPRO™ SFM medium (Gibco, 12309019). The ExpiFectamine™ CHO reagent solution was immediately added slowly to the plasmid solution. The mixture was inverted to be well mixed. The mixed solution of plasmid and transfection reagent was slowly added dropwise while shaking the flask. The cells were cultured in an 8% $CO_2$ shaker at 37° C. for 8-9 days. The Cell viability was observed after 8 days.

The culture was collected and centrifuged at 3300 g for 10 min, and then the supernatant was collected and centrifuged at high speed to remove impurities. A gravity column (Bio-Rad, 7311550) containing MabSelect™ (GE Healthcare Life Science, 71-5020-91 AE) was equilibrated with PBS (pH 7.4) and rinsed with 2-5 column volumes of PBS. The supernatant sample was loaded onto a column. The column was rinsed with 5-10 column volumes of PBS. The target protein was eluted with 0.1 M glycine (pH 3.5). The eluate was adjusted to neutrality with Tris-HCl (pH 8.0), and concentrated and buffer exchanged into PBS buffer with an ultrafiltration tube (Millipore, UFC901024) to obtain a purified antibody solution. Then, the purified antibody solution was subjected to concentration determination using Nano-Drop (Thermo Scientific™ NanoDrop™ One), subpackaged and stored for later use.

9.2. Antibody Characterization by SEC-HPLC, HIC-HPLC and DSF

A proper amount of the purified sample above was loaded onto an analytical SEC column TSKgel G3000SWx1 (HPLC system model: Agilent 1260 Infinity II) for the measurement of purity. In this method, the following parameters and conditions were used: mobile phase: 1×PBS, pH 7.4 (Sangon, E607016); room temperature; flow rate: 1.0 mL/min; sample concentration: 1 mg/mL; injection volume: 20 μL; detection wavelength: 280 nm. After being recorded, the chromatogram was integrated using ChemStation software and relevant data were calculated. An analysis was generated, with the retention times reported for different components in the sample.

A proper amount of the purified sample above was loaded onto an analytical HIC column TSKgel Butyl-NPR 4.6*35 (HPLC system model: Agilent 1260 Infinity II) for the measurement of purity and hydrophobicity. The method consisted of a linear gradient from 100% mobile phase A (20 mM PB, 1.8 M $(NH4)_2SO_4$, pH 6.0) to 100% mobile phase B (20 mM PB, pH 6.0) within 16 min. The flow rate was set at 0.7 mL/min, the sample concentration was 1 mg/mL, the injection volume was 20 μL, and the detection wavelength was 280 nm. After being recorded, the chromatogram was integrated using ChemStation software and relevant data were calculated. An analysis was generated, with the retention times reported for different components in the sample.

In this example, the thermal denaturation temperature (Tm) of a protein molecule was measured by differential scanning fluorimetry (DSF). 10 μg of protein was added to a 96-well PCR plate (Thermo, AB-0700/W), followed by the addition of 2 μL of 100× diluted dye SYPROTM (Invitrogen, 2008138), and then buffer was added to give a final volume of 40 μL per well. The PCR plate was sealed, placed in a real-time fluorescent quantitative PCR instrument (Bio-Rad CFX96 PCR System), incubated at 25° C. for 5 min, then gradually warmed from 25° C. to 95° C. at a gradient of 0.2° C./0.2 min, and cooled to 25° C. at the end of the test. The FRET scanning mode was used and data analysis was performed using Bio-Rad CFX Maestro software to calculate the Tm of the sample. The results of the above characterization are shown in Table 17 below.

TABLE 17

Characterization of the CLDN18.2 × CD3 bispecific antibodies

| Antibody | SEC-HPLC purity (%) | HIC-HPLC purity (%) | HIC-HPLC retention time (min) | Tm1 (° C.) | Tm2 (° C.) |
|---|---|---|---|---|---|
| PR004549 | 93.4 | 100.0 | 19.0 | 56.0 | NA |
| PR004603 | 100.0 | 100.0 | 19.2 | 50.0 | 66.8 |
| PR005072 | 99.1 | 100.0 | 16.4 | 59.0 | 64.2 |
| PR005076 | 97.8 | 92.1 | 18.3 | 50.2 | 66.8 |
| PR005397 | 100.0 | 100.0 | 16.2 | 52.0 | 59.0 |
| PR005398 | 98.9 | 100.0 | 16.7 | 54.2 | 67.8 |
| PR005399 | 86.0 | 100.0 | 16.5 | 53.8 | 67.8 |
| PR005401 | 99.6 | 100.0 | 16.1 | 60.0 | 67.4 |
| PR005411 | 100.0 | 100.0 | 16.2 | 60.2 | 67.4 |
| PR005422 | 99.7 | 100.0 | 18.0 | 48.4 | 66.4 |
| PR005518 | 64.0 | 100.0 | 16.0 | 53.4 | 64.4 |
| PR005519 | 68.9 | 100.0 | 15.9 | 53.4 | 64.2 |
| PR005520 | 89.7 | 100.0 | 16.4 | 54.0 | 62.8 |
| PR005521 | 89.0 | 100.0 | 16.3 | 54.8 | 62.6 |
| PR005522 | 100.0 | 100.0 | 16.5 | 52.0 | 63.8 |
| PR005525 | 99.7 | 100.0 | 16.4 | 63.2 | 66.4 |
| PR005354 | 99.8 | | | | |
| PR006023 | 100.0 | 100.0 | 16.0 | 59.2 | 65.8 |
| PR006292 | 99.4 | 100.0 | 15.9 | 59.6 | 66.8 |
| PR006293 | 99.0 | 100.0 | 16.0 | 59.8 | 65.8 |
| PR006384 | 100.0 | 100.0 | 15.9 | 59.2 | 67.0 |
| PR007079 | 99.4 | 100.0 | 16.1 | 55.6 | 66.4 |
| PR007080 | 97.8 | 100.0 | 16.0 | 59.6 | 66.8 |
| PR007081 | 95.8 | 100.0 | 16.2 | 56.2 | 66.6 |
| PR007082 | 98.5 | 86.10 | 16.1 | 60.8 | 66.8 |
| PR007083 | 84.5 | 100.0 | 16.1 | 51.8 | 67.6 |
| Trastuzumab | 100.0 | 100.0 | 16.0 | 67.8 | 79.2 |

Example 10

Binding Affinity of CLDN18.2×CD3 Bispecific Antibodies to Cells

Antibodies were assayed for binding affinity by FACS. Test cells include HEK293/hCLDN18.2, HEK293/hCLDN18.1, NUGC4_D8 and Jurkat cells. The binding affinity was determined as follows: cells were centrifuged at 300 g for 5 min and then resuspended in FACS buffer (PBS containing 2% FBS). The cell density was adjusted to $10^6$ cells/mL, and 50 μL of the cell suspension was added to each well of a 96-well plate. Antibodies were diluted to different concentrations with FACS buffer, and 50 μL of the antibody dilution was added to each well of the 96-well plate. After 2 h of incubation at 4° C., the plate was washed twice with FACS buffer. Then, an FACS buffer containing an APC-conjugated goat anti-human IgG secondary antibody (final concentration of 1.5 μg/mL, Jackson, 109-605-098) was added. After 1 h of incubation at 4° C., the plate was washed twice with FACS buffer. The cells were resuspended in fixative solution, and then the fluorescence of the cells was monitored using an FACS instrument (ACEA NovoCyte). FIG. 5 and Table 18 show the binding affinity of antibodies to the cells. All the test antibodies can bind to CLDN18.2 and CD3-expressing cells, and do not bind to CLDN18.1-expressing cells.

TABLE 18

The binding affinity of CLDN18.2 × CD3 bispecific antibodies for cells

| Antibody | Titer $EC_{50}$ (nM) | | |
|---|---|---|---|
| | NUGC4_D8 | HEK293/hCLDN18.2 | Jurkat |
| PR004549 | NA | 50.4 | 3.6 |
| PR004603 | NA | 33.1 | NA |
| PR005072 | 90.7 | 15.7 | NA |
| PR005076 | NA | NA | NA |
| PR005397 | 27.5 | 12.8 | NA |
| PR005398 | 19.4 | 20.4 | NA |
| PR005399 | NA | 25.3 | 81.9 |
| PR005401 | 13.1 | 17.5 | NA |
| PR005411 | 20.5 | 16.0 | 85.9 |
| PR005422 | NA | NA | NA |
| PR005518 | 20.5 | | NA |
| PR005519 | 13.9 | | NA |
| PR005520 | 13.9 | | NA |

TABLE 18-continued

The binding affinity of CLDN18.2 × CD3 bispecific antibodies for cells

| | Titer EC$_{50}$ (nM) | | |
|---|---|---|---|
| Antibody | NUGC4_D8 | HEK293/hCLDN18.2 | Jurkat |
| PR005521 | 13.9 | | NA |
| PR005522 | 13.9 | | NA |
| PR005525 | 12.6 | | 26.8 |
| PR005354 | 12.6 | | NA |
| PR006023 | 31.3 | | 40.6 |
| PR006292 | 70.1 | 11.5 | NA |
| PR006293 | 78.0 | | 65.0 |
| PR006384 | 51.4 | 14.4 | NA |
| PR007079 | 73.2 | NA | NA |
| PR007080 | 46.7 | NA | NA |
| PR007081 | 49.3 | NA | NA |
| PR007082 | 44.2 | NA | 41.0 |
| PR007083 | NA | 9.6 | NA |

Note:
the blanks in the table indicate that the molecule was not subjected to an affinity assay for HEK293/hCLDN18.2 cells; NA indicates a failure to obtain EC$_{50}$ by fitting for the molecule in an affinity assay for HEK293/hCLDN18.2 cells.

Example 11

TDCC Activity of CLDN18.2×CD3 Bispecific Antibodies

CLDN18.2×CD3 bispecific antibodies were assayed for TDCC efficacy against NUGC4_D4, SNU620, IM95 and HEK293/hCLDN 18.1 cells using CytoTox 96® non-radioactive cytotoxicity assay kit (Promega, G1780). T cells were isolated from human PBMCs using human total T cell isolation kit (Miltenyi, 130-096-535). The human T cells and the target cells were resuspended in medium (RPMI1640+ 5% FBS). The target cell density was adjusted to 3×10$^5$ cells/mL, and the T cell density was adjusted to 1.2×10$^6$/mL. 50 µL of each type of the cells was added to the wells of a 96-well plate (effector-to-target ratio of 4:1). A test antibody was diluted with medium (RPMI1640+5% FBS) to different concentrations, and 50 µL was added to the wells of the 96-well plate. The samples were incubated at 37° C. for 48 h, and then 10× Triton-X 100 lysate (RPMI1640+5% FBS+ 10% Triton-X 100) was added to the target cell maximum LDH release control well and volume correction control well. The mixture was well mixed and incubated at 37° C. for 0.5 h. The 96-well plate was centrifuged at 400 g for 4 min. 50 µL of the supernatant was taken, and then LDH chromogenic solution was added at a concentration of 50 µL/well. After the mixture was left standing in the absence of light at room temperature for 20 min, the plate was read on MD StakMax (OD$_{490}$). PR004549 was used as a positive control for CLDN18.2 target cells, PR004313 as a positive control for CLDN18.1 target cells, and PR004312 antibody as a negative control. For the calculation of the results, corrected readings were calculated first. The reading of the medium background control well was subtracted from the readings of the experimental wells, target cell spontaneous release LDH control well and effector cell spontaneous release LDH control well, and then the reading of the volume correction control well was subtracted from the reading of the target cell maximum LDH release control well. TDCC activity (%)=(corrected reading of experimental well−corrected reading of effector cell spontaneous release LDH control well−corrected reading of target cell spontaneous release LDH control well)/(corrected reading of target cell maximum LDH release control well−corrected reading of target cell spontaneous release LDH control well)×100. FIG. 6 shows the TDCC activity of the test antibodies, and the values are detailed in Table 19. In NUGC4_D8 cells highly endogenously expressing CLDN18.2, the test antibodies can induce higher or comparable TDCC activity compared to PR004549. Whereas, in IM95 cells lowly expressing CLDN18.2, the test antibodies induce lower TDCC activity compared to PR004549. SNU620 cells have a mutation from methionine to leucine at amino acid 149 of CLDN18.2, representing a subset of gastric cancer patients with the CLDN18.2 mutation, and the test antibodies can induce higher or comparable TDCC activity compared to PR004549. The test antibodies failed to elicit a TDCC effect against HEK293/hCLDN 18.1 cells.

TABLE 19

The TDCC activity of CLDN18.2 × CD3 bispecific antibodies

| | Titer EC$_{50}$ (pM) | | |
|---|---|---|---|
| Antibody | NUGC4_D8 | IM95 | SNU620 |
| PR004549 | 32.0-502 | 109-159 | 55.9-66.2 |
| PR004603 | 251 | NA | 17.8 |
| PR005072 | 142 | NA | 34.5 |
| PR005076 | 102 | | |
| PR005397 | 10.0 | NA | 31.6 |
| PR005398 | 9.00 | NA | 18.3 |
| PR005399 | 14.8 | | 41.1 |
| PR005401 | 6.40 | | 25.8 |
| PR005411 | 11.0 | NA | 38.5 |
| PR005422 | 21.9 | NA | 313.0 |
| PR005518 | 30.6 | | |
| PR005519 | 32.9 | NA | 70.5 |
| PR005520 | 22.4 | | |
| PR005521 | 73.9 | NA | 41.0 |
| PR005522 | 186 | | |
| PR005525 | 28.9 | | |
| PR005354 | 11.0 | | |
| PR006023 | 48.5 | | |
| PR006292 | 185 | NA | 112.7 |
| PR006293 | 87.0 | 460 | 18.5 |
| PR006384 | 57.9 | 938 | 57.1 |

Example 12

Binding Affinity of Antibodies to Human Fc Receptor Proteins by BLI Method

The binding kinetics between proteins and antibodies was analyzed by the Biolayer Interferometry (BLI) technique using an Octet Red 96e (Fortebio) system. The rotation speed was set at 1000 rpm for the system. 10× kinetics buffer (ForteBio, Cat #18-1105) was diluted to 1× kinetics buffer for affinity assay and dilution of samples. FAB2G sensor (Fortebio, 18-5125) arranged in line was equilibrated in a test buffer for 10 min and then used to capture antibodies (PR002725, PR005397, PR006384, PR005411, PR006292, PR006023 and PR006293) at a capture height of 1 nm. After equilibrated in the buffer for 120 s, the FAB2G sensor was allowed to bind to 2-fold serially diluted human Fc receptor protein. The protein concentration and binding and dissociation time are shown in Table 20. Finally, the FAB2G sensor was immersed in a 10 mM glycine-hydrochloric acid solution at pH 1.5 for regeneration to elute the proteins bound to the sensor. The affinity assays of antibodies for FcRn were performed under the conditions of both pH 6.0 buffer and pH 7.4 buffer. For PR004549, the capture sensor is ProL (Fortebio, 18-5085). When data analysis was performed using Octet Data Analysis software (Fortebio, version 11.0), 0 nM was used as a reference hole, and reference subtraction was performed; the "1:1 Global fitting" method was selected to fit the data, and the kinetics parameters of the binding of proteins to antibodies were calculated, with kon(1/Ms) values, kdis(1/s) values and KD(M) values obtained. For the interactions of fast binding and fast dissociation, the "steady state" method was selected to fit the data to obtain KD(M) values. The binding affinity of the antibodies to human Fc receptor proteins is shown in Table 21.

TABLE 20

Information about the Fc receptor proteins and experimental parameters

| Fc receptor protein | Catalog No. | Manufacturer | Test concentration (nM) | Binding time/ dissociation time |
|---|---|---|---|---|
| Human CD64 | CM60 | NovoProtein | 200-12.5* | 60 s/20 s |
| Human FcRn | CI01 | Scientific Co., Ltd. | 400-25 (pH 6.0) 1000-62.5 (pH 7.4) | 60 s/20 s |
| Human CD32a | CS35 | | 10000-625 | 30 s/20 s |
| Human CD32b | C444 | | 10000-625 | 30 s/20 s |
| Human CD16a(F) | CS11 | | 10000-625 | 60 s/20 s |
| Human CD16a(V) | C441 | | 6000-375 | 60 s/20 s |

*For antibody PR002725, the test concentration of CD64 was 40-1.25 nM

TABLE 21

The binding affinity of antibodies to Human Fc receptor proteins

| Fc receptor | Antibody | Concentration (nM) | KD(M) | kon(1/Ms) | kdis(1/s) | Full R^2 |
|---|---|---|---|---|---|---|
| Human CD64 | PR002725 | 40-1.25 | 9.13E−11 | 1.42E+06 | 1.30E−04 | 0.9978 |
| | PR004549 | 200-25 | 9.62E−06 | 6.00E+04 | 5.77E−01 | 0.9814 |
| | PR005397 | 200-12.5 | 5.06E−08 | 8.66E+05 | 4.38E−02 | 0.9951 |
| | PR006384 | 800-50 | NA[1] | | | |
| | PR005411 | 200-12.5 | 4.71E−08 | 8.85E+05 | 4.17E−02 | 0.9934 |
| | PR006292 | 800-50 | NA[1] | | | |
| | PR006023 | 200-12.5 | 5.39E−08 | 8.74E+05 | 4.71E−02 | 0.9952 |
| | PR006293 | 800-50 | NA[1] | | | |
| Human CD16a(V) | PR002725 | 400-25 | 1.29E−07 | 5.85E+05 | 7.57E−02 | 0.9944 |
| | PR004549 | 6000-375 | NA[1] | | | |
| | PR005397 | 6000-375 | 1.80E−06 | NA[2] | NA[2] | 0.9218 |
| | PR006384 | 6000-375 | NA[1] | | | |
| | PR005411 | 6000-375 | 2.30E−06 | NA[2] | NA[2] | 0.9126 |
| | PR006292 | 6000-375 | NA[1] | | | |
| | PR006023 | 6000-375 | 3.00E−06 | NA[2] | NA[2] | 0.9002 |
| | PR006293 | 6000-375 | NA[1] | | | |
| Human CD16a(F) | PR002725 | 10000-625 | 2.10E−06 | NA[2] | NA[2] | 0.9884 |
| | PR004549 | | NA[1] | | | |
| | PR005397 | | | | | |
| | PR006384 | | | | | |
| | PR005411 | | | | | |
| | PR006292 | | | | | |
| | PR006023 | | | | | |
| | PR006293 | | | | | |
| Human FcRn pH 6.0 | PR002725 | 400-25 | 1.55E−07 | 3.46E+05 | 5.37E−02 | 0.9906 |
| | PR004549 | 400-25 | 2.06E−07 | 2.80E+05 | 5.77E−01 | 0.9852 |
| | PR005397 | 400-25 | 1.82E−07 | 3.22E+05 | 5.86E−02 | 0.9907 |
| | PR006384 | 400-25 | 2.10E−07 | 2.89E+05 | 6.08E−02 | 0.9898 |
| | PR005411 | 400-25 | 2.15E−07 | 3.00E+05 | 6.44E−02 | 0.9879 |
| | PR006292 | 400-25 | 2.00E−07 | 3.05E+05 | 6.09E−02 | 0.9895 |
| | PR006023 | 400-25 | 2.10E−07 | 2.98E+05 | 6.26E−02 | 0.9889 |
| | PR006293 | 400-25 | 2.17E−07 | 2.91E+05 | 6.32E−02 | 0.9886 |
| Human FcRn pH 7.4 | PR002725 | 1000-62.5 | NA[1] | | | |
| | PR004549 | | | | | |
| | PR005397 | | | | | |
| | PR006384 | | | | | |
| | PR005411 | | | | | |
| | PR006292 | | | | | |
| | PR006023 | | | | | |
| | PR006293 | | | | | |

TABLE 21-continued

The binding affinity of antibodies to Human Fc receptor proteins

| Fc receptor | Antibody | Concentration (nM) | KD(M) | kon(1/Ms) | kdis(1/s) | Full R^2 |
|---|---|---|---|---|---|---|
| Human CD32a(H) | PR002725 PR004549 PR005397 PR006384 PR005411 PR006292 PR006023 PR006293 | 10000-625 | 7.40E−07 | NA[2] NA[1] | NA[2] | 0.9828 |
| Human CD32b | PR002725 PR004549 PR005397 PR006384 PR005411 PR006292 PR006023 PR006293 | 10000-625 | 2.60E−06 | NA[2] NA[1] | NA[2] | 0.9981 |

NA[1]: There is no binding of the antibody to the protein
NA[2]: The antibody binds to the receptor protein in a fast binding and fast dissociation mode; the fitting method adopted is steady state fitting, without kon/kdis values.

Example 13

Binding Affinity of Antibodies to CD3 Proteins of Different Species by BLI Method The binding kinetics between proteins and antibodies was analyzed by the Biolayer Interferometry (BLI) technique using an Octet Red 96e (Fortebio) system. Human CD3E (Acro, CDE-H5223), cynomolgus CD3E (Acro, CDE-05226) and murine CD3E (Acro, CDE-M5256) were mixed with biotin (Thermo Scientific, A39257) in a molar ratio of 1:3. The mixture was incubated at 4° C. overnight, and then excess biotin was removed to obtain biotinylated CD3E. The rotation speed was set at 1000 rpm for the system. 10× kinetics buffer (ForteBio, Cat #18-1105) was diluted to 1× kinetics buffer for affinity assay and dilution of samples. SA sensor (Fortebio, 18-5019) arranged in line was equilibrated in a test buffer for 10 min and then used to capture CD3 with a biotin label or biotinylated CD3 at a capture height of 0.2 nm. After being equilibrated in the buffer for 120 s, the SA sensor with captured CD3 was allowed to bind to 2-fold serially diluted antibodies. The antibody concentration is shown in Table 22, and binding and dissociation time were set to 180 s and 300 s. Finally, the SA sensor was immersed in a 10 mM glycine-hydrochloric acid solution at pH 1.5 for regeneration to elute the antibodies bound to the sensor. Antibody anti-CD3e 48-2B (santa cruz biotechnology's SC-1174) is a murine positive antibody. When data analysis was performed using Octet Data Analysis software (Fortebio, version 11.0), 0 nM was used as a reference hole, and reference subtraction was performed; the "1:1 Global fitting" method was selected to fit the data, and the kinetics parameters of the binding of proteins to antibodies were calculated, with kon(1/Ms) values, kdis(1/s) values and KD(M) values obtained. For the interactions of fast binding and fast dissociation, the "steady state" method was selected to fit the data to obtain KD(M) values. The binding affinity of the antibodies to CD3 proteins of different species is shown in Table 23. PR002199 was derived from the anti-BCMA(TNB308902)×CD3(TNB_F2B) bispecific antibody in the patent WO2018052503 of Teneobio. PR004931 was derived from the anti-CEA×CD3 bispecific antibody in the patent WO2017055389A1 of Roche.

TABLE 22

Information about the CD3 receptor proteins and experimental parameters

| Protein | Catalog No. | Manufacturer |
|---|---|---|
| Biotinylated human CD3E&D | CDD-H82W6 | Acro biosystems |
| Human CD3Ec | CDE-H5223 | |
| Biotinylated cynomolgus CD3E&D | CDD-C82W6 | |
| Cynomolgus CD3E | CDE-C5226 | |
| Biotinylated murine CD3E&D | CDD-M82W5 | |

TABLE 23

The binding affinity of the antibodies to CD3 proteins of different species

| Protein | Antibody | Concentration (nM) | KD(M) | kon(1/Ms) | kdis(1/s) | Full R^2 |
|---|---|---|---|---|---|---|
| Human CD3E | PR004549 | 20-1.25 | 4.10E−09 | 1.59E+05 | 6.52E−04 | 0.9986 |
| | PR004931 | 100-6.25 | 3.08E−08 | 7.31E+04 | 2.25E−03 | 0.9992 |
| | PR006292 | 100-6.25 | 9.90E−08 | 9.89E+04 | 9.78E−03 | 0.9971 |
| | PR006293 | 100-6.25 | 3.17E−08 | 6.81E+04 | 2.16E−03 | 0.9993 |
| | PR006384 | 100-6.25 | 1.51E−07 | 8.54E+04 | 1.29E−02 | 0.9981 |
| Biotinylated human CD3E&D | PR002199 | 200-12.5 | 2.41E−07 | 2.15E+05 | 5.18E−02 | 0.9834 |
| | PR004549 | 30-1.875 | 6.15E−09 | 9.65E+04 | 5.93E−04 | 0.9988 |
| | PR004931 | 100-6.25 | 3.37E−08 | 4.07E+04 | 1.37E−03 | 0.9973 |
| | PR006292 | 100-6.25 | 1.44E−07 | 8.47E+04 | 1.22E−02 | 0.9972 |
| | PR006384 | 100-6.25 | 1.32E−07 | 9.02E+04 | 1.19E−02 | 0.9985 |

TABLE 23-continued

The binding affinity of the antibodies to CD3 proteins of different species

| Protein | Antibody | Concentration (nM) | KD(M) | kon(1/Ms) | kdis(1/s) | Full R^2 |
|---|---|---|---|---|---|---|
| Cynomolgus CD3E | PR004549 | 20-1.25 | 9.75E−09 | 4.03E+04 | 3.93E−04 | 0.9998 |
| | PR004931 | 100-6.25 | 2.59E−08 | 7.03E+04 | 1.82E−03 | 0.9995 |
| | PR006292 | 100-6.25 | 1.40E−07 | 7.51E+04 | 1.05E−02 | 0.9952 |
| | PR006293 | 100-6.25 | 3.24E−08 | 6.07E+04 | 1.97E−03 | 0.9995 |
| | PR006384 | 100-6.25 | 1.65E−07 | 7.40E+04 | 1.22E−02 | 0.9970 |
| Biotinylated cynomolgus CD3E&D | PR004549 | 30-1.875 | 1.30E−08 | 1.79E+04 | 2.33E−04 | 0.9995 |
| | PR004931 | 100-6.25 | 2.13E−08 | 4.16E+04 | 8.83E−04 | 0.9972 |
| | PR006292 | 100-6.25 | 1.13E−07 | 8.57E+04 | 9.65E−03 | 0.9991 |
| | PR006384 | 100-6.25 | 1.52E−07 | 6.22E+04 | 9.42E−03 | 0.9986 |
| Biotinylated murine CD3E&D | anti-CD3e(48-2B) | 40-2.5 | 1.71E−10 | 8.03E+05 | 1.37E−04 | 0.9940 |
| | PR004549 | 120-7.5 | NA[1] | | | |
| | PR006384 | 120-7.5 | | | | |
| | PR006292 | 120-7.5 | | | | |
| | PR004931 | 120-7.5 | | | | |

NA[1]: There is no binding of the antibody to the protein

Example 14

Figure 7:
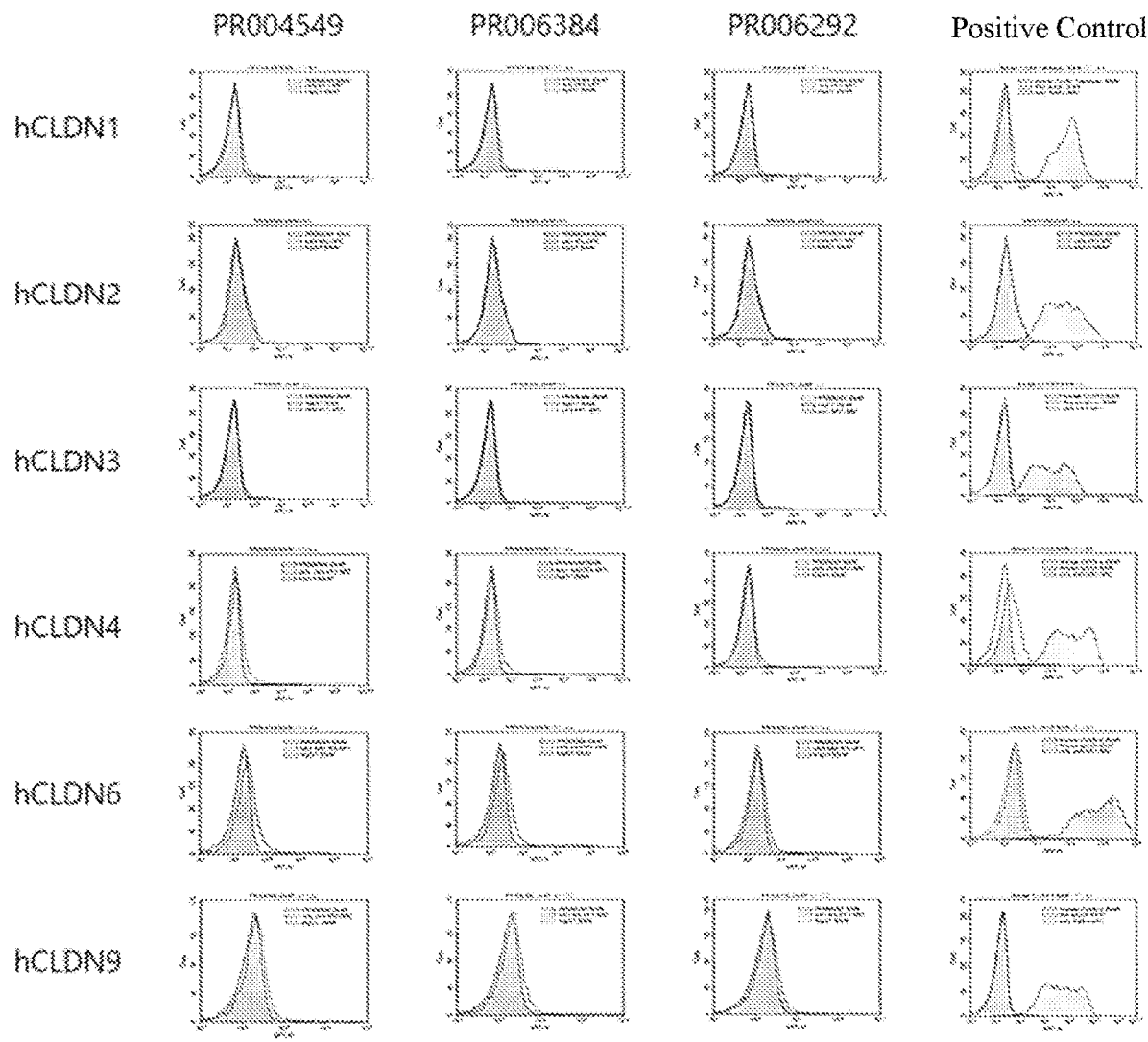
FIG. 7 shows the binding affinity of CLDN18.2×CD3 bispecific antibodies for cells overexpressing human CLDN18.2 paralogous family protein CLDN1, CLDN2, CLDN3, CLDN4, CLDN6 and CLDN9.

Binding Affinity of CLDN18.2×CD3 Bispecific Antibodies to Human CLDN18.2 Paralogous Proteins Antibodies were assayed for binding affinity to human CLDN18.2 paralogous proteins by FACS (ACEA Novo-Cyte). CLDN1, CLDN2, CLDN3, CLDN4, CLDN6 and CLDN9 genes of the human CLDN18.2 paralogous family were transiently transfected into HEK293 cells. Information about plasmids is shown in Table 24. The binding affinity was determined as follows: cells were centrifuged at 300 g for 5 min and then resuspended in FACS buffer (PBS containing 2% FBS). The cell density was adjusted to 10^6 cells/mL, and 50 μL of the cell suspension was added to each well of a 96-well plate. An antibody was diluted to 60 nM with FACS buffer, and 50 μL of the antibody dilution was added to each well of the 96-well plate. After 2 h of incubation at 4° C., the plate was washed twice with FACS buffer. Then, an FACS buffer containing a secondary antibody was added. After 1 h of incubation at 4° C., the plate was washed twice with FACS buffer. The cells were resuspended in fixative solution, and run FACS. Information about the positive control antibody, negative control antibody and secondary antibody was shown in Table 25. PR005080 was clone 1A2 antibody (produced in-house, see EP3567053A1) used as the positive control for CLDN2 binding. The FACS results are shown in FIG. 7, showing that there was no non-specific binding of PR006384 and PR006292 to CLDN1, CLDN2, CLDN3, CLDN4, CLDN6 and CLDN9 of the human CLDN18.2 paralogous family protein.

TABLE 24

Information about the expression plasmids of CLDN18.2 paralogous genes

| Name | Supplier | Catalog No. |
|---|---|---|
| pcDNA3.1_hCLDN9_NM_020982 | genscript | NM_020982.4 |
| pcDNA3.1_hCLDN6_NM_021195 | genscript | NM_021195.5 |
| pcDNA3.1_hCLDN4_NM_001305 | genscript | NM_001305.4 |
| pcDNA3.1_hCLDN3_NM_001306 | genscript | NM_001306.4 |
| pcDNA3.1_hCLDN2_NM_001171092 | genscript | NM_001171092.1 |
| pcDNA3.1_hCLDN1_NM_021101 | genscript | NM_021101.5 |

TABLE 25

Information about the flow cytometry antibodies

| Name | Supplier | Catalog No. |
|---|---|---|
| Human Claudin-1 Antibody | R&D | MAB4618 |
| Human Claudin-3 Antibody | R&D | MAB4620 |
| Human Claudin-4 Antibody | R&D | MAB4219 |
| Human Claudin-6 Antibody | R&D | MAB3656 |
| Human Claudin-9 Antibody | antibodies-online | ABIN1720917 |
| Rat IgG2A | R&D | MAB006 |
| Mouse IgG2A | R&D | MAB003 |
| Mouse IgG2B | R&D | MAB004 |
| Rat IgG2B | R&D | MAB0061 |
| Human Claudin-2 Antibody (PR005080) | Produced in-house | |
| Iso hIgG1 | CrownBio | C0001-4 |
| Alexa Fluor ® 647 AffiniPure Goat Anti-Human IgG, Fcγ fragment specific | Jackson | 109-605-098 |
| Alexa Fluor ® 647 AffiniPure Goat Anti-Mouse IgG (subclasses 1 + 2a + 2b + 3), Fcγ Fragment Specific | Jackson | 115-605-164 |
| Alexa Fluor ® 647 AffiniPure Goat Anti-Rat IgG, Fcγ fragment specific | Jackson | 112-605-071 |

Example 15

Figure 8A:
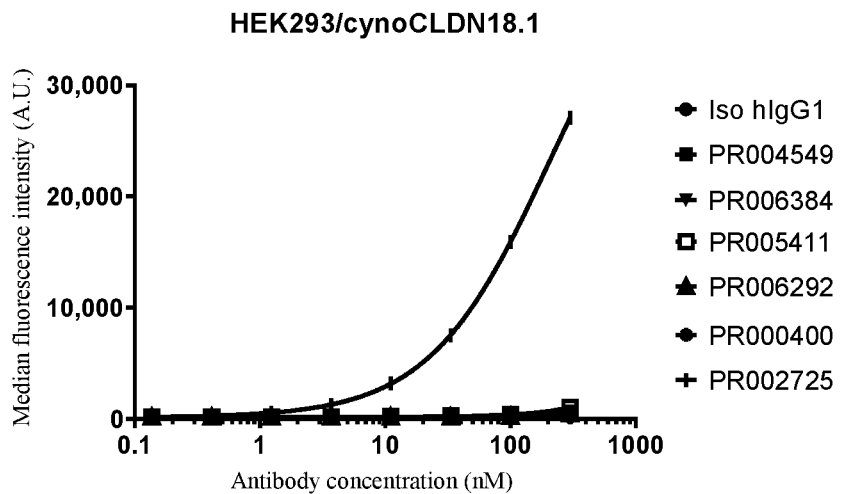
FIGS. 8a-c show the binding affinity of CLDN18.2×CD3 bispecific antibodies for (a) HEK293/cynoCLDN18.1, (b) HEK293/cynoCLDN18.2, and (c) cynomolgus CD3+ T cells.
Figure 8B:
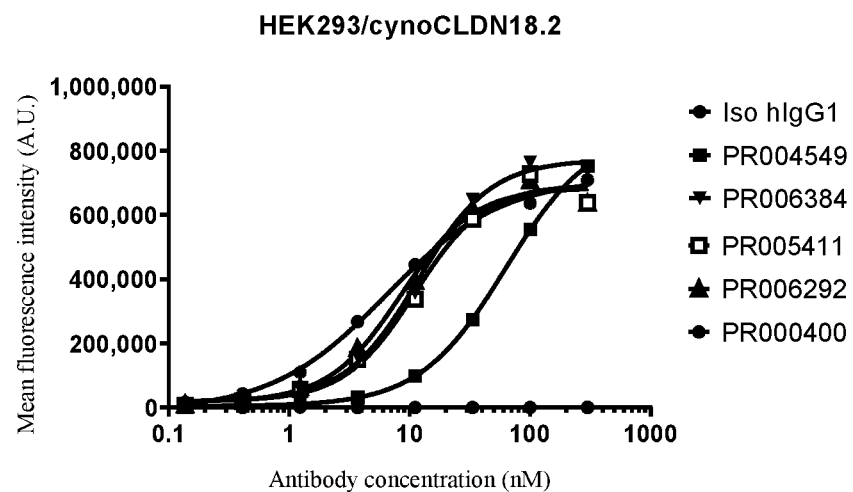
Figure 8C:
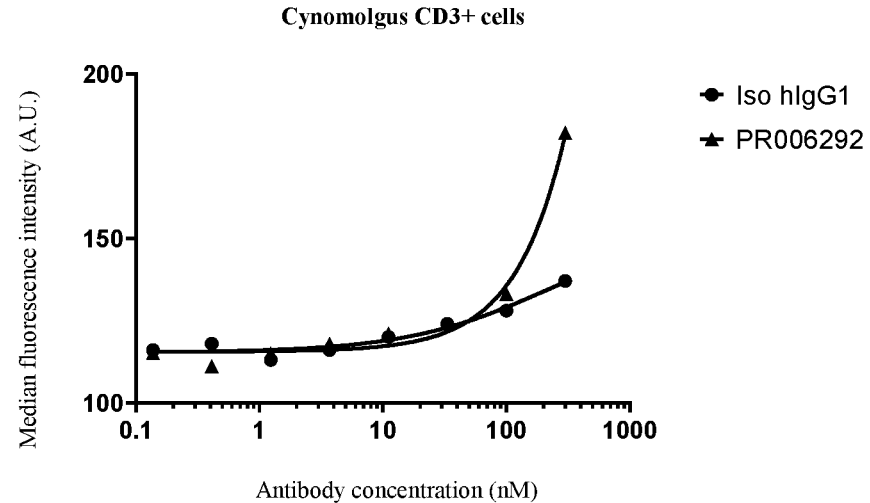

Binding Affinity of CLDN18.2×CD3 Bispecific Antibodies to Cynomolgus Target Proteins Antibodies were assayed for binding affinity by FACS. Test cells include cynomolgus CLDN18.2-expressing HEK293 cells (HEK293/cynoCLDN18.2), cynomolgus CLDN18.1-overexpressing HEK293 cells (HEK293/cyno-CLDN18.1) and cynomolgus CD3 positive T cells. CD3 positive T cells were isolated from cynomolgus PBMCs using a non-human primate CD3 cell isolation kit (Miltenyi, 130-092-012). The binding affinity was determined as follows: cells were centrifuged at 300 g for 5 min and then resuspended in FACS buffer (PBS containing 2% FBS). The cell density was adjusted to $10^6$ cells/mL, and 50 μL of the cell suspension was added to each well of a 96-well plate. Antibodies were diluted to different concentrations with FACS buffer, and 50 μL of the antibody dilution was added to each well of the 96-well plate. After 2 h of incubation at 4° C., the plate was washed twice with FACS buffer. Then, an FACS buffer containing an APC-conjugated goat anti-human IgG secondary antibody (final concentration of 1.5 μg/mL, Jackson, 109-605-098) was added. After 1 h of incubation at 4° C., the plate was washed twice with FACS buffer. The cells were resuspended in fixative solution and run FACS (ACEA NovoCyte). FIG. 8 and Table 26 show the binding affinity of antibodies to HEK293 cells overexpressing cynomolgus CLDN18.1 and CLDN18.2, as well as CD3 positive T cells in cynomolgus PBMCs. All the test antibodies can bind to CLDN18.2 and CD3-expressing cells, and do not bind to CLDN18.1-expressing cells.

TABLE 26

The binding affinity of CLDN18.2 × CD3 bispecific antibodies to cells

|  | Titer $EC_{50}$ (nM) | |
| --- | --- | --- |
| Antibody | HEK293/cynoCLDN18.2 | CD3+ T cell |
| PR004549 | 62.8 | |
| PR005411 | 11.1 | |
| PR006292 | 8.50 | NA |
| PR006384 | 11.7 | |
| PR000400 | 6.50 | |

Example 16

Figure 9:
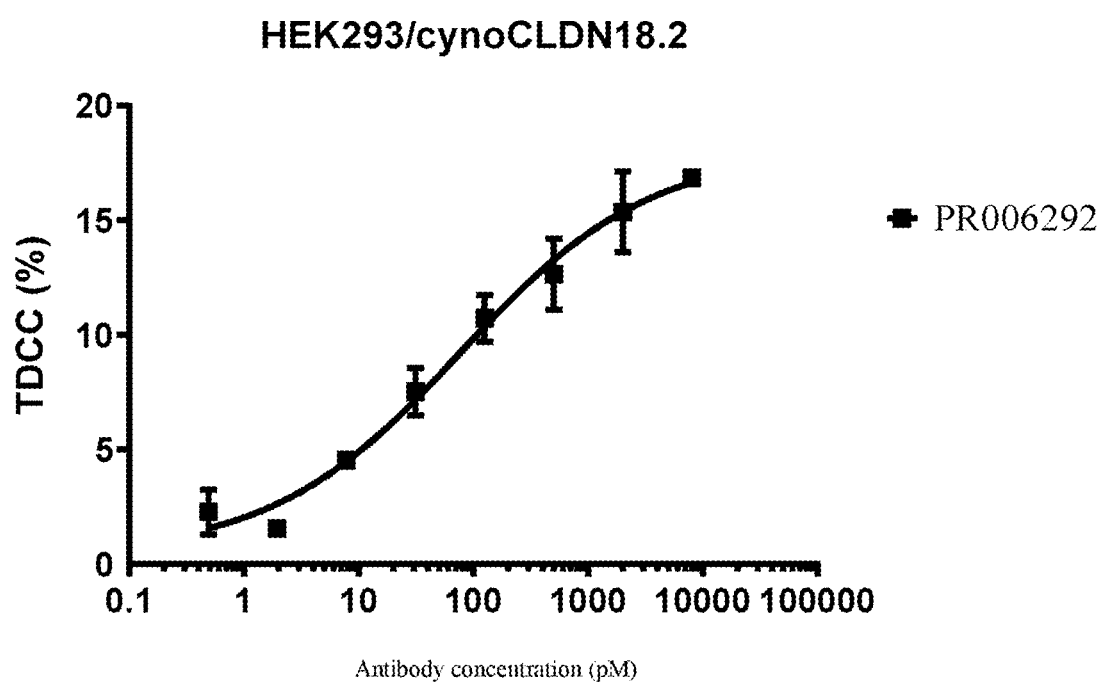
FIG. 9 shows the TDCC activity of CLDN18.2×CD3 bispecific antibodies against HEK293/cynoCLDN18.2 cells by cyno T cells.

TDCC Activity of CLDN18.2×CD3 Bispecific Antibodies Against Cynomolgus CLDN18.2-Expressing Cells CLDN18.2×CD3 bispecific antibodies were assayed for activity of eliciting a TDCC effect against HEK293/cyno-CLDN18.2 using a CytoTox 96® non-radioactive cytotoxicity assay kit (Promega, G1780). CD3 positive T cells were isolated from cynomolgus PBMCs using a non-human primate CD3 cell isolation kit (Miltenyi, 130-092-012). The cynomolgus T cells and target cells were resuspended in medium (RPMI1640+5% FBS). The target cell density was adjusted to $3\times10^5$ cells/mL, and the T cell density was adjusted to $1.2\times10^6$/mL. 50 μL of each type of the cells was added to the wells of a 96-well plate (effector-to-target ratio of 4:1). A test antibody was diluted with medium (RPMI1640+5% FBS) to different concentrations, and 50 μL was added to the wells of the 96-well plate. The samples were incubated at 37° C. for 24 h, and then 10× Triton-X 100 lysate (RPMI1640+5% FBS+10% Triton-X 100) was added to the target cell maximum LDH release control well and volume correction control well. The mixture was well mixed and incubated at 37° C. for 0.5 h. The 96-well plate was centrifuged at 400 g for 4 min. 50 μL of the supernatant was taken, and then LDH chromogenic solution was added at a concentration of 50 μL/well. After the mixture was left standing in the absence of light at room temperature for 20 min, the plate was read on MD StakMax ($OD_{490}$). For the calculation of the results, corrected readings were calculated first. The reading of the medium background control well was subtracted from the readings of the experimental wells, target cell spontaneous release LDH control well and effector cell spontaneous release LDH control well, and then the reading of the volume correction control well was subtracted from the reading of the target cell maximum LDH release control well. TDCC activity (%)=(corrected reading of experimental well−corrected reading of effector cell spontaneous release LDH control well−corrected reading of target cell spontaneous release LDH control well)/(corrected reading of target cell maximum LDH release control well−corrected reading of target cell spontaneous release LDH control well)×100. FIG. 9 shows the TDCC activity induced by antibodies against HEK293/cynoCLDN18.2. The specific values are shown in Table 27.

TABLE 27

The TDCC activity of CLDN18.2 × CD3 bispecific antibodies

| Antibody | $EC_{50}$ (pM) HEK293/cynoCLDN18.2 |
| --- | --- |
| PR006292 | 76.8 |

Example 17

In Vitro Cytokine Release Assay

Figure 10A:
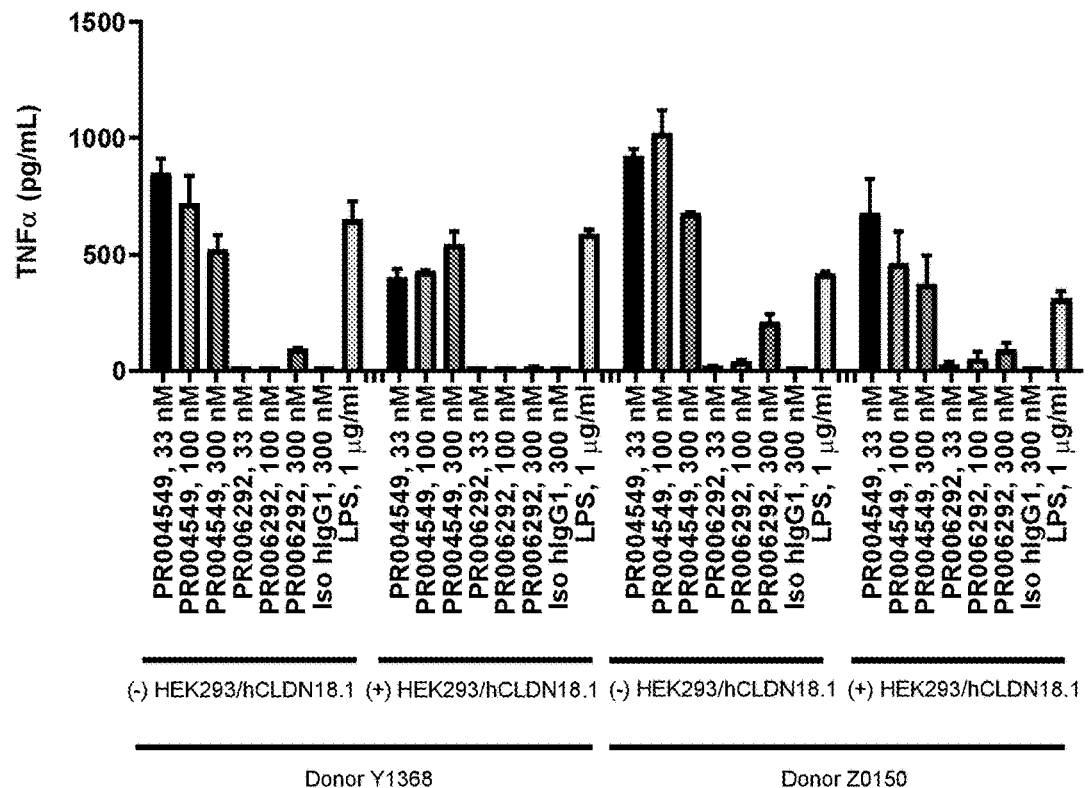
FIGS. 10a-b show the release of cytokines induced by CLDN18.2×CD3 bispecific antibodies in vitro. (a) TNFα, and (b) IL-6.
Figure 10B:
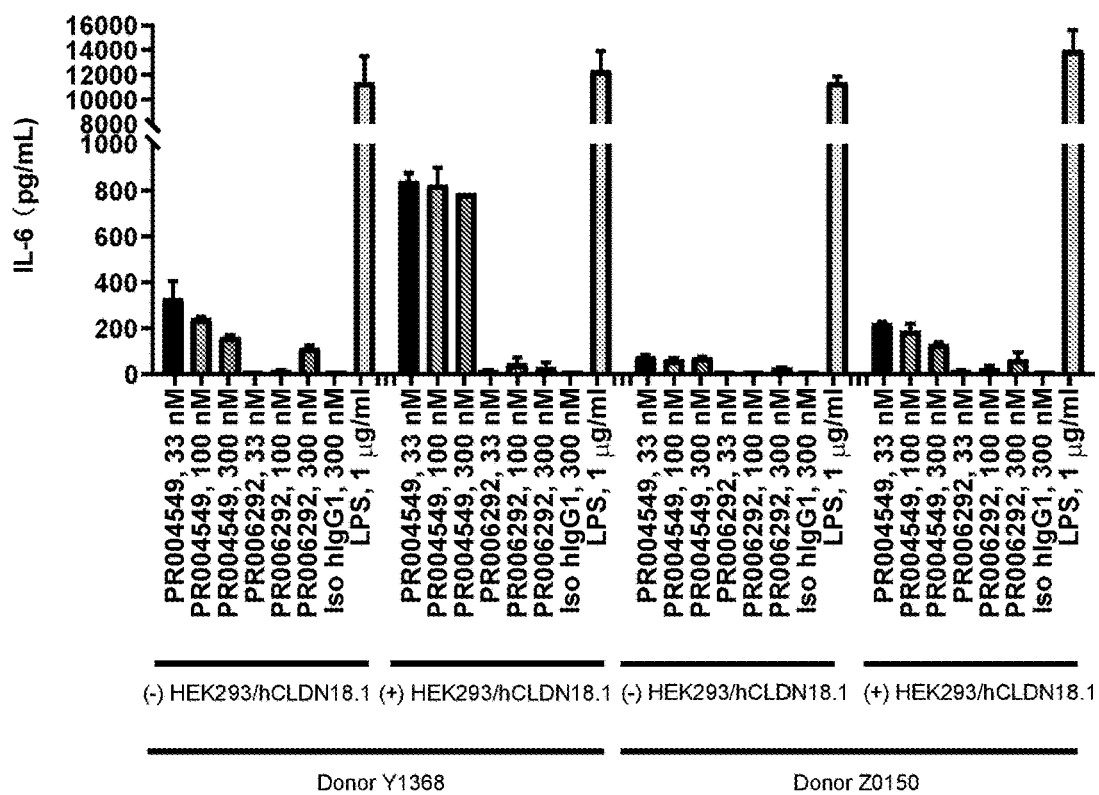

CLDN18.2×CD3 bispecific antibodies were assayed for in vitro induced cytokine release using human PBMCs, so as to predict the safety of the antibodies. PBMCs were incubated with antibodies in either presence or absence of HEK293/hCLDN18.1 cells. PBMCs and HEK293/hCLDN18.1 were resuspended in medium (RPMI1640+10% FBS). The density of HEK293/hCLDN18.1 cells was adjusted to $1.5\times10^6$ cells/mL, and the cell density of PBMCs was adjusted to $2\times10^6$/mL. 100 μL HEK293/hCLDN18.1 cells and 200 μL PBMCs were added to the wells of 48-well plate. Test antibodies were diluted with medium (RPMI1640+10% FBS) to different concentrations, and 100 μL was added to the wells of the 48-well plate to a final volume of 400 μL. LPS (Sigma, L6529) was used as the positive control. Iso hIgG1 (CrownBio, C0001-4) antibody was used as the negative control. The samples were incubated at 37° C. for 24 h. The supernatant was centrifuged at 300 g for 10 min, and 300 μL of the supernatant was harvested. The concentrations of IL-6 (Invitrogen, 88-7066) and TNF-α (Invitrogen, 88-7346) in the supernatant were quantified by ELISA. FIG. 10 shows cytokine release induced by antibodies in vitro. The release of IL-6 and TNF-α induced by PR004549 is higher than that induced by PR006292 in the absence of CLDN18.2 target cells, indicating better safety profile of PR006292

Example 18

ADCC Activity of CLDN18.2×CD3 Bispecific Antibodies

Figure 11A:
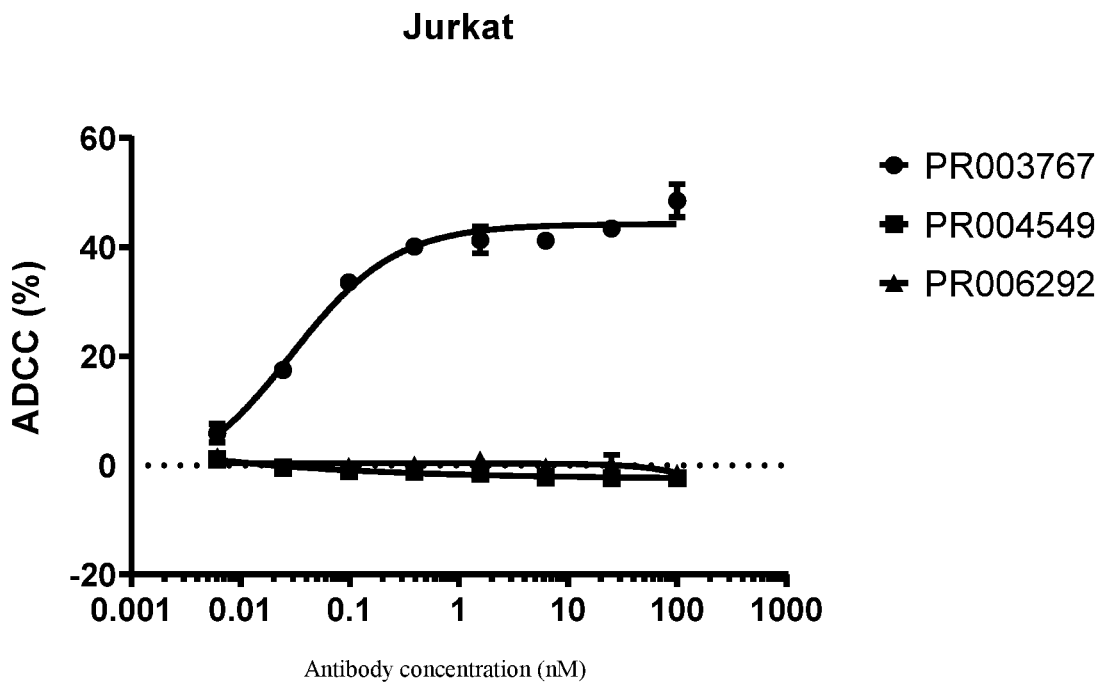
FIGS. 11a-b show the ADCC activity of CLDN18.2×CD3 bispecific antibodies against (a) Jurkat and (b) NUGC4_D8 cells.

CLDN18.2×CD3 bispecific antibodies were assayed for activity of eliciting ADCC effect against Jurkat cells and HEK293/hCLDN 18.2 using a CytoTox 96® non-radioactive cytotoxicity assay kit (Promega, G1780). Human PBMCs were centrifuged at 300 g for 10 min and cultured in a medium (RPMI1640+10% FBS) overnight. NK cells were isolated from the human PBMCs using a human NK cell isolation kit (Miltenyi, 130-092-657). Jurkat cells were centrifuged at 300 g for 5 min and human NK cells at 300 g for 10 min. Then the cells were resuspended in medium (RPMI1640+5% FBS). The target cell density was adjusted to $3\times10^5$ cells/mL, and the NK cell density was adjusted to $1.8\times10^6$/mL. 50 μL of each type of the cells was added to the wells of 96-well plate (effector-to-target ratio of 6:1). Test antibodies were diluted with medium (RPMI1640+5% FBS) to different concentrations, and 50 μL was added to the wells of the 96-well plate. The samples were incubated at 37° C. for 5 h, and then 10× Triton-X 100 lysate (RPMI1640+5% FBS+10% Triton-X 100) was added to the target cell maximum LDH release control well and volume correction control well. The mixture was well mixed and incubated at 37° C. for 0.5 h. The 96-well plate was centrifuged at 300 g for 5 min. 50 μL of the supernatant was taken, and then LDH chromogenic solution was added at a concentration of 50 μL/well. After the mixture was left standing in the absence of light at room temperature for 20 min, the plate was read on MD StakMax ($OD_{490}$). PRO03767 was used as the positive control and Iso hIgG1 (CrownBio, C0001-4) antibody as the negative control. For the calculation of the results, corrected readings were calculated first. The reading of the medium background control well was subtracted from the readings of the experimental wells, target cell spontaneous release LDH control well and effector cell spontaneous release LDH control well, and then the reading of the volume correction control well was subtracted from the reading of the target cell maximum LDH release control well. ADCC activity (%)=(corrected reading of experimental well−corrected reading of effector cell spontaneous release LDH control well−corrected reading of target cell spontaneous release LDH control well)/(corrected reading of target cell maximum LDH release control well−corrected reading of target cell spontaneous release LDH control well)×100. FIG. 11(a) shows the ADCC activity of antibodies against Jurkat cells. PR006292 and PR004549 were unable to elicit ADCC effects against Jurkat cells.

Figure 11B:
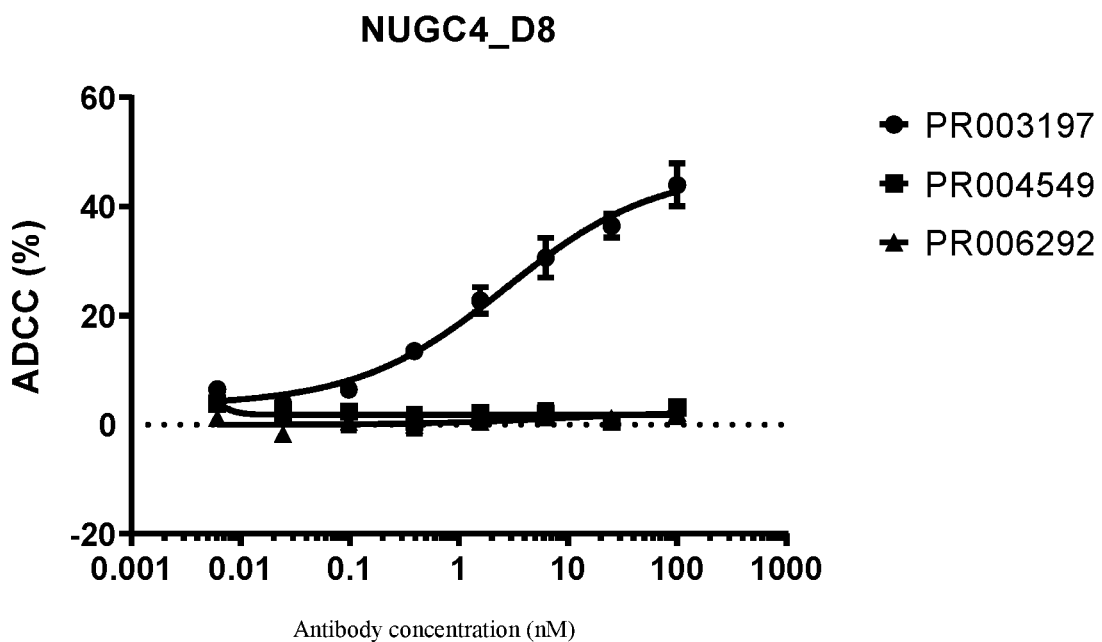

CLDN18.2×CD3 bispecific antibodies were assayed for activity of eliciting an ADCC effect against NUGC4_D8 using NK92/CD16a cells. NUGC4_D8 and NK92/CD16a were resuspended in a medium (RPMI1640+5% FBS). The target cell density was adjusted to $3\times10^5$ cells/mL, and the NK92/CD16a cell density was adjusted to $1.8\times10^6$/mL. 50 μL of each type of the cells was added to the wells of a 96-well plate (effector-to-target ratio of 6:1). Test antibodies were diluted with medium (RPMI1640+5% FBS) to different concentrations, and 50 μL was added to the wells of the 96-well plate. The samples were incubated at 37° C. for 5 h. PR003197 was used as a positive control. FIG. 11(b) shows the ADCC activity of antibodies against NUGC4_D8. PR006292 and PR004549 were unable to elicit ADCC effects against NUGC4_D8 cells.

Example 19

CDC Activity of CLDN18.2×CD3 Bispecific Antibodies

Figure 12A:
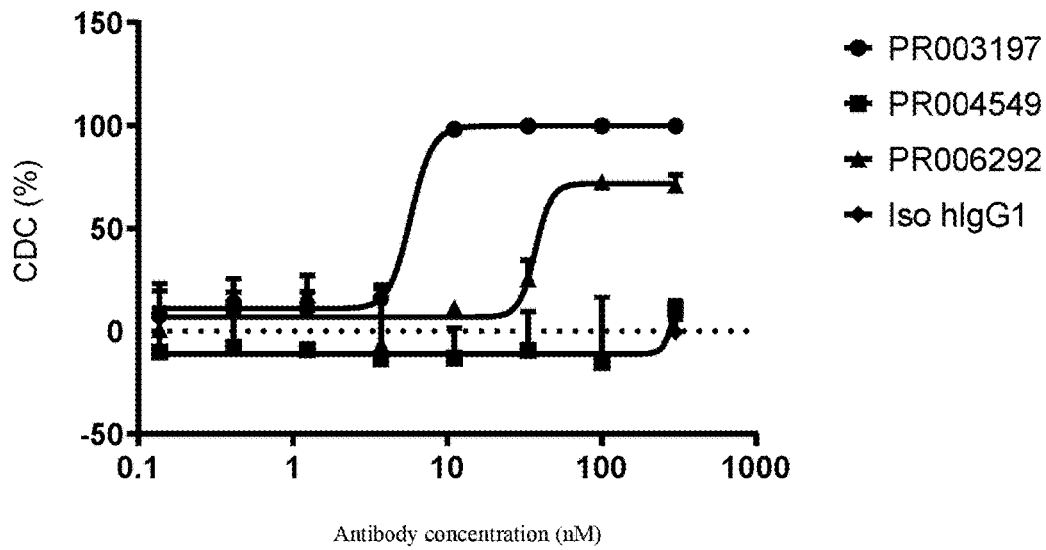
FIGS. 12a-b show the CDC activity of CLDN18.2×CD3 bispecific antibodies against (a) HEK293/hCLDN18.2 and (b) Jurkat cells.
Figure 12B:
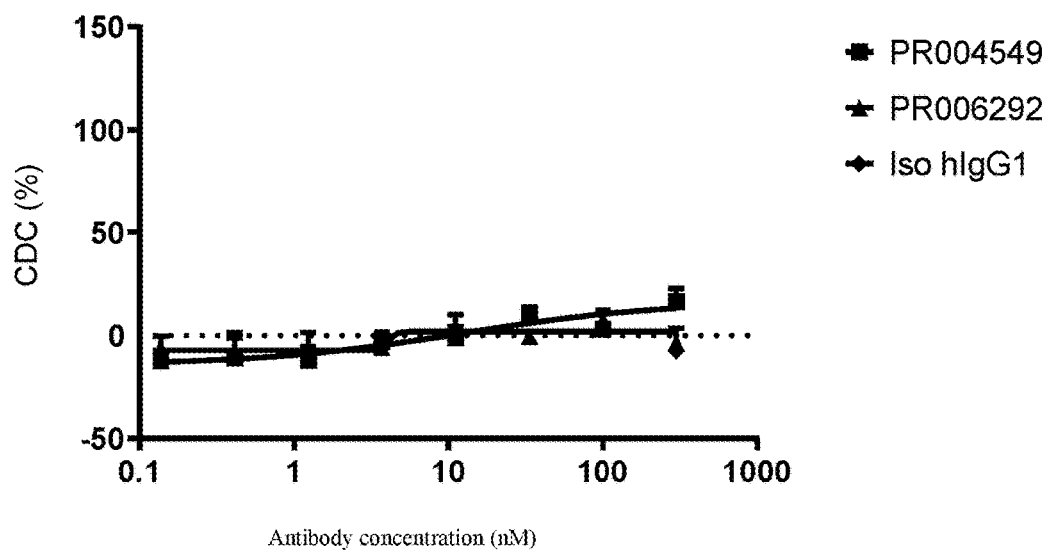

CLDN18.2 antibodies were assayed for CDC effects against HEK293/hCLDN18.2 and Jurkat cells using a CellTiter-Glo luminescent cell viability assay kit (Promega, G7573). The target cells were centrifuged at 300 g for 5 min and then resuspended in RPMI1640 serum-free medium. The target cell density was adjusted to $2\times10^5$ cells/mL, and 25 μL of the cell suspension was added to each well of a 96-well plate. The antibodies were diluted to different concentrations with the serum-free medium, and 25 μL of the antibody dilution was added to each well of the 96-well plate. 50 μL of normal human serum (Access cell culture, 515) was added to a final concentration of 50%, and the resulting mixture was incubated at 37° C. for 24 h. The 96-well plate was left standing at room temperature for 30 min, and 100 μL of CellTiter-Glo chromogenic solution was added to each well at room temperature. Then, the sample was incubated in the absence of light at room temperature for 10 min. The plate was read with PE Enspire. CDC activity (%)=[1−(luminescent sample)/(luminescent mock control)]×100. An IMAB362 analogue was used as a positive control and Iso hIgG1 (CrownBio, C0001-4) antibody as the negative control. FIG. 12 shows the CDC activity of PR006292 antibody against Jurkat cells and human CLDN18.2-overexpressing HEK293 cells. PR006292 induced a greater CDC effect than that induced by PR004549 in HEK293/hCLDN18.2, whereas no CDC activity was observed in Jurkat cells. The CDC activity of CLDN18.2×CD3 bispecific antibodies is specifically shown in Table 28.

TABLE 28

The CDC activity of CLDN18.2 × CD3 bispecific antibodies

| Cell | | PR006292 | PR004549 |
|---|---|---|---|
| HEK293/hCLDN18.2 | Maximum killing rate (%) | 71.8 | 0.00 |
| | $EC_{50}$ (nM) | 37.1 | NA |
| Jurkat | Maximum killing rate (%) | 0.00 | 0.00 |
| | $EC_{50}$ (nM) | NA | NA |

Example 20

Competitive Binding Activity of CLDN18.2×CD3 Bispecific Antibodies

This example is to study the binding of anti-human CLDN18.2 bispecific antibodies to the epitope region of a human CLDN18.2 antigen. Competitive binding experiments were performed at the cellular level using human CLDN18.2-overexpressing HEK293/hCLDN18.2 cells. Briefly, the anti-human CLDN18.2 antibodies PR000400 and PR004549 were biotinylated using a biotinylation kit (ThermoFisher, A35358) according to the instructions. To a 96-well V-bottom plate (Corning, 3894) were added cells at $2\times10^6$ cells/mL and a suspension of human CLDN18.2-overexpressing HEK293T/hCLDN18.2 cells at 50 μL/well, followed by the addition of 25 μL of biotinylated anti-human CLDN18.2 antibody PR000400 or PR004549. The mixture was well mixed and incubated at 4° C. for 30 min. 25 μL of the corresponding serially diluted non-biotinylated anti-human CLDN18.2 antibody was added. The mixture was well mixed and incubated at 4° C. for 1 h. The cells in each well were washed twice with 200 μL of pre-cooled FACS buffer (2% BSA in DPBS) and centrifuged at 500 g at 4° C. for 5 min, and then the supernatant was discarded. A fluorescent secondary antibody (Jackson ImmunoResearch, 016-540-084, 1:500) was added. The mixture was incubated at 4° C. in the absence of light for 1 h. The cells in each well were washed twice with 200 μL of pre-cooled FACS buffer (2% BSA in DPBS) and centrifuged at 500 g at 4° C. for 5 min, and then the supernatant was discarded. Finally, the cells in each well were resuspended in 200 μL of pre-cooled FACS buffer, and the fluorescence signal values were read using a ACEA_NovoCyte. The inhibition rate was calculated using the formula, inhibition rate (%)=(A−B)/A×100 (note: A: fluorescence signal after interaction of biotinylated antibody with ISO (hIgG1) (Crownbio, c0001-4); B: fluorescence signal after interaction of biotinylated antibody with non-biotinylated antibody).

Figure 13A:
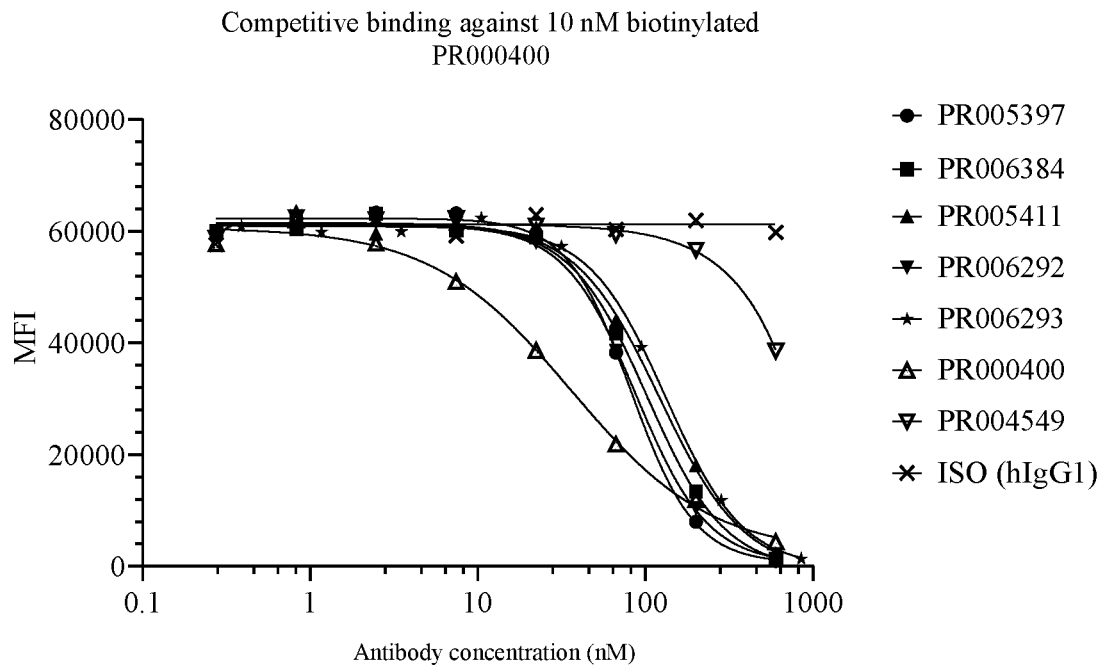
FIGS. 13a-b show the competitive binding activity of CLDN18.2×CD3 bispecific antibodies against (a) PR000400 and (b) PR004549 for HEK293/hCLDN18.2 cells.
Figure 13B:
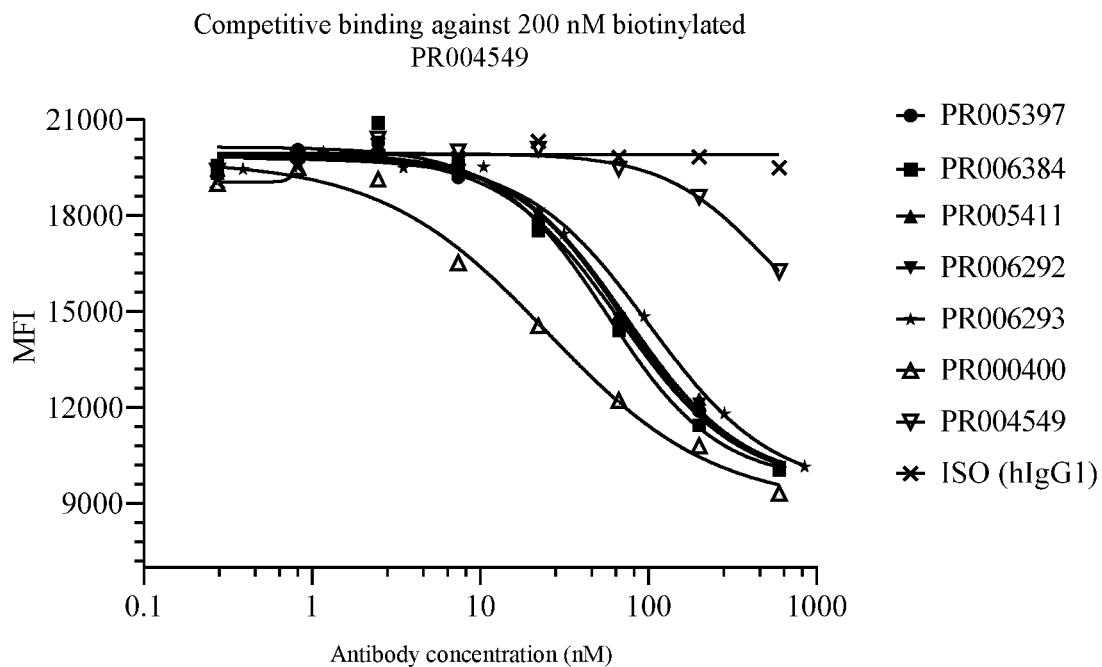

As shown in FIG. 13 and Table 29, the anti-CLDN18.2 bispecific antibodies of the present invention are all able to block the binding of PR000400 or PR004549 to human CLDN18.2, and the detected blocking ability of the antibodies increases with the antibody concentration in a positively correlated manner, indicating that these antibodies have very similar epitopes to those of PR000400 and PR004549. The test antibodies have low binding affinity for HEK293/hCLDN18.1 cells. From the above results, it can be inferred that the test antibodies bind to human CLDN18.2 protein at ECL1 (Extracellular loop 1) rather than ECL2.

TABLE 29

The competitive binding ability of CLDN18.2 antibodies against antibodies PR000400 and PR004549

| Antibody | 10 nM biotinylated PR000400 | | 200 nM biotinylated PR004549 | |
|---|---|---|---|---|
| | IC50 (nM) | Maximum inhibition rate (%) | IC50 (nM) | Maximum inhibition rate (%) |
| PR005397 | 81.8 | 98.4 | 67.5 | 48.0 |
| PR006384 | 103 | 97.8 | 56.7 | 48.5 |
| PR005411 | 122 | 96.2 | 74.4 | 48.0 |
| PR006292 | 87.7 | 97.7 | 70.8 | 48.1 |
| PR006293 | 132 | 97.8 | 100 | 48.0 |
| PR000400 | 36.2 | 92.7 | 25.2 | 52.3 |
| PR004549 | NA | 35.5 | NA | 16.7 |
| ISO hIgG1 | NA | 0.00 | NA | 0.00 |

Example 21

Pharmacokinetics Study on CLDN18.2×CD3 Bispecific Antibodies

Pharmacokinetics studies were carried out as follows using BALB/c nude mice. 6 female BALB/c nude mice weighing 18-22 g were selected and received an antibody dosing by intravenous injection at dose of 5 mg/kg. The whole blood of 3 mice in one group was collected prior to the administration and 15 min, 24 h (1 day), 4 days and 10 days after the administration, and the whole blood of 3 mice in the other group was collected prior to the administration and 5 h, 2 days, 7 days and 14 days after the administration. The whole blood was left standing for 30 min to coagulate, and then centrifuged. The isolated serum sample was cryopreserved at −80° C. until it was taken for analysis. The drug concentration in the mouse serum was quantified by ELISA. The total ELISA (total method) was performed by capturing human Fc-containing antibodies in mouse serum using goat anti-human Fc polyclonal antibody and detected by HRP-labeled goat anti-human Fc secondary antibody. The CLDN18.2 binding domain ELISA (Free X method) was performed by capturing CLDN18.2 binding domain-containing antibodies in the mouse serum using CLDN18.2 protein and detected by HRP-labeled goat anti-human Fc secondary antibody. The plasma concentration data were analyzed using Phoenix WinNonlin software (version 8.2) by non-compartmental analysis (NCA) to evaluate the pharmacokinetic parameters.

Figure 14:
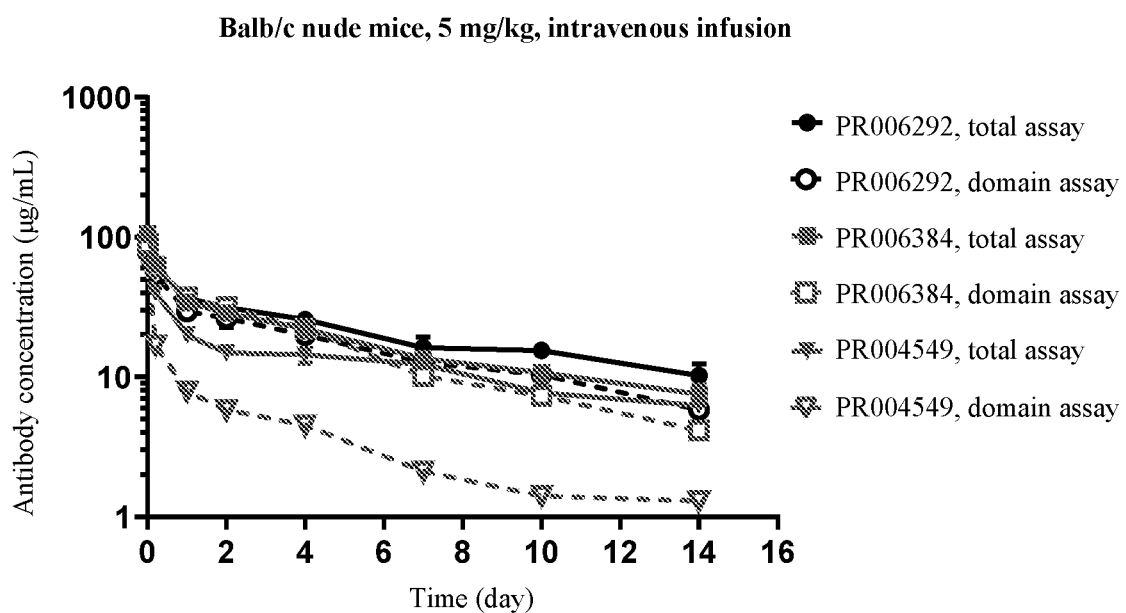
FIG. 14 shows the pharmacokinetics of CLDN18.2×CD3 bispecific antibodies.

The pharmacokinetics of PR006292, PR006384 and PR004549 is shown in FIG. 14, and the pharmacokinetic parameters are shown in Table 30. PR006292 and PR006384 are superior to PR004549 in stability in mice, and have long half-lives and high drug exposure amount in mice.

TABLE 30

Pharmacokinetic parameters of PR006292, PR006384 and PR004549

| | PR004549 | | PR006292 | | PR006384 | |
|---|---|---|---|---|---|---|
| Method | Total assay | Domain assay | Total assay | Domain assay | Total assay | Domain assay |
| $T_{1/2}$ (h) | 7,395 ± 606 | 5,714 ± 464 | 7,395 ± 606 | 5,714 ± 464 | 6,352 ± 325 | 5,751 ± 192 |
| $V_d$ (mL/kg) | 100 | 77.2 | 100 | 77.2 | 100 | 90.5 |
| $AUC_{all}$ (μg/mL h) | 106 | 94.1 | 106 | 94.1 | 106 | 89.7 |
| AUC (%)* | 121 | 132 | 121 | 132 | 141 | 112 |
| Cl (mL/h/kg) | 0.5 | 0.73 | 0.5 | 0.73 | 0.59 | 0.76 |
| $C_0$ (μg/mL) | 173 | 135 | 173 | 135 | 198 | 130 |

*AUC (%) = AUC/AUC$_{(total\ assay;\ mean\ value)}$ × 100

Example 22

In Vivo Pharmacodynamics Studies on CLDN18.2×CD3 Bispecific Antibodies

NUGC4_D8 Tumor Model

In vivo pharmacodynamics studies were carried out by using NCG mice to re-establish the NUGC4_D8 tumor model of human PBMC immune system. The method is specifically as follows. On the day of cell inoculation, each NCG mouse was subcutaneously inoculated with NUGC4_D8 cells and PBMCs. When the mean tumor volume of each group of mice reached 90 mm$^3$, the mice were divided into groups, and a total of one administration was performed through tail veins. After the start of administration, the body weight and the tumor volume were measured twice a week. The tumor volume was calculated as follows: tumor volume (mm$^3$)=0.5×long diameter of tumor× short diameter of tumor$^2$. The data were analyzed using t-test.

Figure 15A:
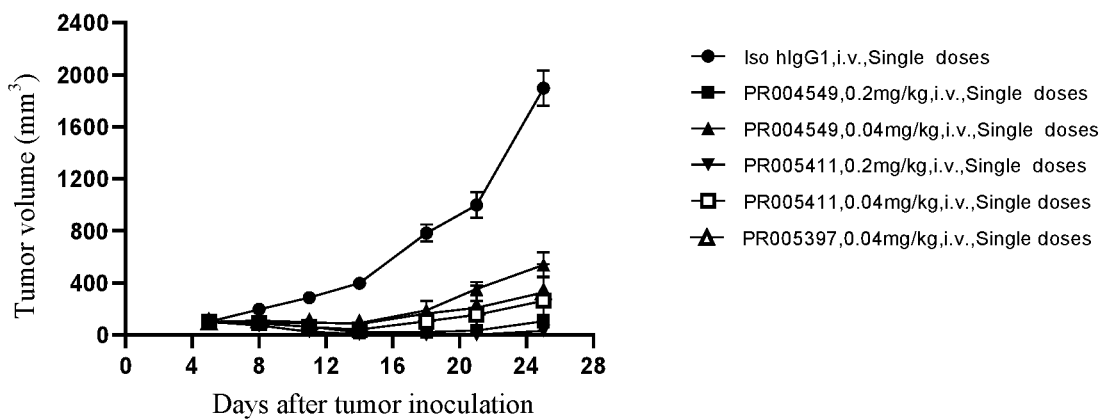
FIGS. 15a-e show in vivo pharmacodynamics studies in (a-b) NUGC4_D8 PBMC, (c) SNU620 PBMC, and (d) HuP-T4 PBMC tumor models and (e) in vivo cytokine storm study on CLDN18.2×CD3 bispecific antibodies.

The in vivo anti-tumor effects of PR005397, PR005411 and PR004549 are shown in FIG. 15(a). Specifically, the mean tumor volume of the Iso hIgG1 control group of mice at day 25 after inoculation was 1897 mm$^3$. The mean tumor volume of the test drug PR004549 (0.2 mg/kg) treatment group at day 25 after inoculation was 104 mm$^3$, showing a significant difference (p value <0.0001) from that of the Iso hIgG1 control group, with the tumor growth inhibition rate TGI (%) being 94.48%. The mean tumor volume of the test drug PR004549 (0.04 mg/kg) treatment group at day 25 after inoculation was 538 mm$^3$, showing a significant difference (p value <0.0001) from that of the Iso hIgG1 control group, with the tumor growth inhibition rate TGI (%) being 71.61%. The mean tumor volume of the test drug PR005411 (0.2 mg/kg) treatment group at day 25 after inoculation was 30 mm$^3$, showing a significant difference (p value <0.0001) from that of the Iso hIgG1 control group, with the tumor growth inhibition rate TGI (%) being 98.39%. The mean tumor volume of the test drug PR005411 (0.04 mg/kg) treatment group at day 25 after inoculation was 263 mm$^3$, showing a significant difference (p value <0.0001) from that of the Iso hIgG1 control group, with the tumor growth inhibition rate TGI (%) being 86.1%. The mean tumor volume of the test drug PR005397 (0.04 mg/kg) treatment group at day 25 after inoculation was 327 mm$^3$, showing a significant difference (p value <0.0001) from that of the Iso hIgG1 control group, with the tumor growth inhibition rate TGI (%) being 82.75%. Throughout the treatment, the animals showed good tolerance for the drugs, with no great weight loss and animals' death occurred. The in vivo anti-tumor effects of PR005397 and PR005411 are superior to that of PR004549.

Figure 15B:
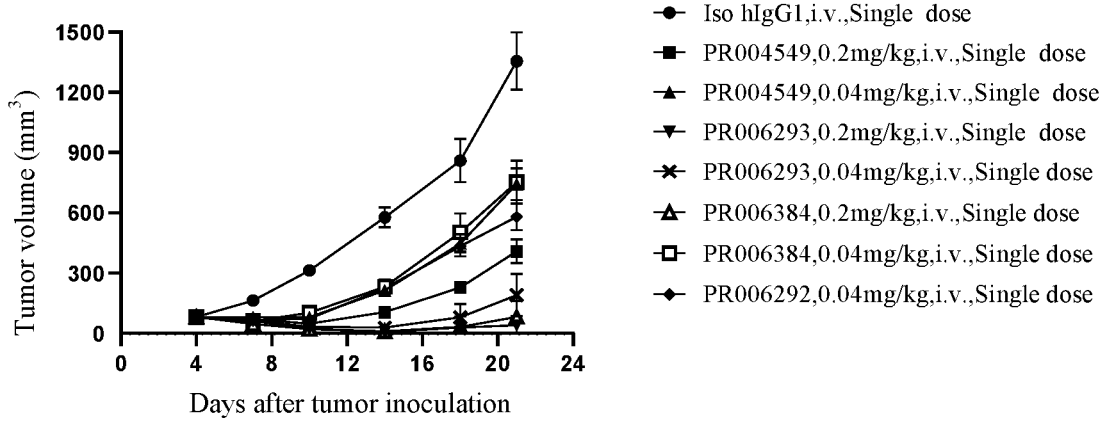

The in vivo anti-tumor effects of PR006292, PR006293, PR006384 and PR004549 are shown in FIG. 15(b). Specifically, the mean tumor volume of the Iso hIgG1 control group of mice at day 25 after inoculation was 1355 mm$^3$. The mean tumor volume of the test drug PR004549 (0.2 mg/kg) treatment group at day 25 after inoculation was 408 mm$^3$, showing a significant difference (p value=0.0001) from that of the Iso hIgG1 control group, with the tumor growth inhibition rate TGI (%) being 69.83%. The mean tumor volume of the test drug PR004549 (0.04 mg/kg) treatment group at day 25 after inoculation was 743 mm$^3$, showing a significant difference (p value=0.0037) from that of the Iso hIgG1 control group, with the tumor growth inhibition rate TGI (%) being 45.15%. The mean tumor volume of the test drug PR006293 (0.2 mg/kg) treatment group at day 25 after inoculation was 39 mm$^3$, showing a significant difference (p value<0.0001) from that of the Iso hIgG1 control group, with the tumor growth inhibition rate TGI (%) being 97.06%. The mean tumor volume of the test drug PR006293 (0.04 mg/kg) treatment group at day 25 after inoculation was 190 mm$^3$, showing a significant difference (p value<0.0001) from that of the Iso hIgG1 control group, with the tumor growth inhibition rate TGI (%) being 85.96%. The mean tumor volume of the test drug PR006384 (0.2 mg/kg) treatment group at day 25 after inoculation was 81 mm$^3$, showing a significant difference (p value<0.0001) from that of the Iso hIgG1 control group, with the tumor growth inhibition rate TGI (%) being 94%. The mean tumor volume of the test drug PR006384 (0.04 mg/kg) treatment group at day 25 after inoculation was 752 mm$^3$, showing a significant difference (p value=0.0071) from that of the Iso hIgG1 control group, with the tumor growth inhibition rate TGI (%) being 44.47%. The mean tumor volume of the test drug PR006292 (0.04 mg/kg) treatment group at day 25 after inoculation was 580 mm$^3$, showing a significant difference (p value=0.0006) from that of the Iso hIgG1 control group, with the tumor growth inhibition rate TGI (%) being 57.15%. Throughout the treatment, the animals showed good tolerance for the drugs, with no great weight loss and animals' death occurred. The in vivo anti-tumor effects of PR006292, PR006293 and PR006384 are superior to that of PR004549.

SNU620 PBMC Tumor Model

In vivo pharmacodynamics studies were carried out by using NCG mice to re-establish the SNU620 tumor model of human PBMC immune system. The method is specifically as follows. On the day of cell inoculation, each NCG mouse was subcutaneously inoculated with SNU620 tumor cells. When the mean tumor volume of each group of mice reached 70 mm$^3$, the mice were divided into groups, and a total of four administrations were performed through tail veins. After the start of administration, the body weight and the tumor volume were measured twice a week. The tumor volume was calculated as follows: tumor volume (mm$^3$) =0.5×long diameter of tumor×short diameter of tumor$^2$. The data were analyzed using t-test.

Figure 15C:
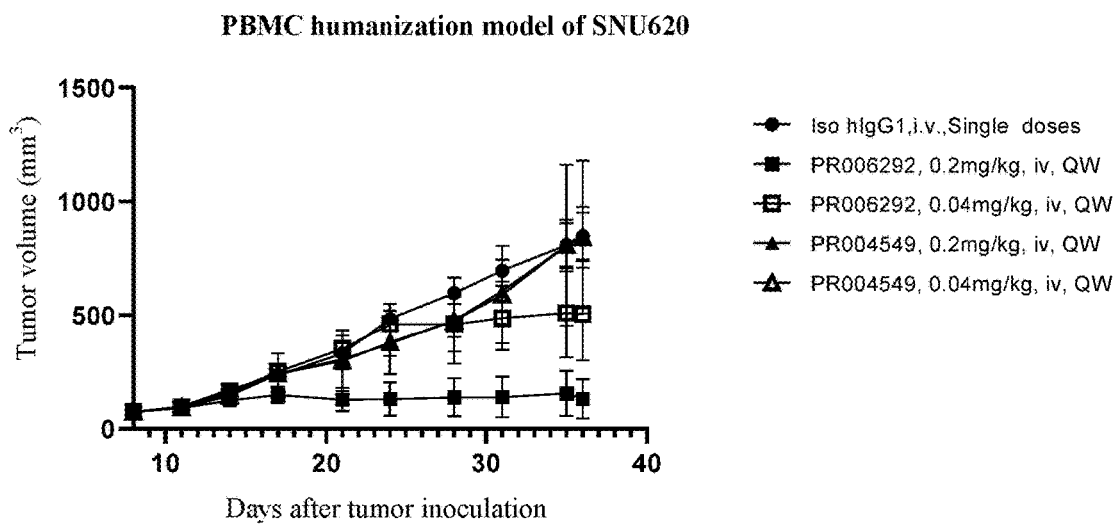

The in vivo anti-tumor effects of PR006292 and PR004549 are shown in FIG. 15(c). Specifically, the mean tumor volume of the Iso hIgG1 control group of mice at day 36 after inoculation was 847 mm$^3$. The mean tumor volume of the test drug PR006292 (0.2 mg/kg) treatment group at day 36 after inoculation was 131 mm$^3$, showing a significant difference (p value=0.0076) from that of the Iso hIgG1 control group, with the tumor growth inhibition rate TGI (%) being 84.53%. The mean tumor volume of the test drug PR006292 (0.04 mg/kg) treatment group at day 36 after inoculation was 505 mm$^3$, showing no significant difference (p value=0.3856) from that of the Iso hIgG1 control group, with the tumor growth inhibition rate TGI (%) being 40.36%. The mean tumor volume of the test drug PR004549 (0.2 mg/kg) treatment group at day 36 after inoculation was 858 mm$^3$, showing a significant difference (p value>0.9999) from that of the Iso hIgG1 control group, with the tumor growth inhibition rate TGI (%) being −1.28%. The mean tumor volume of the test drug PR004549 (0.04 mg/kg) treatment group at day 36 after inoculation was 844 mm$^3$, showing a significant difference (p value>0.9999) from that of the Iso hIgG1 control group, with the tumor growth inhibition rate TGI (%) being 0.39%. Throughout the treatment, the animals showed good tolerance for the drugs, with no great weight loss and animals' death occurred.

HuP-T4 PBMC Tumor Model

In vivo pharmacodynamics studies were carried out by using NCG mice to re-establish the HuP-T4 tumor model of human PBMC immune system. The method is specifically as follows. On the day of cell inoculation, each NCG mouse was subcutaneously inoculated with HuP-T4 tumor cells. When the mean tumor volume of each group of mice reached 130 mm$^3$, the mice were divided into groups, and a total of four administrations were performed through tail veins. After the start of administration, the body weight and the tumor volume were measured twice a week. The tumor volume was calculated as follows: tumor volume (mm$^3$) =0.5×long diameter of tumor×short diameter of tumor$^2$. The data were analyzed using t-test.

Figure 15D:
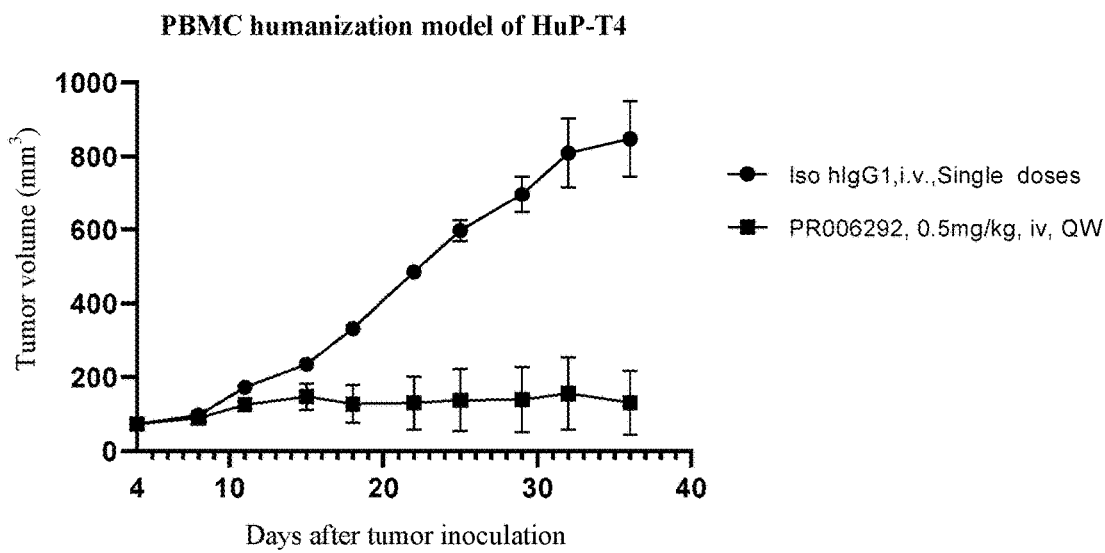

The in vivo anti-tumor effect of PR006292 is shown in FIG. 15(d). Specifically, the mean tumor volume of the Iso hIgG1 control group of mice at day 36 after inoculation was 1059 mm$^3$. The mean tumor volume of the test drug PR006292 (0.5 mg/kg) treatment group at day 36 after inoculation was 129 mm$^3$, showing a significant difference (p value=0.0022) from that of the Iso hIgG1 control group, with the tumor growth inhibition rate TGI (%) being 87.75%. Throughout the treatment, the animals showed good tolerance for the drugs, with no great weight loss and animals' death occurred.

In Vivo Cytokine Release Test in Mouse

In vivo cytokine storm studies were carried out by using NCG mice to re-establish the human PBMC immune system. The method is specifically as follows. Each NCG mouse was intravenously injected with 2×10$^7$ human PBMCs, and at next day, intravenously administered with PR006292, PR004549 and control IgG1 antibodies. Blood was taken to collect serum at hr 0 (before administration), 4 and 24 hrs after administration. The MSD method was utilized to detect the levels of a plurality of cytokines in the serum, including IFN-γ, IL-10, IL-12p70, IL-13, IL-1β, IL-2, IL-4, IL-6, IL-8 and TNF-α. The data were analyzed using t-test.

Figure 15E:
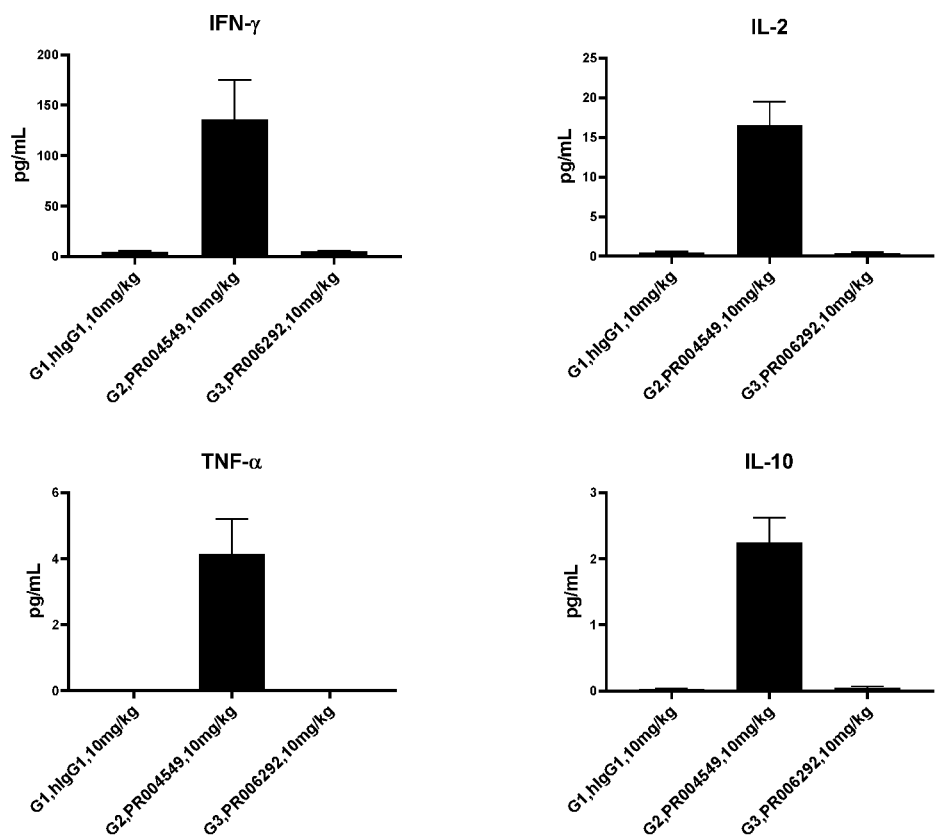

FIG. 15(e) shows the expression of a part of the cytokines that were detectable in the mouse serum 4 hrs after injection of the antibodies. The results showed that PR006292 induced a lower release of the cytokines such as IFN-γ, IL-2 and TNF-α compared to the control antibody PR004549, indicating a better safety.

---

The invention claimed is:

1. A CLDN18.2-targeting antibody comprising a heavy chain variable region comprising HCDR1, HCDR2 and HCDR3, wherein the HCDR1 comprises an amino acid sequence as set forth in SEQ ID NO: 16, the HCDR2 comprises an amino acid sequence as set forth in SEQ ID NO: 51, and the HCDR3 comprises an amino acid sequence as set forth in SEQ ID NO: 78.

2. The antibody according to claim 1, wherein the heavy chain variable region further comprises framework regions, among which the HFR1 comprises an amino acid sequence as set forth in SEQ ID NO: 6, the HFR2 comprises an amino acid sequence as set forth in SEQ ID NO: 29, the HFR3 comprises an amino acid sequence as set forth in SEQ ID NO: 64, and the HFR4 comprises an amino acid sequence as set forth in SEQ ID NO: 86.

3. The antibody according to claim 1, wherein the heavy chain variable region comprises an amino acid sequence as set forth in SEQ ID NO: 162.

4. The antibody according to claim 1, wherein the antibody further comprises a heavy chain constant region.

5. A bispecific antibody comprising a first protein functional region targeting CD3 and a second protein functional region targeting CLDN18.2; wherein the second protein functional region comprises a heavy chain variable region comprising HCDR1, HCDR2 and HCDR3, wherein the HCDR1, the HCDR2 and the HCDR3 comprise amino acid sequences as set forth in SEQ ID NO: 16, SEQ ID NO: 51 and SEQ ID NO: 78, respectively.

6. The bispecific antibody according to claim 5, wherein the first protein functional region comprises a light chain variable region comprising LCDR1, LCDR2 and LCDR3 as set forth in SEQ ID NO: 101, SEQ ID NO: 116 and SEQ ID NO: 131, respectively, and a heavy chain variable region comprising HCDR1, HCDR2 and HCDR3 as set forth in SEQ ID NO: 11, SEQ ID NO: 38 and SEQ ID NO: 72, respectively.

7. The bispecific antibody according to claim 5, wherein the bispecific antibody comprises three polypeptide chains in the following form:
a first polypeptide chain as shown in formula:
$VH_{CLDN18.2}$-linker peptide-$VH_{CLDN18.2}$-hinge-CH2-CH3, wherein the linker peptide comprises an amino acid sequence as set forth in SEQ ID NO: 246; a second polypeptide chain as shown in formula: $VH_{CD3}$-CH1-hinge-CH2-CH3; and a third polypeptide chain as shown in formula: $VL_{CD3}$-CL.

8. The bispecific antibody according to claim 7, wherein the first polypeptide chain comprises an amino acid sequence as set forth in SEQ ID NO: 236, the second polypeptide chain comprises an amino acid sequence as set forth in SEQ ID NO: 235, and the third polypeptide chain comprises an amino acid sequence as set forth in SEQ ID NO: 200.

9. A pharmaceutical composition comprising the antibody according to claim 1, and
a pharmaceutically acceptable carrier; wherein
the pharmaceutical composition further comprises one or more of the group consisting of a hormonal agent, a small molecule-targeted agent, a proteasome inhibitor, an imaging agent, a diagnostic agent, a chemotherapeutic agent, an oncolytic drug, a cytotoxic agent, a cytokine, an activator of a costimulatory molecule, an inhibitor of an inhibitory molecule, and a vaccine.

10. A kit of parts comprising a kit A and a kit B,
wherein: the kit A comprises the antibody according to claim 1; and
the kit B comprises other anti-tumor antibodies or a pharmaceutical composition comprising the other anti-tumor antibodies, and/or one or more of the group consisting of a hormonal agent, a small molecule-targeted agent, a proteasome inhibitor, an imaging agent, a diagnostic agent, a chemotherapeutic agent, an oncolytic drug, a cytotoxic agent, a cytokine, an activator of a co-stimulatory molecule, an inhibitor of an inhibitory molecule, and a vaccine.

11. The bispecific antibody according to claim 5, wherein the CLDN18.2-targeting heavy chain variable region comprises an amino acid sequence as set forth in SEQ ID NO: 162.

12. The bispecific antibody according to claim 6, wherein the CD3-targeting functional region comprises a heavy chain variable region comprising an amino acid sequence as set forth in SEQ ID NO: 149 and a light chain variable region comprising an amino acid sequence as set forth in SEQ ID NO: 168.

13. A pharmaceutical composition comprising the bispecific antibody according to claim 5, and a pharmaceutically acceptable carrier.

14. The pharmaceutical composition of claim 13, further comprising one or more other anti-tumor antibodies, and/or one or more of the group consisting of a hormonal agent, a small molecule-targeted agent, a proteasome inhibitor, an imaging agent, a diagnostic agent, a chemotherapeutic agent, an oncolytic drug, a cytotoxic agent, a cytokine, an activator of a costimulatory molecule, an inhibitor of an inhibitory molecule, and a vaccine.

15. A pharmaceutical composition comprising the bispecific antibody according to claim 8, and a pharmaceutically acceptable carrier.

16. The pharmaceutical composition of claim 15, further comprising one or more other anti-tumor antibodies, and/or one or more of the group consisting of a hormonal agent, a small molecule-targeted agent, a proteasome inhibitor, an imaging agent, a diagnostic agent, a chemotherapeutic agent, an oncolytic drug, a cytotoxic agent, a cytokine, an activator of a costimulatory molecule, an inhibitor of an inhibitory molecule, and a vaccine.

17. A kit of parts comprising a kit A and a kit B, wherein:
the kit A
comprises a pharmaceutical composition comprising the bispecific antibody
according to claim 5; and
the kit B comprises a pharmaceutical composition comprising one or more other anti-tumor antibodies, and/or one or more of the group consisting of a hormonal agent, a small molecule-targeted agent, a proteasome inhibitor, an imaging agent, a diagnostic agent, a chemotherapeutic agent, an oncolytic drug, a cytotoxic agent, a cytokine, an activator of a co-stimulatory molecule, an inhibitor of an inhibitory molecule, and a vaccine.

* * * * *

SEQUENCE LISTING

```
Sequence total quantity: 250
SEQ ID NO: 1            moltype = AA  length = 25
FEATURE                 Location/Qualifiers
REGION                  1..25
                        note = PR000325 HFWR1 Chothia
source                  1..25
                        mol_type = protein
                        organism = synthetic construct
SEQUENCE: 1
QVQLVQSGAE VKKPGQSLRI SCKGA                                           25

SEQ ID NO: 2            moltype = AA  length = 25
FEATURE                 Location/Qualifiers
REGION                  1..25
                        note = PR000400 HFWR1 Chothia
source                  1..25
                        mol_type = protein
                        organism = synthetic construct
SEQUENCE: 2
QVQLQQPGAE LVRPGASVKL SCKAS                                           25

SEQ ID NO: 3            moltype = AA  length = 25
FEATURE                 Location/Qualifiers
REGION                  1..25
                        note = PR001848 HFWR1 Chothia, PR001861 HFWR1 Chothia,
                         PR002725HFWR1 Chothia, PR002726 HFWR1 Chothia
source                  1..25
                        mol_type = protein
                        organism = synthetic construct
SEQUENCE: 3
EVQLLESGGG LVQPGGSLRL SCAAS                                           25

SEQ ID NO: 4            moltype = AA  length = 25
FEATURE                 Location/Qualifiers
REGION                  1..25
                        note = PR003767 HFWR1 Chothia
source                  1..25
                        mol_type = protein
                        organism = synthetic construct
SEQUENCE: 4
EVRLQQSGPD LIKPGASVKM SCKAS                                           25

SEQ ID NO: 5            moltype = AA  length = 25
FEATURE                 Location/Qualifiers
REGION                  1..25
                        note = PR003886 HFWR1 Chothia
source                  1..25
                        mol_type = protein
                        organism = synthetic construct
SEQUENCE: 5
```

```
EVQLVESGGG LVQPGGSLKL SCAAS                                              25

SEQ ID NO: 6            moltype = AA  length = 25
FEATURE                 Location/Qualifiers
REGION                  1..25
                        note = PR004227 HFWR1 Chothia, PR004533 HFWR1 Chothia,
                         PR004536HFWR1 Chothia, PR004540 HFWR1 Chothia, PR004949
                         HFWR1Chothia, PR004950 HFWR1 Chothia, PR004952 HFWR1
                         Chothia,PR007242 HFWR1 Chothia, PR007243
source                  1..25
                        mol_type = protein
                        organism = synthetic construct
SEQUENCE: 6
EVQLVESGGG LVQPGGSLRL SCAAS                                              25

SEQ ID NO: 7            moltype = AA  length = 25
FEATURE                 Location/Qualifiers
REGION                  1..25
                        note = PR004953 HFWR1 Chothia
source                  1..25
                        mol_type = protein
                        organism = synthetic construct
SEQUENCE: 7
EVQLVESGGG VVQPGRSLRL SCAAS                                              25

SEQ ID NO: 8            moltype = AA  length = 26
FEATURE                 Location/Qualifiers
REGION                  1..26
                        note = PR005080 HFWR1 Chothia
source                  1..26
                        mol_type = protein
                        organism = synthetic construct
SEQUENCE: 8
QVKLLQSGAA LVPKPGDSMK MSCKAS                                             26

SEQ ID NO: 9            moltype = AA  length = 7
FEATURE                 Location/Qualifiers
REGION                  1..7
                        note = PR000325 HCDR1 Chothia
source                  1..7
                        mol_type = protein
                        organism = synthetic construct
SEQUENCE: 9
GYSFSTY                                                                   7

SEQ ID NO: 10           moltype = AA  length = 7
FEATURE                 Location/Qualifiers
REGION                  1..7
                        note = PR000400 HCDR1 Chothia
source                  1..7
                        mol_type = protein
                        organism = synthetic construct
SEQUENCE: 10
GYTFTSY                                                                   7

SEQ ID NO: 11           moltype = AA  length = 7
FEATURE                 Location/Qualifiers
REGION                  1..7
                        note = PR001848 HCDR1 Chothia, PR003886 HCDR1 Chothia
source                  1..7
                        mol_type = protein
                        organism = synthetic construct
SEQUENCE: 11
GFTFSTY                                                                   7

SEQ ID NO: 12           moltype = AA  length = 7
FEATURE                 Location/Qualifiers
REGION                  1..7
                        note = PR001861 HCDR1 Chothia
source                  1..7
                        mol_type = protein
                        organism = synthetic construct
SEQUENCE: 12
GFSFSSF                                                                   7

SEQ ID NO: 13           moltype = AA  length = 7
FEATURE                 Location/Qualifiers
REGION                  1..7
                        note = PR002725 HCDR1 Chothia
```

```
                                    source                  1..7
                                                            mol_type = protein
                                                            organism = synthetic construct
SEQUENCE: 13
GFTFSGY                                                                                            7

SEQ ID NO: 14           moltype = AA  length = 7
FEATURE                 Location/Qualifiers
REGION                  1..7
                        note = PR002726 HCDR1 Chothia
source                  1..7
                        mol_type = protein
                        organism = synthetic construct
SEQUENCE: 14
GFTFSSF                                                                                            7

SEQ ID NO: 15           moltype = AA  length = 7
FEATURE                 Location/Qualifiers
REGION                  1..7
                        note = PR003767 HCDR1 Chothia
source                  1..7
                        mol_type = protein
                        organism = synthetic construct
SEQUENCE: 15
GYTFTGY                                                                                            7

SEQ ID NO: 16           moltype = AA  length = 7
FEATURE                 Location/Qualifiers
REGION                  1..7
                        note = PR004227 HCDR1 Chothia, PR004533 HCDR1 Chothia,
                         PR004536HCDR1 Chothia, PR004952 HCDR1 Chothia, PR004953
                         HCDR1Chothia, PR007242 HCDR1 Chothia, PR007243 HCDR1
                         Chothia,PR007244 HCDR1 Chothia, PR007245
source                  1..7
                        mol_type = protein
                        organism = synthetic construct
SEQUENCE: 16
GFTFSSY                                                                                            7

SEQ ID NO: 17           moltype = AA  length = 7
FEATURE                 Location/Qualifiers
REGION                  1..7
                        note = PR004540 HCDR1 Chothia
source                  1..7
                        mol_type = protein
                        organism = synthetic construct
SEQUENCE: 17
GFTFSIY                                                                                            7

SEQ ID NO: 18           moltype = AA  length = 7
FEATURE                 Location/Qualifiers
REGION                  1..7
                        note = PR004949 HCDR1 Chothia, PR004950 HCDR1 Chothia
source                  1..7
                        mol_type = protein
                        organism = synthetic construct
SEQUENCE: 18
GFTFSAY                                                                                            7

SEQ ID NO: 19           moltype = AA  length = 7
FEATURE                 Location/Qualifiers
REGION                  1..7
                        note = PR005080 HCDR1 Chothia
source                  1..7
                        mol_type = protein
                        organism = synthetic construct
SEQUENCE: 19
GYTFTHD                                                                                            7

SEQ ID NO: 20           moltype = AA  length = 19
FEATURE                 Location/Qualifiers
REGION                  1..19
                        note = PR000325 HFWR2 Chothia
source                  1..19
                        mol_type = protein
                        organism = synthetic construct
SEQUENCE: 20
WIGWVRQMPG KGLEWMGII                                                                              19
```

```
SEQ ID NO: 21              moltype = AA   length = 19
FEATURE                    Location/Qualifiers
REGION                     1..19
                           note = PR000400 HFWR2 Chothia
source                     1..19
                           mol_type = protein
                           organism = synthetic construct
SEQUENCE: 21
WINWVKQRPG QGLEWIGNI                                                           19

SEQ ID NO: 22              moltype = AA   length = 19
FEATURE                    Location/Qualifiers
REGION                     1..19
                           note = PR001848 HFWR2 Chothia
source                     1..19
                           mol_type = protein
                           organism = synthetic construct
SEQUENCE: 22
AMNWVRQAPG KGLEWVSRI                                                           19

SEQ ID NO: 23              moltype = AA   length = 19
FEATURE                    Location/Qualifiers
REGION                     1..19
                           note = PR001861 HFWR2 Chothia
source                     1..19
                           mol_type = protein
                           organism = synthetic construct
SEQUENCE: 23
AMSWVRQAPG KGLEWVSAL                                                           19

SEQ ID NO: 24              moltype = AA   length = 19
FEATURE                    Location/Qualifiers
REGION                     1..19
                           note = PR002725 HFWR2 Chothia
source                     1..19
                           mol_type = protein
                           organism = synthetic construct
SEQUENCE: 24
VMSWVRQAPG KGLEWVSAI                                                           19

SEQ ID NO: 25              moltype = AA   length = 19
FEATURE                    Location/Qualifiers
REGION                     1..19
                           note = PR002726 HFWR2 Chothia
source                     1..19
                           mol_type = protein
                           organism = synthetic construct
SEQUENCE: 25
VMSWVRQAPG KGLEWVSTI                                                           19

SEQ ID NO: 26              moltype = AA   length = 19
FEATURE                    Location/Qualifiers
REGION                     1..19
                           note = PR003767 HFWR2 Chothia
source                     1..19
                           mol_type = protein
                           organism = synthetic construct
SEQUENCE: 26
VMHWVKQRPG QGLEWIGFI                                                           19

SEQ ID NO: 27              moltype = AA   length = 19
FEATURE                    Location/Qualifiers
REGION                     1..19
                           note = PR003886 HFWR2 Chothia
source                     1..19
                           mol_type = protein
                           organism = synthetic construct
SEQUENCE: 27
AMNWVRQASG KGLEWVGRI                                                           19

SEQ ID NO: 28              moltype = AA   length = 19
FEATURE                    Location/Qualifiers
REGION                     1..19
                           note = PR004227 HFWR2 Chothia
source                     1..19
                           mol_type = protein
                           organism = synthetic construct
SEQUENCE: 28
WMHWVRQAPG KGLEWVSYI                                                           19
```

```
SEQ ID NO: 29            moltype = AA  length = 19
FEATURE                  Location/Qualifiers
REGION                   1..19
                         note = PR004533 HFWR2 Chothia, PR004950 HFWR2 Chothia,
                         PR007242HFWR2 Chothia, PR007243 HFWR2 Chothia, PR007244
                         HFWR2Chothia, PR007245 HFWR2 Chothia, PR007246 HFWR2
                         Chothia,PR007248 HFWR2 Chothia
source                   1..19
                         mol_type = protein
                         organism = synthetic construct
SEQUENCE: 29
WMHWVRQVPG KGLVWVSRI                                                            19

SEQ ID NO: 30            moltype = AA  length = 19
FEATURE                  Location/Qualifiers
REGION                   1..19
                         note = PR004536 HFWR2 Chothia, PR007247 HFWR2 Chothia
source                   1..19
                         mol_type = protein
                         organism = synthetic construct
SEQUENCE: 30
WMYWVRQVPG KGLVWVSHI                                                            19

SEQ ID NO: 31            moltype = AA  length = 19
FEATURE                  Location/Qualifiers
REGION                   1..19
                         note = PR004540 HFWR2 Chothia
source                   1..19
                         mol_type = protein
                         organism = synthetic construct
SEQUENCE: 31
WMHWVRQVPG KGLVLVSRI                                                            19

SEQ ID NO: 32            moltype = AA  length = 19
FEATURE                  Location/Qualifiers
REGION                   1..19
                         note = PR004949 HFWR2 Chothia
source                   1..19
                         mol_type = protein
                         organism = synthetic construct
SEQUENCE: 32
WMHWVRQVPG RGLVWVSRI                                                            19

SEQ ID NO: 33            moltype = AA  length = 19
FEATURE                  Location/Qualifiers
REGION                   1..19
                         note = PR004952 HFWR2 Chothia
source                   1..19
                         mol_type = protein
                         organism = synthetic construct
SEQUENCE: 33
WMHWVRQAPG KGLVWVSRI                                                            19

SEQ ID NO: 34            moltype = AA  length = 19
FEATURE                  Location/Qualifiers
REGION                   1..19
                         note = PR004953 HFWR2 Chothia
source                   1..19
                         mol_type = protein
                         organism = synthetic construct
SEQUENCE: 34
GMHWVRQAPG KGLEWVAVI                                                            19

SEQ ID NO: 35            moltype = AA  length = 19
FEATURE                  Location/Qualifiers
REGION                   1..19
                         note = PR005080 HFWR2 Chothia
source                   1..19
                         mol_type = protein
                         organism = synthetic construct
SEQUENCE: 35
IIHWVRQSHG KSLEWIGYI                                                            19

SEQ ID NO: 36            moltype = AA  length = 6
FEATURE                  Location/Qualifiers
REGION                   1..6
                         note = PR000325 HCDR2 Chothia
source                   1..6
```

```
                    mol_type = protein
                    organism = synthetic construct
SEQUENCE: 36
YPDDSD                                                                    6

SEQ ID NO: 37       moltype = AA   length = 6
FEATURE             Location/Qualifiers
REGION              1..6
                    note = PR000400 HCDR2 Chothia
source              1..6
                    mol_type = protein
                    organism = synthetic construct
SEQUENCE: 37
YPSDSY                                                                    6

SEQ ID NO: 38       moltype = AA   length = 8
FEATURE             Location/Qualifiers
REGION              1..8
                    note = PR001848 HCDR2 Chothia, PR003886 HCDR2 Chothia
source              1..8
                    mol_type = protein
                    organism = synthetic construct
SEQUENCE: 38
RSKYNNYA                                                                  8

SEQ ID NO: 39       moltype = AA   length = 6
FEATURE             Location/Qualifiers
REGION              1..6
                    note = PR001861 HCDR2 Chothia, PR002725 HCDR2 Chothia
source              1..6
                    mol_type = protein
                    organism = synthetic construct
SEQUENCE: 39
SGSGGS                                                                    6

SEQ ID NO: 40       moltype = AA   length = 6
FEATURE             Location/Qualifiers
REGION              1..6
                    note = PR002726 HCDR2 Chothia
source              1..6
                    mol_type = protein
                    organism = synthetic construct
SEQUENCE: 40
SGSGRS                                                                    6

SEQ ID NO: 41       moltype = AA   length = 6
FEATURE             Location/Qualifiers
REGION              1..6
                    note = PR003767 HCDR2 Chothia
source              1..6
                    mol_type = protein
                    organism = synthetic construct
SEQUENCE: 41
NPYNDD                                                                    6

SEQ ID NO: 42       moltype = AA   length = 6
FEATURE             Location/Qualifiers
REGION              1..6
                    note = PR004227 HCDR2 Chothia
source              1..6
                    mol_type = protein
                    organism = synthetic construct
SEQUENCE: 42
NNDGSS                                                                    6

SEQ ID NO: 43       moltype = AA   length = 6
FEATURE             Location/Qualifiers
REGION              1..6
                    note = PR004533 HCDR2 Chothia, PR004949 HCDR2 Chothia,
                    PR004950HCDR2 Chothia, PR004952 HCDR2 Chothia
source              1..6
                    mol_type = protein
                    organism = synthetic construct
SEQUENCE: 43
NSDGSR                                                                    6

SEQ ID NO: 44       moltype = AA   length = 6
FEATURE             Location/Qualifiers
REGION              1..6
```

```
                          note = PR004536 HCDR2 Chothia
source                    1..6
                          mol_type = protein
                          organism = synthetic construct
SEQUENCE: 44
NSDGST                                                                    6

SEQ ID NO: 45             moltype = AA  length = 6
FEATURE                   Location/Qualifiers
REGION                    1..6
                          note = PR004540 HCDR2 Chothia
source                    1..6
                          mol_type = protein
                          organism = synthetic construct
SEQUENCE: 45
SSDGNY                                                                    6

SEQ ID NO: 46             moltype = AA  length = 6
FEATURE                   Location/Qualifiers
REGION                    1..6
                          note = PR004953 HCDR2 Chothia
source                    1..6
                          mol_type = protein
                          organism = synthetic construct
SEQUENCE: 46
GYDGRN                                                                    6

SEQ ID NO: 47             moltype = AA  length = 6
FEATURE                   Location/Qualifiers
REGION                    1..6
                          note = PR005080 HCDR2 Chothia
source                    1..6
                          mol_type = protein
                          organism = synthetic construct
SEQUENCE: 47
NPYNGG                                                                    6

SEQ ID NO: 48             moltype = AA  length = 6
FEATURE                   Location/Qualifiers
REGION                    1..6
                          note = PR007242 HCDR2 Chothia
source                    1..6
                          mol_type = protein
                          organism = synthetic construct
SEQUENCE: 48
NFDSSR                                                                    6

SEQ ID NO: 49             moltype = AA  length = 6
FEATURE                   Location/Qualifiers
REGION                    1..6
                          note = PR007243 HCDR2 Chothia
source                    1..6
                          mol_type = protein
                          organism = synthetic construct
SEQUENCE: 49
SSAGSR                                                                    6

SEQ ID NO: 50             moltype = AA  length = 6
FEATURE                   Location/Qualifiers
REGION                    1..6
                          note = PR007244 HCDR2 Chothia
source                    1..6
                          mol_type = protein
                          organism = synthetic construct
SEQUENCE: 50
DSRGSR                                                                    6

SEQ ID NO: 51             moltype = AA  length = 6
FEATURE                   Location/Qualifiers
REGION                    1..6
                          note = PR007245 HCDR2 Chothia
source                    1..6
                          mol_type = protein
                          organism = synthetic construct
SEQUENCE: 51
SSDASR                                                                    6

SEQ ID NO: 52             moltype = AA  length = 6
FEATURE                   Location/Qualifiers
```

```
                          -continued

REGION                    1..6
                          note = PR007246 HCDR2 Chothia
source                    1..6
                          mol_type = protein
                          organism = synthetic construct
SEQUENCE: 52
SSTGSR                                                                  6

SEQ ID NO: 53             moltype = AA  length = 6
FEATURE                   Location/Qualifiers
REGION                    1..6
                          note = PR007247 HCDR2 Chothia
source                    1..6
                          mol_type = protein
                          organism = synthetic construct
SEQUENCE: 53
NPLGST                                                                  6

SEQ ID NO: 54             moltype = AA  length = 6
FEATURE                   Location/Qualifiers
REGION                    1..6
                          note = PR007248 HCDR2 Chothia
source                    1..6
                          mol_type = protein
                          organism = synthetic construct
SEQUENCE: 54
NHDSSR                                                                  6

SEQ ID NO: 55             moltype = AA  length = 41
FEATURE                   Location/Qualifiers
REGION                    1..41
                          note = PR000325 HFWR3 Chothia
source                    1..41
                          mol_type = protein
                          organism = synthetic construct
SEQUENCE: 55
TRYSPSFEGQ VTISVDKSIT TAYLHWSSLK ASDTAIYYCA R                           41

SEQ ID NO: 56             moltype = AA  length = 41
FEATURE                   Location/Qualifiers
REGION                    1..41
                          note = PR000400 HFWR3 Chothia
source                    1..41
                          mol_type = protein
                          organism = synthetic construct
SEQUENCE: 56
TNYNQKFKDK ATLTVDKSSS TAYMQLSSPT SEDSAVYYCT R                           41

SEQ ID NO: 57             moltype = AA  length = 41
FEATURE                   Location/Qualifiers
REGION                    1..41
                          note = PR001848 HFWR3 Chothia
source                    1..41
                          mol_type = protein
                          organism = synthetic construct
SEQUENCE: 57
TYYADSVKDR FTISRDDSKS TLYLQMNSLR AEDTAVYYCV R                           41

SEQ ID NO: 58             moltype = AA  length = 41
FEATURE                   Location/Qualifiers
REGION                    1..41
                          note = PR001861 HFWR3 Chothia
source                    1..41
                          mol_type = protein
                          organism = synthetic construct
SEQUENCE: 58
TYYTDSVKGR FTVSRDNSKN TLYLQMNSLR AEDTAIYYCA N                           41

SEQ ID NO: 59             moltype = AA  length = 41
FEATURE                   Location/Qualifiers
REGION                    1..41
                          note = PR002725 HFWR3 Chothia
source                    1..41
                          mol_type = protein
                          organism = synthetic construct
SEQUENCE: 59
KYYADSVKGR FTISRDNSKN TLYLQMNSLR AEDTAVYYCA K                           41

SEQ ID NO: 60             moltype = AA  length = 41
```

```
FEATURE              Location/Qualifiers
REGION               1..41
                     note = PR002726 HFWR3 Chothia
source               1..41
                     mol_type = protein
                     organism = synthetic construct
SEQUENCE: 60
TYYADSVKGR FTISRDNSKN TLHLQMNSLR AEDTAVYYCA K                    41

SEQ ID NO: 61        moltype = AA  length = 41
FEATURE              Location/Qualifiers
REGION               1..41
                     note = PR003767 HFWR3 Chothia
source               1..41
                     mol_type = protein
                     organism = synthetic construct
SEQUENCE: 61
IQSNERFRGK ATLTSDKSST TAYMELSSLT SEDSAVYYCA R                    41

SEQ ID NO: 62        moltype = AA  length = 41
FEATURE              Location/Qualifiers
REGION               1..41
                     note = PR003886 HFWR3 Chothia
source               1..41
                     mol_type = protein
                     organism = synthetic construct
SEQUENCE: 62
TYYADSVKDR FTISRDDSKN TAYLQMNSLK TEDTAVYYCT R                    41

SEQ ID NO: 63        moltype = AA  length = 41
FEATURE              Location/Qualifiers
REGION               1..41
                     note = PR004227 HFWR3 Chothia
source               1..41
                     mol_type = protein
                     organism = synthetic construct
SEQUENCE: 63
TRYADSVKGR FTISRDNAKN TLYLQMNSLR AEDTAVYYCT E                    41

SEQ ID NO: 64        moltype = AA  length = 41
FEATURE              Location/Qualifiers
REGION               1..41
                     note = PR004533 HFWR3 Chothia, PR004950 HFWR3 Chothia,
                       PR004952HFWR3 Chothia, PR007242 HFWR3 Chothia, PR007243
                       HFWR3Chothia, PR007244 HFWR3 Chothia, PR007245 HFWR3
                       Chothia,PR007246 HFWR3 Chothia, PR007248
source               1..41
                     mol_type = protein
                     organism = synthetic construct
SEQUENCE: 64
TIYADSVKGR FTISRDNAKN TLYLQMNSLR AEDTAVYYCA R                    41

SEQ ID NO: 65        moltype = AA  length = 41
FEATURE              Location/Qualifiers
REGION               1..41
                     note = PR004536 HFWR3 Chothia, PR007247 HFWR3 Chothia
source               1..41
                     mol_type = protein
                     organism = synthetic construct
SEQUENCE: 65
TQYADSVKGR FTISRDNAKN MLYLQMNSLR AEDTAVYYCA R                    41

SEQ ID NO: 66        moltype = AA  length = 41
FEATURE              Location/Qualifiers
REGION               1..41
                     note = PR004540 HFWR3 Chothia
source               1..41
                     mol_type = protein
                     organism = synthetic construct
SEQUENCE: 66
TSYADSVKGR FTISRDNAKN TLYLQMNSLR AEDTAVYLCA R                    41

SEQ ID NO: 67        moltype = AA  length = 41
FEATURE              Location/Qualifiers
REGION               1..41
                     note = PR004949 HFWR3 Chothia
source               1..41
                     mol_type = protein
                     organism = synthetic construct
```

```
SEQUENCE: 67
TIYADSVKGR FTISRDNAKN TLYLQMNSLR AEDTAVYLCA R                          41

SEQ ID NO: 68           moltype = AA  length = 41
FEATURE                 Location/Qualifiers
REGION                  1..41
                        note = PR004953 HFWR3 Chothia
source                  1..41
                        mol_type = protein
                        organism = synthetic construct
SEQUENCE: 68
KYYADSVKGR FTISRDNSKN TLFLQMDNLR AEDTALYYCA R                          41

SEQ ID NO: 69           moltype = AA  length = 41
FEATURE                 Location/Qualifiers
REGION                  1..41
                        note = PR005080 HFWR3 Chothia
source                  1..41
                        mol_type = protein
                        organism = synthetic construct
SEQUENCE: 69
TNYNEKFKTK ATMTVDKPSS TAYLELTRVS SEASAIYYCA T                          41

SEQ ID NO: 70           moltype = AA  length = 8
FEATURE                 Location/Qualifiers
REGION                  1..8
                        note = PR000325 HCDR3 Chothia
source                  1..8
                        mol_type = protein
                        organism = synthetic construct
SEQUENCE: 70
LVGGAPAY                                                                8

SEQ ID NO: 71           moltype = AA  length = 9
FEATURE                 Location/Qualifiers
REGION                  1..9
                        note = PR000400 HCDR3 Chothia
source                  1..9
                        mol_type = protein
                        organism = synthetic construct
SEQUENCE: 71
SWRGNSFDY                                                               9

SEQ ID NO: 72           moltype = AA  length = 14
FEATURE                 Location/Qualifiers
REGION                  1..14
                        note = PR001848 HCDR3 Chothia, PR003886 HCDR3 Chothia
source                  1..14
                        mol_type = protein
                        organism = synthetic construct
SEQUENCE: 72
HGNFGNSYVS WFAY                                                        14

SEQ ID NO: 73           moltype = AA  length = 10
FEATURE                 Location/Qualifiers
REGION                  1..10
                        note = PR001861 HCDR3 Chothia
source                  1..10
                        mol_type = protein
                        organism = synthetic construct
SEQUENCE: 73
WGGGTGIFEF                                                             10

SEQ ID NO: 74           moltype = AA  length = 10
FEATURE                 Location/Qualifiers
REGION                  1..10
                        note = PR002725 HCDR3 Chothia
source                  1..10
                        mol_type = protein
                        organism = synthetic construct
SEQUENCE: 74
GDIAVLLFDY                                                             10

SEQ ID NO: 75           moltype = AA  length = 11
FEATURE                 Location/Qualifiers
REGION                  1..11
                        note = PR002726 HCDR3 Chothia
source                  1..11
                        mol_type = protein
```

```
                            -continued organism = synthetic construct
SEQUENCE: 75
DAAAAGTKFD Y                                                            11

SEQ ID NO: 76           moltype = AA   length = 15
FEATURE                 Location/Qualifiers
REGION                  1..15
                        note = PR003767 HCDR3 Chothia
source                  1..15
                        mol_type = protein
                        organism = synthetic construct
SEQUENCE: 76
GAGYNFDGAY RFFDF                                                        15

SEQ ID NO: 77           moltype = AA   length = 11
FEATURE                 Location/Qualifiers
REGION                  1..11
                        note = PR004227 HCDR3 Chothia
source                  1..11
                        mol_type = protein
                        organism = synthetic construct
SEQUENCE: 77
APPYGNYERD Y                                                            11

SEQ ID NO: 78           moltype = AA   length = 12
FEATURE                 Location/Qualifiers
REGION                  1..12
                        note = PR004533 HCDR3 Chothia, PR004950 HCDR3 Chothia,
                         PR007242HCDR3 Chothia, PR007243 HCDR3 Chothia, PR007244
                         HCDR3Chothia, PR007245 HCDR3 Chothia, PR007246 HCDR3
                         Chothia,PR007248 HCDR3 Chothia
source                  1..12
                        mol_type = protein
                        organism = synthetic construct
SEQUENCE: 78
GEDHDILTGY PI                                                           12

SEQ ID NO: 79           moltype = AA   length = 14
FEATURE                 Location/Qualifiers
REGION                  1..14
                        note = PR004536 HCDR3 Chothia, PR007247 HCDR3 Chothia
source                  1..14
                        mol_type = protein
                        organism = synthetic construct
SEQUENCE: 79
DFPVLGGSHF DFQH                                                         14

SEQ ID NO: 80           moltype = AA   length = 12
FEATURE                 Location/Qualifiers
REGION                  1..12
                        note = PR004540 HCDR3 Chothia, PR004949 HCDR3 Chothia
source                  1..12
                        mol_type = protein
                        organism = synthetic construct
SEQUENCE: 80
GEDHDMLTGY PV                                                           12

SEQ ID NO: 81           moltype = AA   length = 12
FEATURE                 Location/Qualifiers
REGION                  1..12
                        note = PR004952 HCDR3 Chothia
source                  1..12
                        mol_type = protein
                        organism = synthetic construct
SEQUENCE: 81
GEDHDILTGY PV                                                           12

SEQ ID NO: 82           moltype = AA   length = 14
FEATURE                 Location/Qualifiers
REGION                  1..14
                        note = PR004953 HCDR3 Chothia
source                  1..14
                        mol_type = protein
                        organism = synthetic construct
SEQUENCE: 82
HFPSLPGTTD TFDI                                                         14

SEQ ID NO: 83           moltype = AA   length = 5
FEATURE                 Location/Qualifiers
```

```
REGION              1..5
                    note = PR005080 HCDR3 Chothia
source              1..5
                    mol_type = protein
                    organism = synthetic construct
SEQUENCE: 83
GSFDY                                                                    5

SEQ ID NO: 84       moltype = AA   length = 11
FEATURE             Location/Qualifiers
REGION              1..11
                    note = PR000325 HFWR4 Chothia, PR001848 HFWR4 Chothia,
                     PR001861HFWR4 Chothia, PR002725 HFWR4 Chothia, PR002726
                     HFWR4Chothia, PR003886 HFWR4 Chothia, PR004227 HFWR4
                     Chothia,PR004536 HFWR4 Chothia, PR007247
source              1..11
                    mol_type = protein
                    organism = synthetic construct
SEQUENCE: 84
WGQGTLVTVS S                                                             11

SEQ ID NO: 85       moltype = AA   length = 11
FEATURE             Location/Qualifiers
REGION              1..11
                    note = PR000400 HFWR4 Chothia, PR003767 HFWR4 Chothia
source              1..11
                    mol_type = protein
                    organism = synthetic construct
SEQUENCE: 85
WGQGTTLTVS S                                                             11

SEQ ID NO: 86       moltype = AA   length = 11
FEATURE             Location/Qualifiers
REGION              1..11
                    note = PR004533 HFWR4 Chothia, PR004540 HFWR4 Chothia,
                     PR007242HFWR4 Chothia, PR007243 HFWR4 Chothia, PR007244
                     HFWR4Chothia, PR007245 HFWR4 Chothia, PR007246 HFWR4
                     Chothia,PR007248 HFWR4 Chothia
source              1..11
                    mol_type = protein
                    organism = synthetic construct
SEQUENCE: 86
RGQGTTVTVS S                                                             11

SEQ ID NO: 87       moltype = AA   length = 11
FEATURE             Location/Qualifiers
REGION              1..11
                    note = PR004949 HFWR4 Chothia, PR004950 HFWR4 Chothia
source              1..11
                    mol_type = protein
                    organism = synthetic construct
SEQUENCE: 87
RGQGTMVTVS S                                                             11

SEQ ID NO: 88       moltype = AA   length = 11
FEATURE             Location/Qualifiers
REGION              1..11
                    note = PR004952 HFWR4 Chothia
source              1..11
                    mol_type = protein
                    organism = synthetic construct
SEQUENCE: 88
RGQGATVTVS S                                                             11

SEQ ID NO: 89       moltype = AA   length = 11
FEATURE             Location/Qualifiers
REGION              1..11
                    note = PR004953 HFWR4 Chothia
source              1..11
                    mol_type = protein
                    organism = synthetic construct
SEQUENCE: 89
RGPGTMVTVS S                                                             11

SEQ ID NO: 90       moltype = AA   length = 11
FEATURE             Location/Qualifiers
REGION              1..11
                    note = PR005080 HFWR4 Chothia
source              1..11
```

```
                        mol_type = protein
                        organism = synthetic construct
SEQUENCE: 90
WGQGVMVTVS S                                                        11

SEQ ID NO: 91           moltype = AA  length = 22
FEATURE                 Location/Qualifiers
REGION                  1..22
                        note = PR000325 LFWR1 Chothia
source                  1..22
                        mol_type = protein
                        organism = synthetic construct
SEQUENCE: 91
QSALTQPASV SGSPGQSITI SC                                            22

SEQ ID NO: 92           moltype = AA  length = 23
FEATURE                 Location/Qualifiers
REGION                  1..23
                        note = PR000400 LFWR1 Chothia
source                  1..23
                        mol_type = protein
                        organism = synthetic construct
SEQUENCE: 92
DIVMTQSPSS LTVTAGEKVT MSC                                           23

SEQ ID NO: 93           moltype = AA  length = 22
FEATURE                 Location/Qualifiers
REGION                  1..22
                        note = PR001848 LFWR1 Chothia, PR003886 LFWR1 Chothia
source                  1..22
                        mol_type = protein
                        organism = synthetic construct
SEQUENCE: 93
QAVVTQEPSL TVSPGGTVTL TC                                            22

SEQ ID NO: 94           moltype = AA  length = 23
FEATURE                 Location/Qualifiers
REGION                  1..23
                        note = PR001861 LFWR1 Chothia
source                  1..23
                        mol_type = protein
                        organism = synthetic construct
SEQUENCE: 94
EIVMTQSPAT LSVSPGERAT LSC                                           23

SEQ ID NO: 95           moltype = AA  length = 23
FEATURE                 Location/Qualifiers
REGION                  1..23
                        note = PR002725 LFWR1 Chothia
source                  1..23
                        mol_type = protein
                        organism = synthetic construct
SEQUENCE: 95
EMVMTQSPAT LSVSPGERAT LSC                                           23

SEQ ID NO: 96           moltype = AA  length = 23
FEATURE                 Location/Qualifiers
REGION                  1..23
                        note = PR002726 LFWR1 Chothia
source                  1..23
                        mol_type = protein
                        organism = synthetic construct
SEQUENCE: 96
EIVLTQSPAT LSLSPGERAT LSC                                           23

SEQ ID NO: 97           moltype = AA  length = 23
FEATURE                 Location/Qualifiers
REGION                  1..23
                        note = PR003767 LFWR1 Chothia
source                  1..23
                        mol_type = protein
                        organism = synthetic construct
SEQUENCE: 97
DVVMTQSPLS LPVSLGDQAS ISC                                           23

SEQ ID NO: 98           moltype = AA  length = 23
FEATURE                 Location/Qualifiers
REGION                  1..23
                        note = PR005080 LFWR1 Chothia
```

```
source                  1..23
                        mol_type = protein
                        organism = synthetic construct
SEQUENCE: 98
DVVLTQTPGS LSLAIGQSAS ISC                                              23

SEQ ID NO: 99           moltype = AA  length = 14
FEATURE                 Location/Qualifiers
REGION                  1..14
                        note = PR000325 LCDR1 Chothia
source                  1..14
                        mol_type = protein
                        organism = synthetic construct
SEQUENCE: 99
SGSSSDIGRY DYVS                                                        14

SEQ ID NO: 100          moltype = AA  length = 17
FEATURE                 Location/Qualifiers
REGION                  1..17
                        note = PR000400 LCDR1 Chothia
source                  1..17
                        mol_type = protein
                        organism = synthetic construct
SEQUENCE: 100
KSSQSLLNSG NQKNYLT                                                     17

SEQ ID NO: 101          moltype = AA  length = 14
FEATURE                 Location/Qualifiers
REGION                  1..14
                        note = PR001848 LCDR1 Chothia, PR003886 LCDR1 Chothia
source                  1..14
                        mol_type = protein
                        organism = synthetic construct
SEQUENCE: 101
RSSTGAVTTS NYAN                                                        14

SEQ ID NO: 102          moltype = AA  length = 11
FEATURE                 Location/Qualifiers
REGION                  1..11
                        note = PR001861 LCDR1 Chothia
source                  1..11
                        mol_type = protein
                        organism = synthetic construct
SEQUENCE: 102
RASQSVRSYL A                                                           11

SEQ ID NO: 103          moltype = AA  length = 11
FEATURE                 Location/Qualifiers
REGION                  1..11
                        note = PR002725 LCDR1 Chothia
source                  1..11
                        mol_type = protein
                        organism = synthetic construct
SEQUENCE: 103
RASQSVSRNL A                                                           11

SEQ ID NO: 104          moltype = AA  length = 11
FEATURE                 Location/Qualifiers
REGION                  1..11
                        note = PR002726 LCDR1 Chothia
source                  1..11
                        mol_type = protein
                        organism = synthetic construct
SEQUENCE: 104
RASQSVSSYL A                                                           11

SEQ ID NO: 105          moltype = AA  length = 16
FEATURE                 Location/Qualifiers
REGION                  1..16
                        note = PR003767 LCDR1 Chothia
source                  1..16
                        mol_type = protein
                        organism = synthetic construct
SEQUENCE: 105
RSSQRLVHSN GNTYLH                                                      16

SEQ ID NO: 106          moltype = AA  length = 16
FEATURE                 Location/Qualifiers
REGION                  1..16
```

```
                        note = PR005080 LCDR1 Chothia
source                  1..16
                        mol_type = protein
                        organism = synthetic construct
SEQUENCE: 106
KSSQSLLGTS GKTFLN                                                    16

SEQ ID NO: 107          moltype = AA  length = 15
FEATURE                 Location/Qualifiers
REGION                  1..15
                        note = PR000325 LFWR2 Chothia
source                  1..15
                        mol_type = protein
                        organism = synthetic construct
SEQUENCE: 107
WYQHYPDKAP KLIIY                                                     15

SEQ ID NO: 108          moltype = AA  length = 15
FEATURE                 Location/Qualifiers
REGION                  1..15
                        note = PR000400 LFWR2 Chothia
source                  1..15
                        mol_type = protein
                        organism = synthetic construct
SEQUENCE: 108
WYQQKPGQPP KLLIY                                                     15

SEQ ID NO: 109          moltype = AA  length = 15
FEATURE                 Location/Qualifiers
REGION                  1..15
                        note = PR001848 LFWR2 Chothia, PR003886 LFWR2 Chothia
source                  1..15
                        mol_type = protein
                        organism = synthetic construct
SEQUENCE: 109
WVQQKPGQAP RGLIG                                                     15

SEQ ID NO: 110          moltype = AA  length = 15
FEATURE                 Location/Qualifiers
REGION                  1..15
                        note = PR001861 LFWR2 Chothia, PR002726 LFWR2 Chothia
source                  1..15
                        mol_type = protein
                        organism = synthetic construct
SEQUENCE: 110
WYQQKPGQAP RLLIY                                                     15

SEQ ID NO: 111          moltype = AA  length = 15
FEATURE                 Location/Qualifiers
REGION                  1..15
                        note = PR002725 LFWR2 Chothia
source                  1..15
                        mol_type = protein
                        organism = synthetic construct
SEQUENCE: 111
WFQQKPGQAP RLLIY                                                     15

SEQ ID NO: 112          moltype = AA  length = 15
FEATURE                 Location/Qualifiers
REGION                  1..15
                        note = PR003767 LFWR2 Chothia
source                  1..15
                        mol_type = protein
                        organism = synthetic construct
SEQUENCE: 112
WYLQKPGQSP KLLIY                                                     15

SEQ ID NO: 113          moltype = AA  length = 15
FEATURE                 Location/Qualifiers
REGION                  1..15
                        note = PR005080 LFWR2 Chothia
source                  1..15
                        mol_type = protein
                        organism = synthetic construct
SEQUENCE: 113
WILQRPGQSP ERLIY                                                     15

SEQ ID NO: 114          moltype = AA  length = 7
FEATURE                 Location/Qualifiers
```

```
REGION                  1..7
                        note = PR000325 LCDR2 Chothia
source                  1..7
                        mol_type = protein
                        organism = synthetic construct
SEQUENCE: 114
EVKHRPS                                                                   7

SEQ ID NO: 115          moltype = AA  length = 7
FEATURE                 Location/Qualifiers
REGION                  1..7
                        note = PR000400 LCDR2 Chothia
source                  1..7
                        mol_type = protein
                        organism = synthetic construct
SEQUENCE: 115
WASTRES                                                                   7

SEQ ID NO: 116          moltype = AA  length = 7
FEATURE                 Location/Qualifiers
REGION                  1..7
                        note = PR001848 LCDR2 Chothia, PR003886 LCDR2 Chothia
source                  1..7
                        mol_type = protein
                        organism = synthetic construct
SEQUENCE: 116
GTNKRAP                                                                   7

SEQ ID NO: 117          moltype = AA  length = 7
FEATURE                 Location/Qualifiers
REGION                  1..7
                        note = PR001861 LCDR2 Chothia, PR002725 LCDR2 Chothia
source                  1..7
                        mol_type = protein
                        organism = synthetic construct
SEQUENCE: 117
GASTRAT                                                                   7

SEQ ID NO: 118          moltype = AA  length = 7
FEATURE                 Location/Qualifiers
REGION                  1..7
                        note = PR002726 LCDR2 Chothia
source                  1..7
                        mol_type = protein
                        organism = synthetic construct
SEQUENCE: 118
DASNRAT                                                                   7

SEQ ID NO: 119          moltype = AA  length = 7
FEATURE                 Location/Qualifiers
REGION                  1..7
                        note = PR003767 LCDR2 Chothia
source                  1..7
                        mol_type = protein
                        organism = synthetic construct
SEQUENCE: 119
RVSNRFP                                                                   7

SEQ ID NO: 120          moltype = AA  length = 7
FEATURE                 Location/Qualifiers
REGION                  1..7
                        note = PR005080 LCDR2 Chothia
source                  1..7
                        mol_type = protein
                        organism = synthetic construct
SEQUENCE: 120
QVSKLYS                                                                   7

SEQ ID NO: 121          moltype = AA  length = 32
FEATURE                 Location/Qualifiers
REGION                  1..32
                        note = PR000325 LFWR3 Chothia
source                  1..32
                        mol_type = protein
                        organism = synthetic construct
SEQUENCE: 121
GISHRFSASK SGNTASLTIS ELQPGDEADY YC                                      32

SEQ ID NO: 122          moltype = AA  length = 32
```

```
FEATURE                 Location/Qualifiers
REGION                  1..32
                        note = PR000400 LFWR3 Chothia
source                  1..32
                        mol_type = protein
                        organism = synthetic construct
SEQUENCE: 122
GVPDRFTGSG SGTDFTLTIS SVQAEDLAVY YC                                 32

SEQ ID NO: 123          moltype = AA   length = 32
FEATURE                 Location/Qualifiers
REGION                  1..32
                        note = PR001848 LFWR3 Chothia, PR003886 LFWR3 Chothia
source                  1..32
                        mol_type = protein
                        organism = synthetic construct
SEQUENCE: 123
WTPARFSGSL LGDKAALTLL GAQPEDEAEY FC                                 32

SEQ ID NO: 124          moltype = AA   length = 32
FEATURE                 Location/Qualifiers
REGION                  1..32
                        note = PR001861 LFWR3 Chothia
source                  1..32
                        mol_type = protein
                        organism = synthetic construct
SEQUENCE: 124
GIPARFSGSG SGTEFTLTIS SLQSEDFAVY HC                                 32

SEQ ID NO: 125          moltype = AA   length = 32
FEATURE                 Location/Qualifiers
REGION                  1..32
                        note = PR002725 LFWR3 Chothia
source                  1..32
                        mol_type = protein
                        organism = synthetic construct
SEQUENCE: 125
GIPARFSGSG SGTEFTLTIS SLQSEDFAVY YC                                 32

SEQ ID NO: 126          moltype = AA   length = 32
FEATURE                 Location/Qualifiers
REGION                  1..32
                        note = PR002726 LFWR3 Chothia
source                  1..32
                        mol_type = protein
                        organism = synthetic construct
SEQUENCE: 126
GIPARFSGSG SGTDFTLTIS SLEPEDFAVY YC                                 32

SEQ ID NO: 127          moltype = AA   length = 32
FEATURE                 Location/Qualifiers
REGION                  1..32
                        note = PR003767 LFWR3 Chothia
source                  1..32
                        mol_type = protein
                        organism = synthetic construct
SEQUENCE: 127
GVPDRFSGSG SGTDFTLKIS RVEAEDLGIY FC                                 32

SEQ ID NO: 128          moltype = AA   length = 32
FEATURE                 Location/Qualifiers
REGION                  1..32
                        note = PR005080 LFWR3 Chothia
source                  1..32
                        mol_type = protein
                        organism = synthetic construct
SEQUENCE: 128
EVPDRFSGSG SETEFTLKIS RVEAEDLGVY YC                                 32

SEQ ID NO: 129          moltype = AA   length = 10
FEATURE                 Location/Qualifiers
REGION                  1..10
                        note = PR000325 LCDR3 Chothia
source                  1..10
                        mol_type = protein
                        organism = synthetic construct
SEQUENCE: 129
ASYTESKTYI                                                          10
```

| | | |
|---|---|---|
| SEQ ID NO: 130<br>FEATURE<br>REGION<br><br>source<br><br><br>SEQUENCE: 130<br>QNDYSYPFT | moltype = AA   length = 9<br>Location/Qualifiers<br>1..9<br>note = PR000400 LCDR3 Chothia<br>1..9<br>mol_type = protein<br>organism = synthetic construct<br><br> | <br><br><br><br><br><br><br><br>9 |
| SEQ ID NO: 131<br>FEATURE<br>REGION<br><br>source<br><br><br>SEQUENCE: 131<br>ALWYSNLWV | moltype = AA   length = 9<br>Location/Qualifiers<br>1..9<br>note = PR001848 LCDR3 Chothia, PR003886 LCDR3 Chothia<br>1..9<br>mol_type = protein<br>organism = synthetic construct<br><br> | <br><br><br><br><br><br><br><br>9 |
| SEQ ID NO: 132<br>FEATURE<br>REGION<br><br>source<br><br><br>SEQUENCE: 132<br>QQYNNWPLT | moltype = AA   length = 9<br>Location/Qualifiers<br>1..9<br>note = PR001861 LCDR3 Chothia, PR002725 LCDR3 Chothia<br>1..9<br>mol_type = protein<br>organism = synthetic construct<br><br> | <br><br><br><br><br><br><br><br>9 |
| SEQ ID NO: 133<br>FEATURE<br>REGION<br><br>source<br><br><br>SEQUENCE: 133<br>QQRSNWPLT | moltype = AA   length = 9<br>Location/Qualifiers<br>1..9<br>note = PR002726 LCDR3 Chothia<br>1..9<br>mol_type = protein<br>organism = synthetic construct<br><br> | <br><br><br><br><br><br><br><br>9 |
| SEQ ID NO: 134<br>FEATURE<br>REGION<br><br>source<br><br><br>SEQUENCE: 134<br>SQSTHVPYT | moltype = AA   length = 9<br>Location/Qualifiers<br>1..9<br>note = PR003767 LCDR3 Chothia<br>1..9<br>mol_type = protein<br>organism = synthetic construct<br><br> | <br><br><br><br><br><br><br><br>9 |
| SEQ ID NO: 135<br>FEATURE<br>REGION<br><br>source<br><br><br>SEQUENCE: 135<br>WQGIHFPHT | moltype = AA   length = 9<br>Location/Qualifiers<br>1..9<br>note = PR005080 LCDR3 Chothia<br>1..9<br>mol_type = protein<br>organism = synthetic construct<br><br> | <br><br><br><br><br><br><br><br>9 |
| SEQ ID NO: 136<br>FEATURE<br>REGION<br><br>source<br><br><br>SEQUENCE: 136<br>FGGGTKVTVL | moltype = AA   length = 10<br>Location/Qualifiers<br>1..10<br>note = PR000325 LFWR4 Chothia<br>1..10<br>mol_type = protein<br>organism = synthetic construct<br><br> | <br><br><br><br><br><br><br><br>10 |
| SEQ ID NO: 137<br>FEATURE<br>REGION<br><br>source<br><br><br>SEQUENCE: 137<br>FGSGTKLEIK | moltype = AA   length = 10<br>Location/Qualifiers<br>1..10<br>note = PR000400 LFWR4 Chothia<br>1..10<br>mol_type = protein<br>organism = synthetic construct<br><br> | <br><br><br><br><br><br><br><br>10 |

-continued

```
SEQ ID NO: 138          moltype = AA   length = 10
FEATURE                 Location/Qualifiers
REGION                  1..10
                        note = PR001848 LFWR4 Chothia, PR003886 LFWR4 Chothia
source                  1..10
                        mol_type = protein
                        organism = synthetic construct
SEQUENCE: 138
FGGGTKLTVL                                                              10

SEQ ID NO: 139          moltype = AA   length = 10
FEATURE                 Location/Qualifiers
REGION                  1..10
                        note = PR001861 LFWR4 Chothia, PR002725 LFWR4 Chothia,
                         PR002726 LFWR4 Chothia
source                  1..10
                        mol_type = protein
                        organism = synthetic construct
SEQUENCE: 139
FGGGTKVEIK                                                              10

SEQ ID NO: 140          moltype = AA   length = 10
FEATURE                 Location/Qualifiers
REGION                  1..10
                        note = PR003767 LFWR4 Chothia
source                  1..10
                        mol_type = protein
                        organism = synthetic construct
SEQUENCE: 140
FGGGTKLEIK                                                              10

SEQ ID NO: 141          moltype = AA   length = 10
FEATURE                 Location/Qualifiers
REGION                  1..10
                        note = PR005080 LFWR4 Chothia
source                  1..10
                        mol_type = protein
                        organism = synthetic construct
SEQUENCE: 141
FGAGTKLELK                                                              10

SEQ ID NO: 142          moltype = AA   length = 117
FEATURE                 Location/Qualifiers
REGION                  1..117
                        note = PR000325 VH
source                  1..117
                        mol_type = protein
                        organism = synthetic construct
SEQUENCE: 142
QVQLVQSGAE VKKPGQSLRI SCKGAGYSFS TYWIGWVRQM PGKGLEWMGI IYPDDSDTRY        60
SPSFEGQVTI SVDKSITTAY LHWSSLKASD TAIYYCARLV GGAPAYWGQG TLVTVSS          117

SEQ ID NO: 143          moltype = AA   length = 118
FEATURE                 Location/Qualifiers
REGION                  1..118
                        note = PR000400 VH
source                  1..118
                        mol_type = protein
                        organism = synthetic construct
SEQUENCE: 143
QVQLQQPGAE LVRPGASVKL SCKASGYTFT SYWINWVKQR PGQGLEWIGN IYPSDSYTNY        60
NQKFKDKATL TVDKSSSTAY MQLSSPTSED SAVYYCTRSW RGNSFDYWGQ GTTLTVSS         118

SEQ ID NO: 144          moltype = AA   length = 125
FEATURE                 Location/Qualifiers
REGION                  1..125
                        note = PR001848 VH
source                  1..125
                        mol_type = protein
                        organism = synthetic construct
SEQUENCE: 144
EVQLLESGGG LVQPGGSLRL SCAASGFTFS TYAMNWVRQA PGKGLEWVSR IRSKYNNYAT        60
YYADSVKDRF TISRDDSKST LYLQMNSLRA EDTAVYYCVR HGNFGNSYVS WFAYWGQGTL      120
VTVSS                                                                  125

SEQ ID NO: 145          moltype = AA   length = 119
FEATURE                 Location/Qualifiers
REGION                  1..119
```

```
                        note = PR001861 VH
source                  1..119
                        mol_type = protein
                        organism = synthetic construct
SEQUENCE: 145
EVQLLESGGG LVQPGGSLRL SCAASGFSFS SFAMSWVRQA PGKGLEWVSA LSGSGGSTYY  60
TDSVKGRFTV SRDNSKNTLY LQMNSLRAED TAIYYCANWG GGTGIFEFWG QGTLVTVSS  119

SEQ ID NO: 146          moltype = AA   length = 119
FEATURE                 Location/Qualifiers
REGION                  1..119
                        note = PR002725 VH
source                  1..119
                        mol_type = protein
                        organism = synthetic construct
SEQUENCE: 146
EVQLLESGGG LVQPGGSLRL SCAASGFTFS GYVMSWVRQA PGKGLEWVSA ISGSGGSKYY  60
ADSVKGRFTI SRDNSKNTLY LQMNSLRAED TAVYYCAKGD IAVLLFDYWG QGTLVTVSS  119

SEQ ID NO: 147          moltype = AA   length = 120
FEATURE                 Location/Qualifiers
REGION                  1..120
                        note = PR002726 VH
source                  1..120
                        mol_type = protein
                        organism = synthetic construct
SEQUENCE: 147
EVQLLESGGG LVQPGGSLRL SCAASGFTFS SFVMSWVRQA PGKGLEWVST ISGSGRSTYY  60
ADSVKGRFTI SRDNSKNTLH LQMNSLRAED TAVYYCAKDA AAAGTKFDYW GQGTLVTVSS 120

SEQ ID NO: 148          moltype = AA   length = 124
FEATURE                 Location/Qualifiers
REGION                  1..124
                        note = PR003767 VH
source                  1..124
                        mol_type = protein
                        organism = synthetic construct
SEQUENCE: 148
EVRLQQSGPD LIKPGASVKM SCKASGYTFT GYVMHWVKQR PGQGLEWIGF INPYNDDIQS  60
NERFRGKATL TSDKSSTTAY MELSSLTSED SAVYYCARGA GYNFDGAYRF FDFWGQGTTL 120
TVSS                                                              124

SEQ ID NO: 149          moltype = AA   length = 125
FEATURE                 Location/Qualifiers
REGION                  1..125
                        note = PR003886 VH
source                  1..125
                        mol_type = protein
                        organism = synthetic construct
SEQUENCE: 149
EVQLVESGGG LVQPGGSLKL SCAASGFTFS TYAMNWVRQA SGKGLEWVGR IRSKYNNYAT  60
YYADSVKDRF TISRDDSKNT AYLQMNSLKT EDTAVYYCTR HGNFGNSYVS WFAYWGQGTL 120
VTVSS                                                             125

SEQ ID NO: 150          moltype = AA   length = 120
FEATURE                 Location/Qualifiers
REGION                  1..120
                        note = PR004227 VH
source                  1..120
                        mol_type = protein
                        organism = synthetic construct
SEQUENCE: 150
EVQLVESGGG LVQPGGSLRL SCAASGFTFS SYWMHWVRQA PGKGLEWVSY INNDGSSTRY  60
ADSVKGRFTI SRDNAKNTLY LQMNSLRAED TAVYYCTEAP PYGNYERDYW GQGTLVTVSS 120

SEQ ID NO: 151          moltype = AA   length = 121
FEATURE                 Location/Qualifiers
REGION                  1..121
                        note = PR004533 VH
source                  1..121
                        mol_type = protein
                        organism = synthetic construct
SEQUENCE: 151
EVQLVESGGG LVQPGGSLRL SCAASGFTFS SYWMHWVRQV PGKGLVWVSR INSDGSRTIY  60
ADSVKGRFTI SRDNAKNTLY LQMNSLRAED TAVYYCARGE DHDILTGYPI RGQGTTVTVS 120
S                                                                 121

SEQ ID NO: 152          moltype = AA   length = 123
FEATURE                 Location/Qualifiers
```

```
REGION                    1..123
                          note = PR004536 VH
source                    1..123
                          mol_type = protein
                          organism = synthetic construct
SEQUENCE: 152
EVQLVESGGG LVQPGGSLRL SCAASGFTFS SYWMYWVRQV PGKGLVWVSH INSDGSTTQY    60
ADSVKGRFTI SRDNAKNMLY LQMNSLRAED TAVYYCARDF PVLGGSHFDF QHWGQGTLVT   120
VSS                                                                 123

SEQ ID NO: 153            moltype = AA  length = 121
FEATURE                   Location/Qualifiers
REGION                    1..121
                          note = PR004540 VH
source                    1..121
                          mol_type = protein
                          organism = synthetic construct
SEQUENCE: 153
EVQLVESGGG LVQPGGSLRL SCAASGFTFS IYWMHWVRQV PGKGLVLVSR ISSDGNYTSY    60
ADSVKGRFTI SRDNAKNTLY LQMNSLRAED TAVYLCARGE DHDMLTGYPV RGQGTTVTVS   120
S                                                                   121

SEQ ID NO: 154            moltype = AA  length = 121
FEATURE                   Location/Qualifiers
REGION                    1..121
                          note = PR004949 VH
source                    1..121
                          mol_type = protein
                          organism = synthetic construct
SEQUENCE: 154
EVQLVESGGG LVQPGGSLRL SCAASGFTFS AYWMHWVRQV PGRGLVWVSR INSDGSRTIY    60
ADSVKGRFTI SRDNAKNTLY LQMNSLRAED TAVYLCARGE DHDMLTGYPV RGQGTMVTVS   120
S                                                                   121

SEQ ID NO: 155            moltype = AA  length = 121
FEATURE                   Location/Qualifiers
REGION                    1..121
                          note = PR004950 VH
source                    1..121
                          mol_type = protein
                          organism = synthetic construct
SEQUENCE: 155
EVQLVESGGG LVQPGGSLRL SCAASGFTFS AYWMHWVRQV PGKGLVWVSR INSDGSRTIY    60
ADSVKGRFTI SRDNAKNTLY LQMNSLRAED TAVYYCARGE DHDILTGYPI RGQGTMVTVS   120
S                                                                   121

SEQ ID NO: 156            moltype = AA  length = 121
FEATURE                   Location/Qualifiers
REGION                    1..121
                          note = PR004952 VH
source                    1..121
                          mol_type = protein
                          organism = synthetic construct
SEQUENCE: 156
EVQLVESGGG LVQPGGSLRL SCAASGFTFS SYWMHWVRQA PGKGLVWVSR INSDGSRTIY    60
ADSVKGRFTI SRDNAKNTLY LQMNSLRAED TAVYYCARGE DHDILTGYPV RGQGATVTVS   120
S                                                                   121

SEQ ID NO: 157            moltype = AA  length = 123
FEATURE                   Location/Qualifiers
REGION                    1..123
                          note = PR004953 VH
source                    1..123
                          mol_type = protein
                          organism = synthetic construct
SEQUENCE: 157
EVQLVESGGG VVQPGRSLRL SCAASGFTFS SYGMHWVRQA PGKGLEWVAV IGYDGRNKYY    60
ADSVKGRFTI SRDNSKNTLF LQMDNLRAED TALYYCARHF PSLPGTTDTF DIRGPGTMVT   120
VSS                                                                 123

SEQ ID NO: 158            moltype = AA  length = 115
FEATURE                   Location/Qualifiers
REGION                    1..115
                          note = PR005080 VH
source                    1..115
                          mol_type = protein
                          organism = synthetic construct
SEQUENCE: 158
QVKLLQSGAA LVPKPGDSMK MSCKASGYTF THDIIHWVRQ SHGKSLEWIG YINPYNGGTN    60
```

```
YNEKFKTKAT MTVDKPSSTA YLELTRVSSE ASAIYYCATG SFDYWGQGVM VTVSS         115

SEQ ID NO: 159          moltype = AA  length = 121
FEATURE                 Location/Qualifiers
REGION                  1..121
                        note = PR007242 VH
source                  1..121
                        mol_type = protein
                        organism = synthetic construct
SEQUENCE: 159
EVQLVESGGG LVQPGGSLRL SCAASGFTFS SYWMHWVRQV PGKGLVWVSR INFDSSRTIY    60
ADSVKGRFTI SRDNAKNTLY LQMNSLRAED TAVYYCARGE DHDILTGYPI RGQGTTVTVS    120
S                                                                   121

SEQ ID NO: 160          moltype = AA  length = 121
FEATURE                 Location/Qualifiers
REGION                  1..121
                        note = PR007243 VH
source                  1..121
                        mol_type = protein
                        organism = synthetic construct
SEQUENCE: 160
EVQLVESGGG LVQPGGSLRL SCAASGFTFS SYWMHWVRQV PGKGLVWVSR ISSAGSRTIY    60
ADSVKGRFTI SRDNAKNTLY LQMNSLRAED TAVYYCARGE DHDILTGYPI RGQGTTVTVS    120
S                                                                   121

SEQ ID NO: 161          moltype = AA  length = 121
FEATURE                 Location/Qualifiers
REGION                  1..121
                        note = PR007244 VH
source                  1..121
                        mol_type = protein
                        organism = synthetic construct
SEQUENCE: 161
EVQLVESGGG LVQPGGSLRL SCAASGFTFS SYWMHWVRQV PGKGLVWVSR IDSRGSRTIY    60
ADSVKGRFTI SRDNAKNTLY LQMNSLRAED TAVYYCARGE DHDILTGYPI RGQGTTVTVS    120
S                                                                   121

SEQ ID NO: 162          moltype = AA  length = 121
FEATURE                 Location/Qualifiers
REGION                  1..121
                        note = PR007245 VH
source                  1..121
                        mol_type = protein
                        organism = synthetic construct
SEQUENCE: 162
EVQLVESGGG LVQPGGSLRL SCAASGFTFS SYWMHWVRQV PGKGLVWVSR ISSDASRTIY    60
ADSVKGRFTI SRDNAKNTLY LQMNSLRAED TAVYYCARGE DHDILTGYPI RGQGTTVTVS    120
S                                                                   121

SEQ ID NO: 163          moltype = AA  length = 121
FEATURE                 Location/Qualifiers
REGION                  1..121
                        note = PR007246 VH
source                  1..121
                        mol_type = protein
                        organism = synthetic construct
SEQUENCE: 163
EVQLVESGGG LVQPGGSLRL SCAASGFTFS SYWMHWVRQV PGKGLVWVSR ISSTGSRTIY    60
ADSVKGRFTI SRDNAKNTLY LQMNSLRAED TAVYYCARGE DHDILTGYPI RGQGTTVTVS    120
S                                                                   121

SEQ ID NO: 164          moltype = AA  length = 123
FEATURE                 Location/Qualifiers
REGION                  1..123
                        note = PR007247 VH
source                  1..123
                        mol_type = protein
                        organism = synthetic construct
SEQUENCE: 164
EVQLVESGGG LVQPGGSLRL SCAASGFTFS SYWMYWVRQV PGKGLVWVSH INPLGSTTQY    60
ADSVKGRFTI SRDNAKNMLY LQMNSLRAED TAVYYCARDF PVLGGSHFDF QHWGQGTLVT    120
VSS                                                                 123

SEQ ID NO: 165          moltype = AA  length = 121
FEATURE                 Location/Qualifiers
REGION                  1..121
                        note = PR007248 VH
source                  1..121
```

```
                        mol_type = protein
                        organism = synthetic construct
SEQUENCE: 165
EVQLVESGGG LVQPGGSLRL SCAASGFTFS SYWMHWVRQV PGKGLVWVSR INHDSSRTIY      60
ADSVKGRFTI SRDNAKNTLY LQMNSLRAED TAVYYCARGE DHDILTGYPI RGQGTTVTVS     120
S                                                                    121

SEQ ID NO: 166          moltype = AA  length = 110
FEATURE                 Location/Qualifiers
REGION                  1..110
                        note = PR000325 VL
source                  1..110
                        mol_type = protein
                        organism = synthetic construct
SEQUENCE: 166
QSALTQPASV SGSPGQSITI SCSGSSSDIG RYDYVSWYQH YPDKAPKLII YEVKHRPSGI      60
SHRFSASKSG NTASLTISEL QPGDEADYYC ASYTESKTYI FGGGTKVTVL                110

SEQ ID NO: 167          moltype = AA  length = 113
FEATURE                 Location/Qualifiers
REGION                  1..113
                        note = PR000400 VL
source                  1..113
                        mol_type = protein
                        organism = synthetic construct
SEQUENCE: 167
DIVMTQSPSS LTVTAGEKVT MSCKSSQSLL NSGNQKNYLT WYQQKPGQPP KLLIYWASTR      60
ESGVPDRFTG SGSGTDFTLT ISSVQAEDLA VYYCQNDYSY PFTFGSGTKL EIK            113

SEQ ID NO: 168          moltype = AA  length = 109
FEATURE                 Location/Qualifiers
REGION                  1..109
                        note = PR001848 VL, PR003886 VL
source                  1..109
                        mol_type = protein
                        organism = synthetic construct
SEQUENCE: 168
QAVVTQEPSL TVSPGGTVTL TCRSSTGAVT TSNYANWVQQ KPGQAPRGLI GGTNKRAPWT      60
PARFSGSLLG DKAALTLLGA QPEDEAEYFC ALWYSNLWVF GGGTKLTVL                 109

SEQ ID NO: 169          moltype = AA  length = 107
FEATURE                 Location/Qualifiers
REGION                  1..107
                        note = PR001861 VL
source                  1..107
                        mol_type = protein
                        organism = synthetic construct
SEQUENCE: 169
EIVMTQSPAT LSVSPGERAT LSCRASQSVR SYLAWYQQKP GQAPRLLIYG ASTRATGIPA      60
RFSGSGSGTE FTLTISSLQS EDFAVYHCQQ YNNWPLTFGG GTKVEIK                   107

SEQ ID NO: 170          moltype = AA  length = 107
FEATURE                 Location/Qualifiers
REGION                  1..107
                        note = PR002725 VL
source                  1..107
                        mol_type = protein
                        organism = synthetic construct
SEQUENCE: 170
EMVMTQSPAT LSVSPGERAT LSCRASQSVS RNLAWFQQKP GQAPRLLIYG ASTRATGIPA      60
RFSGSGSGTE FTLTISSLQS EDFAVYYCQQ YNNWPLTFGG GTKVEIK                   107

SEQ ID NO: 171          moltype = AA  length = 107
FEATURE                 Location/Qualifiers
REGION                  1..107
                        note = PR002726 VL
source                  1..107
                        mol_type = protein
                        organism = synthetic construct
SEQUENCE: 171
EIVLTQSPAT LSLSPGERAT LSCRASQSVS SYLAWYQQKP GQAPRLLIYD ASNRATGIPA      60
RFSGSGSGTD FTLTISSLEP EDFAVYYCQQ RSNWPLTFGG GTKVEIK                   107

SEQ ID NO: 172          moltype = AA  length = 112
FEATURE                 Location/Qualifiers
REGION                  1..112
                        note = PR003767 VL
source                  1..112
                        mol_type = protein
```

```
                        organism   = synthetic construct
SEQUENCE: 172
DVVMTQSPLS LPVSLGDQAS ISCRSSQRLV HSNGNTYLHW YLQKPGQSPK LLIYRVSNRF     60
PGVPDRFSGS GSGTDFTLKI SRVEAEDLGI YFCSQSTHVP YTFGGGTKLE IK            112

SEQ ID NO: 173          moltype = AA   length = 112
FEATURE                 Location/Qualifiers
REGION                  1..112
                        note = PR005080 VL
source                  1..112
                        mol_type = protein
                        organism = synthetic construct
SEQUENCE: 173
DVVLTQTPGS LSLAIGQSAS ISCKSSQSLL GTSGKTFLNW ILQRPGQSPE RLIYQVSKLY     60
SEVPDRFSGS GSETEFTLKI SRVEAEDLGV YYCWQGIHFP HTFGAGTKLE LK            112

SEQ ID NO: 174          moltype = AA   length = 447
FEATURE                 Location/Qualifiers
REGION                  1..447
                        note = PR000325 HC
source                  1..447
                        mol_type = protein
                        organism = synthetic construct
SEQUENCE: 174
QVQLVQSGAE VKKPGQSLRI SCKGAYSFS TYWIGWVRQM PGKGLEWMGI IYPDDSDTRY      60
SPSFEGQVTI SVDKSITTAY LHWSSLKASD TAIYYCARLV GGAPAYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSREEMTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                       447

SEQ ID NO: 175          moltype = AA   length = 448
FEATURE                 Location/Qualifiers
REGION                  1..448
                        note = PR000400 HC
source                  1..448
                        mol_type = protein
                        organism = synthetic construct
SEQUENCE: 175
QVQLQQPGAE LVRPGASVKL SCKASGYTFT SYWINWVKQR PGQGLEWIGN IYPSDSYTNY     60
NQKFKDKATL TVDKSSSTAY MQLSSPTSED SAVYYCTRSW RGNSFDYWGQ GTTLTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVY TLPPSREEMT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGK                                      448

SEQ ID NO: 176          moltype = AA   length = 455
FEATURE                 Location/Qualifiers
REGION                  1..455
                        note = PR001848 HC
source                  1..455
                        mol_type = protein
                        organism = synthetic construct
SEQUENCE: 176
EVQLLESGGG LVQPGGSLRL SCAASGFTFS TYAMNWVRQA PGKGLEWVSR IRSKYNNYAT     60
YYADSVKDRF TISRDDSKST LYLQMNSLRA EDTAVYYCVR HGNFGNSYVS WFAYWGQGTL    120
VTVSSASTKG PSVFPLAPSS KSTSGGTAAL GCLVKDYFPE PVTVSWNSGA LTSGVHTFPA    180
VLQSSGLYSL SSVVTPSSS LGTQTYICNV NHKPSNTKVD KKVEPKSCDK THTCPPCPAP    240
EAAGGPSVFL FPPKPKDTLM ISRTPEVTCV VVDVSHEDPE VKFNWYVDGV EVHNAKTKPR    300
EEQYNSTYRV VSVLTVLHQD WLNGKEYKCK VSNKALGAPI EKTISKAKGQ PREPQVYTLP    360
PSREEMTKNQ VSLTCLVKGF YPSDIAVEWE SNGQPENNYK TTPPVLDSDG SFFLYSKLTV    420
DKSRWQQGNV FSCSVMHEAL HNHYTQKSLS LSPGK                              455

SEQ ID NO: 177          moltype = AA   length = 449
FEATURE                 Location/Qualifiers
REGION                  1..449
                        note = PR001861 HC
source                  1..449
                        mol_type = protein
                        organism = synthetic construct
SEQUENCE: 177
EVQLLESGGG LVQPGGSLRL SCAASGFSFS SFAMSWVRQA PGKGLEWVSA LSGSGGSTYY     60
TDSVKGRFTV SRDNSKNTLY LQMNSLRAED TAIYYCANWG GGTGIFEFWG QGTLVTVSSA    120
STKGPSVFPL APSSKSTSGG TAALGCLVKD YFPEPVTVSW NSGALTSGVH TPAVLQSSG    180
LYSLSSVVTV PSSLGTQTY ICNVNHKPSN TKVDKKVEPK SCDKTHTCPP CPAPELLGGP    240
```

```
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                      449

SEQ ID NO: 178          moltype = AA  length = 449
FEATURE                 Location/Qualifiers
REGION                  1..449
                        note = PR002725 HC
source                  1..449
                        mol_type = protein
                        organism = synthetic construct
SEQUENCE: 178
EVQLLESGGG LVQPGGSLRL SCAASGFTFS GYVMSWVRQA PGKGLEWVSA ISGSGGSKYY     60
ADSVKGRFTI SRDNSKNTLY LQMNSLRAED TAVYYCAKGD IAVLLFDYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                      449

SEQ ID NO: 179          moltype = AA  length = 450
FEATURE                 Location/Qualifiers
REGION                  1..450
                        note = PR002726 HC
source                  1..450
                        mol_type = protein
                        organism = synthetic construct
SEQUENCE: 179
EVQLLESGGG LVQPGGSLRL SCAASGFTFS SFVMSWVRQA PGKGLEWVST ISGSGRSTYY     60
ADSVKGRFTI SRDNSKNTLH LQMNSLRAED TAVYYCAKDA AAAGTKFDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                     450

SEQ ID NO: 180          moltype = AA  length = 454
FEATURE                 Location/Qualifiers
REGION                  1..454
                        note = PR003767 HC
source                  1..454
                        mol_type = protein
                        organism = synthetic construct
SEQUENCE: 180
EVRLQQSGPD LIKPGASVKM SCKASGYTFT GYVMHWVKQR PGQGLEWIGF INPYNDDIQS     60
NERFRGKATL TSDKSSTTAY MELSSLTSED SAVYYCARGA GYNFDGAYRF FDFWGQGTTL    120
TVSSASTKGP SVFPLAPSSK STSGGTAALG CLVKDYFPEP VTVSWNSGAL TSGVHTFPAV    180
LQSSGLYSLS SVVTVPSSSL GTQTYICNVN HKPSNTKVDK KVEPKSCDKT HTCPPCPAPE    240
LLGGPDVFLF PPKPKDTLMI SRTPEVTCVV VDVSHEDPEV KFNWYVDGVE VHNAKTKPRE    300
EQYNSTYRVV SVLTVLHQDW LNGKEYKCKV SNKALPAPEE KTISKAKGQP REPQVYTLPP    360
SREEMTKNQV SLTCLVKGFY PSDIAVEWES NGQPENNYKT TPPVLDSDGS FFLYSKLTVD    420
KSRWQQGNVF SCSVMHEALH NHYTQKSLSL SPGK                                454

SEQ ID NO: 181          moltype = AA  length = 455
FEATURE                 Location/Qualifiers
REGION                  1..455
                        note = PR003886 HC
source                  1..455
                        mol_type = protein
                        organism = synthetic construct
SEQUENCE: 181
EVQLVESGGG LVQPGGSLKL SCAASGFTFS TYAMNWVRQA SGKGLEWVGR IRSKYNNYAT     60
YYADSVKDRF TISRDDSKNT AYLQMNSLKT EDTAVYYCTR HGNFGNSYVS WFAYWGQGTL    120
VTVSSASTKG PSVFPLAPSS KSTSGGTAAL GCLVKDYFPE PVTVSWNSGA LTSGVHTFPA    180
VLQSSGLYSL SSVVTVPSSS LGTQTYICNV NHKPSNTKVD KKVEPKSCDK THTCPPCPAP    240
EAAGGPSVFL FPPKPKDTLM ISRTPEVTCV VVDVSHEDPE VKFNWYVDGV EVHNAKTKPR    300
EEQYNSTYRV VSVLTVLHQD WLNGKEYKCK VSNKALPAPI EKTISKAKGQ PREPQVYTLP    360
PSREEMTKNQ VSLTCLVKGF YPSDIAVEWE SNGQPENNYK TTPPVLDSDG SFFLYSKLTV    420
DKSRWQQGNV FSCSVMHEAL HNHYTQKSLS LSPGK                               455

SEQ ID NO: 182          moltype = AA  length = 357
FEATURE                 Location/Qualifiers
REGION                  1..357
                        note = PR004227 HC
source                  1..357
                        mol_type = protein
```

```
                            organism = synthetic construct
SEQUENCE: 182
EVQLVESGGG LVQPGGSLRL SCAASGFTFS SYWMHWVRQA PGKGLEWVSY INNDGSSTRY       60
ADSVKGRFTI SRDNAKNTLY LQMNSLRAED TAVYYCTEAP PYGNYERDYW GQGTLVTVSS      120
GQAGQEPKSS DKTHTCPPCP APELLGGPSV FLFPPKPKDT LMISRTPEVT CVVVDVSHED      180
PEVKFNWYVD GVEVHNAKTK PREEQYNSTY RVVSVLTVLH QDWLNGKEYK CKVSNKALPA      240
PIEKTISKAK GQPREPQVYT LPPSREEMTK NQVSLTCLVK GFYPSDIAVE WESNGQPENN      300
YKTTPPVLDS DGSFFLYSKL TVDKSRWQQG NVFSCSVMHE ALHNHYTQKS LSLSPGK         357

SEQ ID NO: 183          moltype = AA  length = 353
FEATURE                 Location/Qualifiers
REGION                  1..353
                        note = PR004533 HC
source                  1..353
                        mol_type = protein
                        organism = synthetic construct
SEQUENCE: 183
EVQLVESGGG LVQPGGSLRL SCAASGFTFS SYWMHWVRQV PGKGLVWVSR INSDGSRTIY       60
ADSVKGRFTI SRDNAKNTLY LQMNSLRAED TAVYYCARGE DHDILTGYPI RGQGTTVTVS      120
SEPKSSDKTH TCPPCPAPEL LGGPSVFLFP PKPKDTLMIS RTPEVTCVVV DVSHEDPEVK      180
FNWYVDGVEV HNAKTKPREE QYNSTYRVVS VLTVLHQDWL NGKEYKCKVS NKALPAPIEK      240
TISKAKGQPR EPQVYTLPPS REEMTKNQVS LTCLVKGFYP SDIAVEWESN GQPENNYKTT      300
PPVLDSDGSF FLYSKLTVDK SRWQQGNVFS CSVMHEALHN HYTQKSLSLS PGK             353

SEQ ID NO: 184          moltype = AA  length = 355
FEATURE                 Location/Qualifiers
REGION                  1..355
                        note = PR004536 HC
source                  1..355
                        mol_type = protein
                        organism = synthetic construct
SEQUENCE: 184
EVQLVESGGG LVQPGGSLRL SCAASGFTFS SYWMYWVRQV PGKGLVWVSH INSDGSTTQY       60
ADSVKGRFTI SRDNAKNMLY LQMNSLRAED TAVYYCARDF PVLGGSHPDF QHWGQGTLVT      120
VSSEPKSSDK THTCPPCPAP ELLGGPSVFL FPPKPKDTLM ISRTPEVTCV VVDVSHEDPE      180
VKFNWYVDGV EVHNAKTKPR EEQYNSTYRV VSVLTVLHQD WLNGKEYKCK VSNKALPAPI      240
EKTISKAKGQ PREPQVYTLP PSREEMTKNQ VSLTCLVKGF YPSDIAVEWE SNGQPENNYK      300
TTPPVLDSDG SFFLYSKLTV DKSRWQQGNV FSCSVMHEAL HNHYTQKSLS LSPGK           355

SEQ ID NO: 185          moltype = AA  length = 353
FEATURE                 Location/Qualifiers
REGION                  1..353
                        note = PR004540 HC
source                  1..353
                        mol_type = protein
                        organism = synthetic construct
SEQUENCE: 185
EVQLVESGGG LVQPGGSLRL SCAASGFTFS IYWMHWVRQV PGKGLVLVSR ISSDGNYTSY       60
ADSVKGRFTI SRDNAKNTLY LQMNSLRAED TAVYLCARGE DHDMLTGYPV RGQGTTVTVS      120
SEPKSSDKTH TCPPCPAPEL LGGPSVFLFP PKPKDTLMIS RTPEVTCVVV DVSHEDPEVK      180
FNWYVDGVEV HNAKTKPREE QYNSTYRVVS VLTVLHQDWL NGKEYKCKVS NKALPAPIEK      240
TISKAKGQPR EPQVYTLPPS REEMTKNQVS LTCLVKGFYP SDIAVEWESN GQPENNYKTT      300
PPVLDSDGSF FLYSKLTVDK SRWQQGNVFS CSVMHEALHN HYTQKSLSLS PGK             353

SEQ ID NO: 186          moltype = AA  length = 353
FEATURE                 Location/Qualifiers
REGION                  1..353
                        note = PR004949 HC
source                  1..353
                        mol_type = protein
                        organism = synthetic construct
SEQUENCE: 186
EVQLVESGGG LVQPGGSLRL SCAASGFTFS AYWMHWVRQV PGRGLVWVSR INSDGSRTIY       60
ADSVKGRFTI SRDNAKNTLY LQMNSLRAED TAVYLCARGE DHDMLTGYPV RGQGTMVTVS      120
SEPKSSDKTH TCPPCPAPEL LGGPSVFLFP PKPKDTLMIS RTPEVTCVVV DVSHEDPEVK      180
FNWYVDGVEV HNAKTKPREE QYNSTYRVVS VLTVLHQDWL NGKEYKCKVS NKALPAPIEK      240
TISKAKGQPR EPQVYTLPPS REEMTKNQVS LTCLVKGFYP SDIAVEWESN GQPENNYKTT      300
PPVLDSDGSF FLYSKLTVDK SRWQQGNVFS CSVMHEALHN HYTQKSLSLS PGK             353

SEQ ID NO: 187          moltype = AA  length = 353
FEATURE                 Location/Qualifiers
REGION                  1..353
                        note = PR004950 HC
source                  1..353
                        mol_type = protein
                        organism = synthetic construct
SEQUENCE: 187
EVQLVESGGG LVQPGGSLRL SCAASGFTFS AYWMHWVRQV PGKGLVWVSR INSDGSRTIY       60
ADSVKGRFTI SRDNAKNTLY LQMNSLRAED TAVYYCARGE DHDILTGYPI RGQGTMVTVS      120
```

```
SEPKSSDKTH TCPPCPAPEL LGGPSVFLFP PKPKDTLMIS RTPEVTCVVV DVSHEDPEVK    180
FNWYVDGVEV HNAKTKPREE QYNSTYRVVS VLTVLHQDWL NGKEYKCKVS NKALPAPIEK    240
TISKAKGQPR EPQVYTLPPS REEMTKNQVS LTCLVKGFYP SDIAVEWESN GQPENNYKTT    300
PPVLDSDGSF FLYSKLTVDK SRWQQGNVFS CSVMHEALHN HYTQKSLSLS PGK           353

SEQ ID NO: 188          moltype = AA  length = 353
FEATURE                 Location/Qualifiers
REGION                  1..353
                        note = PR004952 HC
source                  1..353
                        mol_type = protein
                        organism = synthetic construct
SEQUENCE: 188
EVQLVESGGG LVQPGGSLRL SCAASGFTFS SYWMHWVRQA PGKGLVWVSR INSDGSRTIY     60
ADSVKGRFTI SRDNAKNTLY LQMNSLRAED TAVYYCARGE DHDILTGYPV RGQGATVTVS    120
SEPKSSDKTH TCPPCPAPEL LGGPSVFLFP PKPKDTLMIS RTPEVTCVVV DVSHEDPEVK    180
FNWYVDGVEV HNAKTKPREE QYNSTYRVVS VLTVLHQDWL NGKEYKCKVS NKALPAPIEK    240
TISKAKGQPR EPQVYTLPPS REEMTKNQVS LTCLVKGFYP SDIAVEWESN GQPENNYKTT    300
PPVLDSDGSF FLYSKLTVDK SRWQQGNVFS CSVMHEALHN HYTQKSLSLS PGK           353

SEQ ID NO: 189          moltype = AA  length = 355
FEATURE                 Location/Qualifiers
REGION                  1..355
                        note = PR004953 HC
source                  1..355
                        mol_type = protein
                        organism = synthetic construct
SEQUENCE: 189
EVQLVESGGG VVQPGRSLRL SCAASGFTFS SYGMHWVRQA PGKGLEWVAV IGYDGRNKYY     60
ADSVKGRFTI SRDNSKNTLF LQMDNLRAED TALYYCARHF PSLPGTTDTF DIRGPGTMVT    120
VSSEPKSSDK THTCPPCPAP ELLGGPSVFL FPPKPKDTLM ISRTPEVTCV VVDSHEDPE     180
VKFNWYVDGV EVHNAKTKPR EEQYNSTYRV VSVLTVLHQD WLNGKEYKCK VSNKALPAPI    240
EKTISKAKGQ PREPQVYTLP PSREEMTKNQ VSLTCLVKGF YPSDIAVEWE SNGQPENNYK    300
TTPPVLDSDG SFFLYSKLTV DKSRWQQGNV FSCSVMHEAL HNHYTQKSLS LSPGK         355

SEQ ID NO: 190          moltype = AA  length = 445
FEATURE                 Location/Qualifiers
REGION                  1..445
                        note = PR005080 HC
source                  1..445
                        mol_type = protein
                        organism = synthetic construct
SEQUENCE: 190
QVKLLQSGAA LVPKPGDSMK MSCKASGYTF THDIIHWVRQ SHGKSLEWIG YINPYNGGTN     60
YNEKFKTKAT MTVDKPSSTA YLELTRVSSE ASAIYYCATG SFDYWGQGVM VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KKVEPKSCDK THTCPPCPAP ELLGGPSVFL    240
FPPKPKDTLM ISRTPEVTCV VVDSHEDPE VKFNWYVDGV EVHNAKTKPR EEQYNSTYRV     300
VSVLTVLHQD WLNGKEYKCK VSNKALPAPI EKTISKAKGQ PREPQVYTLP PSREEMTKNQ    360
VSLTCLVKGF YPSDIAVEWE SNGQPENNYK TTPPVLDSDG SFFLYSKLTV DKSRWQQGNV    420
FSCSVMHEAL HNHYTQKSLS LSPGK                                          445

SEQ ID NO: 191          moltype = AA  length = 353
FEATURE                 Location/Qualifiers
REGION                  1..353
                        note = PR007242 HC
source                  1..353
                        mol_type = protein
                        organism = synthetic construct
SEQUENCE: 191
EVQLVESGGG LVQPGGSLRL SCAASGFTFS SYWMHWVRQV PGKGLVWVSR INFDSSRTIY     60
ADSVKGRFTI SRDNAKNTLY LQMNSLRAED TAVYYCARGE DHDILTGYPI RGQGTTVTVS    120
SEPKSSDKTH TCPPCPAPEL LGGPSVFLFP PKPKDTLMIS RTPEVTCVVV DVSHEDPEVK    180
FNWYVDGVEV HNAKTKPREE QYNSTYRVVS VLTVLHQDWL NGKEYKCKVS NKALPAPIEK    240
TISKAKGQPR EPQVYTLPPS REEMTKNQVS LTCLVKGFYP SDIAVEWESN GQPENNYKTT    300
PPVLDSDGSF FLYSKLTVDK SRWQQGNVFS CSVMHEALHN HYTQKSLSLS PGK           353

SEQ ID NO: 192          moltype = AA  length = 353
FEATURE                 Location/Qualifiers
REGION                  1..353
                        note = PR007243 HC
source                  1..353
                        mol_type = protein
                        organism = synthetic construct
SEQUENCE: 192
EVQLVESGGG LVQPGGSLRL SCAASGFTFS SYWMHWVRQV PGKGLVWVSR ISSAGSRTIY     60
ADSVKGRFTI SRDNAKNTLY LQMNSLRAED TAVYYCARGE DHDILTGYPI RGQGTTVTVS    120
SEPKSSDKTH TCPPCPAPEL LGGPSVFLFP PKPKDTLMIS RTPEVTCVVV DVSHEDPEVK    180
FNWYVDGVEV HNAKTKPREE QYNSTYRVVS VLTVLHQDWL NGKEYKCKVS NKALPAPIEK    240
```

```
TISKAKGQPR EPQVYTLPPS REEMTKNQVS LTCLVKGFYP SDIAVEWESN GQPENNYKTT    300
PPVLDSDGSF FLYSKLTVDK SRWQQGNVFS CSVMHEALHN HYTQKSLSLS PGK           353

SEQ ID NO: 193          moltype = AA  length = 353
FEATURE                 Location/Qualifiers
REGION                  1..353
                        note = PR007244 HC
source                  1..353
                        mol_type = protein
                        organism = synthetic construct
SEQUENCE: 193
EVQLVESGGG LVQPGGSLRL SCAASGFTFS SYWMHWVRQV PGKGLVWVSR IDSRGSRTIY     60
ADSVKGRFTI SRDNAKNTLY LQMNSLRAED TAVYYCARGE DHDILTGYPI RGQGTTVTVS    120
SEPKSSDKTH TCPPCPAPEL LGGPSVFLFP PKPKDTLMIS RTPEVTCVVV DVSHEDPEVK    180
FNWYVDGVEV HNAKTKPREE QYNSTYRVVS VLTVLHQDWL NGKEYKCKVS NKALPAPIEK    240
TISKAKGQPR EPQVYTLPPS REEMTKNQVS LTCLVKGFYP SDIAVEWESN GQPENNYKTT    300
PPVLDSDGSF FLYSKLTVDK SRWQQGNVFS CSVMHEALHN HYTQKSLSLS PGK           353

SEQ ID NO: 194          moltype = AA  length = 353
FEATURE                 Location/Qualifiers
REGION                  1..353
                        note = PR007245 HC
source                  1..353
                        mol_type = protein
                        organism = synthetic construct
SEQUENCE: 194
EVQLVESGGG LVQPGGSLRL SCAASGFTFS SYWMHWVRQV PGKGLVWVSR ISSDASRTIY     60
ADSVKGRFTI SRDNAKNTLY LQMNSLRAED TAVYYCARGE DHDILTGYPI RGQGTTVTVS    120
SEPKSSDKTH TCPPCPAPEL LGGPSVFLFP PKPKDTLMIS RTPEVTCVVV DVSHEDPEVK    180
FNWYVDGVEV HNAKTKPREE QYNSTYRVVS VLTVLHQDWL NGKEYKCKVS NKALPAPIEK    240
TISKAKGQPR EPQVYTLPPS REEMTKNQVS LTCLVKGFYP SDIAVEWESN GQPENNYKTT    300
PPVLDSDGSF FLYSKLTVDK SRWQQGNVFS CSVMHEALHN HYTQKSLSLS PGK           353

SEQ ID NO: 195          moltype = AA  length = 353
FEATURE                 Location/Qualifiers
REGION                  1..353
                        note = PR007246 HC
source                  1..353
                        mol_type = protein
                        organism = synthetic construct
SEQUENCE: 195
EVQLVESGGG LVQPGGSLRL SCAASGFTFS SYWMHWVRQV PGKGLVWVSR ISSTGSRTIY     60
ADSVKGRFTI SRDNAKNTLY LQMNSLRAED TAVYYCARGE DHDILTGYPI RGQGTTVTVS    120
SEPKSSDKTH TCPPCPAPEL LGGPSVFLFP PKPKDTLMIS RTPEVTCVVV DVSHEDPEVK    180
FNWYVDGVEV HNAKTKPREE QYNSTYRVVS VLTVLHQDWL NGKEYKCKVS NKALPAPIEK    240
TISKAKGQPR EPQVYTLPPS REEMTKNQVS LTCLVKGFYP SDIAVEWESN GQPENNYKTT    300
PPVLDSDGSF FLYSKLTVDK SRWQQGNVFS CSVMHEALHN HYTQKSLSLS PGK           353

SEQ ID NO: 196          moltype = AA  length = 355
FEATURE                 Location/Qualifiers
REGION                  1..355
                        note = PR007247 HC
source                  1..355
                        mol_type = protein
                        organism = synthetic construct
SEQUENCE: 196
EVQLVESGGG LVQPGGSLRL SCAASGFTFS SYWMYWVRQV PGKGLVWVSH INPLGSTTQY     60
ADSVKGRFTI SRDNAKNMLY LQMNSLRAED TAVYYCARDF PVLGGSHFDF QHWGQGTLVT    120
VSSEPKSSDK THTCPPCPAP ELLGGPSVFL FPPKPKDTLM ISRTPEVTCV VVDVSHEDPE    180
VKFNWYVDGV EVHNAKTKPR EEQYNSTYRV VSVLTVLHQD WLNGKEYKCK VSNKALPAPI    240
EKTISKAKGQ PREPQVYTLP PSREEMTKNQ VSLTCLVKGF YPSDIAVEWE SNGQPENNYK    300
TTPPVLDSDG SFFLYSKLTV DKSRWQQGNV FSCSVMHEAL HNHYTQKSLS LSPGK         355

SEQ ID NO: 197          moltype = AA  length = 353
FEATURE                 Location/Qualifiers
REGION                  1..353
                        note = PR007248 HC
source                  1..353
                        mol_type = protein
                        organism = synthetic construct
SEQUENCE: 197
EVQLVESGGG LVQPGGSLRL SCAASGFTFS SYWMHWVRQV PGKGLVWVSR INHDSSRTIY     60
ADSVKGRFTI SRDNAKNTLY LQMNSLRAED TAVYYCARGE DHDILTGYPI RGQGTTVTVS    120
SEPKSSDKTH TCPPCPAPEL LGGPSVFLFP PKPKDTLMIS RTPEVTCVVV DVSHEDPEVK    180
FNWYVDGVEV HNAKTKPREE QYNSTYRVVS VLTVLHQDWL NGKEYKCKVS NKALPAPIEK    240
TISKAKGQPR EPQVYTLPPS REEMTKNQVS LTCLVKGFYP SDIAVEWESN GQPENNYKTT    300
PPVLDSDGSF FLYSKLTVDK SRWQQGNVFS CSVMHEALHN HYTQKSLSLS PGK           353

SEQ ID NO: 198          moltype = AA  length = 216
```

```
FEATURE                 Location/Qualifiers
REGION                  1..216
                        note = PR000325 LC
source                  1..216
                        mol_type = protein
                        organism = synthetic construct
SEQUENCE: 198
QSALTQPASV SGSPGQSITI SCSGSSSDIG RYDYVSWYQH YPDKAPKLII YEVKHRPSGI      60
SHRFSASKSG NTASLTISEL QPGDEADYYC ASYTESKTYI FGGGTKVTVL GQPKAAPSVT     120
LFPPSSEELQ ANKATLVCLI SDFYPGAVTV AWKADSSPVK AGVETTTPSK QSNNKYAASS     180
YLSLTPEQWK SHRSYSCQVT HEGSTVEKTV APTECS                              216

SEQ ID NO: 199          moltype = AA  length = 220
FEATURE                 Location/Qualifiers
REGION                  1..220
                        note = PR000400 LC
source                  1..220
                        mol_type = protein
                        organism = synthetic construct
SEQUENCE: 199
DIVMTQSPSS LTVTAGEKVT MSCKSSQSLL NSGNQKNYLT WYQQKPGQPP KLLIYWASTR      60
ESGVPDRFTG SGSGTDFTLT ISSVQAEDLA VYYCQNDYSY PFTFGSGTKL EIKRTVAAPS     120
VFIFPPSDEQ LKSGTASVVC LLNNFYPREA KVQWKVDNAL QSGNSQESVT EQDSKDSTYS     180
LSSTLTLSKA DYEKHKVYAC EVTHQGLSSP VTKSFNRGEC                           220

SEQ ID NO: 200          moltype = AA  length = 215
FEATURE                 Location/Qualifiers
REGION                  1..215
                        note = PR001848 LC, PR003886 LC, PR004312 Chain,
                          PR004313Chain, PR004603 Chain, PR005072 Chain, PR005076
                          Chain,PR005354 Chain, PR005397 Chain, PR005398 Chain,
                          PR005399Chain, PR005401 Chain, PR005411 Chain
source                  1..215
                        mol_type = protein
                        organism = synthetic construct
SEQUENCE: 200
QAVVTQEPSL TVSPGGTVTL TCRSSTGAVT TSNYANWVQQ KPGQAPRGLI GGTNKRAPWT      60
PARFSGSLLG DKAALTLLGA QPEDEAEYFC ALWYSNLWVF GGGTKLTVLG QPKAAPSVTL     120
FPPSSEELQA NKATLVCLIS DFYPGAVTVA WKADSSPVKA GVETTTPSKQ SNNKYAASSY     180
LSLTPEQWKS HRSYSCQVTH EGSTVEKTVA PTECS                                215

SEQ ID NO: 201          moltype = AA  length = 214
FEATURE                 Location/Qualifiers
REGION                  1..214
                        note = PR001861 LC
source                  1..214
                        mol_type = protein
                        organism = synthetic construct
SEQUENCE: 201
EIVMTQSPAT LSVSPGERAT LSCRASQSVR SYLAWYQQKP GQAPRLLIYG ASTRATGIPA      60
RFSGSGSGTE FTLTISSLQS EDFAVYHCQQ YNNWPLTFGG GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 202          moltype = AA  length = 214
FEATURE                 Location/Qualifiers
REGION                  1..214
                        note = PR002725 LC
source                  1..214
                        mol_type = protein
                        organism = synthetic construct
SEQUENCE: 202
EMVMTQSPAT LSVSPGERAT LSCRASQSVS RNLAWFQQKP GQAPRLLIYG ASTRATGIPA      60
RFSGSGSGTE FTLTISSLQS EDFAVYYCQQ YNNWPLTFGG GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 203          moltype = AA  length = 214
FEATURE                 Location/Qualifiers
REGION                  1..214
                        note = PR002726 LC
source                  1..214
                        mol_type = protein
                        organism = synthetic construct
SEQUENCE: 203
EIVLTQSPAT LSLSPGERAT LSCRASQSVS SYLAWYQQKP GQAPRLLIYD ASNRATGIPA      60
RFSGSGSGTD FTLTISSLEP EDFAVYYCQQ RSNWPLTFGG GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214
```

```
SEQ ID NO: 204          moltype = AA  length = 219
FEATURE                 Location/Qualifiers
REGION                  1..219
                        note = PR003767 LC
source                  1..219
                        mol_type = protein
                        organism = synthetic construct
SEQUENCE: 204
DVVMTQSPLS LPVSLGDQAS ISCRSSQRLV HSNGNTYLHW YLQKPGQSPK LLIYRVSNRF    60
PGVPDRFSGS GSGTDFTLKI SRVEAEDLGI YFCSQSTHVP YTFGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 205          moltype = AA  length = 219
FEATURE                 Location/Qualifiers
REGION                  1..219
                        note = PR005080 LC
source                  1..219
                        mol_type = protein
                        organism = synthetic construct
SEQUENCE: 205
DVVLTQTPGS LSLAIGQSAS ISCKSSQSLL GTSGKTFLNW ILQRPGQSPE RLIYQVSKLY    60
SEVPDRFSGS GSETEFTLKI SRVEAEDLGV YYCWQGIHFP HTFGAGTKLE LKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 206          moltype = AA  length = 214
FEATURE                 Location/Qualifiers
REGION                  1..214
                        note = PR002199 Chain
source                  1..214
                        mol_type = protein
                        organism = synthetic construct
SEQUENCE: 206
EIVMTQSPAT LSVSPGERAT LSCRASQSVS SNLAWYQQKP GQAPRLLIYG ASTRATGIPA    60
RFSGSGSGTE FTLTISSLQS EDFAVYYCQQ YNNWPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 207          moltype = AA  length = 453
FEATURE                 Location/Qualifiers
REGION                  1..453
                        note = PR002199 Chain
source                  1..453
                        mol_type = protein
                        organism = synthetic construct
SEQUENCE: 207
EVQLVESGGG LVQPGRSLRL SCAASGFTFD DYAMHWVRQA PGKGLEWVSG ISWNSGSIGY    60
ADSVKGRFTI SRDNAKNSLY LQMNSLRAED TALYYCAKDS RGYGDYRLGG AYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALGAPIEK TISKAKGQPR EPQVYTLPPC   360
REEMTKNQVS LWCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 208          moltype = AA  length = 477
FEATURE                 Location/Qualifiers
REGION                  1..477
                        note = PR002199 Chain
source                  1..477
                        mol_type = protein
                        organism = synthetic construct
SEQUENCE: 208
EVQLLESGGG LVQPGGSLRL SCAASGFTVS SYGMSWVRQA PGKGPEWVSG IRGSDGSTYY    60
ADSVKGRFTI SRDNSKNTLY LQMNSLRAED TAVYYCAKQG ENDGPFDHRG QGTLVTVSSG   120
GGGSEVQLLE SGGGLVQPGG SLRLSCAASG FTVSSYGMSW VRQAPGKGPE WVSGIRGSDG   180
STYYADSVKG RFTISRDNSK NTLYLQMNSL RAEDTAVYYC AKQGENDGPF DHRGQGTLVT   240
VSSASEPKSS DKTHTCPPCP APEAAGGPSV FLFPPKPKDT LMISRTPEVT CVVVDVSHED   300
PEVKFNWYVD GVEVHNAKTK PREEQYNSTY RVVSVLTVLH QDWLNGKEYK CKVSNKALGA   360
PIEKTISKAK GQPREPQVCT LPPSREEMTK NQVSLCAVK GFYPSDIAVE WESNGQPENN   420
YKTTPPVLDS DGSFFLVSKL TVDKSRWQQG NVFSCSVMHE ALHNHYTQKS LSLSPGK      477

SEQ ID NO: 209          moltype = AA  length = 455
FEATURE                 Location/Qualifiers
REGION                  1..455
                        note = PR004312 Chain, PR004313 Chain, PR005354 Chain,
                        PR006023Chain
```

```
source                          1..455
                                mol_type = protein
                                organism = synthetic construct
SEQUENCE: 209
EVQLLESGGG LVQPGGSLRL SCAASGFTFS TYAMNWVRQA PGKGLEWVSR IRSKYNNYAT    60
YYADSVKDRF TISRDDSKST LYLQMNSLRA EDTAVYYCVR HGNFGNSYVS WFAYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PCREEMTKNQ VSLWCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 210                  moltype = AA   length = 481
FEATURE                         Location/Qualifiers
REGION                          1..481
                                note = PR004312 Chain
source                          1..481
                                mol_type = protein
                                organism = synthetic construct
SEQUENCE: 210
QVQLVQSGAE VKKPGQSLRI SCKGAGYSFS TYWIGWVRQM PGKGLEWMGI IYPDDSDTRY    60
SPSFEGQVTI SVDKSITTAY LHWSSLKASD TAIYYCARLV GGAPAYWGQG TLVTVSSGGG   120
GSGGGGSGGG GSGGGGSQSA LTQPASVSGS PGQSITISCS GSSSDIGRYD YVSWYQHYPD   180
KAPKLIIYEV KHRPSGISHR FSASKSGNTA SLTISELQPG DEADYYCASY TESKTYIFGG   240
GTKVTVLASE PKSSDKTHTC PPCPAPEAAG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVCTLPPSRE EMTKNQVSLS CAVKGFYPSD IAVEWESNGQ   420
PENNYKTTPP VLDSDGSFFL VSKLTVDKSR WQQGNVFSCS VMHEALHNHY TQKSLSLSPG   480
K                                                                   481

SEQ ID NO: 211                  moltype = AA   length = 480
FEATURE                         Location/Qualifiers
REGION                          1..480
                                note = PR004313 Chain
source                          1..480
                                mol_type = protein
                                organism = synthetic construct
SEQUENCE: 211
EVQLLESGGG LVQPGGSLRL SCAASGFSFS SFAMSWVRQA PGKGLEWVSA LSGSGGSTYY    60
TDSVKGRFTV SRDNSKNTLY LQMNSLRAED TAIYYCANWG GGTGIFEFWG QGTLVTVSSG   120
GGGSGGGGSG GGGSGGGGSE IVMTQSPATL SVSPGERATL SCRASQSVRS YLAWYQQKPG   180
QAPRLLIYGA STRATGIPAR FSGSGSGTEF TLTISSLQSE DFAVHCQQY NNWPLTFGGG   240
TKVEIKASEP KSSDKTHTCP PCPAPEAAGG PSVFLFPPKP KDTLMISRTP EVTCVVVDVS   300
HEDPEVKFNW YVDGVEVHNA KTKPREEQYN STYRVVSVLT VLHQDWLNGK EYKCKVSNKA   360
LPAPIEKTIS KAKGQPREPQ VCTLPPSREE MTKNQVSLSC AVKGFYPSDI AVEWESNGQP   420
ENNYKTTPPV LDSDGSFFLV SKLTVDKSRW QQGNVFSCSV MHEALHNHYT QKSLSLSPGK   480

SEQ ID NO: 212                  moltype = AA   length = 988
FEATURE                         Location/Qualifiers
REGION                          1..988
                                note = PR004549 Chain
source                          1..988
                                mol_type = protein
                                organism = synthetic construct
SEQUENCE: 212
QVQLVQSGAE VKKPGASVKV SCKASGYTFT GYYMHWVRQA PGQCLEWMGW INPNSGGTKY    60
AQKFQGRVTM TRDTSISTAY MELSRLRSDD TAVYYCARDR ITVAGTYYYY GMDVWGQGTT   120
VTVSSGGGGS GGGGSGGGGS DIQMTQSPSS VSASVGDRVT ITCRASQGVN NWLAWYQQKP   180
GKAPKLLIYT ASSLQSGVPS RFSGSGSGTD FTLTIRSLQP EDFATYYCQQ ANSFPITFGC   240
GTRLEIKSGG GSEVQLVES GGGLVQPGGS LKLSCAASGF TFNKYAMNWV RQAPGKGLEW   300
VARIRSKYNN YATYYADSVK DRFTISRDDS KNTAYLQMNN LKTEDTAVYY CVRHGNFGNS   360
YISYWAYWGQ GTLVTVSSGG GGSGGGGSGG GGSQTVVTQE PSLTVSPGGT VTLTCGSSTG   420
AVTSGNYPNW VQQKPGQAPR GLIGGTKFLA PGTPARFSGS LLGGKAALTL SGVQPEDEAE   480
YYCVLWYSNR WVFGGGTKLT VLGGGGDKTH TCPPCPAPEL LGGPSVFLFP PKPKDTLMIS   540
RTPEVTCVVV DVSHEDPEVK FNWYVDGVEV HNAKTKPCEE QYGSTYRCVS VLTVLHQDWL   600
NGKEYKCKVS NKALPAPIEK TISKAKGQPR EPQVYTLPPS REEMTKNQVS LTCLVKGFYP   660
SDIAVEWESN GQPENNYKTT PPVLDSDGSF FLYSKLTVDK SRWQQGNVFS CSVMHEALHN   720
HYTQKSLSLS PGGGGSGGGG SGGGGSGGGG SGGGGSGGGG SDKTHTCPPC PAPELLGGPS   780
VFLFPPKPKD TLMISRTPEV TCVVVDVSHE DPEVKFNWYV DGVEVHNAKT KPCEEQYGST   840
YRCVSVLTVL HQDWLNGKEY KCKVSNKALP APIEKTISKA KGQPREPQVY TLPPSREEMT   900
KNQVSLTCLV KGFYPSDIAV EWESNGQPEN NYKTTPPVLD SDGSFFLYSK LTVDKSRWQQ   960
GNVFSCSVMH EALHNHYTQK SLSLSPGK                                      988

SEQ ID NO: 213                  moltype = AA   length = 455
FEATURE                         Location/Qualifiers
REGION                          1..455
                                note = PR004603 Chain, PR005072 Chain, PR005076 Chain,
                                PR005397Chain, PR005398 Chain, PR005399 Chain, PR005401
```

```
                        Chain,PR005411 Chain, PR005422 Chain, PR005525 Chain
source                  1..455
                        mol_type = protein
                        organism = synthetic construct
SEQUENCE: 213
EVQLVESGGG LVQPGGSLKL SCAASGFTFS TYAMNWVRQA SGKGLEWVGR IRSKYNNYAT    60
YYADSVKDRF TISRDDSKNT AYLQMNSLKT EDTAVYYCTR HGNFGNSYVS WFAYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PCREEMTKNQ VSLWCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 214          moltype = AA   length = 489
FEATURE                 Location/Qualifiers
REGION                  1..489
                        note = PR004603 Chain
source                  1..489
                        mol_type = protein
                        organism = synthetic construct
SEQUENCE: 214
EVQLVESGGG LVQPGGSLRL SCAASGFTFS SYWMHWVRQA PGKGLEWVSY INNDGSSTRY    60
ADSVKGRFTI SRDNAKNTLY LQMNSLRAED TAVYYCTEAP PYGNYERDYW GQGTLVTVSS   120
GGGGSGGGGS GGGGSEVQLV ESGGGLVQPG GSLRLSCAAS GFTFSSYWMH WVRQAPGKGL   180
EWVSYINNDG SSTRYADSVK GRFTISRDNA KNTLYLQMNS LRAEDTAVYY CTEAPPYGNY   240
ERDYWGQGTL VTVSSASEPK SSDKTHTCPP CPAPEAAGGP SVFLFPPKPK DTLMISRTPE   300
VTCVVVDVSH EDPEVKFNWY VDGVEVHNAK TKPREEQYNS TYRVVSVLTV LHQDWLNGKE   360
YKCKVSNKAL PAPIEKTISK AKGQPREPQV CTLPPSREEM TKNQVSLSCA VKGFYPSDIA   420
VEWESNGQPE NNYKTTPPVL DSDGSFFLVS KLTVDKSRWQ QGNVFSCSVM HEALHNHYTQ   480
KSLSLSPGK                                                           489

SEQ ID NO: 215          moltype = AA   length = 214
FEATURE                 Location/Qualifiers
REGION                  1..214
                        note = PR004931 Chain
source                  1..214
                        mol_type = protein
                        organism = synthetic construct
SEQUENCE: 215
QAVVTQEPSL TVSPGGTVTL TCGSSTGAVT TSNYANWVQE KPGQAFRGLI GGTNKRAPGT    60
PARFSGSLLG GKAALTLSGA QPEDEAEYYC ALWYSNLWVF GGGTKLTVLS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKE SNTKVDKKVE PKSC                                214

SEQ ID NO: 216          moltype = AA   length = 215
FEATURE                 Location/Qualifiers
REGION                  1..215
                        note = PR004931 Chain
source                  1..215
                        mol_type = protein
                        organism = synthetic construct
SEQUENCE: 216
DIQMTQSPSS LSASVGDRVT ITCKASAAVG TYVAWYQQKP GKAPKLLIYS ASYRKRGVPS    60
RFSGSGSGTD FTLTISSLQP EDFATYYCHQ YYTYPLFTFG QGTKLEIKRT VAAPSVFIFP   120
PSDEQLKSGT ASVVCLLNNE YPREAKVQWK VDNALQSGNS QESVTEQDSK DSTYSLSSTL   180
TLSKADYEKH KVYACEVTHQ GLSSPVTKSF NRGEC                               215

SEQ ID NO: 217          moltype = AA   length = 451
FEATURE                 Location/Qualifiers
REGION                  1..451
                        note = PR004931 Chain
source                  1..451
                        mol_type = protein
                        organism = synthetic construct
SEQUENCE: 217
QVQLVQSGAE VKKPGASVKV SCKASGYTFT EFGMNWVRQA PGQGLEWMGW INTKTGEATY    60
VEEFKGRVTF TTDTSTSTAY MELRSLRSDD TAVYYCARWD FAYYVEAMDY WGQGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALGAPIEKTI SKAKGQPREP QVCTLPPSRE   360
EMTKNQVSLS CAVKGFYPSD IAVEWESNGQ PENNYKTTPP VLDSDGSFFL VSKLTVDKSR   420
WQQGNVFSCS VMHEALHNHY TQKSLSLSPG K                                   451

SEQ ID NO: 218          moltype = AA   length = 694
FEATURE                 Location/Qualifiers
REGION                  1..694
                        note = PR004931 Chain
```

```
source                  1..694
                        mol_type = protein
                        organism = synthetic construct
SEQUENCE: 218
QVQLVQSGAE VKKPGASVKV SCKASGYTFT EFGMNWVRQA PGQGLEWMGW INTKTGEATY      60
VEEFKGRVTF TTDTSTSTAY MELRSLRSDD TAVYYCARWD FAYYVEAMDY WGQGTTVTVS     120
SASTKGPSVF PLAPSSKSTS GGTAALGCLV KDYFPEPVTV SWNSGALTSG VHTFPAVLQS     180
SGLYSLSSVV TVPSSSLGTQ TYICNVNHKP SNTKVDKKVE PKSCDGGGGS GGGGSEVQLL     240
ESGGGLVQPG GSLRLSCAAS GFTFSTYAMN WVRQAPGKGL EWVSRIRSKY NNYATYYADS     300
VKGRFTISRD DSKNTLYLQM NSLRAEDTAV YYCVRHGNFG NSYVSWFAYW GQGTLVTVSS     360
ASVAAPSVFI FPPSDEQLKS GTASVVCLLN NFYPREAKVQ WKVDNALQSG NSQESVTEQD     420
SKDSTYSLSS TLTLSKADYE KHKVYACEVT HQGLSSPVTK SFNRGECDKT HTCPPCPAPE     480
AAGGPSVFLF PPKPKDTLMI SRTPEVTCVV VDVSHEDPEV KFNWYVDGVE VHNAKTKPRE     540
EQYNSTYRVV SVLTVLHQDW LNGKEYKCKV SNKALGAPIE KTISKAKGQP REPQVYTLPP     600
CREEMTKNQV SLWCLVKGFY PSDIAVEWES NGQPENNYKT TPPVLDSDGS FFLYSKLTVD     660
KSRWQQGNVF SCSVMHEALH NHYTQKSLSL SPGK                                 694

SEQ ID NO: 219          moltype = AA  length = 491
FEATURE                 Location/Qualifiers
REGION                  1..491
                        note = PR005072 Chain, PR005354 Chain, PR005520 Chain,
                         PR005521Chain, PR005522 Chain
source                  1..491
                        mol_type = protein
                        organism = synthetic construct
SEQUENCE: 219
EVQLVESGGG LVQPGGSLRL SCAASGFTFS SYWMHWVRQV PGKGLVWVSR INSDGSRTIY      60
ADSVKGRFTI SRDNAKNTLY LQMNSLRAED TAVYYCARGE DHDILTGYPI RGQGTTVTVS     120
SGGGGSGGGG SGGGGSEVQL VESGGGLVQP GGSLRLSCAA SGFTFSSYWM HWVRQVPGKG     180
LVWVSRINSD GSRTIYADSV KGRFTISRDN AKNTLYLQMN SLRAEDTAVY YCARGEDHDI     240
LTGYPIRGQG TTVTVSSASE PKSSDKTHTC PPCPAPEAAG GPSVFLFPPK PKDTLMISRT     300
PEVTCVVVDV SHEDPEVKFN WYVDGVEVHN AKTKPREEQY NSTYRVVSVL TVLHQDWLNG     360
KEYKCKVSNK ALPAPIEKTI SKAKGQPREP QVCTLPPSRE EMTKNQVSLS CAVKGFYPSD     420
IAVEWESNGQ PENNYKTTPP VLDSDGSFFL VSKLTVDKSR WQQGNVFSCS VMHEALHNHY     480
TQKSLSLSPG K                                                          491

SEQ ID NO: 220          moltype = AA  length = 495
FEATURE                 Location/Qualifiers
REGION                  1..495
                        note = PR005076 Chain
source                  1..495
                        mol_type = protein
                        organism = synthetic construct
SEQUENCE: 220
EVQLVESGGG LVQPGGSLRL SCAASGFTFS SYWMYWVRQV PGKGLVWVSH INSDGSTTQY      60
ADSVKGRFTI SRDNAKNMLY LQMNSLRAED TAVYYCARDF PVLGGSHFDF QHWGQGTLVT     120
VSSGGGGSGG GGSGGGGSEV QLVESGGGLV QPGGSLRLSC AASGFTFSSY WMYWVRQVPG     180
KGLVWVSHIN SDGSTTQYAD SVKGRFTISR DNAKNMLYLQ MNSLRAEDTA VYYCARDFPV     240
LGGSHFDFQH WGQGTLVTVS SASEPKSSDK THTCPPCPAP EAAGGPSVFL FPPKPKDTLM     300
ISRTPEVTCV VVDVSHEDPE VKFNWYVDGV EVHNAKTKPR EEQYNSTYRV VSVLTVLHQD     360
WLNGKEYKCK VSNKALPAPI EKTISKAKGQ PREPQVCTLP PSREEMTKNQ VSLSCAVKGF     420
YPSDIAVEWE SNGQPENNYK TTPPVLDSDG SFFLVSKLTV DKSRWQQGNV FSCSVMHEAL     480
HNHYTQKSLS LSPGK                                                      495

SEQ ID NO: 221          moltype = AA  length = 491
FEATURE                 Location/Qualifiers
REGION                  1..491
                        note = PR005397 Chain, PR006023 Chain
source                  1..491
                        mol_type = protein
                        organism = synthetic construct
SEQUENCE: 221
EVQLVESGGG LVQPGGSLRL SCAASGFTFS SYWMHWVRQV PGKGLVWVSR ISSTGSRTIY      60
ADSVKGRFTI SRDNAKNTLY LQMNSLRAED TAVYYCARGE DHDILTGYPI RGQGTTVTVS     120
SGGGGSGGGG SGGGGSEVQL VESGGGLVQP GGSLRLSCAA SGFTFSSYWM HWVRQVPGKG     180
LVWVSRISST GSRTIYADSV KGRFTISRDN AKNTLYLQMN SLRAEDTAVY YCARGEDHDI     240
LTGYPIRGQG TTVTVSSASE PKSSDKTHTC PPCPAPEAAG GPSVFLFPPK PKDTLMISRT     300
PEVTCVVVDV SHEDPEVKFN WYVDGVEVHN AKTKPREEQY NSTYRVVSVL TVLHQDWLNG     360
KEYKCKVSNK ALPAPIEKTI SKAKGQPREP QVCTLPPSRE EMTKNQVSLS CAVKGFYPSD     420
IAVEWESNGQ PENNYKTTPP VLDSDGSFFL VSKLTVDKSR WQQGNVFSCS VMHEALHNHY     480
TQKSLSLSPG K                                                          491

SEQ ID NO: 222          moltype = AA  length = 491
FEATURE                 Location/Qualifiers
REGION                  1..491
                        note = PR005398 Chain
source                  1..491
                        mol_type = protein
                        organism = synthetic construct
```

```
SEQUENCE: 222
EVQLVESGGG LVQPGGSLRL SCAASGFTFS SYWMHWVRQV PGKGLVWVSR INFDSSRTIY    60
ADSVKGRFTI SRDNAKNTLY LQMNSLRAED TAVYYCARGE DHDILTGYPI RGQGTTVTVS   120
SGGGGSGGGG SGGGGSEVQL VESGGGLVQP GGSLRLSCAA SGFTFSSYWM HWVRQVPGKG   180
LVWVSRINFD SSRTIYADSV KGRFTISRDN AKNTLYLQMN SLRAEDTAVY YCARGEDHDI   240
LTGYPIRGQG TTVTVSSASE PKSSDKTHTC PPCPAPEAAG GPSVFLFPPK PKDTLMISRT   300
PEVTCVVVDV SHEDPEVKFN WYVDGVEVHN AKTKPREEQY NSTYRVVSVL TVLHQDWLNG   360
KEYKCKVSNK ALPAPIEKTI SKAKGQPREP QVCTLPPSRE EMTKNQVSLS CAVKGFYPSD   420
IAVEWESNGQ PENNYKTTPP VLDSDGSFFL VSKLTVDKSR WQQGNVFSCS VMHEALHNHY   480
TQKSLSLSPG K                                                       491

SEQ ID NO: 223          moltype = AA  length = 491
FEATURE                 Location/Qualifiers
REGION                  1..491
                        note = PR005399 Chain
source                  1..491
                        mol_type = protein
                        organism = synthetic construct
SEQUENCE: 223
EVQLVESGGG LVQPGGSLRL SCAASGFTFS SYWMHWVRQV PGKGLVWVSR ISSAGSRTIY    60
ADSVKGRFTI SRDNAKNTLY LQMNSLRAED TAVYYCARGE DHDILTGYPI RGQGTTVTVS   120
SGGGGSGGGG SGGGGSEVQL VESGGGLVQP GGSLRLSCAA SGFTFSSYWM HWVRQVPGKG   180
LVWVSRISSA GSRTIYADSV KGRFTISRDN AKNTLYLQMN SLRAEDTAVY YCARGEDHDI   240
LTGYPIRGQG TTVTVSSASE PKSSDKTHTC PPCPAPEAAG GPSVFLFPPK PKDTLMISRT   300
PEVTCVVVDV SHEDPEVKFN WYVDGVEVHN AKTKPREEQY NSTYRVVSVL TVLHQDWLNG   360
KEYKCKVSNK ALPAPIEKTI SKAKGQPREP QVCTLPPSRE EMTKNQVSLS CAVKGFYPSD   420
IAVEWESNGQ PENNYKTTPP VLDSDGSFFL VSKLTVDKSR WQQGNVFSCS VMHEALHNHY   480
TQKSLSLSPG K                                                       491

SEQ ID NO: 224          moltype = AA  length = 491
FEATURE                 Location/Qualifiers
REGION                  1..491
                        note = PR005401 Chain
source                  1..491
                        mol_type = protein
                        organism = synthetic construct
SEQUENCE: 224
EVQLVESGGG LVQPGGSLRL SCAASGFTFS SYWMHWVRQV PGKGLVWVSR IDSRGSRTIY    60
ADSVKGRFTI SRDNAKNTLY LQMNSLRAED TAVYYCARGE DHDILTGYPI RGQGTTVTVS   120
SGGGGSGGGG SGGGGSEVQL VESGGGLVQP GGSLRLSCAA SGFTFSSYWM HWVRQVPGKG   180
LVWVSRIDSR GSRTIYADSV KGRFTISRDN AKNTLYLQMN SLRAEDTAVY YCARGEDHDI   240
LTGYPIRGQG TTVTVSSASE PKSSDKTHTC PPCPAPEAAG GPSVFLFPPK PKDTLMISRT   300
PEVTCVVVDV SHEDPEVKFN WYVDGVEVHN AKTKPREEQY NSTYRVVSVL TVLHQDWLNG   360
KEYKCKVSNK ALPAPIEKTI SKAKGQPREP QVCTLPPSRE EMTKNQVSLS CAVKGFYPSD   420
IAVEWESNGQ PENNYKTTPP VLDSDGSFFL VSKLTVDKSR WQQGNVFSCS VMHEALHNHY   480
TQKSLSLSPG K                                                       491

SEQ ID NO: 225          moltype = AA  length = 491
FEATURE                 Location/Qualifiers
REGION                  1..491
                        note = PR005411 Chain
source                  1..491
                        mol_type = protein
                        organism = synthetic construct
SEQUENCE: 225
EVQLVESGGG LVQPGGSLRL SCAASGFTFS SYWMHWVRQV PGKGLVWVSR ISSDASRTIY    60
ADSVKGRFTI SRDNAKNTLY LQMNSLRAED TAVYYCARGE DHDILTGYPI RGQGTTVTVS   120
SGGGGSGGGG SGGGGSEVQL VESGGGLVQP GGSLRLSCAA SGFTFSSYWM HWVRQVPGKG   180
LVWVSRISSD ASRTIYADSV KGRFTISRDN AKNTLYLQMN SLRAEDTAVY YCARGEDHDI   240
LTGYPIRGQG TTVTVSSASE PKSSDKTHTC PPCPAPEAAG GPSVFLFPPK PKDTLMISRT   300
PEVTCVVVDV SHEDPEVKFN WYVDGVEVHN AKTKPREEQY NSTYRVVSVL TVLHQDWLNG   360
KEYKCKVSNK ALPAPIEKTI SKAKGQPREP QVCTLPPSRE EMTKNQVSLS CAVKGFYPSD   420
IAVEWESNGQ PENNYKTTPP VLDSDGSFFL VSKLTVDKSR WQQGNVFSCS VMHEALHNHY   480
TQKSLSLSPG K                                                       491

SEQ ID NO: 226          moltype = AA  length = 495
FEATURE                 Location/Qualifiers
REGION                  1..495
                        note = PR005422 Chain
source                  1..495
                        mol_type = protein
                        organism = synthetic construct
SEQUENCE: 226
EVQLVESGGG LVQPGGSLRL SCAASGFTFS SYWMYWVRQV PGKGLVWVSH INPLGSTTQY    60
ADSVKGRFTI SRDNAKNMLY LQMNSLRAED TAVYYCARDF PVLGGSHFDF QHWGQGTLVT   120
VSSGGGGSGG GGSGGGGSEV QLVESGGGLV QPGGSLRLSC AASGFTFSSY WMYWVRQVPG   180
KGLVWVSHIN PLGSTTQYAD SVKGRFTISR DNAKNMLYLQ MNSLRAEDTA VYYCARDFPV   240
LGGSHFDFQH WGQGTLVTVS SASEPKSSDK THTCPPCPAP EAAGGPSVFL FPPKPKDTLM   300
ISRTPEVTCV VVDVSHEDPE VKFNWYVDGV EVHNAKTKPR EEQYNSTYRV VSVLTVLHQD   360
```

-continued

```
WLNGKEYKCK VSNKALPAPI EKTISKAKGQ PREPQVCTLP PSREEMTKNQ VSLSCAVKGF    420
YPSDIAVEWE SNGQPENNYK TTPPVLDSDG SFFLVSKLTV DKSRWQQGNV FSCSVMHEAL    480
HNHYTQKSLS LSPGK                                                    495

SEQ ID NO: 227          moltype = AA   length = 355
FEATURE                 Location/Qualifiers
REGION                  1..355
                        note = PR005518 Chain, PR005519 Chain
source                  1..355
                        mol_type = protein
                        organism = synthetic construct
SEQUENCE: 227
EVQLVESGGG LVQPGGSLRL SCAASGFTFS SYWMHWVRQV PGKGLVWVSR INSDGSRTIY     60
ADSVKGRFTI SRDNAKNTLY LQMNSLRAED TAVYYCARGE DHDILTGYPI RGQGTTVTVS    120
SASEPKSSDK THTCPPCPAP EAAGGPSVFL FPPKPKDTLM ISRTPEVTCV VVDVSHEDPE    180
VKFNWYVDGV EVHNAKTKPR EEQYNSTYRV VSVLTVLHQD WLNGKEYKCK VSNKALPAPI    240
EKTISKAKGQ PREPQVCTLP PSREEMTKNQ VSLSCAVKGF YPSDIAVEWE SNGQPENNYK    300
TTPPVLDSDG SFFLVSKLTV DKSRWQQGNV FSCSVMHEAL HNHYTQKSLS LSPGK         355

SEQ ID NO: 228          moltype = AA   length = 599
FEATURE                 Location/Qualifiers
REGION                  1..599
                        note = PR005518 Chain
source                  1..599
                        mol_type = protein
                        organism = synthetic construct
SEQUENCE: 228
EVQLVESGGG LVQPGGSLRL SCAASGFTFS SYWMHWVRQV PGKGLVWVSR INSDGSRTIY     60
ADSVKGRFTI SRDNAKNTLY LQMNSLRAED TAVYYCARGE DHDILTGYPI RGQGTTVTVS    120
SASEPKSSDK THTCPPCPAP EAAGGPSVFL FPPKPKDTLM ISRTPEVTCV VVDVSHEDPE    180
VKFNWYVDGV EVHNAKTKPR EEQYNSTYRV VSVLTVLHQD WLNGKEYKCK VSNKALPAPI    240
EKTISKAKGQ PREPQVYTLP PCREEMTKNQ VSLWCLVKGF YPSDIAVEWE SNGQPENNYK    300
TTPPVLDSDG SFFLYSKLTV DKSRWQQGNV FSCSVMHEAL HNHYTQKSLS LSPGGGGGSG    360
GGGSGGGGSR TEVQLLESGG GLVQPGGSLR LSCAASGFTF STYAMNWVRQ APGKGLEWVS    420
RIRSKYNNYA TYYADSVKDR FTISRDDSKS TLYLQMNSLR AEDTAVYYCV RHGNFGNSYV    480
SWFAYWGQGT LVTVSSASTK GPSVFPLAPS SKSTSGGTAA LGCLVKDYFP EPVTVSWNSG    540
ALTSGVHTFP AVLQSSGLYS LSSVVTVPSS SLGTQTYICN VNHKPSNTKV DKKVEPKSC    599

SEQ ID NO: 229          moltype = AA   length = 228
FEATURE                 Location/Qualifiers
REGION                  1..228
                        note = PR005519 Chain, PR005521 Chain
source                  1..228
                        mol_type = protein
                        organism = synthetic construct
SEQUENCE: 229
EVQLLESGGG LVQPGGSLRL SCAASGFTFS TYAMNWVRQA PGKGLEWVSR IRSKYNNYAT     60
YYADSVKDRF TISRDDSKST LYLQMNSLRA EDTAVYYCVR HGNFGNSYVS WFAYWGQGTL    120
VTVSSASTKG PSVFPLAPSS KSTSGGTAAL GCLVKDYFPE PVTVSWNSGA LTSGVHTFPA    180
VLQSSGLYSL SSVVTVPSSS LGTQTYICNV NHKPSNTKVD KKVEPKSC                 228

SEQ ID NO: 230          moltype = AA   length = 586
FEATURE                 Location/Qualifiers
REGION                  1..586
                        note = PR005519 Chain
source                  1..586
                        mol_type = protein
                        organism = synthetic construct
SEQUENCE: 230
EVQLVESGGG LVQPGGSLRL SCAASGFTFS SYWMHWVRQV PGKGLVWVSR INSDGSRTIY     60
ADSVKGRFTI SRDNAKNTLY LQMNSLRAED TAVYYCARGE DHDILTGYPI RGQGTTVTVS    120
SASEPKSSDK THTCPPCPAP EAAGGPSVFL FPPKPKDTLM ISRTPEVTCV VVDVSHEDPE    180
VKFNWYVDGV EVHNAKTKPR EEQYNSTYRV VSVLTVLHQD WLNGKEYKCK VSNKALPAPI    240
EKTISKAKGQ PREPQVYTLP PCREEMTKNQ VSLWCLVKGF YPSDIAVEWE SNGQPENNYK    300
TTPPVLDSDG SFFLYSKLTV DKSRWQQGNV FSCSVMHEAL HNHYTQKSLS LSPGGGGGSG    360
GGGSGGGGSR TQAVVTQEPS LTVSPGGTVT LTCRSSTGAV TTSNYANWVQ QKPGQAPRGL    420
IGGTNKRAPW TPARFSGSLL GDKAALTLLG AQPEDEAEYF CALWYSNLWV FGGGTKLTVL    480
GQPKAAPSVT LFPPSSEELQ ANKATLVCLI SDFYPGAVTV AWKADSSPVK AGVETTTPSK    540
QSNNKYAASS YLSLTPEQWK SHRSYSCQVT HEGSTVEKTV APTECS                  586

SEQ ID NO: 231          moltype = AA   length = 735
FEATURE                 Location/Qualifiers
REGION                  1..735
                        note = PR005520 Chain
source                  1..735
                        mol_type = protein
                        organism = synthetic construct
SEQUENCE: 231
EVQLVESGGG LVQPGGSLRL SCAASGFTFS SYWMHWVRQV PGKGLVWVSR INSDGSRTIY     60
```

```
ADSVKGRFTI SRDNAKNTLY LQMNSLRAED TAVYYCARGE DHDILTGYPI RGQGTTVTVS    120
SGGGGSGGGG SGGGGSEVQL VESGGGLVQP GGSLRLSCAA SGFTFSSYWM HWVRQVPGKG    180
LVWVSRINSD GSRTIYADSV KGRFTISRDN AKNTLYLQMN SLRAEDTAVY YCARGEDHDI    240
LTGYPIRGQG TTVTVSSASE PKSSDKTHTC PPCPAPEAAG GPSVFLFPPK PKDTLMISRT    300
PEVTCVVVDV SHEDPEVKFN WYVDGVEVHN AKTKPREEQY NSTYRVVSVL TVLHQDWLNG    360
KEYKCKVSNK ALPAPIEKTI SKAKGQPREP QVYTLPPCRE EMTKNQVSLW CLVKGFYPSD    420
IAVEWESNGQ PENNYKTTPP VLDSDGSFFL YSKLTVDKSR WQQGNVFSCS VMHEALHNHY    480
TQKSLSLSPG GGGGSGGGGS GGGGSRTEVQ LLESGGGLVQ PGGSLRLSCA ASGFTFSTYA    540
MNWVRQAPGK GLEWVSRIRS KYNNYATYYA DSVKDRFTIS RDDSKSTLYL QMNSLRAEDT    600
AVYYCVRHGN FGNSYVSWFA YWGQGTLVTV SSASTKGPSV FPLAPSSKST SGGTAALGCL    660
VKDYFPEPVT VSWNSGALTS GVHTFPAVLQ SSGLYSLSSV VTVPSSSLGT QTYICNVNHK    720
PSNTKVDKKV EPKSC                                                    735

SEQ ID NO: 232        moltype = AA  length = 722
FEATURE               Location/Qualifiers
REGION                1..722
                      note = PR005521 Chain
source                1..722
                      mol_type = protein
                      organism = synthetic construct
SEQUENCE: 232
EVQLVESGGG LVQPGGSLRL SCAASGFTFS SYWMHWVRQV PGKGLVWVSR INSDGSRTIY     60
ADSVKGRFTI SRDNAKNTLY LQMNSLRAED TAVYYCARGE DHDILTGYPI RGQGTTVTVS    120
SGGGGSGGGG SGGGGSEVQL VESGGGLVQP GGSLRLSCAA SGFTFSSYWM HWVRQVPGKG    180
LVWVSRINSD GSRTIYADSV KGRFTISRDN AKNTLYLQMN SLRAEDTAVY YCARGEDHDI    240
LTGYPIRGQG TTVTVSSASE PKSSDKTHTC PPCPAPEAAG GPSVFLFPPK PKDTLMISRT    300
PEVTCVVVDV SHEDPEVKFN WYVDGVEVHN AKTKPREEQY NSTYRVVSVL TVLHQDWLNG    360
KEYKCKVSNK ALPAPIEKTI SKAKGQPREP QVYTLPPCRE EMTKNQVSLW CLVKGFYPSD    420
IAVEWESNGQ PENNYKTTPP VLDSDGSFFL YSKLTVDKSR WQQGNVFSCS VMHEALHNHY    480
TQKSLSLSPG GGGGSGGGGS GGGGSRTQAV VTQEPSLTVS PGGTVTLTCR SSTGAVTTSN    540
YANWVQQKPG QAPRGLIGGT NKRAPWTPAR FSGSLLGDKA ALTLLGAQPE DEAEYFCALW    600
YSNLWVFGGG TKLTVLGQPK AAPSVTLFPP SSEELQANKA TLVCLISDFY PGAVTVAWKA    660
DSSPVKAGVE TTTPSKQSNN KYAASSYLSL TPEQWKSHRS YSCQVTHEGS TVEKTVAPTE    720
CS                                                                  722

SEQ ID NO: 233        moltype = AA  length = 591
FEATURE               Location/Qualifiers
REGION                1..591
                      note = PR005522 Chain
source                1..591
                      mol_type = protein
                      organism = synthetic construct
SEQUENCE: 233
EVQLVESGGG LVQPGGSLRL SCAASGFTFS SYWMHWVRQV PGKGLVWVSR INSDGSRTIY     60
ADSVKGRFTI SRDNAKNTLY LQMNSLRAED TAVYYCARGE DHDILTGYPI RGQGTTVTVS    120
SGGGGSGGGG SGGGGSEVQL LESGGGLVQP GGSLRLSCAA SGFTFSTYAM NWVRQAPGKG    180
LEWVSRIRSK YNNYATYYAD SVKDRFTISR DDSKSTLYLQ MNSLRAEDTA VYYCVRHGNF    240
GNSYVSWFAY WGQGTLVTVS SASTKGPSVF PLAPSSKSTS GGTAALGCLV KDYFPEPVTV    300
SWNSGALTSG VHTFPAVLQS SGLYSLSSVV TVPSSSLGTQ TYICNVNHKP SNTKVDKKVE    360
PKSCDKTHTC PPCPAPEAAG GPSVFLFPPK PKDTLMISRT PEVTCVVVDV SHEDPEVKFN    420
WYVDGVEVHN AKTKPREEQY NSTYRVVSVL TVLHQDWLNG KEYKCKVSNK ALPAPIEKTI    480
SKAKGQPREP QVYTLPPCRE EMTKNQVSLW CLVKGFYPSD IAVEWESNGQ PENNYKTTPP    540
VLDSDGSFFL YSKLTVDKSR WQQGNVFSCS VMHEALHNHY TQKSLSLSPG K             591

SEQ ID NO: 234        moltype = AA  length = 627
FEATURE               Location/Qualifiers
REGION                1..627
                      note = PR005525 Chain
source                1..627
                      mol_type = protein
                      organism = synthetic construct
SEQUENCE: 234
EVQLVESGGG LVQPGGSLRL SCAASGFTFS SYWMHWVRQV PGKGLVWVSR INSDGSRTIY     60
ADSVKGRFTI SRDNAKNTLY LQMNSLRAED TAVYYCARGE DHDILTGYPI RGQGTTVTVS    120
SGGGGSGGGG SGGGGSEVQL VESGGGLVQP GGSLRLSCAA SGFTFSSYWM HWVRQVPGKG    180
LVWVSRINSD GSRTIYADSV KGRFTISRDN AKNTLYLQMN SLRAEDTAVY YCARGEDHDI    240
LTGYPIRGQG TTVTVSSGGG GSGGGGSGGG GSEVQLVESG GGLVQPGGSL RLSCAASGFT    300
FSSYWMHWVR QVPGKGLVWV SRINSDGSRT IYADSVKGRF TISRDNAKNT LYLQMNSLRA    360
EDTAVYYCAR GEDHDILTGY PIRGQGTTVT VSSASEPKSS DKTHTCPPCP APEAAGGPSV    420
FLFPPKPKDT LMISRTPEVT CVVVDVSHED PEVKFNWYVD GVEVHNAKTK PREEQYNSTY    480
RVVSVLTVLH QDWLNGKEYK CKVSNKALPA PIEKTISKAK GQPREPQVCT LPPSREEMTK    540
NQVSLSCAVK GFYPSDIAVE WESNGQPENN YKTTPPVLDS DGSFFLVSKL TVDKSRWQQG    600
NVFSCSVMHE ALHNHYTQKS LSLSPGK                                       627

SEQ ID NO: 235        moltype = AA  length = 455
FEATURE               Location/Qualifiers
REGION                1..455
                      note = PR006292 Chain, PR006384 Chain, PR007079 Chain,
                      PR007080Chain, PR007081 Chain, PR007082 Chain, PR007083
```

```
                            Chain
source                      1..455
                            mol_type = protein
                            organism = synthetic construct
SEQUENCE: 235
EVQLVESGGG LVQPGGSLKL SCAASGFTFS TYAMNWVRQA SGKGLEWVGR IRSKYNNYAT    60
YYADSVKDRF TISRDDSKNT AYLQMNSLKT EDTAVYYCTR HGNFGNSYVS WFAYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
EAAGAPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PCREEMTKNQ VSLWCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 236              moltype = AA  length = 491
FEATURE                     Location/Qualifiers
REGION                      1..491
                            note = PR006292 Chain, PR006293 Chain
source                      1..491
                            mol_type = protein
                            organism = synthetic construct
SEQUENCE: 236
EVQLVESGGG LVQPGGSLRL SCAASGFTFS SYWMHWVRQV PGKGLVWVSR ISSDASRTIY    60
ADSVKGRFTI SRDNAKNTLY LQMNSLRAED TAVYYCARGE DHDILTGYPI RGQGTTVTVS   120
SGGGGSGGGG SGGGGSEVQL VESGGGLVQP GGSLRLSCAA SGFTFSSYWM HWVRQVPGKG   180
LVWVSRISSD ASRTIYADSV KGRFTISRDN AKNTLYLQMN SLRAEDTAVY YCARGEDHDI   240
LTGYPIRGQG TTVTVSSASE PKSSDKTHTC PPCPAPEAAG APSVFLFPPK PKDTLMISRT   300
PEVTCVVVDV SHEDPEVKFN WYVDGVEVHN AKTKPREEQY NSTYRVVSVL TVLHQDWLNG   360
KEYKCKVSNK ALPAPIEKTI SKAKGQPREP QVCTLPPSRE EMTKNQVSLS CAVKGFYPSD   420
IAVEWESNGQ PENNYKTTPP VLDSDGSFFL VSKLTVDKSR WQQGNVFSCS VMHEALHNHY   480
TQKSLSLSPG K                                                       491

SEQ ID NO: 237              moltype = AA  length = 455
FEATURE                     Location/Qualifiers
REGION                      1..455
                            note = PR006293 Chain
source                      1..455
                            mol_type = protein
                            organism = synthetic construct
SEQUENCE: 237
EVQLLESGGG LVQPGGSLRL SCAASGFTFS TYAMNWVRQA PGKGLEWVSR IRSKYNNYAT    60
YYADSVKDRF TISRDDSKST LYLQMNSLRA EDTAVYYCVR HGNFGNSYVS WFAYWGQGTL   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
EAAGAPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PCREEMTKNQ VSLWCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 238              moltype = AA  length = 491
FEATURE                     Location/Qualifiers
REGION                      1..491
                            note = PR006384 Chain
source                      1..491
                            mol_type = protein
                            organism = synthetic construct
SEQUENCE: 238
EVQLVESGGG LVQPGGSLRL SCAASGFTFS SYWMHWVRQV PGKGLVWVSR ISSTGSRTIY    60
ADSVKGRFTI SRDNAKNTLY LQMNSLRAED TAVYYCARGE DHDILTGYPI RGQGTTVTVS   120
SGGGGSGGGG SGGGGSEVQL VESGGGLVQP GGSLRLSCAA SGFTFSSYWM HWVRQVPGKG   180
LVWVSRISST GSRTIYADSV KGRFTISRDN AKNTLYLQMN SLRAEDTAVY YCARGEDHDI   240
LTGYPIRGQG TTVTVSSASE PKSSDKTHTC PPCPAPEAAG APSVFLFPPK PKDTLMISRT   300
PEVTCVVVDV SHEDPEVKFN WYVDGVEVHN AKTKPREEQY NSTYRVVSVL TVLHQDWLNG   360
KEYKCKVSNK ALPAPIEKTI SKAKGQPREP QVCTLPPSRE EMTKNQVSLS CAVKGFYPSD   420
IAVEWESNGQ PENNYKTTPP VLDSDGSFFL VSKLTVDKSR WQQGNVFSCS VMHEALHNHY   480
TQKSLSLSPG K                                                       491

SEQ ID NO: 239              moltype = AA  length = 491
FEATURE                     Location/Qualifiers
REGION                      1..491
                            note = PR007079 Chain
source                      1..491
                            mol_type = protein
                            organism = synthetic construct
SEQUENCE: 239
EVQLVESGGG LVQPGGSLRL SCAASGFTFS SYWMHWVRQV PGKGLVWVSR ISSAGSRTIY    60
ADSVKGRFTI SRDNAKNTLY LQMNSLRAED TAVYYCARGE DHDILTGYPI RGQGTTVTVS   120
SGGGGSGGGG SGGGGSEVQL VESGGGLVQP GGSLRLSCAA SGFTFSSYWM HWVRQVPGKG   180
LVWVSRISSA GSRTIYADSV KGRFTISRDN AKNTLYLQMN SLRAEDTAVY YCARGEDHDI   240
```

```
LTGYPIRGQG TTVTVSSASE PKSSDKTHTC PPCPAPEAAG APSVFLFPPK PKDTLMISRT     300
PEVTCVVVDV SHEDPEVKFN WYVDGVEVHN AKTKPREEQY NSTYRVVSVL TVLHQDWLNG     360
KEYKCKVSNK ALPAPIEKTI SKAKGQPREP QVCTLPPSRE EMTKNQVSLS CAVKGFYPSD    420
IAVEWESNGQ PENNYKTTPP VLDSDGSFFL VSKLTVDKSR WQQGNVFSCS VMHEALHNHY    480
TQKSLSLSPG K                                                          491

SEQ ID NO: 240          moltype = AA   length = 491
FEATURE                 Location/Qualifiers
REGION                  1..491
                        note = PR007080 Chain
source                  1..491
                        mol_type = protein
                        organism = synthetic construct
SEQUENCE: 240
EVQLVESGGG LVQPGGSLRL SCAASGFTFS SYWMHWVRQV PGKGLVWVSR IDSRGSRTIY     60
ADSVKGRFTI SRDNAKNTLY LQMNSLRAED TAVYYCARGE DHDILTGYPI RGQGTTVTVS    120
SGGGGSGGGG SGGGGSEVQL VESGGGLVQP GGSLRLSCAA SGFTFSSYWM HWVRQVPGKG    180
LVWVSRIDSR GSRTIYADSV KGRFTISRDN AKNTLYLQMN SLRAEDTAVY YCARGEDHDI    240
LTGYPIRGQG TTVTVSSASE PKSSDKTHTC PPCPAPEAAG APSVFLFPPK PKDTLMISRT    300
PEVTCVVVDV SHEDPEVKFN WYVDGVEVHN AKTKPREEQY NSTYRVVSVL TVLHQDWLNG    360
KEYKCKVSNK ALPAPIEKTI SKAKGQPREP QVCTLPPSRE EMTKNQVSLS CAVKGFYPSD    420
IAVEWESNGQ PENNYKTTPP VLDSDGSFFL VSKLTVDKSR WQQGNVFSCS VMHEALHNHY    480
TQKSLSLSPG K                                                          491

SEQ ID NO: 241          moltype = AA   length = 491
FEATURE                 Location/Qualifiers
REGION                  1..491
                        note = PR007081 Chain
source                  1..491
                        mol_type = protein
                        organism = synthetic construct
SEQUENCE: 241
EVQLVESGGG LVQPGGSLRL SCAASGFTFS SYWMHWVRQV PGKGLVWVSR INFDSSRTIY     60
ADSVKGRFTI SRDNAKNTLY LQMNSLRAED TAVYYCARGE DHDILTGYPI RGQGTTVTVS    120
SGGGGSGGGG SGGGGSEVQL VESGGGLVQP GGSLRLSCAA SGFTFSSYWM HWVRQVPGKG    180
LVWVSRINFD SSRTIYADSV KGRFTISRDN AKNTLYLQMN SLRAEDTAVY YCARGEDHDI    240
LTGYPIRGQG TTVTVSSASE PKSSDKTHTC PPCPAPEAAG APSVFLFPPK PKDTLMISRT    300
PEVTCVVVDV SHEDPEVKFN WYVDGVEVHN AKTKPREEQY NSTYRVVSVL TVLHQDWLNG    360
KEYKCKVSNK ALPAPIEKTI SKAKGQPREP QVCTLPPSRE EMTKNQVSLS CAVKGFYPSD    420
IAVEWESNGQ PENNYKTTPP VLDSDGSFFL VSKLTVDKSR WQQGNVFSCS VMHEALHNHY    480
TQKSLSLSPG K                                                          491

SEQ ID NO: 242          moltype = AA   length = 491
FEATURE                 Location/Qualifiers
REGION                  1..491
                        note = PR007082 Chain
source                  1..491
                        mol_type = protein
                        organism = synthetic construct
SEQUENCE: 242
EVQLVESGGG LVQPGGSLRL SCAASGFTFS SYWMHWVRQV PGKGLVWVSR INHDSSRTIY     60
ADSVKGRFTI SRDNAKNTLY LQMNSLRAED TAVYYCARGE DHDILTGYPI RGQGTTVTVS    120
SGGGGSGGGG SGGGGSEVQL VESGGGLVQP GGSLRLSCAA SGFTFSSYWM HWVRQVPGKG    180
LVWVSRINHD SSRTIYADSV KGRFTISRDN AKNTLYLQMN SLRAEDTAVY YCARGEDHDI    240
LTGYPIRGQG TTVTVSSASE PKSSDKTHTC PPCPAPEAAG APSVFLFPPK PKDTLMISRT    300
PEVTCVVVDV SHEDPEVKFN WYVDGVEVHN AKTKPREEQY NSTYRVVSVL TVLHQDWLNG    360
KEYKCKVSNK ALPAPIEKTI SKAKGQPREP QVCTLPPSRE EMTKNQVSLS CAVKGFYPSD    420
IAVEWESNGQ PENNYKTTPP VLDSDGSFFL VSKLTVDKSR WQQGNVFSCS VMHEALHNHY    480
TQKSLSLSPG K                                                          491

SEQ ID NO: 243          moltype = AA   length = 491
FEATURE                 Location/Qualifiers
REGION                  1..491
                        note = PR007083 Chain
source                  1..491
                        mol_type = protein
                        organism = synthetic construct
SEQUENCE: 243
EVQLVESGGG LVQPGGSLRL SCAASGFTFS SYWMHWVRQV PGKGLVWVCR ISSDASRTIY     60
ADSVKGRFTC SRDNAKNTLY LQMNSLRAED TAVYYCARGE DHDILTGYPI RGQGTTVTVS    120
SGGGGSGGGG SGGGGSEVQL VESGGGLVQP GGSLRLSCAA SGFTFSSYWM HWVRQVPGKG    180
LVWVCRISSD ASRTIYADSV KGRFTCSRDN AKNTLYLQMN SLRAEDTAVY YCARGEDHDI    240
LTGYPIRGQG TTVTVSSASE PKSSDKTHTC PPCPAPEAAG APSVFLFPPK PKDTLMISRT    300
PEVTCVVVDV SHEDPEVKFN WYVDGVEVHN AKTKPREEQY NSTYRVVSVL TVLHQDWLNG    360
KEYKCKVSNK ALPAPIEKTI SKAKGQPREP QVCTLPPSRE EMTKNQVSLS CAVKGFYPSD    420
IAVEWESNGQ PENNYKTTPP VLDSDGSFFL VSKLTVDKSR WQQGNVFSCS VMHEALHNHY    480
TQKSLSLSPG K                                                          491

SEQ ID NO: 244          moltype = AA   length = 5
```

```
FEATURE              Location/Qualifiers
REGION               1..5
                     note = Linker peptide GS_5
source               1..5
                     mol_type = protein
                     organism = synthetic construct
SEQUENCE: 244
GGGGS                                                                    5

SEQ ID NO: 245       moltype = AA  length = 10
FEATURE              Location/Qualifiers
REGION               1..10
                     note = Linker peptide GS_10
source               1..10
                     mol_type = protein
                     organism = synthetic construct
SEQUENCE: 245
GGGGSGGGGS                                                              10

SEQ ID NO: 246       moltype = AA  length = 15
FEATURE              Location/Qualifiers
REGION               1..15
                     note = Linker peptide GS_15
source               1..15
                     mol_type = protein
                     organism = synthetic construct
SEQUENCE: 246
GGGGSGGGGS GGGGS                                                        15

SEQ ID NO: 247       moltype = AA  length = 20
FEATURE              Location/Qualifiers
REGION               1..20
                     note = Linker peptide GS_20
source               1..20
                     mol_type = protein
                     organism = synthetic construct
SEQUENCE: 247
GGGGSGGGGS GGGGSGGGGS                                                   20

SEQ ID NO: 248       moltype = AA  length = 25
FEATURE              Location/Qualifiers
REGION               1..25
                     note = Linker peptide GS_25
source               1..25
                     mol_type = protein
                     organism = synthetic construct
SEQUENCE: 248
GGGGSGGGGS GGGGSGGGGS GGGGS                                             25

SEQ ID NO: 249       moltype = DNA  length = 24
FEATURE              Location/Qualifiers
misc_feature         1..24
                     note = PCR primer-1
source               1..24
                     mol_type = other DNA
                     organism = synthetic construct
SEQUENCE: 249
ggtgtccagt gtsaggtgca gctg                                              24

SEQ ID NO: 250       moltype = DNA  length = 29
FEATURE              Location/Qualifiers
misc_feature         1..29
                     note = PCR primer-2
source               1..29
                     mol_type = other DNA
                     organism = synthetic construct
SEQUENCE: 250
aatccctggg cactgaagag acggtgacc                                         29
```